US012799170B2

(12) United States Patent
Combier et al.

(10) Patent No.: US 12,799,170 B2
(45) Date of Patent: *Nov. 17, 2026

(54) MICROPEPTIDES AND USE OF SAME FOR MODULATING GENE EXPRESSION

(71) Applicants: UNIVERSITE PAUL SABATIER TOULOUSE III, Toulouse Cedex (FR); CENTRE NATIONAL DE LA RECHERCHE SCIENTIFIQUE, Paris Cedex (FR)

(72) Inventors: Jean-Philippe Combier, Castanet Tolosan (FR); Dominique Lauressergues, Toulouse (FR); Guillaume Becard, Odars (FR); François Payre, Pompertuzat (FR); Serge Plaza, Ramonville Saint Agne (FR); Jérôme Cavaille, Ramonville Saint Agne (FR)

(73) Assignees: UNIVERSITE PAUL SABATIER TOULOUSE III, Toulouse (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 206 days.

This patent is subject to a terminal disclaimer.

(21) Appl. No.: 18/668,366

(22) Filed: May 20, 2024

(65) Prior Publication Data

US 2024/0301014 A1 Sep. 12, 2024

Related U.S. Application Data

(63) Continuation of application No. 16/595,926, filed on Oct. 8, 2019, now Pat. No. 12,024,543, which is a continuation of application No. 14/320,703, filed on Jul. 1, 2014, now abandoned.

(30) Foreign Application Priority Data

Oct. 31, 2013 (FR) ...................................... 1360727
Jun. 3, 2014 (FR) ...................................... 1455044

(51) Int. Cl.

| | |
|---|---|
| ***C12N 15/113*** | (2010.01) |
| ***A01N 37/46*** | (2006.01) |
| ***A01N 57/16*** | (2006.01) |
| ***A01N 65/00*** | (2009.01) |
| ***A01N 65/08*** | (2009.01) |
| ***A01N 65/20*** | (2009.01) |
| ***A01N 65/28*** | (2009.01) |
| ***A01N 65/44*** | (2009.01) |
| ***C07K 5/10*** | (2006.01) |
| ***C07K 5/103*** | (2006.01) |
| ***C07K 7/06*** | (2006.01) |
| ***C07K 7/08*** | (2006.01) |
| ***C07K 14/415*** | (2006.01) |
| ***C12N 15/63*** | (2006.01) |
| ***C12N 15/82*** | (2006.01) |
| ***C12Q 1/68*** | (2018.01) |
| ***C12Q 1/6895*** | (2018.01) |
| *A61K 38/00* | (2006.01) |
| *A61K 48/00* | (2006.01) |

(52) U.S. Cl.

CPC ............ *C07K 14/415* (2013.01); *A01N 37/46* (2013.01); *A01N 57/16* (2013.01); *A01N 65/00* (2013.01); *A01N 65/08* (2013.01); *A01N 65/20* (2013.01); *A01N 65/28* (2013.01); *A01N 65/44* (2013.01); *C07K 5/10* (2013.01); *C07K 5/1013* (2013.01); *C07K 7/06* (2013.01); *C07K 7/08* (2013.01); *C12N 15/113* (2013.01); *C12N 15/63* (2013.01); *C12N 15/8218* (2013.01); *C12N 15/8261* (2013.01); *C12Q 1/68* (2013.01); *C12Q 1/6895* (2013.01); *A61K 38/00* (2013.01); *A61K 48/00* (2013.01); *C12Q 2600/13* (2013.01); *C12Q 2600/158* (2013.01); *C12Q 2600/178* (2013.01); *Y02A 40/146* (2018.01)

(58) Field of Classification Search

None

See application file for complete search history.

(56) References Cited

PUBLICATIONS

Freidinger, Roger M. "Design and synthesis of novel bioactive peptides and peptidomimetics." Journal of medicinal chemistry 46.26 (2003): 5553-5566. (Year: 2003).*
Hamley, Ian W. "Small bioactive peptides for biomaterials design and therapeutics." Chemical reviews 117.24 (2017): 14015-14041). (Year: 2017).*
"Administer" definition retrieved from dictionary.com website, Dec. 23, 2016.
Ehsan Sabaghian, et al., "An integrated network of *Arabidopsis* growth regulators and its use for gene prioritization", Scientific Reports, 2015, 5: 17617, DOI: 10.10/1038/srep17617, pp. 1-13.
Calvin D. Lietzow, et al., "QTL mapping of parthenocarpic fruit set in North American processing cucumber", Theor Appl Genet, 2016, 129:2387-2401, DOI: 10.1007/s00122-016-2778-z, 15 pages.
C. D. Town, Genbank Accession AC157488, submitted Feb. 17, 2005, annotated Mar. 24, 2007, 45 pages.

(Continued)

*Primary Examiner* — Charles Logsdon
(74) *Attorney, Agent, or Firm* — Maier & Maier, PLLC

(57) ABSTRACT

Process for detecting and identifying micropeptides (miPEPs) encoded by a nucleotide sequence contained in the sequence of the primary transcript of a microRNA and use thereof for modulating gene expression.

10 Claims, 21 Drawing Sheets

Specification includes a Sequence Listing.

(56) References Cited

PUBLICATIONS

Rebecca Schwab, et al., "Enhanced microRNA accumulation through stemloop-adjacent introns", EMBO Reports, vol. 14, No. 7, 2013, pp. 615-621.
David Bielewicz. et al., "Introns of plant primiRNAs enhance miRNA biogenesis", EMBO Reports, vol. 14, No. 7, 2013, pp. 622-628.
Maximo Ibo Galindo, et al., "Peptides Encoded by Short ORFs Control Development and Define a New Eukaryotic Gene Family", PLOS Biology, vol. 5, No. 5, May 2007, pp. 1052-1062, DOI: 10.1371/journal.pbio.0050106.
Yuji Kageyama, et al., "Coding vs non-coding: Translatability of short ORFs found in putative non-coding transcripts", Biochimie 93, 2011, pp. 1981-1986, DOI: 10.1016/j.biochi.2011.06.024.
T. Kondo, et al., "Small Peptides Switch the Transcriptional Activity of Shavenbaby During *Drosophila* Embryogenesis", Science, vol. 329, No. 5989, Jul. 16, 2010, pp. 336-339.
Miriam I. Rosenberg, et al., "Hiding in Plain Sight", Science, vol. 329, No. 5989, Jul. 16, 2010, pp. 284-285.
Jin Dai, et al., "Plant Phenolics: Extraction, Analysis and Their Antioxidant and Anticancer Properties", Molecules, vol. 15, No. 10, 2010, pp. 7313-7352, ISSN: 1420-3049, DOI: 10.3390/molecules15107313.
Wang et al., "A universal and rapid protocol for protein extraction from recalcitrant plant tissues for proteomic analysis", Electrophoresis 2006, vol. 27, pp. 2782-2786.

* cited by examiner

A

B

A) Control plant

B) Plant treated with miPEP 164a

A) Control plant

B) Plant treated with miPEP319a

MICROPEPTIDES AND USE OF SAME FOR MODULATING GENE EXPRESSION

RELATED APPLICATIONS

This application is a continuation of U.S. patent application Ser. No. 16/595,926, filed on Oct. 8, 2019, which is a continuation of U.S. patent application Ser. No. 14/320,703, filed on Jul. 1, 2014, which claims priority under 35 U.S.C. § 119, to French Patent Application Nos. 1360727, filed Oct. 31, 2013, and U.S. Pat. No. 1,455,044, filed Jun. 3, 2014, the disclosures of which are incorporated by reference herein in their entireties.

REFERENCE TO A SEQUENCE LISTING

In accordance with 37 CFR § 1.831, the present specification makes reference to a Sequence Listing submitted electronically as an .xml file named "USCC IPEP2-Sequence Listing.xml", created on May 17, 2024, which is 425,444 bytes in size. The entire contents of the Sequence Listing are hereby incorporated by reference.

FIELD OF THE INVENTION

The present invention relates to micropeptides (peptides encoded by microRNAs or "miPEPs") and use thereof for modulating gene expression.

BACKGROUND OF THE INVENTION

The microRNAs (miRNAs) are small non-coding RNAs, about 21 nucleotides in length after maturation, which control expression of target genes at the post-transcriptional level, by degrading the target mRNA or by inhibiting its translation. The miRNAs occur in plants and animals.

The target genes are often key genes in developmental processes. For example they encode transcription factors or proteins of the proteasome.

The regulation of expression of the miRNAs is very poorly understood, but it is known in particular that the latter involves, like most coding genes, an RNA polymerase II: this enzyme produces a primary transcript, called "pri-miRNA", which is then matured by a protein complex in particular containing the Dicer type enzymes. This maturation leads firstly to the formation of a precursor of miRNA called "pre-miRNA", having a stem-loop secondary structure containing the miRNA and its complementary sequence miRNA*. Then the precursor is matured, which leads to formation of a shorter double-stranded RNA containing the miRNA and the miRNA*. The miRNA is then manipulated by the RISC complex, which cleaves the mRNA of the target gene or inhibits its translation.

Moreover, it has been shown that the presence of introns in the primary transcript of the microRNA increases the expression of the mature microRNA (Schwab et al, *EMBO Rep.*, 14(7): 615-21, 2013). However, owing to experimental difficulties, the primary transcripts of microRNAs, or pri-miRNAs, have received very little study.

About 50% of eukaryotic genes have small open reading frames within their 5'UTR region (5' UnTranslated Region) upstream of the coding sequence. These small open reading frames (or "uORFs" for upstream ORFs) may perform a role of translation regulator, mainly in cis, by modulating the fixation and the rate of the ribosomes on the mRNA, but also in trans by an as yet unknown mechanism, by means of peptides encoded by said uORFs (Combier et al., *Gene Dev*, 22: 1549-1559, 2008). By definition, the uORFS are present upstream of coding genes.

Recently, small ORFs have also been discovered in long intergenic non-coding RNAs (lincRNAs), the putative function of which, if it exists, is not known (Ingolia et al., *Cell*, 147(4): 789-802, 2011; Guttman & Rinn, *Nature*, 482 (7385): 339-46, 2012).

However, no example has yet been reported concerning the existence of ORFs encoding peptides within non-coding microRNAs. Until now, the microRNAs, and by extension their primary transcript, have always been regarded, based on their particular mode of action, as non-coding regulatory RNAs that do not produce any peptide.

SUMMARY OF THE INVENTION

One of the aspects of the invention is to propose peptides capable of modulating the expression of microRNAs.

Another aspect of the invention is to propose a means for modulating the expression of one or more target genes of a microRNA.

The present invention offers the advantage of allowing easier and more effective control of the expression of genes targeted by the microRNAs, through a means other than the microRNA.

The invention thus relates to a process for detecting and identifying a micropeptide (miPEP) encoded by a nucleotide sequence contained in the sequence of the primary transcript of a microRNA, comprising:

a) a step of detecting an open reading frame from 12 to 303 nucleotides in length contained in the sequence of the primary transcript of said microRNA, then b) a step of comparison between:

the accumulation of said microRNA in a specified eukaryotic cell expressing said microRNA, in the presence of a peptide encoded by a nucleotide sequence that is identical or degenerate relative to that of said open reading frame, said peptide being present in the cell independently of transcription of the primary transcript of said microRNA, and the accumulation of said microRNA in a eukaryotic cell of the same type as the aforesaid specified eukaryotic cell expressing said microRNA, in the absence of said peptide, in which a modulation of the accumulation of said microRNA in the presence of said peptide relative to the accumulation of said microRNA in the absence of said peptide indicates the existence of a micropeptide encoded by said open reading frame.

The invention relates in particular to a process for detecting and identifying a micropeptide (miPEP) encoded by a nucleotide sequence contained in the sequence of the primary transcript of a microRNA, comprising:

a) a step of detecting an open reading frame from 15 to 303 nucleotides in length contained in the sequence of the primary transcript of said microRNA, then b) a step of comparison between:

the accumulation of said microRNA in a specified eukaryotic cell expressing said microRNA, in the presence of a peptide encoded by a nucleotide sequence that is identical or degenerate relative to that of said open reading frame, said peptide being present in the cell independently of transcription of the primary transcript of said microRNA, and the accumulation of said microRNA in a eukaryotic cell of the same type as the aforesaid specified eukaryotic cell expressing said microRNA, in the absence of said peptide, in which a modulation of the accumulation of said microRNA in the presence of said peptide relative to the accumulation of said microRNA in the absence of said peptide indicates the existence of a micropeptide encoded by said open reading frame.

BRIEF DESCRIPTION OF THE DRAWINGS

The following figures and examples will illustrate the invention better, but without limiting its scope.

(A) The y-axis indicates the relative expression of MtmiR171b (left-hand columns), of HAM1 (middle columns) or of HAM2 (right-hand columns) in a control plant (white columns) or in a plant in which MtmiR171b is overexpressed (black columns). The error bar corresponds to the standard error of the mean (number of individuals=10). The overexpression of MtmiR171b induces a decrease in the expression of the HAM1 and HAM2 genes.

(B) The y-axis indicates the mean number of lateral roots observed in a control plant (white column) or in a plant in which MtmiR171b is overexpressed (black column). The error bar corresponds to the standard error of the mean (number of individuals=100). The overexpression of MtmiR171b leads to a reduction in the number of lateral roots.

Figure 2:
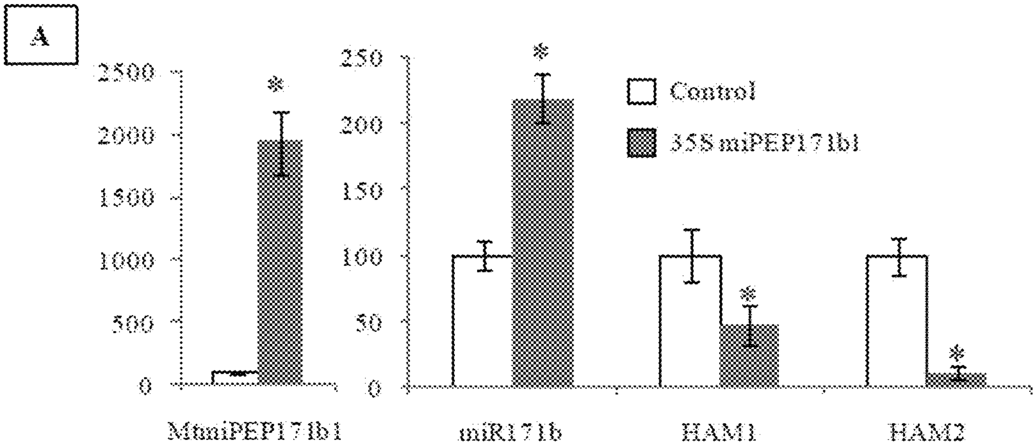
Figure 2:
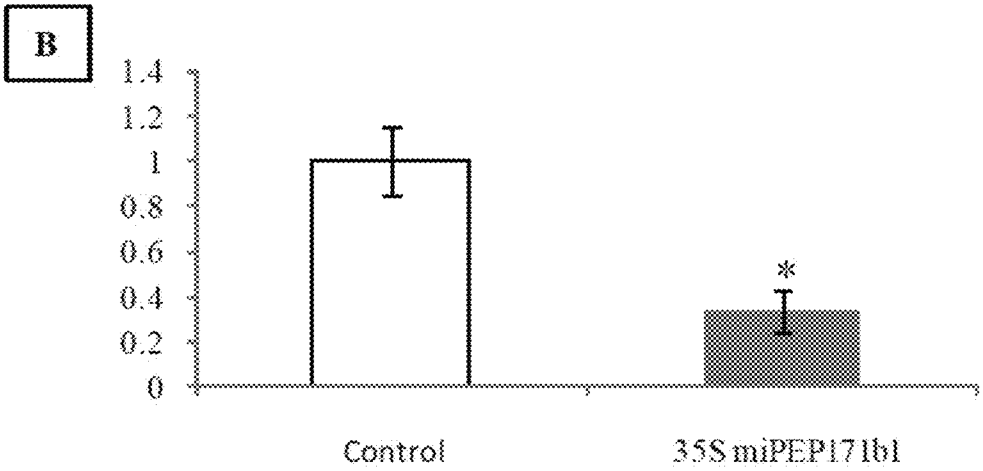

FIG. 2. Effects of overexpression of MtmiPEP171b1 on the expression of MtmiR171b and of the HAM1 and HAM2 genes (A) or on the number of lateral roots (B) in *M. truncatula.*

(A) The y-axis indicates the relative expression of MtmiPEP171b1 (graph on left), miR171b (graph on right, left-hand columns), of HAM1 (accession No. MtGI9-TC114268) (graph on right, middle columns) or of HAM2 (accession No. MtGI9-TC120850) (graph on right, right-hand columns) in a control plant (white columns) or in a plant in which MtmiPEP171b1 is overexpressed (black columns). The error bar corresponds to the standard error of the mean (number of individuals=10). The overexpression of MtmiPEP171b1 induces an increase in the accumulation of MtmiR171b, as well as a decrease in the expression of the HAM1 and HAM2 genes.

(B) The y-axis indicates the mean number of lateral roots observed in a control plant (white column) or in a plant in which MtmiPEP171b1 is overexpressed (black column). The error bar corresponds to the standard error of the mean (number of individuals=100). The overexpression of MtmiPEP171b1 leads to a reduction in the number of lateral roots.

Figure 3:
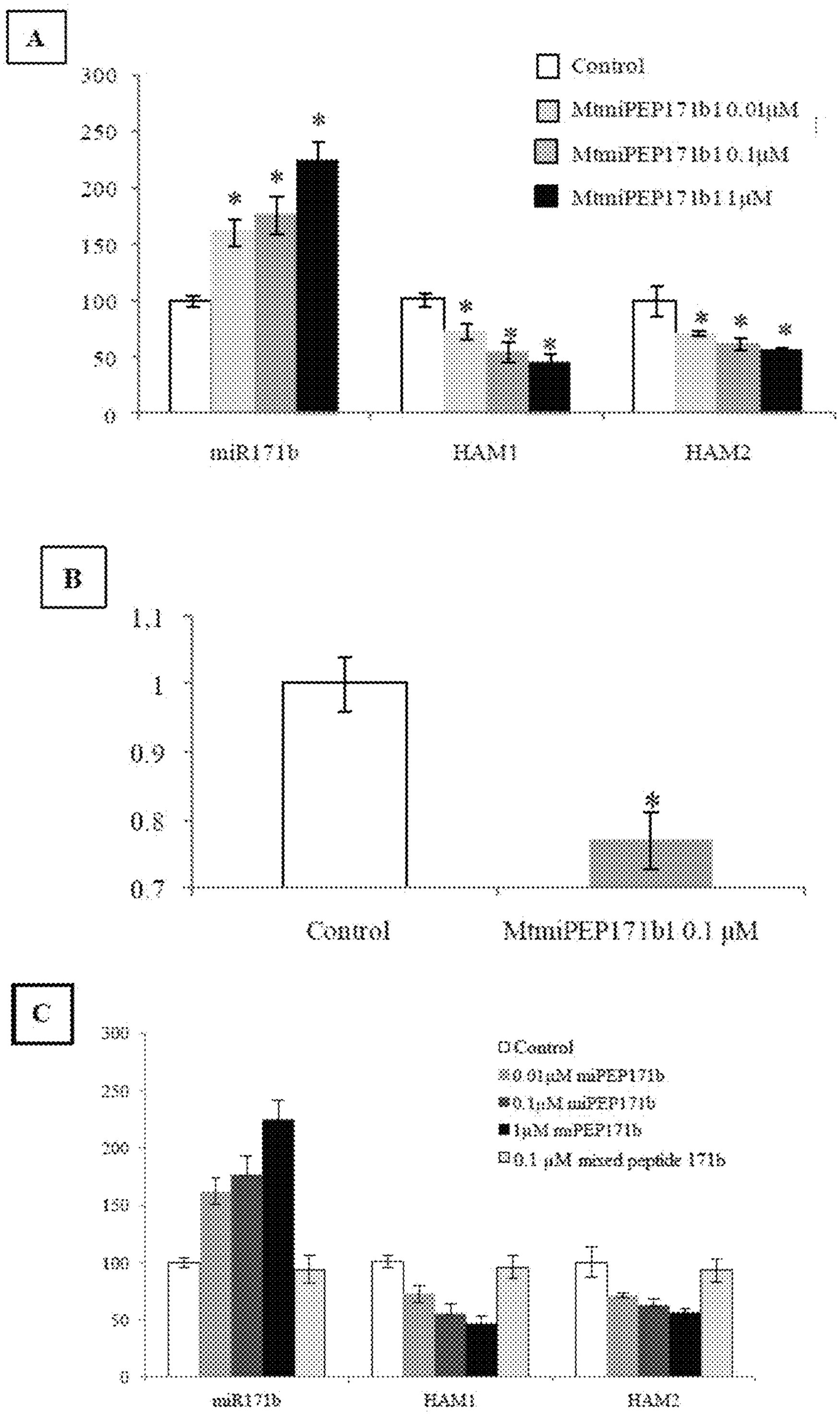

FIG. 3. Effects of MtmiPEP171b1 on the expression of MtmiR171b and the HAM1 and HAM2 genes (A) and on the number of lateral roots (B) in *M. truncatula.*

(A) The y-axis indicates the relative expression of MtmiR171b (left-hand columns), of HAM1 (middle columns) or of HAM2 (right-hand columns) in a control plant (white columns) or in a plant treated by watering once daily for 5 days with MtmiPEP171b1 at 0.01 μM (light grey columns), 0.1 μM (dark grey columns) or 1 μM (black columns). The error bar corresponds to the standard error of the mean (number of individuals=10). Application of MtmiPEP171b1 at different concentrations induces an increase in the accumulation of MtmiR171b, as well as a decrease in the expression of the HAM1 and HAM2 genes.

(B) The y-axis indicates the mean number of lateral roots observed in a control plant (white column) or in a plant treated by watering with MtmiPEP171b1 at 0.1 μM once daily for 5 days (black column). The error bar corresponds to the standard error of the mean (number of individuals=100). Application of MtmiPEP171b1 at 0.1 μM leads to a reduction in the number of lateral roots.

(C) The y-axis indicates the relative expression of MtmiR171b (left-hand columns), of HAM1 (middle columns) or of HAM2 (right-hand columns) in a control plant (white columns) or in a plant treated by watering once daily for 5 days with MtmiPEP171b1 at 0.01 μM (grey columns), 0.1 μM (dark grey columns) or 1 μM (black columns) or with 0.01 μM of a mixed peptide (light grey columns) the amino acid composition of which is identical to miPEP171b but the sequence of which is different. The error bar corresponds to the standard error of the mean (number of individuals=10).

Figure 4:
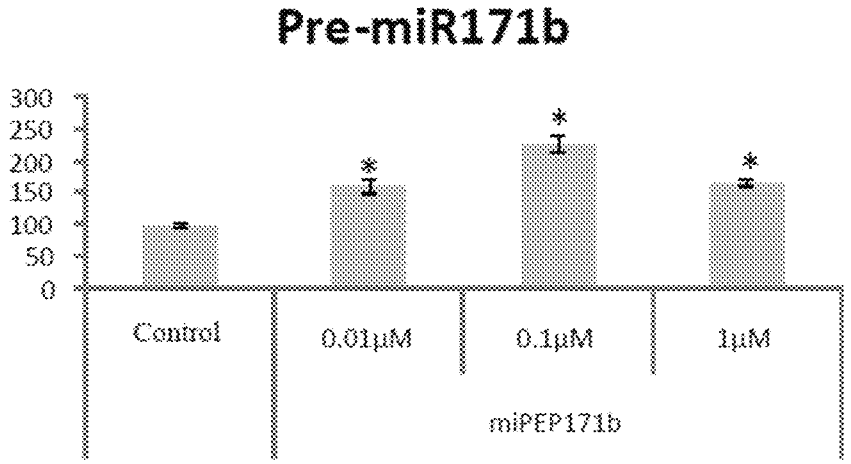
Figure 4:
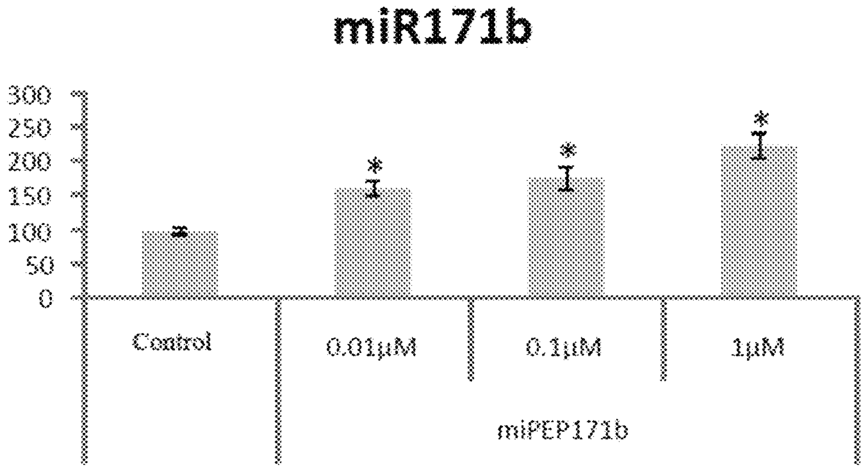

FIG. 4. Effects of MtmiPEP171b1 on the expression of pre-MtmiR171b (A) and of MtmiR171b (B) in *M. truncatula.*

The y-axis indicates the relative expression of the precursors of the different forms of the microRNA in control plants (left-hand column) or in plants treated by watering once daily for 5 days with MtmiPEP171b1 at 0.01 μM, 0.1 μM or 1 μM (right-hand columns). The error bar corresponds to the standard error of the mean (number of individuals=200). Application of MtmiPEP171b1 at different concentrations leads to an increase in the accumulation of pre-MtmiR171b (A) and of MtmiR171b (B).

Figure 5:
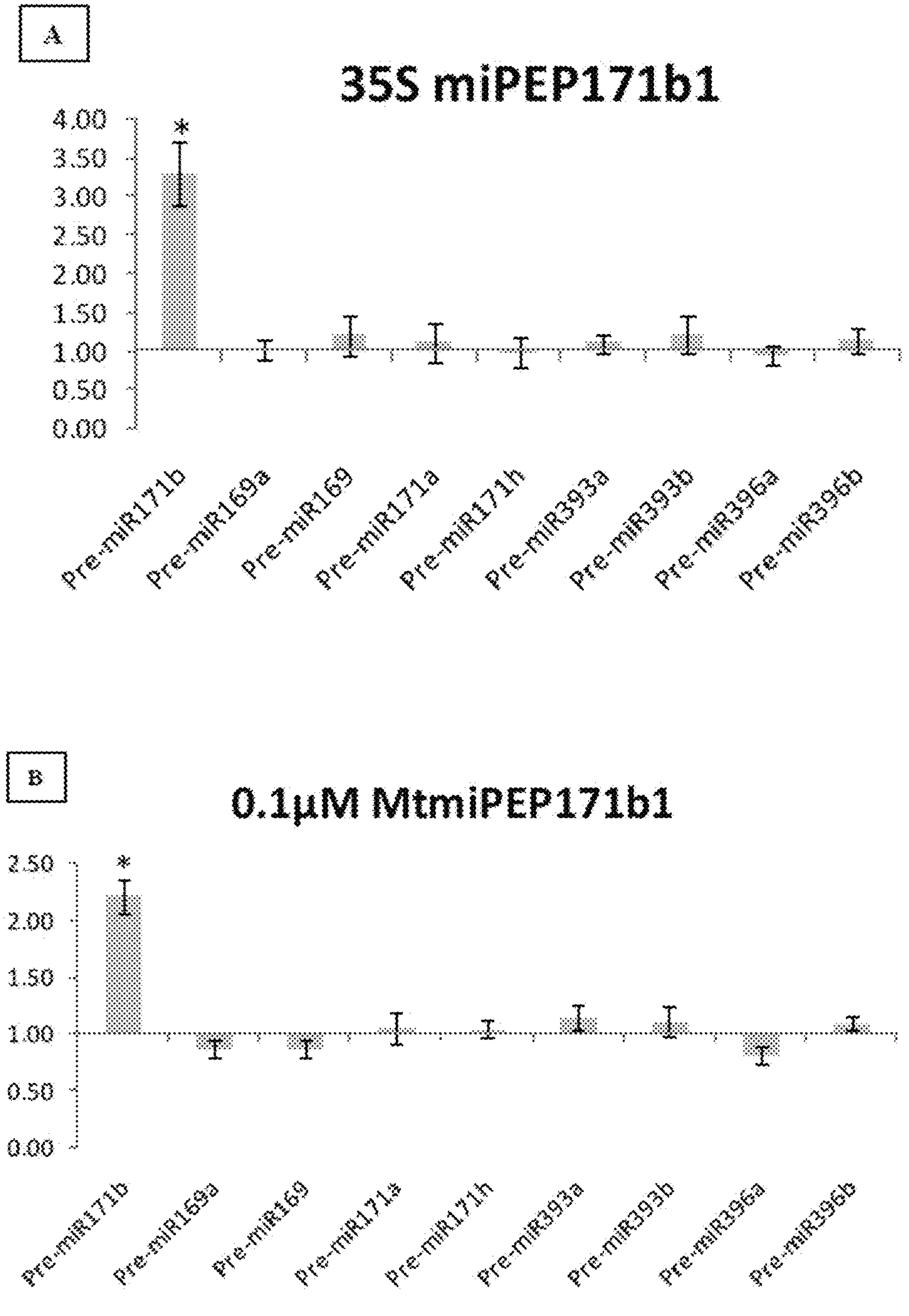

FIG. 5. Effects of overexpression of MtmiPEP171b1 (A) and effects of MtmiPEP171b1 (B) on the expression of different precursors of microRNAs in *M. truncatula.*

The y-axis indicates the ratio of the expression of the precursors of microRNAs in plants overexpressing MtmiPEP171b1 to the expression of these same precursors in control roots (A), or the ratio of the expression of the precursors of microRNAs in plants treated with MtmiPEP171b1 (0.1 μM) to the expression of these same precursors in control roots (B). The different precursors of microRNAs tested are indicated from left to right on the x-axis, namely pre-MtmiR171b (SEQ ID NO: 246), pre-MtmiR169 (SEQ ID NO: 359), pre-MtmiR169a (SEQ ID NO: 360), pre-MtmiR171a (SEQ ID NO: 361), pre-MtmiR171h (SEQ ID NO: 362), pre-MtmiR393a (SEQ ID NO: 363), pre-MtmiR393b (SEQ ID NO: 364), pre-MtmiR396a (SEQ ID NO: 365) and pre-MtmiR396b (SEQ ID NO: 366). The error bar corresponds to the standard error of the mean (number of individuals=10). It is noted that MtmiPEP171b1 only leads to an effect on the accumulation of MtmiR171b and not on the other miRNAs.

Figure 6:
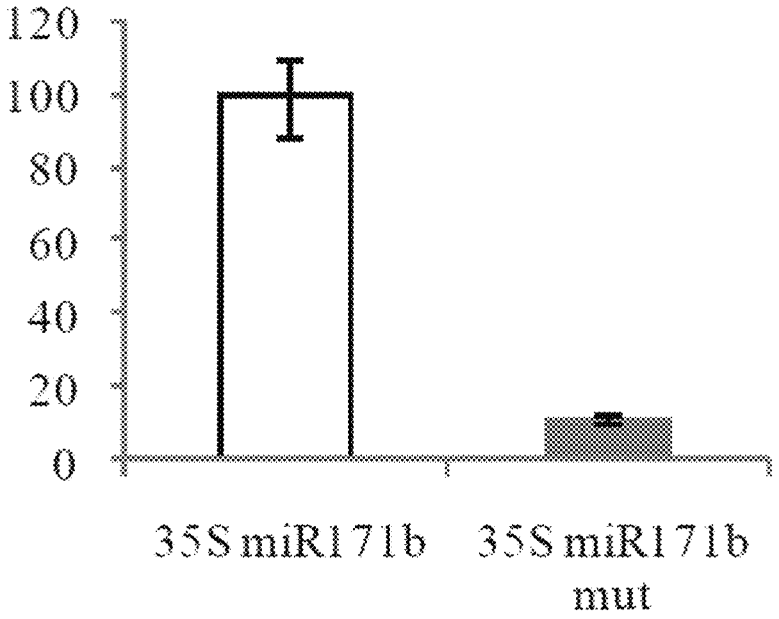

FIG. 6. Effects of translation of MtmiPEP171b1 on the expression of MtmiR171b demonstrated in the model plant *Nicotiana benthamiana*. The y-axis indicates the relative expression of MtmiR171b in tobacco plants transformed in order to express pri-MtmiR171b (white column) or a mutated pri-MtmiR171b in which the codon ATG has been replaced with ATT (black column). The mutated pri-MtmiR171b is therefore incapable of producing MtmiPEP171b1. The error bar corresponds to the standard error of the mean (number of individuals=30). It is noted that the absence of translation of MtmiPEP171b1 leads to a marked decrease in the accumulation of miR171b.

Figure 7:
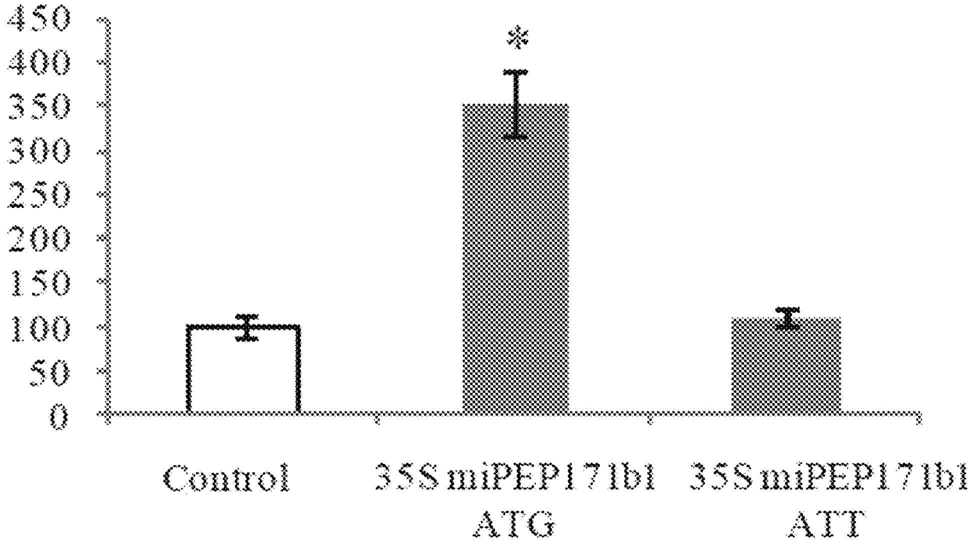

FIG. 7. Effects of overexpression of MtmiPEP171b1 on the expression of pre-MtmiR171b demonstrated in the model plant *Nicotiana benthamiana.*

The y-axis indicates the relative expression of pre-MtmiR171b in tobacco plants that have been transformed in order to express MtmiR171b (left-hand column), MtmiR171b and MtmiPEP171b1 (middle column), or MtmiR171b and a mutated version of MtmiORF171b in which the start codon ATG has been replaced with ATT (right-hand column). The error bar corresponds to the standard error of the mean (number of individuals=30). It is noted that the expression of MtmiPEP171b1 increases the expression of MtmiR171b, and this effect is dependent on the translation of MtmiORF171b to MtmiPEP171b1.

Figure 8:
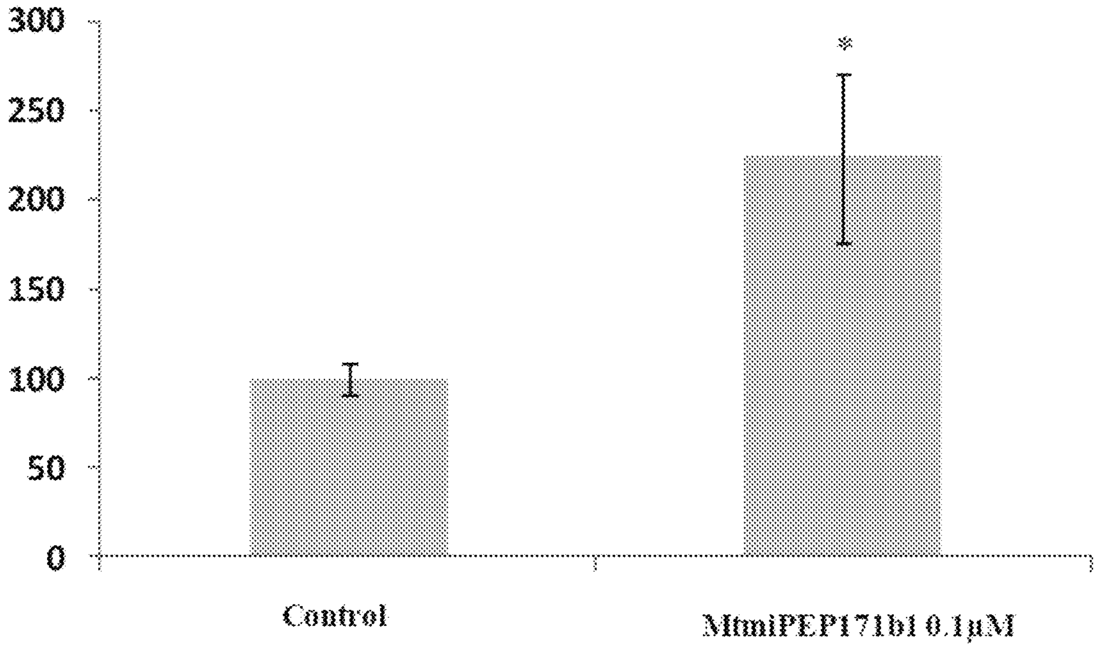

FIG. 8. Effects of MtmiPEP171b1 on the expression of pre-MtmiR171b demonstrated in the model plant *Nicotiana benthamiana.*

The y-axis indicates the relative expression of MtmiR171b in tobacco plants transformed in order to express MtmiR171b onto which MtmiPEP171b1 has been sprayed (0.1 μM) twice, 12 h and then 30 min before sampling (right-hand column) or not (left-hand column). The error bar corresponds to the standard error of the mean (number of individuals=6). The peptide MtmiPEP171b1 applied by spraying induces an increase in the accumulation of MtmiR171b.

Figure 9:
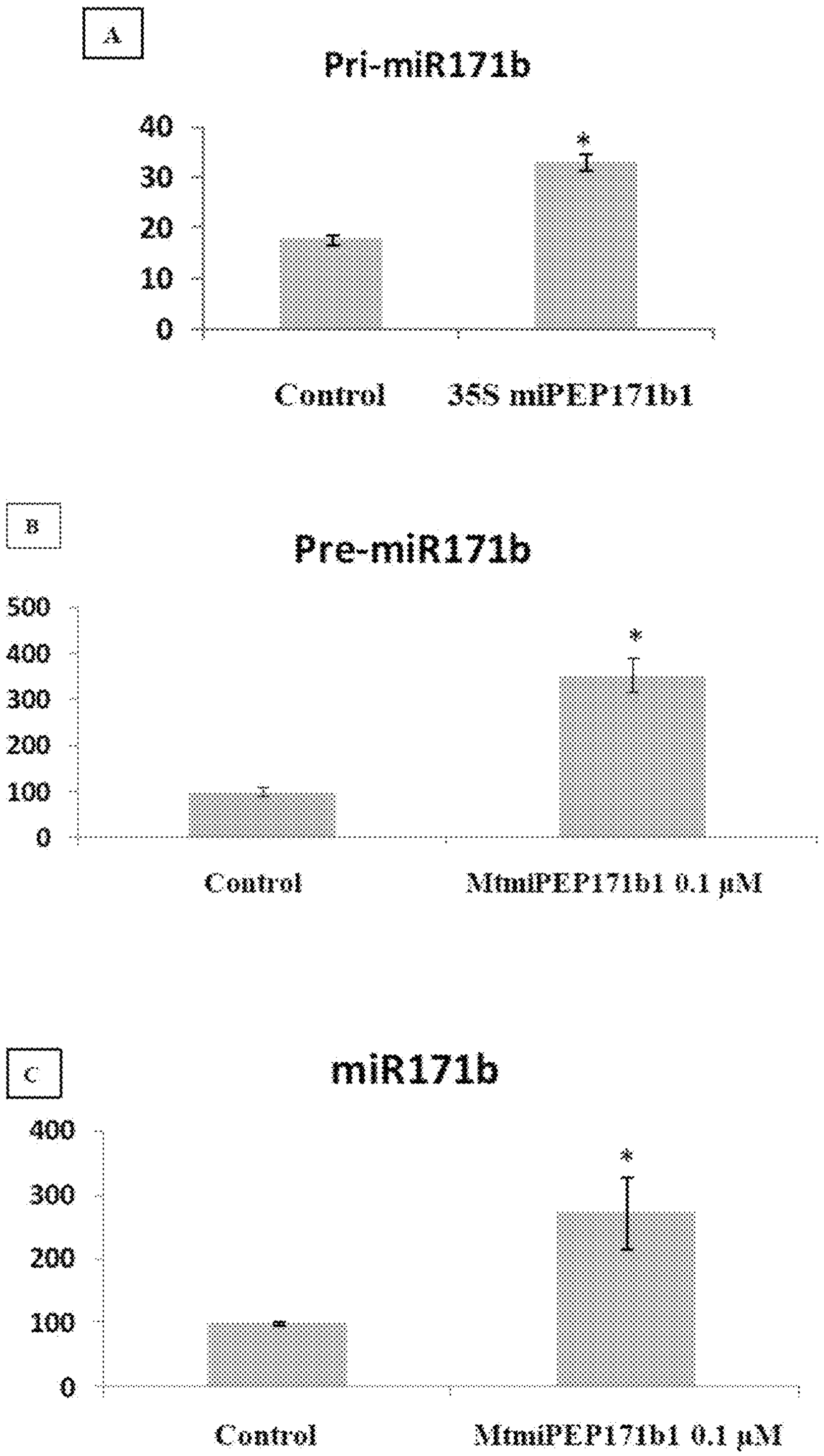

FIG. 9. Effects of MtmiPEP171b1 on the expression of pri-miR171b (A), pre-MtmiR171b (B) and MtmiR171b (C) demonstrated in the model plant *Nicotiana benthamiana.*

The y-axis indicates the relative expression of the precursors of the different forms of the microRNA in tobacco plants modified in order to express MtmiR171b (left-hand column) or modified in order to express MtmiR171b and overexpress MtmiPEP171b1 (right-hand columns, FIG. 9A) or treated with 0.1 μM of miPEP171b1 (FIGS. 9B and C). The error bar corresponds to the standard error of the mean (number of individuals=30). The overexpression of MtmiPEP171b1 or application of miPEP171b1 increases the accumulation of pri-MtmiR171b (A), pre-MtmiR171b (B) and MtmiR171b (C).

Figure 10:
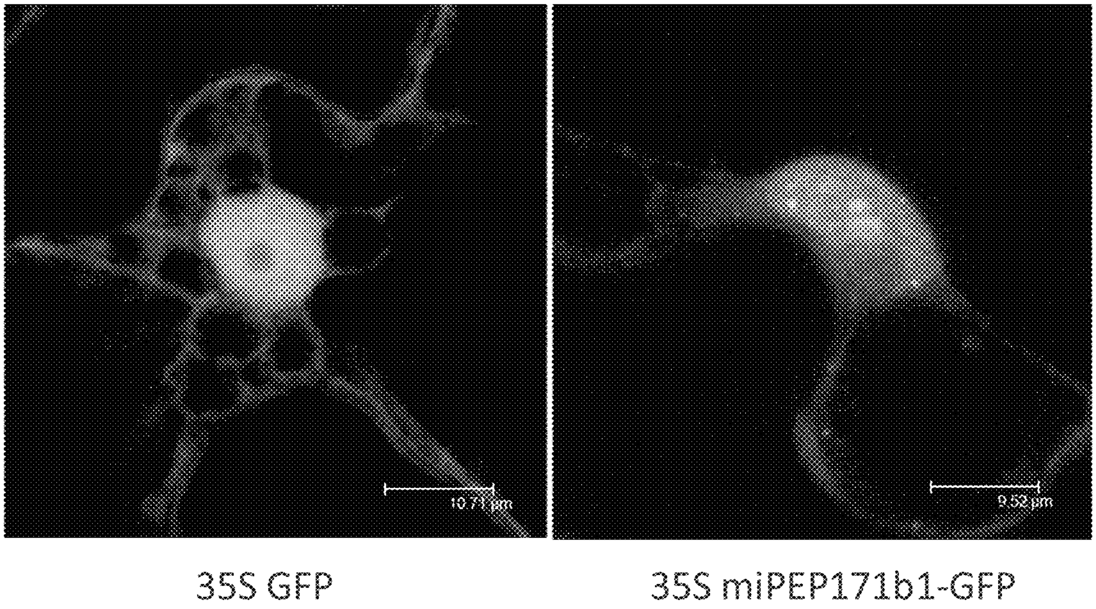

FIG. 10. Localization of MtmiPEP171b1 in tobacco leaf cells that have been modified in order to express MtmiPEP171b1.

The photographs show tobacco leaf cells modified in order to express the protein GFP alone (left panel) or the protein GFP fused to MtmiPEP171b1 (right panel). These observations indicate that MtmiPEP171b1 is localized in small nuclear bodies.

Figure 11:
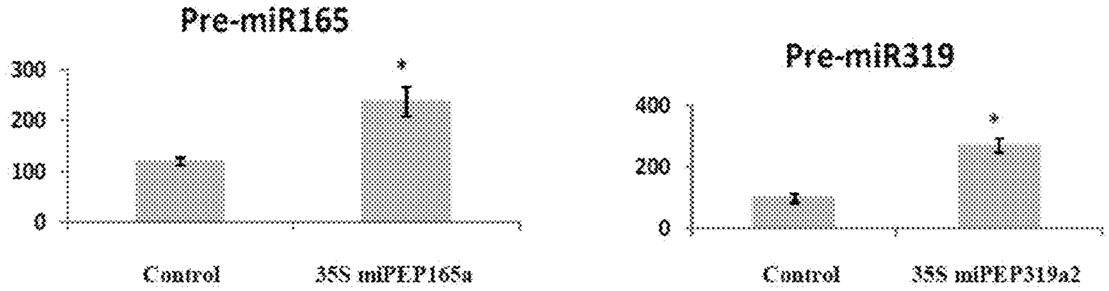

FIG. 11. Effects of the expression of AtmiPEP165a (identified in *Arabidopsis thaliana*) on the expression of AtmiR165a (A), and of the expression of AtmiPEP319a2 (identified in *Arabidopsis thaliana*) on AtmiR319a (B), demonstrated in the model plant of tobacco.

(A) The y-axis indicates the relative expression of AtmiR165a in tobacco plants modified in order to express AtmiR165a (left-hand column) or to express AtmiR165a and AtmiPEP165a (right-hand column).

(B) The y-axis indicates the relative expression of AtmiR319a in tobacco plants modified in order to express AtmiR319a (left-hand column) or in order to express AtmiR319a and AtmiPEP319a (right-hand column).

The error bar corresponds to the standard error of the mean (number of individuals=30).

In both cases, it is noted that the expression of miORF, and therefore the production of miPEP, leads to an increase in the accumulation of pre-miRNA.

Figure 12:
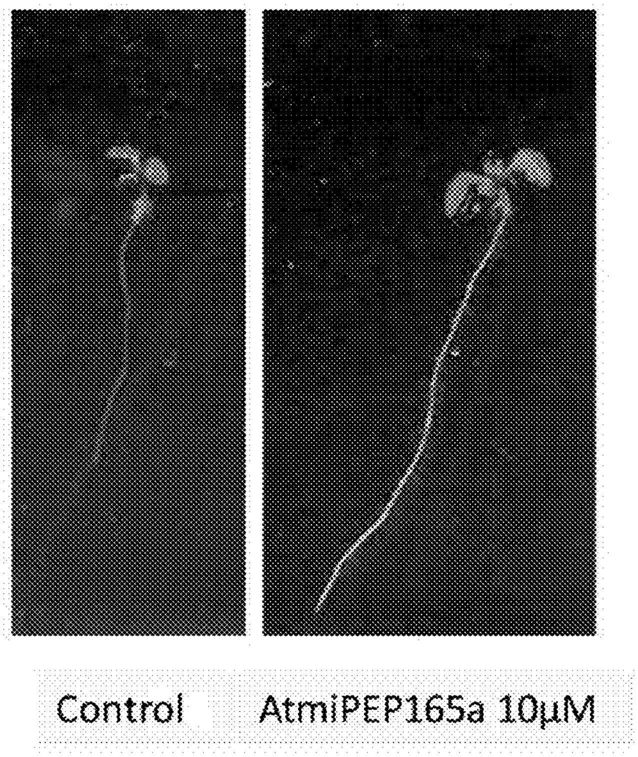
Figure 12:
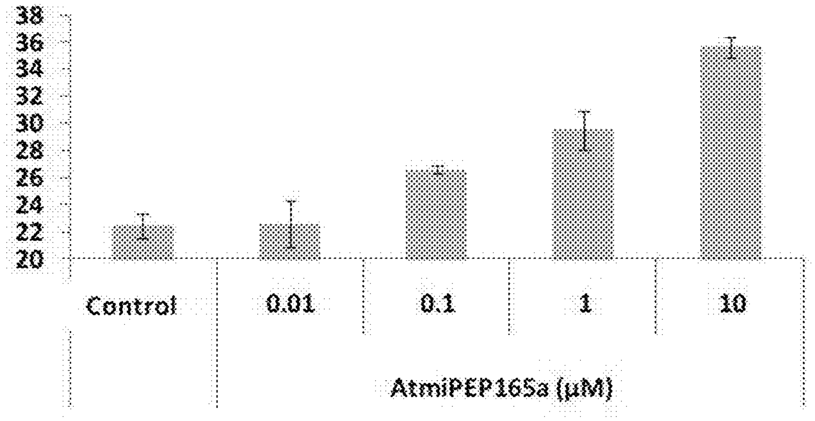

FIG. 12. Effects of treatment with AtmiPEP165a on root growth in *Arabidopsis thaliana.*

The photograph shows two plants of the same age: a control plant (plant on the left) and a plant treated with AtmiPEP165a (plant on the right). The treatment with AtmiPEP165a leads to a phenotype with greatly accelerated root growth in *Arabidopsis thaliana*. The graph shows the expression of pre-miR165 in response to treatment with increasing doses of AtmiPEP165a.

Figure 13:
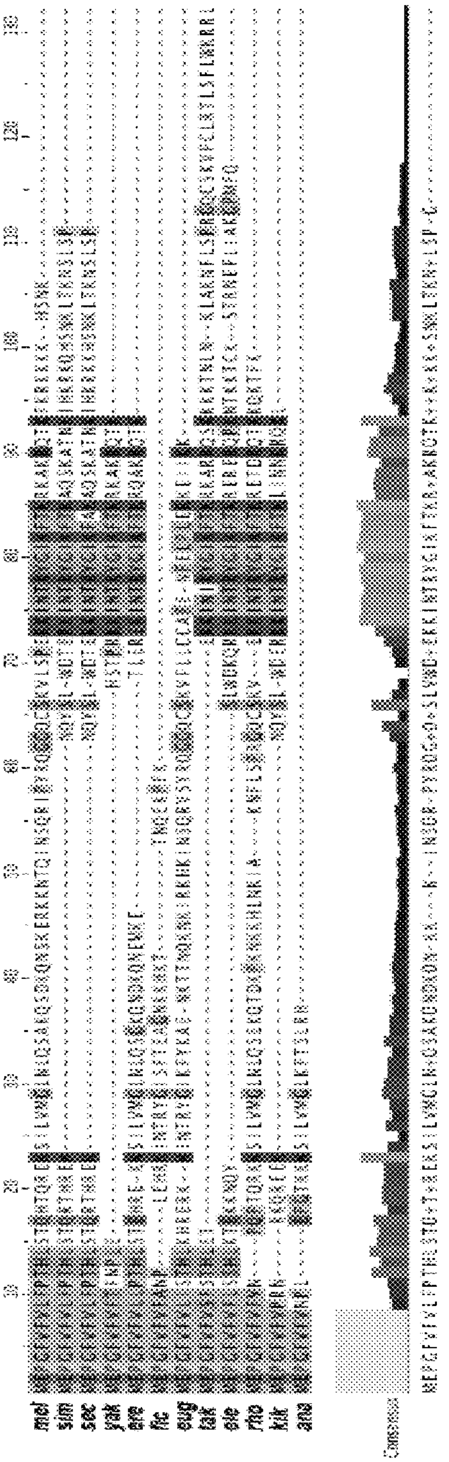

FIG. 13. Conservation of the sequence of miPEP8 identified in *Drosophila.*

The sequences of miPEP8 (SEQ ID NO: 104) were deduced from the sequences of miORF8 (SEQ ID NO: 208) of 12 different *Drosophila* species and were aligned. A histogram shows the conservation of each amino acid between the sequences of miORF8 in the 12 species analysed.

Figure 14:
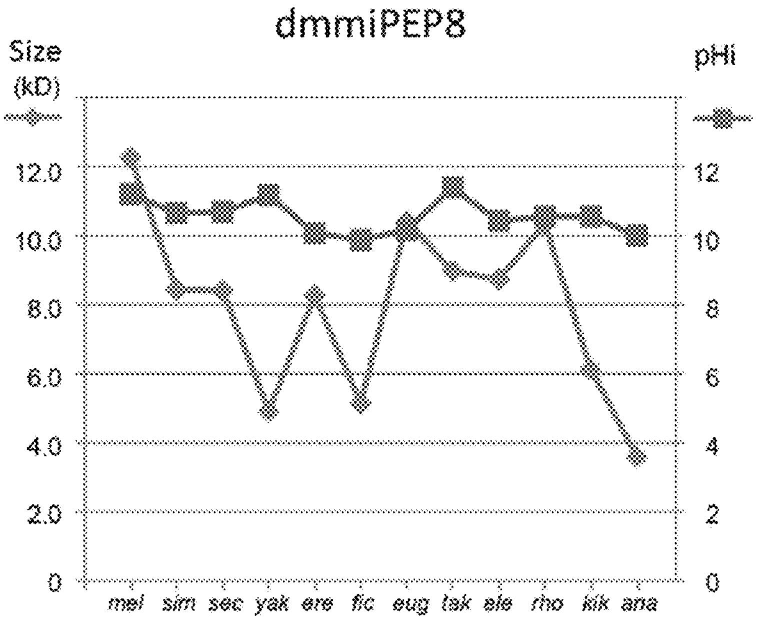

FIG. 14. Evolution of the mass (kDa) and isoelectric point (pI) of miPEP8 in the *Drosophila* species.

The y-axis on the left indicates the size of the miPEP8 (in kD). The y-axis on the right indicates the isoelectric point of the miPEP. The x-axis indicates the origin of the miPEP, i.e. the *Drosophila* species. It is noted that despite a significant change in their size (by more than a factor of 3), the charge of the miPEPs is still very basic (>9.8) in the 12 species studied.

Figure 15:
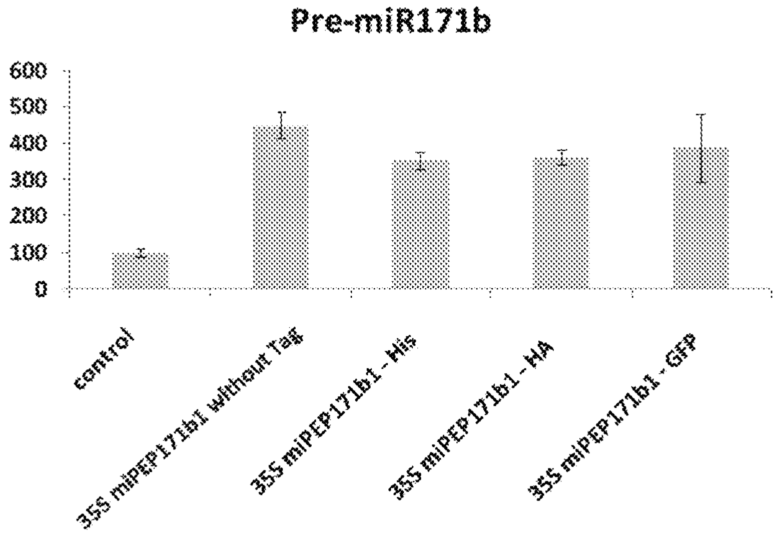

FIG. 15. Effect of the addition of sequences on the function of miPEP.

The tobacco leaves were transformed in order to overexpress miPEP171b. These graphs show that the addition of sequences (tag His, HA or GFP) does not alter the function of miPEP. The y-axis indicates the relative expression of pre-MtmiR171b in tobacco plants that have been transformed in order to express MtmiR171b (left-hand column), MtmiR171b and MtmiPEP171b1 with or without addition of protein tags (right-hand columns). The error bar corresponds to the standard error of the mean (number of individuals=6). It is noted that the expression of MtmiPEP171b1 increases the expression of MtmiR171b, and this effect is independent of the presence of tags.

Figure 16:
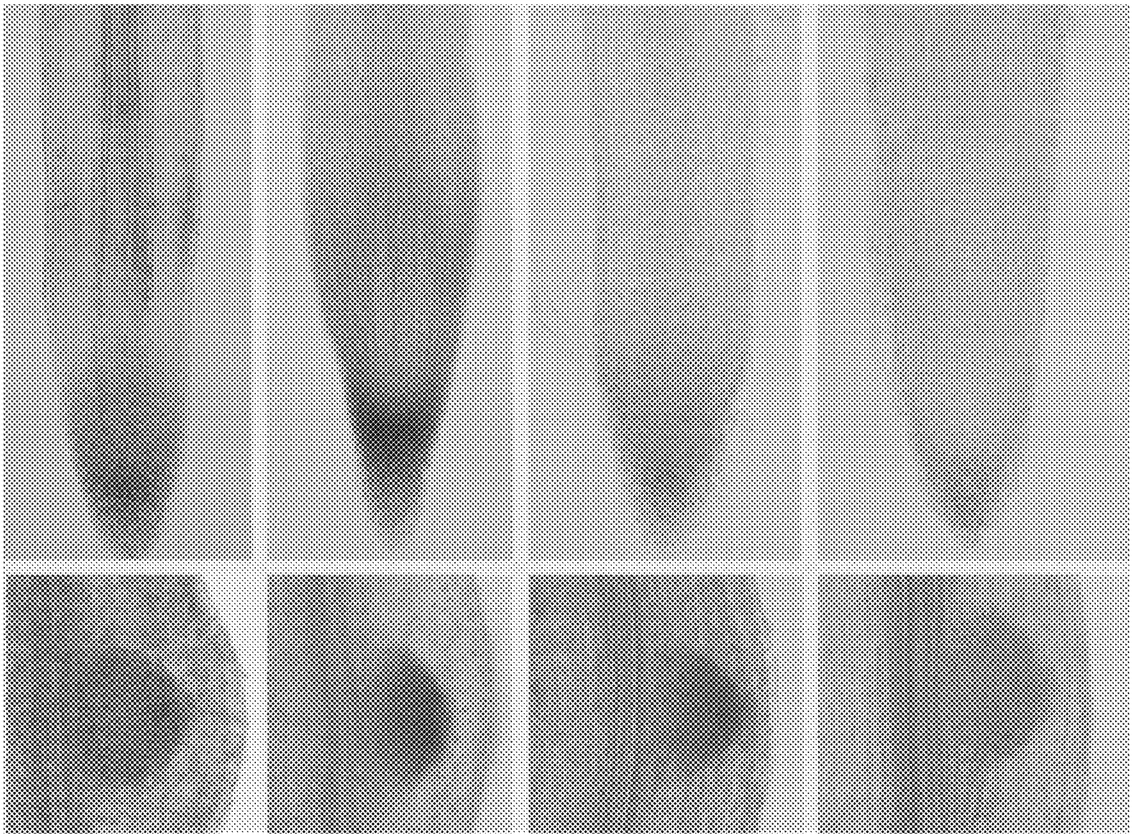

FIG. 16. Expression of MtmiPEP171b1 in the root system of *Medicago truncatula.*

The roots of *Medicago truncatula* were transformed in order to express fusions between GUS protein (in blue) and the promoter of miR17b (A, E), the ATG of miPEP171b1 (B, F), whole miPEP171b1 (C, G) or ATG2 (second ATG located on the precursor, after miPEP) (D, H). It is clear that there is expression of miRNA in the root tips (A) as well as the lateral roots (E). The transcriptional (B, F) and translational (C, G) fusions show an expression of miPEP171b in the same tissues, whereas the next ATG is not active (D, H).

Figure 17:
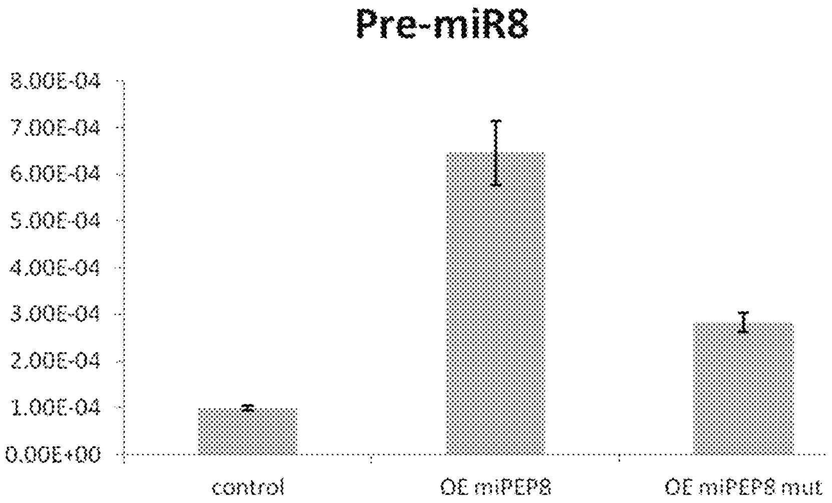

FIG. 17. Expression of DmmiPEP8 in cells of *Drosophila melanogaster*

The cells of *Drosphila melanogaster* were transfected in order to overexpress DmmiPEP8 (OE miPEP8) or miPEP8 of which the translation start codons have been mutated (OE miPEP8 mut). The y-axis indicates the relative expression of Pre-miR8. The error bar corresponds to the standard error of the mean (number of independent experiments=6). It is noted that the expression of DmmiPEP8 increases the expression of DmmiR8, and this effect is linked to the translation of the mRNA.

Figure 18:
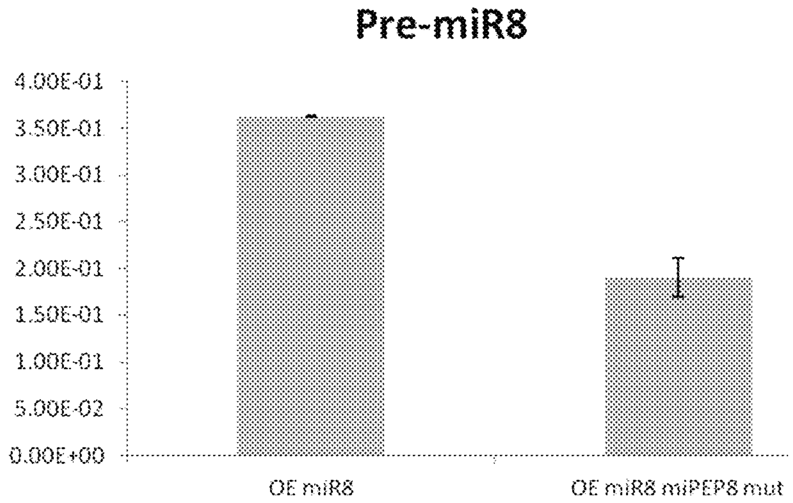

FIG. 18. Impact of DmmiPEP8 on accumulation of DmmiR8 in cells of *D. melanogaster*

The cells of *Drosphila melanogaster* were transfected in order to overexpress wild-type DmmiR8 (OE miR8) or DmmiR8 the translation start codons of which have been mutated (OE miR8 miPEP8 mut). The y-axis indicates the relative expression of Pre-miR8. The error bar corresponds to the standard error of the mean (number of independent experiments=2). It is noted that the presence of DmmiPEP8 increases the expression of DmmiR8.

Figure 19:
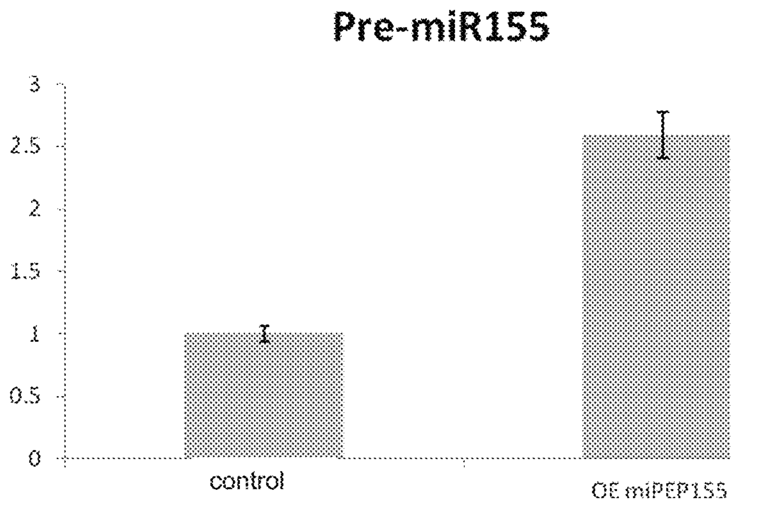

FIG. 19. Impact of HsmiPEP155 on accumulation of HsmiR155 in cells of *Homo sapiens*

HeLa cells of *Homo sapiens* had been transfected in order to overexpress HsmiPEP155 (OE miPEP155). The y-axis indicates the relative expression of Pre-miR155. The error bar corresponds to the standard error of the mean (number of independent experiments=2). It is noted that the expression of HsmiPEP155 increases the expression of HsmiR155.

Figure 20:
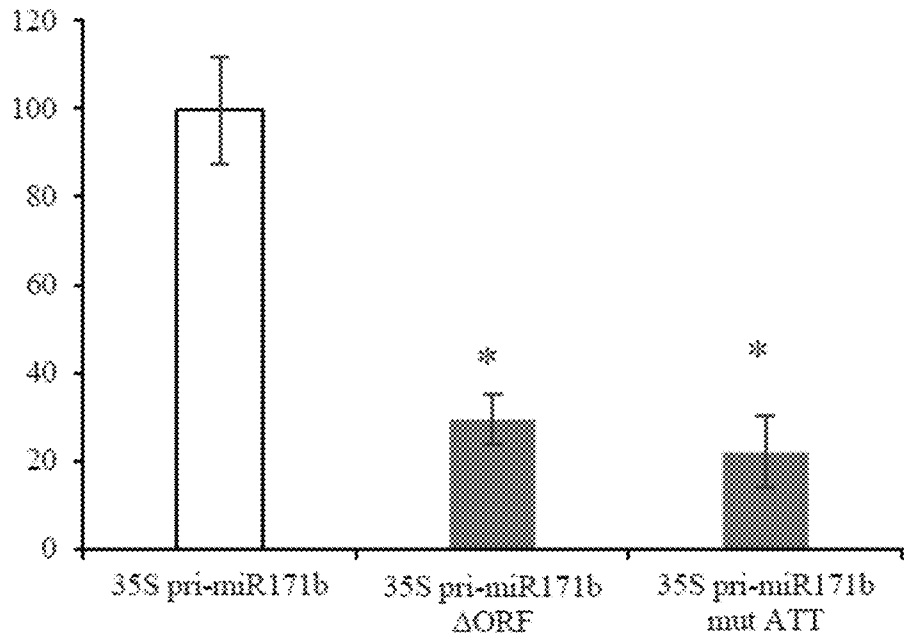

FIG. 20. Effects of translation of MtmiPEP171b1 on the expression of MtmiR171b demonstrated in the model plant *Nicotiana benthamiana.*

The y-axis indicates the relative expression of MtmiR171b in tobacco plants transformed in order to express pri-miR171b (left-hand column), a pri-miR171b in which the miORF171b has been deleted (middle column) or a mutated pri-miR171b in which the codon ATG has been replaced with ATT (right-hand column). The mutated pri-miR171b is therefore incapable of producing miPEP171b1. The error bar corresponds to the standard error of the mean (number of individuals=30). It is noted that the absence of translation of miPEP171b1 leads to a marked decrease in the accumulation of miR171b.

Figure 21:
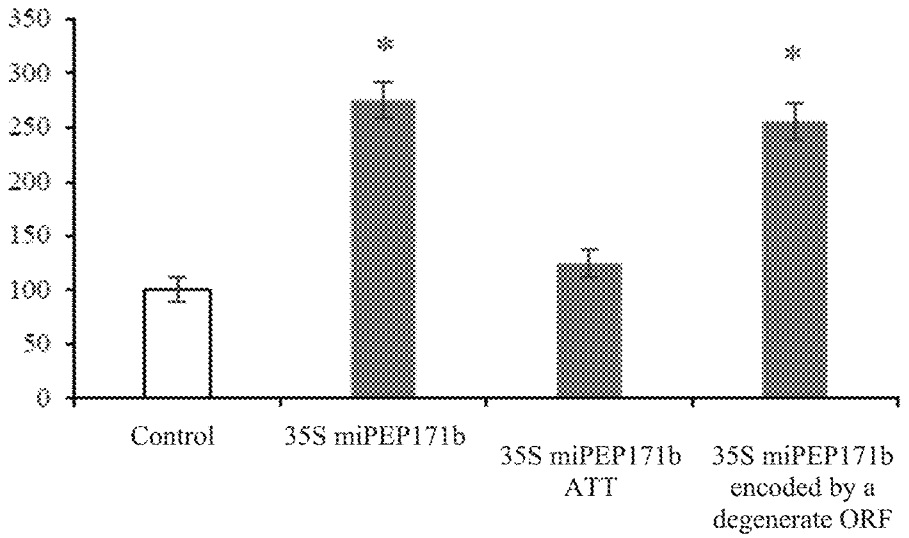

FIG. 21. Effects of overexpression of MtmiPEP171b1 on the expression of MtmiR171b demonstrated in the model plant *Nicotiana benthamiana.*

The y-axis indicates the relative expression of MtmiR171b in tobacco plants that had been transformed with a vector allowing the expression of miPEP171b and either a second empty vector (white column), or a vector allowing the expression of mtmiPEP171b (left black column), or a vector in which the codon ATG of the ORF encoding mtmiPEP171b has been replaced with ATT (middle black column), or a vector in which the nucleotide sequence of the ORF has been mutated without modifying the amino acid sequence of the translated peptide (miPEP encoded by a degenerate ORF) (right black column). The error bar corresponds to the standard error of the mean (number of individuals=30). It is noted that the expression of MtmiPEP171b1 increases the expression of MtmiR171b, and this effect is dependent on the translation of MtmiORF171b to MtmiPEP171b1.

Figure 22:
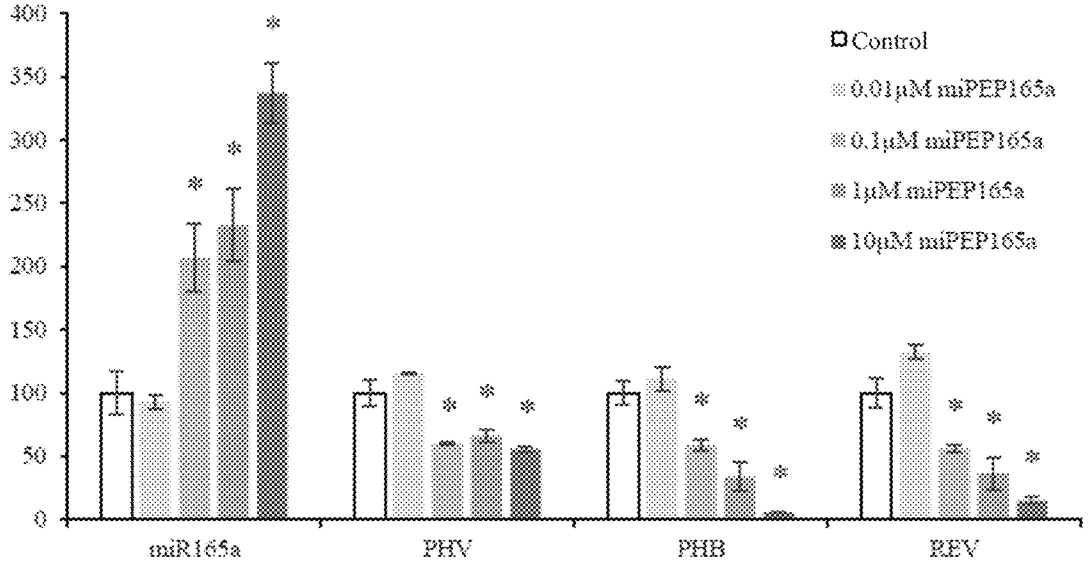

FIG. 22. Effects of AtmiPEP165a on accumulation of AtmiR165a and of its target genes (PHAVOLUTA: PHV, PHABOLUSA: PHB and REVOLUTA: REV).

The y-axis indicates the relative expression of AtmiR165a, PHV, PHB and REV in roots of *Arabidopsis thaliana* treated with water (control) or different concentrations of AtmiPEP165a (0.01 μM, 0.1 μM, 1 μM or 10 μM). The error bar corresponds to the standard error of the mean (number of individuals=10).

The treatment of plants with higher and higher concentrations of AtmiPEP165a demonstrates a dose-dependent effect of the accumulation of AtmiR165a and the negative regulation of its target genes as a function of the quantity of AtmiPEP165a.

Figure 23:
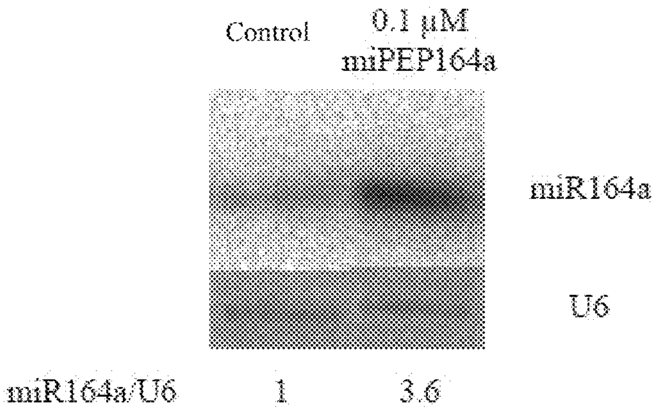

FIG. 23. Effects of treatment with AtmiPEP164a on the expression of AtmiR164a in *A. thaliana.*

The photographs show the results of a Northern blot analysis of the accumulation of AtmiR164a in roots treated with water (control, photograph on left) or with 0.1 μM of a synthetic peptide, having a sequence identical to that of AtmiPEP164a, dissolved in water (0.1 μM miPEP164a). The RNA U6 is used as loading control making it possible to quantify the quantity of AtmiR164a.

This experiment was repeated 4 times independently and led to similar results.

Treatment of shoots of *A. thaliana* with 0.1 μM of miPEP164a leads to an increase in the accumulation of miR164a.

Figure 24:
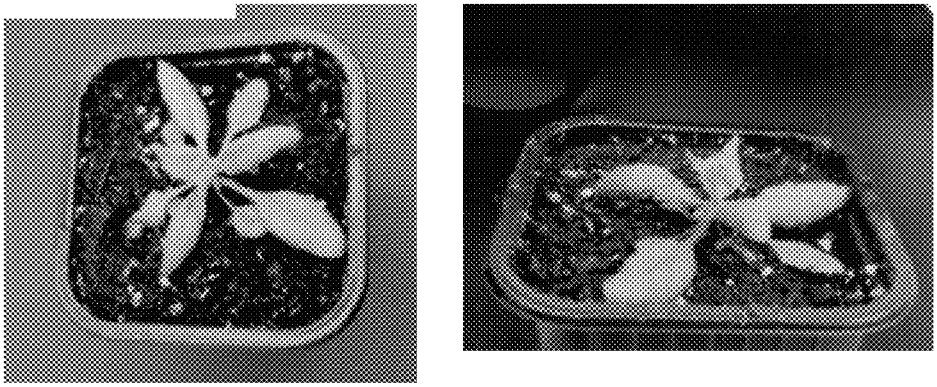
Figure 24:
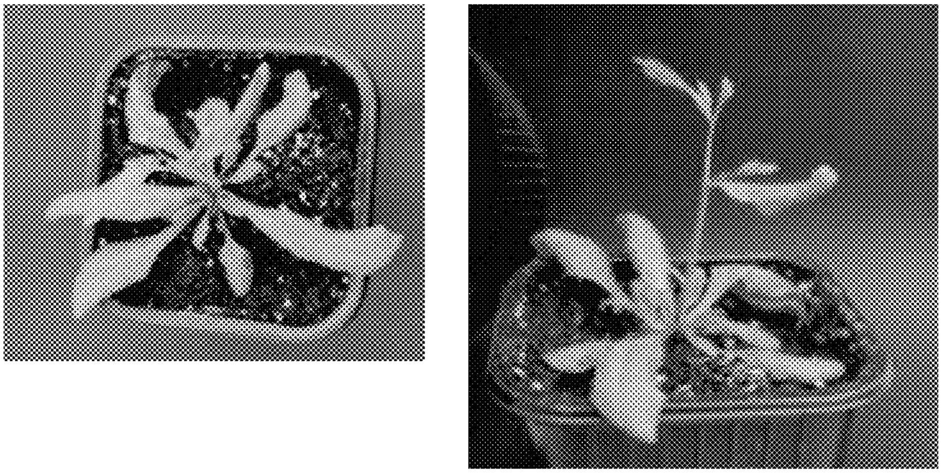

FIG. 24. Effects of treatment with AtmiPEP164a on the growth of *Arabidopsis thaliana.*

The photographs show two plants (top views and side views) after 3 weeks of growth: a control plant watered with water (A), and a plant watered with a composition of 0.1 μM of synthetic peptide corresponding to AtmiPEP164a (B). Watering plants of *Arabidopsis thaliana* with AtmiPEP164a increases plant growth significantly.

Figure 25:
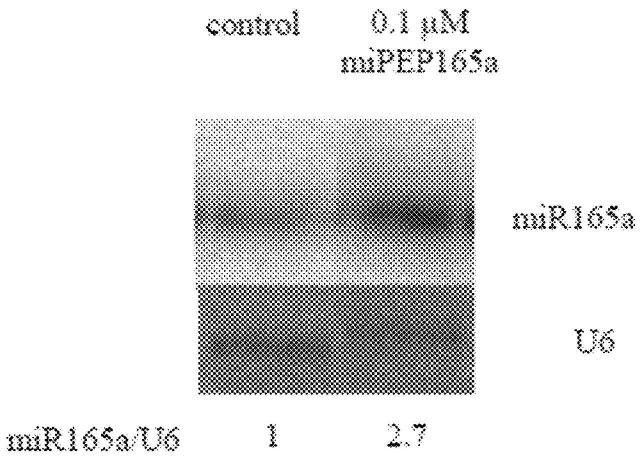

FIG. 25. Effects of treatment with AtmiPEP165a on the expression of AtmiR165a in *A. thaliana.*

The photographs show the results of a Northern blot analysis of the accumulation of AtmiR165a in roots treated with water (control, photograph on left) or with 0.1 μM of a synthetic peptide, having a sequence identical to that of AtmiPEP165a, dissolved in water (0.1 μM miPEP165a). The RNA U6 is used as loading control making it possible to quantify the quantity of AtmiR165a.

This experiment was repeated 4 times independently and led to similar results.

Treatment of *A. thaliana* shoots with 0.1 μM of miPEP165a leads to an increase in the accumulation of miR165a.

Figure 26:
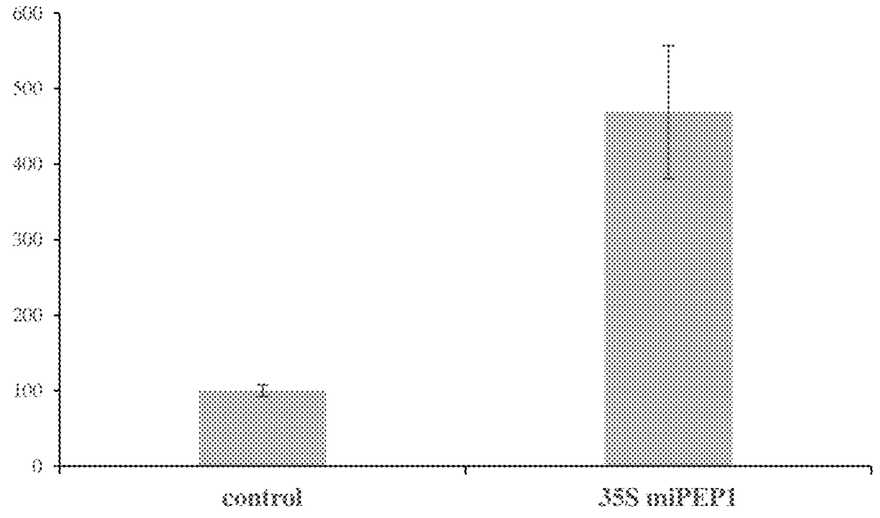

FIG. 26. Effects of overexpression of AtmiPEP319a1 on the expression of AtmiR319a in *A. thaliana.*

The y-axis indicates the relative expression of AtmiR319a in a control plant (left-hand column) or in a plant in which AtmiPEP319a1 is overexpressed (right-hand column). The error bar corresponds to the standard error of the mean (number of individuals=10). The overexpression of AtmiPEP319a1 induces an increase in the accumulation of AtmiR319a.

Figure 27:
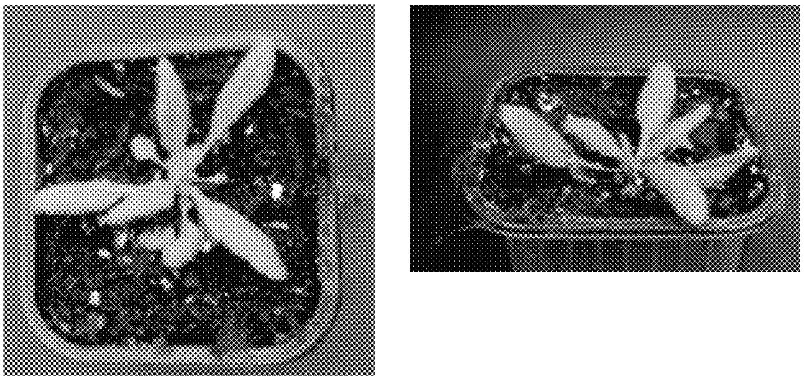
Figure 27:
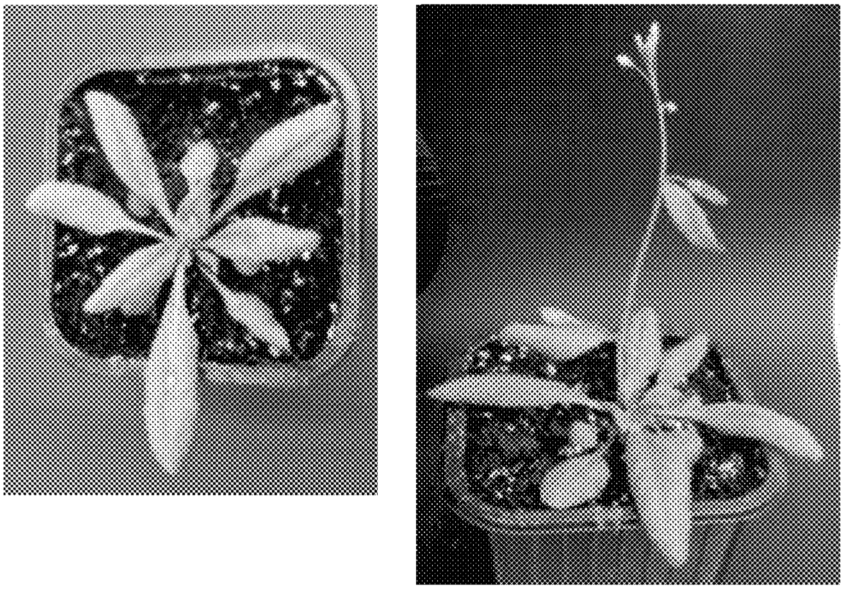

FIG. 27. Effects of treatment with AtmiPEP319a on the growth of *Arabidopsis thaliana.*

The photographs show two plants (top views and side views) after 3 weeks of growth: a control plant watered with water (A), and a plant watered with a composition of 0.1 μM of synthetic peptide corresponding to AtmiPEP319a1 (B). Watering of the plants of *Arabidopsis thaliana* with AtmiPEP319a1 increases plant growth significantly.

Figure 28:
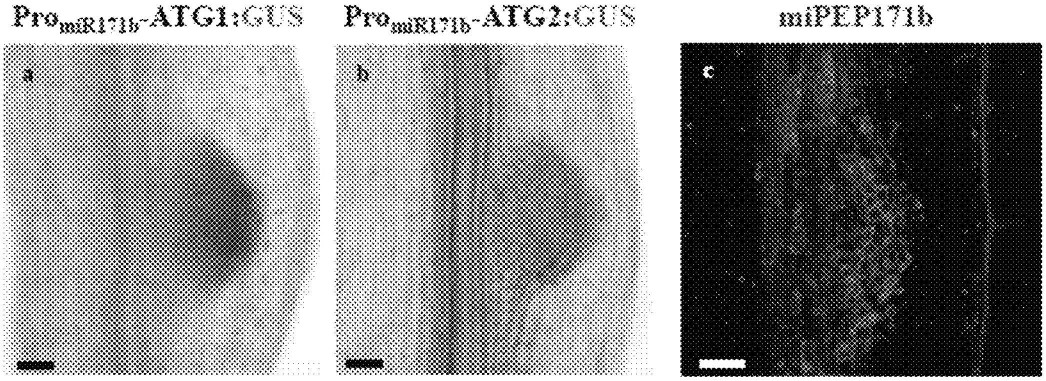

FIG. 28. Immunolocalization.

The roots of *Medicago truncatula* were transformed in order to express fusions between the GUS protein (in blue) and the ATG of miPEP171b (PromiR171b-ATG1:GUS) or ATG2 (second ATG located on the precursor, after miPEP) (PromiR171b-ATG2:GUS). Labelling was also carried out with an anti-miPEP171b antibody (miPEP171b). Immunolocalization of miPEP171b in the roots of *M. truncatula* reveals the presence of miPEP171b in the lateral root initiation sites, showing a co-localization between the microRNA and the corresponding miPEP.

DETAILED DESCRIPTION OF THE INVENTION

In a first step, the process for detecting and identifying a micropeptide therefore consists of detecting, on the primary transcript of a microRNA, the existence of an open reading frame potentially encoding a peptide.

For its part, the second step makes it possible to characterize said peptide, i.e. to determine whether said peptide corresponds to a peptide really produced in the cell, by searching for an effect of said peptide on the accumulation of said microRNA.

In order to demonstrate an effect of the peptide on the accumulation of the microRNA, a large quantity of peptide is introduced into a first cell expressing said microRNA. The accumulation of the microRNA in this first cell is then measured and compared with the accumulation of the microRNA in a second cell identical to the first, but not containing said peptide.

Observation of a variation of the quantities of microRNA between the cells in the presence and in the absence of the peptide thus indicates (i) that there is a peptide encoded on the primary transcript of said microRNA, (ii) that the sequence of this peptide is encoded by the open reading frame identified on the primary transcript of said microRNA, and (iii) that said peptide has an effect on the accumulation of said microRNA.

The invention is therefore based on the unexpected double observation made by the inventors that, on the one hand, there are open reading frames that are able to encode micropeptides present on the primary transcripts of microRNAs, and on the other hand that said micropeptides are capable of modulating the accumulation of said microRNAs.

In particular, the invention relates to a process for detecting and identifying a micropeptide (miPEP) encoded by a nucleotide sequence contained in the sequence of the primary transcript of a microRNA, comprising:

a) a step of detecting an open reading frame from 15 to 303 nucleotides in length contained in the sequence of the primary transcript of said microRNA, then b) a step of comparison between:

the accumulation of said microRNA in a specified eukaryotic cell expressing the primary transcript of said microRNA, in the presence of a peptide encoded by a nucleotide sequence that is identical or degenerate relative to that of said open reading frame, said peptide being present in the cell independently of transcription of the primary transcript of said microRNA, and the accumulation of said microRNA in a eukaryotic cell of the same type as the aforesaid specified eukaryotic cell expressing the primary transcript of said microRNA, in the absence of said peptide, in which a modulation of the accumulation of said microRNA in the presence of said peptide relative to the accumulation of said microRNA in the absence of said peptide indicates the existence of a micropeptide encoded by said open reading frame.

In the invention, the terms "microRNA", "non-coding microRNA" and "miRNA" are equivalent and may be used interchangeably. They define small molecules of RNA of about 21 nucleotides, which are not translated and do not lead to a peptide or a protein.

However, in this mature form, the microRNAs perform a function of regulation of certain genes via post-transcriptional mechanisms, for example by means of the RISC complex.

The primary transcript of the microRNA or "pri-miRNA" corresponds to the RNA molecule obtained directly from transcription of the DNA molecule. Generally, this primary transcript undergoes one or more post-transcriptional modifications, involving for example a particular structure of the RNA or cleavage of certain portions of the RNA by splicing phenomena, and which lead to the precursor form of the microRNA or "pre-miRNA", then to the mature form of the microRNA or "miRNA".

The terms "micropeptides" and "miPEPs" (microRNA encoded PEPtides) are equivalent and may be used interchangeably. They define a peptide that is encoded by an open reading frame present on the primary transcript of a microRNA, and which is capable of modulating the accumulation of said microRNA.

In view of the above definitions, it is important to distinguish on one side, the miRNA which does not encode any peptide and on the other side, the primary transcript of such a miRNA which may encode a miPEP.

This distinction derives from the teaching of the invention and is original in view of the current knowledge about miRNAs.

The micropeptides within the meaning of the present invention are not to be understood as necessarily being small peptides, as "micro" does not correspond to the size of the peptide.

Taking into account the degeneracy of the genetic code, one and the same micropeptide is or may be encoded by several nucleotide sequences. Nucleotide sequences of this kind, differing from one another by at least one nucleotide but encoding one and the same peptide, are called "degenerate sequences".

The terms "open reading frame" or "ORF" are equivalent and may be used interchangeably. They correspond to a nucleotide sequence in a DNA or RNA molecule that may potentially encode a peptide or a protein: said open reading frame begins with a start codon (the start codon generally encoding a methionine), followed by a series of codons (each codon encoding an amino acid), and ends with a stop codon (the stop codon not being translated).

In the invention, the ORFs may be called specifically "miORFs" when they are present on the primary transcripts of microRNA.

The miORFs as defined in the particular invention may have a size from 12 to 303 nucleotides and may encode peptides from 3 to 100 amino acids.

In particular, the miORFs as defined in the invention may have a size from 15 to 303 nucleotides. As an amino acid is encoded by a codon of 3 nucleotides, the miORFs from 15 to 303 nucleotides encode miPEPS from 4 to 100 amino acids.

In particular, the miORFs have a size of:

15, 18, 21, 24, 27, 30, 33, 36, 39, 42, 45, 47, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153, 156, 159, 162, 165, 168, 171, 174, 177, 180, 183, 186, 189, 192, 195, 198, 201, 204, 207, 210, 213, 216, 219, 222, 225, 228, 231, 234, 237, 240, 243, 246, 249, 252, 255, 258, 261, 264, 267, 270, 273, 276, 279, 282, 285, 288, 291, 294, 297, 300 or 303 nucleotides, and encode respectively miPEPs having a size of:

4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 amino acids.

In the invention, "accumulation" means the production of a molecule, such as a microRNA or a micropeptide, in the cell.

Thus, "modulation" of the accumulation of a molecule in a cell corresponds to a modification of the quantity of this molecule present in the cell.

In an embodiment, the invention relates to a process for detecting and identifying a miPEP as defined above, in which the modulation of the accumulation of said microRNA is a decrease or an increase in the accumulation of said microRNA, in particular an increase.

A "decrease in the accumulation" corresponds to a decrease in the quantity of said molecule in the cell.

Conversely, an "increase in the accumulation" corresponds to an increase in the quantity of said molecule in the cell.

In an advantageous embodiment, the invention relates to a process for detecting and identifying a miPEP as defined above, in which the modulation of the accumulation of said microRNA is an increase in the accumulation of said microRNA.

In an embodiment, the invention relates to a process for detecting and identifying a miPEP as defined above, in which the presence of said peptide in the cell results from:

the introduction of a nucleic acid encoding said peptide into the cell, or the introduction of said peptide into the cell.

In order to characterize a miPEP, it is necessary to have a cellular model expressing a microRNA in which said peptide to be tested is present. For this, it is possible to introduce a peptide into the cell, either by bringing the cell into contact with said peptide, or by introducing a nucleic acid encoding said peptide into the cell, and this nucleic acid will then be translated into peptide within the cell.

In an embodiment, the invention relates to a process for detecting and identifying a miPEP as defined above, in which said open reading frame in step a) is contained in the 5' or 3' portion of said primary transcript of the microRNA, preferably in the 5' portion.

The 5' or 3' portions of the primary transcript of the microRNA correspond to the terminal portions of the RNA molecule that are cleaved during maturation of the microRNA.

In an embodiment, the invention relates to a process for detecting and identifying a miPEP as defined above, in which said microRNA is present in a wild-type plant cell.

In the invention, a wild-type plant cell corresponds to a plant cell that has not been genetically modified by humans.

In an embodiment, the invention relates to a process for detecting and identifying a miPEP as defined above, in which said microRNA is present in a wild-type animal cell, and in particular a wild-type human cell or a wild-type *Drosophila* cell.

In the invention, a wild-type animal cell corresponds to an animal cell, and in particular a human cell, that has not been modified genetically by humans.

In an embodiment, the invention relates to a process for detecting and identifying a miPEP as defined above, in which said specified eukaryotic cell and said eukaryotic cell of the same type as the aforesaid specified eukaryotic cell, used in step b, are plant cells of a cruciferous plant such as *Arabidopsis thaliana*, of a leguminous plant such as *Glycine max* (soya), *Medicago truncatula* and *Medicago sativa* (alfalfa) or of a plant of the Solanaceae family such as *Nicotiana benthamiana* (tobacco), *Solanum tuberosum* (potato), *Solanum lycopersicum* (tomato) or *Solanum melongena* (aubergine).

In an embodiment, the invention relates to a process for detecting and identifying a miPEP as defined above, in which said specified eukaryotic cell and said eukaryotic cell of the same type as the aforesaid specified eukaryotic cell, used in step b, are plant cells, preferably cells of *Medicago truncatula, Nicotiana benthamiana* or *Arabidopsis thaliana.*

In an embodiment, the invention relates to a process for detecting and identifying a miPEP as defined above, in which said specified eukaryotic cell and said eukaryotic cell of the same type as the aforesaid specified eukaryotic cell, used in step b, are animal cells, preferably human cells or *Drosophila* cells.

In the process for detecting and identifying a micropeptide as defined above, after identifying an ORF that is able to encode a peptide on the primary transcript of a microRNA, it is necessary to have a cellular model having said microRNA and said peptide, so as to be able to demonstrate a possible effect of the peptide on said microRNA.

Two options are therefore conceivable:

the cellular model in which the miORF has been identified and that in which the effect of the peptide on the miRNA has been demonstrated are identical, or the cellular model in which the miORF has been identified and that in which the effect of the peptide on the miRNA has been demonstrated are different.

In the first option, the cellular model used for observing an effect of the peptide is the same as that in which the primary transcript of said microRNA was isolated. In this cellular model, the specified eukaryotic cells contain said microRNA naturally and only the peptide to be tested has to be introduced into these cells. In this context, said microRNA is qualified as "of endogenous origin" as it exists naturally in the cells. Nevertheless, other copies of a microRNA of endogenous origin may be added to a cell, for example by introducing a vector encoding said microRNA of endogenous origin into the cell.

In the second option, the cellular model used for observing an effect of the peptide is different from that in which the primary transcript of said microRNA was isolated. In this cellular model, the specified eukaryotic cells contain neither the microRNA, nor the peptide to be tested. These two elements must therefore be introduced into these cells. In this context, said microRNA is qualified as "of exogenous origin" as it does not exist naturally in the cells.

In an embodiment, the invention relates to a process for detecting and identifying a miPEP as defined above, in which said microRNA is of endogenous origin in said eukaryotic cell and in said eukaryotic cell of the same type as the aforesaid specified eukaryotic cell, used in step b).

In an embodiment, the invention relates to a process for detecting and identifying a miPEP as defined above in which said microRNA is of exogenous origin in said eukaryotic cell and in said eukaryotic cell of the same type as the aforesaid specified eukaryotic cell, used in step b), said eukaryotic cells containing a vector allowing the expression of said microRNA.

In an embodiment, the invention relates to a process for detecting and identifying a miPEP as defined above, in which the accumulation of said microRNA is determined using quantitative RT-PCR or Northern blot.

In an embodiment, the invention relates to a process for detecting and identifying a miPEP as defined above, in which the accumulation of said microRNA is determined using a DNA or RNA chip.

The accumulation of said microRNA may be determined using the techniques of molecular biology for assaying specific nucleic acid molecules.

In another aspect, the invention also relates to a process for detecting and identifying a microRNA in which the sequence of the primary transcript contains a nucleotide sequence encoding a miPEP, comprising:

a) a step of detecting an open reading frame from 15 to 303 nucleotides in length contained in the sequence of the primary transcript of said microRNA, then b) a step of comparison between:

the accumulation of said microRNA in a specified eukaryotic cell expressing said microRNA, in the presence of a peptide encoded by a nucleotide sequence that is identical or degenerate relative to that of said open reading frame, said peptide being present in the cell independently of transcription of the primary transcript of said microRNA, and the accumulation of said microRNA in a eukaryotic cell, of the same type as the aforesaid specified eukaryotic cell expressing said microRNA, in the absence of said peptide, in which a modulation of the accumulation of said microRNA in the presence of said peptide relative to the accumulation of said microRNA in the absence of said peptide indicates the existence of a microRNA the primary transcript of which contains a nucleotide sequence encoding a micropeptide.

In particular, the invention relates to a process for detecting and identifying a microRNA in which the sequence of the primary transcript contains a nucleotide sequence encoding a miPEP, comprising:

a) a step of detecting an open reading frame from 15 to 303 nucleotides in length contained in the sequence of the primary transcript of said microRNA, then b) a step of comparison between:

the accumulation of said microRNA in a specified eukaryotic cell expressing the primary transcript of said microRNA, in the presence of a peptide encoded by a nucleotide sequence that is identical or degenerate relative to that of said open reading frame, said peptide being present in the cell independently of transcription of the primary transcript of said microRNA, and the accumulation of said microRNA in a eukaryotic cell, of the same type as the aforesaid specified eukaryotic cell expressing the primary transcript of said microRNA, in the absence of said peptide, in which a modulation of the accumulation of said microRNA in the presence of said peptide relative to the accumulation of said microRNA in the absence of said peptide indicates the existence of a microRNA the primary transcript of which contains a nucleotide sequence encoding a micropeptide.

In an embodiment, the invention relates to a process for detecting and identifying a microRNA as defined above, in which the modulation of the accumulation of said microRNA is a decrease or an increase in the accumulation of said microRNA, in particular an increase.

In an embodiment, the invention relates to a process for detecting and identifying a microRNA as defined above, in which the presence of said peptide in the cell results from:

the introduction of a nucleic acid encoding said peptide into the cell, or the introduction of said peptide into the cell.

In an embodiment, the invention relates to a process for detecting and identifying a microRNA as defined above, in which said open reading frame in step a) is contained in the 5' or 3' portion of said primary transcript of the microRNA, preferably in the 5' portion.

In an embodiment, the invention relates to a process for detecting and identifying a microRNA as defined above, in which said microRNA is present in a wild-type plant cell.

In an embodiment, the invention relates to a process for detecting and identifying a microRNA as defined above, in which said microRNA is present in a wild-type animal cell, and in particular a wild-type human cell.

In an embodiment, the invention relates to a process for detecting and identifying a microRNA as defined above, in which said eukaryotic cell, and said eukaryotic cell of the same type as the aforesaid specified eukaryotic cell, used in step b) are plant cells, preferably cells of *Medicago truncatula*.

In an embodiment, the invention relates to a process for detecting and identifying a microRNA as defined above, in which said eukaryotic cell, and said eukaryotic cell of the same type as the aforesaid specified eukaryotic cell, used in step b) are animal cells, preferably *Drosophila* cells.

In an embodiment, the invention relates to a process for detecting and identifying a microRNA as defined above, in which said microRNA is of endogenous origin in said eukaryotic cell and in said eukaryotic cell of the same type as the aforesaid specified eukaryotic cell, used in step b).

In an embodiment, the invention relates to a process for detecting and identifying a microRNA as defined above in which said microRNA is of exogenous origin in said eukaryotic cell and in said eukaryotic cell of the same type as the aforesaid specified eukaryotic cell, used in step b), said eukaryotic cells containing a vector allowing the expression of said microRNA.

In an embodiment, the invention relates to a process for detecting and identifying a microRNA as defined above, in which the accumulation of said microRNA is determined using quantitative RT-PCR or Northern blot.

In an embodiment, the invention relates to a process for detecting and identifying a microRNA as defined above, in which the accumulation of said microRNA is determined using a DNA or RNA chip.

In another aspect, the invention relates to a miPEP as obtained by implementing the process as defined above.

More particularly, the invention relates to a miPEP encoded by a nucleotide sequence as obtained by implementing the process as defined above. In other words, the invention relates to a miPEP encoded by a nucleotide sequence detected and identified by implementing the process as defined above.

Another aspect of the invention also relates to a miPEP of 3 to 100 amino acids, in particular of 4 to 100 amino acids, in particular of 4 to 60 amino acids, preferably of 4 to 40 amino acids, encoded by a nucleotide sequence contained in the primary transcript of a microRNA, said miPEP being capable of modulating the accumulation of said microRNA in a eukaryotic cell.

In particular, the miPEP as defined in the invention is encoded by a miORF of 15 to 303 nucleotides and has a size of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 amino acids, in particular 5, 8, 10, 18, 19, 23, 37, 50 or 59 amino acids.

In particular, the miPEP of the invention has a size in the range from 4 to 10 amino acids, 4 to 20 amino acids, 4 to 30 amino acids, 4 to 40 amino acids, 4 to 50 amino acids, 4 to 60 amino acids, 4 to 70 amino acids, 4 to 80 amino acids, 4 to 90 amino acids, or 4 to 100 amino acids.

Moreover, it should be noted that several miORFS may be identified on the primary transcript of a microRNA, indicating that a primary transcript of microRNA may potentially encode several miPEPs.

It should also be noted that the effect of a miPEP is generally specific to a single microRNA, namely that resulting from the primary transcript encoding said miPEP.

The modulation of the microRNA by said miPEP may be demonstrated after observing a variation in quantities of microRNA between the cells in the presence and in the absence of the miPEP.

In an embodiment, the invention relates to a miPEP as defined above, said nucleotide sequence being contained in the 5' or 3' portion of said primary transcript of a microRNA, preferably in the 5' portion.

In an embodiment, the invention relates to a miPEP as defined above, said nucleotide sequence corresponding to the first open reading frame present on said primary transcript of a microRNA.

In an embodiment, the invention relates to a miPEP as defined above, said miPEP having a basic isoelectric point, preferably above 8.

In an embodiment, the invention relates to a miPEP as defined above, said miPEP having an acidic isoelectric point.

In an embodiment, the invention relates to a miPEP as defined above, said miPEP being selected from the group of peptides consisting of SEQ ID NO: 1 to SEQ ID NO: 104, SEQ ID NO: 375 to SEQ ID NO: 386, and SEQ ID NO: 355 (Table 1).

In an embodiment, the invention relates to a miPEP as defined above, consisting of the amino acid sequence MVT.

In another aspect, the invention relates to a nucleic acid molecule encoding a miPEP as defined above.

In an embodiment, the invention relates to a nucleic acid molecule as defined above, said molecule being selected from the group of nucleic acids consisting of SEQ ID NO: 105 to SEQ ID NO 208, SEQ ID NO: 387 to SEQ ID NO: 399 and SEQ ID NO: 356 (Table 2).

In a particular embodiment, the invention relates to MtmiPEP171b1 (SEQ ID NO: 59) encoded by the nucleotide sequence (SEQ ID NO: 163) contained in the primary transcript of miR171b (SEQ ID NO: 319), said MtmiPEP171b1 being capable of modulating the accumulation of said miR171b in a eukaryotic cell.

In a particular embodiment, the invention relates to AtmiPEP164a1 (SEQ ID NO: 24) encoded by the nucleotide sequence (SEQ ID NO: 128) contained in the primary transcript of miR164a (SEQ ID NO: 297), said AtmiPEP164a1 being capable of modulating the accumulation of said miR164a in a eukaryotic cell.

In a particular embodiment, the invention relates to AtmiPEP165a (SEQ ID NO: 43) encoded by the nucleotide sequence (SEQ ID NO: 147) contained in the primary transcript of miR165a (SEQ ID NO: 305), said miPEP165a being capable of modulating the accumulation of said miR165a in a eukaryotic cell.

In a particular embodiment, the invention relates to AtmiPEP319a1 (SEQ ID NO: 76) encoded by the nucleotide sequence (SEQ ID NO: 180) contained in the primary transcript of miR319a (SEQ ID NO: 331), said AtmiPEP319a1 being capable of modulating the accumulation of said miR319a in a eukaryotic cell.

In a particular embodiment, the invention relates to AtmiPEP319a2 (SEQ ID NO: 77) encoded by the nucleotide sequence (SEQ ID NO: 181) contained in the primary transcript of miR319a (SEQ ID NO: 331), said AtmiPEP319a2 being capable of modulating the accumulation of said miR319a in a eukaryotic cell.

In a particular embodiment, the invention relates to DmmiPEP1a (SEQ ID NO: 102) encoded by the nucleotide sequence (SEQ ID NO: 206) contained in the primary transcript of miR1 (SEQ ID NO: 353), said dmmiPEP1a being capable of modulating the accumulation of said miR1 in a eukaryotic cell.

In a particular embodiment, the invention relates to DmmiPEP1b (SEQ ID NO: 103) encoded by the nucleotide sequence (SEQ ID NO: 207) contained in the primary transcript of miR1 (SEQ ID NO: 353), said dmmiPEP1b being capable of modulating the accumulation of said miR1 in a eukaryotic cell.

In a particular embodiment, the invention relates to dmmiPEP8 (SEQ ID NO: 104) encoded by the nucleotide sequence (SEQ ID NO: 208) contained in the primary transcript of miR8 (SEQ ID NO: 354), said dmmiPEP8 being capable of modulating the accumulation of said miR8 in a eukaryotic cell.

In a particular embodiment, the invention relates to HsmiPEP155 (SEQ ID NO: 355) encoded by the nucleotide sequence (SEQ ID NO: 356) contained in the primary transcript of miR155 (SEQ ID NO: 358), said HsmiPEP155 being capable of modulating the accumulation of said miR155 in a eukaryotic cell.

In another aspect, the invention relates to an isolated peptide, or an isolated and purified peptide, or a synthetic peptide or a recombinant peptide, comprising or consisting of a sequence identical to that of a miPEP, said miPEP in particular being present naturally in a plant, or in an animal, such as humans.

In another aspect, the invention relates to a vector comprising at least one nucleic acid molecule as defined above.

In another aspect, the invention also relates to the use of at least one:

miPEP as defined above, nucleic acid encoding said miPEP, or vector containing said nucleic acid, for modulating the expression of at least one gene in a specified eukaryotic cell, said specified eukaryotic cell being capable of expressing a microRNA, the primary transcript of which contains at least one nucleotide sequence encoding said at least one miPEP and the accumulation of which is modulated by said at least one miPEP, the expression of said at least one gene being regulated by said microRNA.

In another aspect, the invention also relates to the use of at least one:

miPEP of 4 to 100 amino acids, preferably of 4 to 40 amino acids, encoded by a nucleotide sequence contained in the primary transcript of a microRNA, said miPEP being capable of modulating the accumulation of said microRNA in a eukaryotic cell, nucleic acid encoding said miPEP, or vector containing said nucleic acid, for modulating the expression of at least one gene in a specified eukaryotic cell, said specified eukaryotic cell being capable of expressing a microRNA, the primary transcript of which contains at least one nucleotide sequence encoding said at least one miPEP and the accumulation of which is modulated by said at least one miPEP, the expression of said at least one gene being regulated by said microRNA.

The invention is based on the surprising observation made by the inventors that it is possible to modulate the expression of one or more target genes of one and the same microRNA by modulating the accumulation of said microRNA using a miPEP.

In an embodiment, the invention relates to the use as defined above in which said specified eukaryotic cell is a plant cell.

In an embodiment, the invention relates to the use as defined above in which said specified eukaryotic cell is a plant cell of a crucifer such as *Arabidopsis thaliana*, of a leguminous plant such as *Glycine max* (soya), *Medicago truncatula* and *Medicago sativa* (alfalfa) or of a plant of the Solanaceae family such as *Nicotiana benthamiana* (tobacco), *Solanum tuberosum* (potato), *Solanum lycopersicum* (tomato) or *Solanum melongena* (aubergine).

In an embodiment, the invention relates to the use as defined above in which said specified eukaryotic cell is an animal cell, in particular human.

In an embodiment, the invention relates to the use as defined above in which said specified eukaryotic cell is an animal cell, in particular human, said miPEP not being used for surgical or therapeutic treatment of the human body or animal body, nor for modifying the genetic identity of a human being.

In an embodiment, the invention relates to the use as defined above in which said specified eukaryotic cell is an animal cell, said miPEP being used for surgical or therapeutic treatment of the human body or animal body.

In an embodiment, the invention relates to the use as defined above in which said microRNA and said gene are of endogenous origin in said specified eukaryotic cell.

In an embodiment, the invention relates to the use as defined above in which said microRNA and said gene are of exogenous origin in said specified eukaryotic cell, said specified eukaryotic cell containing at least one vector allowing the expression of said microRNA and of said gene.

In the invention, the expressions “of endogenous origin” and “of exogenous origin” are used for distinguishing said microRNAs and/or the genes of different species, in view of the conservation of the sequences between species.

Thus, the term “of endogenous origin” indicates that the microRNA and/or gene may be present naturally in the cell in question. Other copies of the microRNA and/or of the gene of endogenous origin may nevertheless be added artificially to the cell in question, for example by cloning.

Conversely, the term “of exogenous origin” indicates that the microRNA and/or the gene are never present naturally in the cell in question. It is a microRNA and/or a gene identified in another cellular type or in an organism of another species; this microRNA and/or this gene are therefore necessarily introduced artificially into the cell in question.

In the invention, a genetically transformed cell may therefore contain 2 groups of microRNAs and/or of genes potentially similar in terms of sequence, one of endogenous origin and the other of exogenous origin.

In an embodiment, the invention relates to the use as defined above in which the primary transcript of the miRNA and said gene are of exogenous origin in said specified eukaryotic cell, said specified eukaryotic cell containing at least one vector allowing the expression of the primary transcript of the microRNA.

In an embodiment, the invention relates to the use as defined above in which the primary transcript of the miRNA is encoded by a vector introduced into the cell artificially.

In an embodiment, the invention relates to the use as defined above in which said miPEP is selected from the group of peptides consisting of SEQ ID NO: 1 to SEQ ID NO: 104, SEQ ID NO: 375 to SEQ ID NO: 386 and SEQ ID NO: 355 (Table 1).

In an embodiment, the invention relates to the use as defined above in which said miPEP is selected from MtmiPEP171b1 (SEQ ID NO: 59), AtmiPEP164a1 (SEQ ID NO: 24), AtmiPEP165a (SEQ ID NO: 43), AtmiPEP319a1 (SEQ ID NO: 76) and AtmiPEP319a2 (SEQ ID NO: 77).

In an embodiment, the invention relates to the use as defined above in which said miPEP is selected from DmmiPEP1a (SEQ ID NO: 102), DmmiPEP1b (SEQ ID NO: 103) and DmmiPEP8 (SEQ ID NO: 104).

In an embodiment, the invention relates to the use as defined above in which said miPEP is HsmiPEP155a (SEQ ID NO: 355).

In an embodiment, the invention relates to the use as defined above in which said nucleic acid is selected from the group of nucleic acids consisting of SEQ ID NO: 105 to SEQ ID NO: 208 and SEQ ID NO: 356 (Table 2).

In an embodiment, the invention relates to the use as defined above in which said nucleic acid is selected from miORF171b (SEQ ID NO: 163), miORF164a1 (SEQ ID NO: 128), miORF165a (SEQ ID NO: 147), miORF319a1 (SEQ ID NO: 180) and miORF319a2 (SEQ ID NO: 181).

In an embodiment, the invention relates to the use as defined above in which said nucleic acid is selected from miORF1a (SEQ ID NO: 206), miORF1b (SEQ ID NO: 207) and miORF8 (SEQ ID NO: 208).

In an embodiment, the invention relates to the use as defined above in which said nucleic acid is selected from miORF155 (SEQ ID NO: 356).

In an embodiment, the invention relates to the use as defined above in which said microRNA is selected from the group of nucleic acids consisting of SEQ ID NO: 282 to SEQ ID NO: 354 and SEQ ID NO: 358.

In an embodiment, the invention relates to the use as defined above in which said microRNA is selected from miR171b (SEQ ID NO: 319), miR165a (SEQ ID NO: 305) and miR319a (SEQ ID NO: 331).

In an embodiment, the invention relates to the use as defined above in which said microRNA is selected from miR1a (SEQ ID NO: 353) and miR8 (SEQ ID NO: 354).

In an embodiment, the invention relates to the use as defined above in which said microRNA is selected from miR155 (SEQ ID NO: 358).

In another aspect, the invention relates in particular to a process for modulating the expression of a gene regulated by a microRNA in a eukaryotic cell,

- comprising carrying out a step of accumulation of a miPEP in said eukaryotic cell,
  - said miPEP having:
    - a size from 3 to 100 amino acids, preferably 4 to 20 amino acids, and
    - a peptide sequence identical to that encoded by a nucleotide sequence contained in the primary transcript of a microRNA regulating the expression of said gene, and
  - being capable of modulating the accumulation of said microRNA, in which the accumulation of said miPEP in said eukaryotic cell induces a modulation of the expression of said gene relative to the expression of said gene without accumulation of said miPEP.

In particular, the invention relates to a process for modulating the expression of a gene regulated by a microRNA in a eukaryotic cell, comprising carrying out a step of accumulation of a miPEP in said eukaryotic cell, said miPEP having:

a size from 4 to 100 amino acids, preferably 4 to 20 amino acids, and a peptide sequence identical to that encoded by a nucleotide sequence contained in the primary transcript of a microRNA regulating the expression of said gene, and being capable of modulating the accumulation of said microRNA, in which the accumulation of said miPEP in said eukaryotic cell induces a modulation of the expression of said gene relative to the expression of said gene without accumulation of said miPEP.

In an embodiment, the invention relates to a process for modulating the expression of a gene as defined above, in which the accumulation of said miPEP in the cell results from:

introduction of a nucleic acid encoding said miPEP into the cell, or introduction of said miPEP into the cell.

In an embodiment, the invention relates to a process for modulating the expression of a gene as defined above in which said eukaryotic cell is a plant cell.

In an embodiment, the invention relates to a process for modulating the expression of a gene as defined above in which said eukaryotic cell is an animal cell and in particular a human cell.

In an embodiment, the invention relates to a process for modulating the expression of a gene as defined above in which said eukaryotic cell is an animal cell and in particular a human cell, said process not being used for surgical or therapeutic treatment of the human body or animal body, nor for modifying the genetic identity of a human being.

In an embodiment, the invention relates to a process for modulating the expression of a gene as defined above in which said microRNA and said gene are of endogenous origin in said eukaryotic cell.

In an embodiment, the invention relates to a process for modulating the expression of a gene as defined above in which said microRNA and said gene are of exogenous origin in said eukaryotic cell, said eukaryotic cell containing at least one vector allowing the expression of said microRNA and of said gene.

In an embodiment, the invention relates to a process for modulating the expression of a gene as defined above in which said miPEP is selected from the group of peptides consisting of SEQ ID NO: 1 to SEQ ID NO: 104, SEQ ID NO: 375 to SEQ ID NO: 386 and SEQ ID NO: 355.

In a particular embodiment, the invention relates to a process for modulating the expression of a gene regulated by miR171b (SEQ ID NO: 319) in a eukaryotic cell, comprising carrying out a step of accumulation of MtmiPEP171b1 (SEQ ID NO: 59) in said eukaryotic cell, in which the accumulation of said MtmiPEP171b1 in said eukaryotic cell induces a modulation of the expression of said gene relative to the expression of said gene without accumulation of said MtmiPEP171b1.

In a particular embodiment, the invention relates to a process for modulating the expression of a gene regulated by miR171b (SEQ ID NO: 319) in a eukaryotic cell, comprising carrying out a step of accumulation of MtmiPEP171b1 (SEQ ID NO: 59) in said eukaryotic cell, in which the accumulation of said MtmiPEP171b1 in said eukaryotic cell induces a modulation of the expression of said gene relative to the expression of said gene without accumulation of said MtmiPEP171b1, in which said gene is selected from the genes HAM1 (accession No. MtGI9-TC114268) and HAM2 (accession No. MtGI9-TC120850) (accession numbers according to the database *Medicago truncatula* Gene Expression Atlas "MtGEA").

In a particular embodiment, the invention relates to a process for modulating the expression of a gene regulated by miR164a (SEQ ID NO: 297) in a eukaryotic cell, comprising carrying out a step of accumulation of AtmiPEP165a1 (SEQ ID NO: 24) in said eukaryotic cell, in which the accumulation of said AtmiPEP164a1 in said eukaryotic cell induces a modulation of the expression of said gene relative to the expression of said gene without accumulation of said AtmiPEP164a1.

In a particular embodiment, the invention relates to a process for modulating the expression of a gene regulated by miR165a (SEQ ID NO: 305) in a eukaryotic cell, comprising carrying out a step of accumulation of AtmiPEP165a (SEQ ID NO: 43) in said eukaryotic cell, in which the accumulation of said AtmiPEP165a in said eukaryotic cell induces a modulation of the expression of said gene relative to the expression of said gene without accumulation of said AtmiPEP165a.

In a particular embodiment, the invention relates to a process for modulating the expression of a gene regulated by miR319a (SEQ ID NO: 331) in a eukaryotic cell, comprising carrying out a step of accumulation of AtmiPEP319a1 (SEQ ID NO: 76) in said eukaryotic cell, in which the accumulation of said AtmiPEP319a1 in said eukaryotic cell induces a modulation of the expression of said gene relative to the expression of said gene without accumulation of said AtmiPEP319a1.

In a particular embodiment, the invention relates to a process for modulating the expression of a gene regulated by miR319a (SEQ ID NO: 331) in a eukaryotic cell, comprising carrying out a step of accumulation of AtmiPEP319a2 (SEQ ID NO: 77) in said eukaryotic cell, in which the accumulation of said AtmiPEP319a2 in said eukaryotic cell induces a modulation of the expression of said gene relative to the expression of said gene without accumulation of said AtmiPEP319a2.

In a particular embodiment, the invention relates to a process for modulating the expression of a gene regulated by miR1 (SEQ ID NO: 353) in a eukaryotic cell, comprising carrying out a step of accumulation of DmmiPEP1a (SEQ ID NO: 102) in said eukaryotic cell, in which the accumulation of said DmmiPEP1a in said eukaryotic cell induces a modulation of the expression of said gene relative to the expression of said gene without accumulation of said DmmiPEP1a.

In a particular embodiment, the invention relates to a process for modulating the expression of a gene regulated by miR1 (SEQ ID NO: 353) in a eukaryotic cell, comprising carrying out a step of accumulation of DmmiPEP1b (SEQ ID NO: 103) in said eukaryotic cell, in which the accumulation of said DmmiPEP1b in said eukaryotic cell induces a modulation of the expression of said gene relative to the expression of said gene without accumulation of said DmmiPEP1b.

In a particular embodiment, the invention relates to a process for modulating the expression of a gene regulated by miR8 (SEQ ID NO: 354) in a eukaryotic cell, comprising carrying out a step of accumulation of DmmiPEP8 (SEQ ID NO: 104) in said eukaryotic cell, in which the accumulation of said DmmiPEP8 in said eukaryotic cell induces a modulation of the expression of said gene relative to the expression of said gene without accumulation of said DmmiPEP8.

In a particular embodiment, the invention relates to a process for modulating the expression of a gene regulated by miR155 (SEQ ID NO: 358) in a eukaryotic cell, comprising carrying out a step of accumulation of hsmiPEP155 (SEQ ID NO: 355) in said eukaryotic cell, in which the accumulation of said hsmiPEP155 in said eukaryotic cell induces a modulation of the expression of said gene relative to the expression of said gene without accumulation of said hsmiPEP155.

In another aspect, the invention relates to a modified eukaryotic cell containing a peptide identical to a miPEP as defined above, said peptide being present in said eukaryotic cell independently of transcription of the primary transcript of the microRNA bearing the nucleotide sequence encoding said miPEP.

In the invention, by the term "modified eukaryotic cell" is meant that said eukaryotic cell contains a miPEP introduced into the cell artificially, whether as a peptide, or via a vector encoding said miPEP.

In an embodiment, the invention relates to a modified eukaryotic cell as defined above, in which said microRNA is of endogenous origin.

In another embodiment, the invention relates to a modified eukaryotic cell as defined above in which said microRNA is of exogenous origin, said modified eukaryotic cell containing a vector allowing the expression of said microRNA.

In an embodiment, the invention relates to a modified eukaryotic cell as defined above, said cell being a plant cell.

In an embodiment, the invention relates to a modified eukaryotic cell as defined above, in which said plant cell is a cell of *Medicago truncatula* or of *Arabidopsis thaliana*, and said peptide is selected from the group of peptides consisting of SEQ ID NO: 43, SEQ ID NO: 59 and SEQ ID NO: 77.

In an embodiment, the invention relates to a modified eukaryotic cell as defined above, said cell being an animal cell.

In an embodiment, the invention relates to a modified eukaryotic cell as defined above, in which said animal cell is a *Drosophila* cell and said peptide is selected from the group of peptides consisting of SEQ ID NO: 102, SEQ ID NO: 103 and SEQ ID NO: 104.

In an embodiment, the invention relates to a modified eukaryotic cell as defined above, in which said animal cell is a human cell and said peptide consists of SEQ ID NO: 355.

In another aspect, the invention relates to a plant comprising at least one modified eukaryotic cell as defined above.

In another aspect, the invention also relates to a non-human animal organism comprising at least one modified eukaryotic cell as defined above.

In another aspect, the invention relates to a composition comprising at least one:

miPEP as defined above,
nucleic acid encoding said miPEP, or
vector containing said nucleic acid.

In another aspect, the invention relates to a pesticide composition comprising at least one:

miPEP as defined above,
nucleic acid encoding said miPEP, or
vector containing said nucleic acid.

In another aspect, the invention relates to a phytopharmaceutical composition comprising at least one:

miPEP as defined above,
nucleic acid encoding said miPEP, or
vector containing said nucleic acid.

In another aspect, the invention relates to an elicitor composition comprising at least one:

miPEP as defined above,
nucleic acid encoding said miPEP, or
vector containing said nucleic acid.

"Elicitor composition" denotes a composition capable of endowing the plant with better capacity for symbiosis or better resistance to different stresses whether they are of the nature of thermal stress, water stress or chemical stress.

For this purpose, the invention also relates to compositions acting on the growth (inhibition of growth or conversely growth promotion) and the physiology (better capacity for mycorrhization, nodule formation, better tolerance of different stresses) of the plant.

In particular, the invention relates to compositions for promoting plant growth.

In another aspect, the invention relates to a herbicide composition comprising at least one:

miPEP as defined above,
nucleic acid encoding said miPEP, or
vector containing said nucleic acid.

In another aspect, the invention relates to an insecticide composition comprising at least one:

miPEP as defined above,
nucleic acid encoding said miPEP, or
vector containing said nucleic acid.

In another aspect, the invention relates to a composition, in particular a phytosanitary composition, comprising miPEP164a as active ingredient, said miPEP164a preferably consisting of SEQ ID NO: 24.

In another aspect, the invention relates to a composition, in particular a phytosanitary composition, comprising miPEP319a as active ingredient, said miPEP319a preferably consisting of SEQ ID NO: 76.

In another aspect, the invention relates to a composition, in particular a phytosanitary composition, comprising miPEP171b as active ingredient, said miPEP171b preferably consisting of SEQ ID NO: 59.

The solubility properties of the miPEPs are in particular determined by their amino acid composition. The hydrophilic miPEPs can be dissolved and packaged in aqueous solutions, such as water. The hydrophobic miPEPs can be dissolved and packaged in solvents, such as organic solvents.

For treatment of plants with the miPEPS, the organic solvents are solvents that are non-toxic to the plants in small quantities, i.e. they do not have any harmful effect on the development of the plant. Non-limitatively, the organic solvents may be selected from acetonitrile and acetic acid.

The miPEPs can also be dissolved and packaged in mixtures of organic solvents, such as for example a mixture of acetonitrile and acetic acid. In particular, the miPEPs may be dissolved in a solution comprising 50% acetonitrile, 10% acetic acid and 40% water (volume/volume/volume).

Preferably, miPEPs 164a and 165a are dissolved in water, and miPEPs 171b and 319a are dissolved in a solution comprising 50% acetonitrile, 10% acetic acid and 40% water (volume/volume/volume).

Non-limitatively, the compositions, the pesticide compositions, the phytopharmaceutical compositions, the herbicide compositions and the insecticide compositions as defined above may comprise $10^{-9}$ M to $10^{-4}$ M of miPEP, in particular $10^{-9}$ M, $10^{-8}$ M, $10^{-7}$ M, $10^{-6}$ M, $10^{-5}$ M or $10^{-4}$ M of miPEP.

Compositions of higher or lower concentration may also be provided depending on the applications envisaged. For example, compositions comprising $10^{-1}$ M to $10^{-3}$ M of miPEP, in particular $10^{-1}$ M, $10^{-2}$ M or $10^{-3}$ M of miPEP, may be envisaged in the case where the miPEP has to be administered to the plant by spreading.

In another aspect, the invention relates to the use of a composition as defined above, as a herbicide for eradicating plants or slowing their growth, preferably as a herbicide specific to a species or to a genus of plants.

In another aspect, the invention relates to the use of a composition as defined above, as a phytopharmaceutical agent, for promoting the growth and/or development of plants, in particular for modulating the physiological parameters of a plant, in particular the biomass, foliar surface area, flowering, fruit size, production and/or selection of plant seeds, in particular for controlling the parthenocarpy or the monoecism of a plant, or for modifying the physiological parameters of plant seeds, in particular germination, establishment of the root system and resistance to water stress, or for preventing or treating plant diseases, in particular for promoting resistance to infectious diseases.

In another aspect, the invention relates to the use of a composition as defined above, for modulating the physiological parameters of a plant, in particular biomass, foliar surface area, or fruit size.

In an embodiment, the invention relates to the use of a composition as defined above, for thinning of orchards in order to increase fruit size.

In an embodiment, the invention relates to the use of a composition as defined above, for production and/or selection of plant seeds, said composition being used for controlling the parthenocarpy or the monoecism of a plant.

In an embodiment, the invention relates to the use of a composition as defined above, said composition being administered to said plant via the leaves or via the roots.

In an embodiment, the invention relates to the use of a composition as defined above, for production and/or selection of plant seeds.

In an embodiment, the invention relates to the use of a composition as defined above, in which said composition is used for modifying the physiological parameters of said plant seeds, in particular establishment of the root system, germination and resistance to water stress.

In an embodiment, the invention relates to the use of a composition as defined above, in which said composition is applied by dressing or film-coating of said plant seeds.

In another aspect, the invention relates to the use of a composition as defined above, as a pesticide, for eradicating organisms that are harmful to plants or that might be classified as such, in particular as insecticide, arachnicide, molluscicide or rodenticide.

In an embodiment, the invention relates to the use of a composition as defined above, as insecticide.

In an embodiment, the invention relates to the use of a composition as defined above, for eradicating insect pests.

In an embodiment, the invention relates to the use of a composition as defined above, for eradicating animal species classified as harmful or liable to be classified as such, in particular the Muridae, in particular the rat.

In an embodiment, the invention relates to the use of a composition as defined above, as pesticide for eradicating organisms harmful to plants or liable to be classified as such, in particular as insecticide, arachnicide, molluscicide, or rodenticide, in particular by application of said composition to a plant or to a support in contact with the plant.

In another aspect, the invention relates to the use of a composition as defined above, in which said composition is applied to a plant to protect it against insect pests.

In another aspect, the invention relates to the use of a peptide for promoting the growth of a plant, said peptide being introduced into the plant, said peptide having an amino acid sequence comprising or consisting of a sequence identical to that of a miPEP naturally present in said plant, said miPEP naturally present in said plant being a peptide of 4 to 100 amino acids the sequence of which is encoded by an open reading frame located on the primary transcript of a miRNA, said miPEP being capable of modulating the accumulation of said miRNA in said plant, said miRNA regulating the expression of at least one gene involved in the development of the vegetative or reproductive parts of the plant, in particular the roots, stem, leaves or flowers.

The inventors have surprisingly found that the use of peptides the sequence of which comprises or consists of a sequence identical to that of miPEPs encoded on the primary transcripts of miRNAs makes it possible to promote the growth of the plants.

In the invention, the term "plant" refers generally to the whole or part of a plant irrespective of its stage of development (including the plant in the form of a seed or a young shoot), to one or more organs of the plant (for example the leaves, roots, stem, flowers), to one or more cells of the plant, or to a cluster of cells of the plant.

In the invention, the term "growth" refers to the development of the whole or part of a plant over time. The growth of the plant may thus be determined and quantified by monitoring developmental parameters observable for certain parts, cells or organs of the plant, such as the leaves, roots, stems or flowers.

Non-limitatively, the parameters for determining and quantifying the growth of a plant may in particular be:

the size, surface area, volume, mass and the number of leaves, the size and number of flowers, the size of the stem (or spike), the length and number of roots, the earliness of germination, the earliness of budding, the earliness of floral induction (or floral transition), or also the number of cells.

In the case of leguminous plants, plant growth may also be linked to the rate of nodulation, or also to the size and number of nodules on the roots.

Moreover, in the invention, the expression "promote plant growth", or "improve plant growth", indicates:

either an acceleration of development (such as for example a larger leaf size for a plant at a given point in time relative to a reference plant), or an increase in development (such as for example a larger leaf size for a plant that cannot be attained by a reference plant), or an acceleration and an increase in the development of the plant.

It is important to note that the use according to the invention has the advantage of being ecological, in comparison with the chemical methods used conventionally in horticulture or in agriculture, as the miPEP is a peptide that is present naturally in the plant.

The invention also relates to the use of a miPEP introduced into a plant for promoting its growth, said miPEP introduced being a peptide comprising, or consisting of, a sequence identical to that of a miPEP naturally present in said plant, said miPEP naturally present is a peptide of 4 to 100 amino acids, the sequence of which is encoded by an open reading frame located at 5' on the primary transcript of a miRNA, said miPEP being capable of modulating the accumulation of said miRNA in said plant, said miRNA regulating the expression of at least one gene involved in the development of the vegetative or reproductive parts of the plant, in particular the roots, stem, leaves or flowers, the sum total of the quantity of said miPEP introduced and that of said miPEP naturally present being strictly greater than the quantity of said miPEP naturally present.

In the invention, the expression "miPEP introduced" refers to a miPEP introduced into the plant artificially as opposed to the "miPEP present naturally in the plant". The introduction of a miPEP into the plant therefore involves a technological step, which is not a natural phenomenon and corresponds neither to crossing, nor to selection.

The miPEP introduced may be either a peptide produced outside of the plant (for example an isolated and/or purified peptide, a synthetic peptide or a recombinant peptide), or a peptide produced in the plant following the non-natural introduction of a nucleic acid encoding said miPEP into said plant.

The plant into which the miPEP has not been introduced has a basal quantity of said miPEP, which corresponds to the quantity of said miPEP naturally present. The use of a miPEP comprising, or consisting of, a sequence identical to that of said miPEP leads to an increase in the total quantity of miPEP, which modulates the accumulation of the miRNA the primary transcript of which contains the sequence encoding said miPEP.

Moreover, the miPEP introduced is present in the plant and its introduction has no impact on its stability.

In an embodiment, the invention relates to the use as defined above, in which said gene, involved in the development of the vegetative or reproductive parts of the plant, is selected from the group consisting of: NAC1 (Accession No. AT1G56010.1), NAC4 (Accession No. AT5G07680.1), NAC5 (Accession No. AT5G61430.1), CUC1 (Accession No. AT3G15170.1), CUC2 (Accession No. AT5G53950.1), TCP3 (Accession No. AT1G53230.1) and TCP4 (Accession No. AT3G15030.1) (accession numbers according to the database The *Arabidopsis* Information Resource "TAIR").

In particular, the invention relates to the use as defined above, in which said gene involved in the development of the vegetative or reproductive parts of the plant is selected from the group consisting of: NAC1, NAC4, NAC5, CUC1 and CUC2.

In an embodiment, the invention relates to the use as defined above, in which said gene involved in the development of the vegetative or reproductive parts of the plant is selected from the group consisting of: TCP3 and TCP4, In an embodiment, the invention relates to the use as defined above, in which said miRNA is selected from miR164a and mir319a.

In particular, the invention relates to the use as defined above, in which said miR164a has a nucleotide sequence consisting of SEQ ID NO: 297.

In particular, the invention relates to the use as defined above, in which said miR164a has a nucleotide sequence having at least 80% identity, preferably at least 90% identity, with the nucleotide sequence SEQ ID NO: 297.

In an embodiment, the invention relates to the use as defined above, in which said miPEP is AtmiPEP164a1, in particular in which said AtmiPEP164a1 has an amino acid sequence consisting of SEQ ID NO: 24.

In particular, the invention relates to the use as defined above, in which said miR319a has a nucleotide sequence consisting of SEQ ID NO: 331.

In particular, the invention relates to the use as defined above, in which said miR319a has a nucleotide sequence having at least 80% identity, preferably at least 90% identity, with the nucleotide sequence SEQ ID NO: 331.

In an embodiment, the invention relates to the use as defined above, in which said miPEP is AtmiPEP319a1, in particular in which said AtmiPEP319a1 has an amino acid sequence consisting of SEQ ID NO: 76.

In an embodiment, the invention relates to the use as defined above, in which said plant is a crucifer such as *Arabidopsis thaliana*, a leguminous plant such as *Glycine max* (soya), *Medicago truncatula* and *Medicago sativa* (alfalfa) or a plant of the Solanaceae family such as *Nicotiana benthamiana* (tobacco), *Solanum tuberosum* (potato), *Solanum lycopersicum* (tomato) or *Solanum melongena* (aubergine).

In an embodiment, the invention relates to the use as defined above, in which said plant is a crucifer.

In an embodiment, the invention relates to the use as defined above, in which said plant is *Arabidopsis thaliana.*

In an embodiment, the invention relates to the use as defined above, for promoting the growth of an *Arabidopsis thaliana* plant, in which AtmiPEP164a1 is introduced into said *Arabidopsis thaliana* plant, said AtmiPEP164a1 also being naturally present in said *Arabidopsis thaliana* plant, said AtmiPEP164a1 introduced being a peptide the sequence of which comprises or consists of a sequence identical to that of said AtmiPEP164a1 naturally present, said sequence of AtmiPEP164a1 naturally present being encoded by an open reading frame located at 5' on the primary transcript of the miR164a, which miR164a controls the expression of at least one gene involved in the development of the vegetative or reproductive parts of *Arabidopsis thaliana,* the sum total of the quantity of said AtmiPEP164a1 introduced and that of said AtmiPEP164a1 naturally present being strictly greater than the quantity of said AtmiPEP164a1 naturally present in said *Arabidopsis thaliana* plant.

In an embodiment, the invention relates to the use as defined above, for promoting the growth of an *Arabidopsis thaliana* plant, in which the AtmiPEP319a1 is introduced into said *Arabidopsis thaliana* plant, said AtmiPEP319a1 also being naturally present in said *Arabidopsis thaliana* plant, said AtmiPEP319a1 introduced being a peptide the sequence of which comprises or consists of a sequence identical to that of said AtmiPEP319a1 naturally present, said sequence of the AtmiPEP319a1 naturally present being encoded by an open reading frame located at 5' on the primary transcript of the miR319a, which miR319a controls the expression of at least one gene involved in the development of the vegetative or reproductive parts of *Arabidopsis thaliana,* the sum total of the quantity of said AtmiPEP319a1 introduced and that of said AtmiPEP319a1 naturally present being strictly greater than the quantity of said AtmiPEP319a1 naturally present in said *Arabidopsis thaliana* plant.

In an embodiment, the invention relates to the use as defined above, in which said miPEP is introduced into the plant externally, preferably by watering, by spraying or by adding a fertilizer, a compost, a culture substrate or an inert support.

In an embodiment, the invention relates to the use as defined above, in which said miPEP is introduced by watering and by spraying.

In an embodiment, the invention relates to the use as defined above, in which said miPEP is introduced by watering and by adding a fertilizer.

In an embodiment, the invention relates to the use as defined above, in which said miPEP is introduced by spraying and by adding a fertilizer.

In an embodiment, the invention relates to the use as defined above, in which said miPEP is introduced, by watering, by spraying and by adding a fertilizer.

The inventors have in fact unexpectedly found that it is possible to apply a composition comprising a miPEP directly to the plant in order to modulate the accumulation of the corresponding miRNA in the plant, which indicates that the miPEP is captured by the plant.

In an embodiment, the invention relates to the use as defined above, in which the plant is treated with a composition comprising $10^{-9}$ M to $10^{-4}$ M of said miPEP, in particular $10^{-9}$ M, $10^{-8}$ M, $10^{-7}$ M, $10^{-6}$ M, $10^{-5}$ M or $10^{-4}$ M of said miPEP.

Preferably, the compositions have a concentration from $10^{-8}$ M to $10^{-5}$ M for application by watering or by spraying on the plant.

In addition, compositions of higher or lower concentration may be envisaged for treating the plant with the miPEP. As a non-limitative example, compositions of higher concentration comprising $10^{-1}$ M to $10^{-3}$ M, in particular $10^{-2}$ M of miPEP, may be used in the case where the miPEP introduced exogenously is administered to the plant by spreading.

In an embodiment, the invention relates to the use as defined above, in which said miPEP is introduced into the plant by means of a nucleic acid encoding said miPEP, said nucleic acid being introduced into the plant.

In an embodiment, the invention relates to the use as defined above, in which the size of the stem is increased in the plant into which said miPEP has been introduced relative to the size of the stem of an identical plant of the same age into which no miPEP has been introduced, or relative to the size of the stem of an identical plant of the same age into which said miPEP has not been introduced.

In an embodiment, the invention relates to the use as defined above, in which the number of leaves is increased in the plant into which said miPEP has been introduced relative to the number of leaves of an identical plant of the same age into which no miPEP has been introduced, or relative to the number of leaves of an identical plant of the same age into which said miPEP has not been introduced.

In an embodiment, the invention relates to the use as defined above, in which the size of the leaves is increased in the plant into which said miPEP has been introduced relative to the size of the leaves of an identical plant of the same age into which no miPEP has been introduced, or relative to the size of the leaves of an identical plant of the same age into which said miPEP has not been introduced.

In an embodiment, the invention relates to the use as defined above, in which the number of roots is increased in the plant into which said miPEP has been introduced relative to the number of roots of an identical plant of the same age into which no miPEP has been introduced, or relative to the number of roots of an identical plant of the same age into which said miPEP has not been introduced.

In an embodiment, the invention relates to the use as defined above, in which the length of the roots is increased in the plant into which said miPEP has been introduced relative to the length of the roots of an identical plant of the same age into which no miPEP has been introduced, or relative to the length of the roots of an identical plant of the same age into which said miPEP has not been introduced.

In an embodiment, the invention relates to the use as defined above, in which the rate of nodulation is increased in the plant into which said miPEP has been introduced relative to the rate of nodulation of an identical plant of the same age into which no miPEP has been introduced, or relative to the rate of nodulation of an identical plant of the same age into which said miPEP has not been introduced.

In an embodiment, the invention relates to the use as defined above, in which the number of nodules is increased in the plant into which said miPEP has been introduced relative to the number of nodules of an identical plant of the same age into which no miPEP has been introduced, or relative to the number of nodules of an identical plant of the same age into which said miPEP has not been introduced.

The increase in the parameters for determining and quantifying growth in the plant into which the miPEP has been introduced (such as the size of the stem, the number and size of the leaves, the number and length of the roots, the rate of nodulation or also the number of nodules on the roots) is preferably demonstrated by comparison with an identical plant (i.e. a plant of the same species and/or variety), of the same age and grown under the same conditions but into which no miPEP has been introduced.

In another aspect, the invention relates to a process for promoting the growth of a plant, comprising a step of introducing a miPEP into a plant, said miPEP also being present naturally in said plant, said miPEP introduced being a peptide of 4 to 100 amino acids the sequence of which comprises or consists of a sequence identical to that of said miPEP naturally present, said sequence of the miPEP naturally present being encoded by an open reading frame located at 5' on the primary transcript of a miRNA, said miPEP being capable of modulating the accumulation of said miRNA, said miRNA regulating the expression of at least one gene involved in the development of the vegetative or reproductive parts of the plant, in particular the roots, stem, leaves or flowers, the sum total of the quantity of said miPEP introduced and that of said miPEP naturally present being strictly greater than the quantity of said miPEP naturally present.

In an embodiment, the invention relates to a process as defined above, in which said gene involved in the development of the vegetative or reproductive parts of the plant is selected from the group consisting of: NAC1 (Accession No. AT1G56010.1), NAC4 (Accession No. AT5G07680.1), NAC5 (Accession No. AT5G61430.1), CUC1 (Accession No. AT3G15170.1), CUC2 (Accession No. AT5G53950.1), TCP3 (Accession No. AT1G53230.1) and TCP4 (Accession No. AT3G15030.1).

In particular, the invention relates to a process as defined above, in which said gene involved in the development of the vegetative or reproductive parts of the plant is selected from the group consisting of: NAC1, NAC4, NAC5, CUC1 and CUC2.

In an embodiment, the invention relates to a process as defined above, in which said gene involved in the development of the vegetative or reproductive parts of the plant is selected from the group consisting of: TCP3 and TCP4.

In an embodiment, the invention relates to a process as defined above, in which said miRNA is miR164a, in particular in which said miR164a has a nucleotide sequence consisting of SEQ ID NO: 297.

In an embodiment, the invention relates to a process as defined above, in which said miPEP is AtmiPEP164a1, in particular in which said AtmiPEP164a1 has an amino acid sequence consisting of SEQ ID NO: 24.

In an embodiment, the invention relates to a process as defined above, in which said miRNA is miR319a, in particular in which said miR319a has a nucleotide sequence consisting of SEQ ID NO: 331.

In an embodiment, the invention relates to a process as defined above, in which said miPEP is AtmiPEP319a1, in particular in which said AtmiPEP319a1 has an amino acid sequence consisting of SEQ ID NO: 76.

In an embodiment, the invention relates to a process as defined above, in which said plant is a crucifer such as *Arabidopsis thaliana*, a leguminous plant such as *Glycine max* (soya), *Medicago truncatula* and *Medicago sativa* (alfalfa) or a plant of the Solanaceae family such as *Nicotiana benthamiana* (tobacco), *Solanum tuberosum* (potato), *Solanum lycopersicum* (tomato) or *Solanum melongena* (aubergine).

In an embodiment, the invention relates to a process as defined above, in which said plant is a crucifer.

In an embodiment, the invention relates to a process as defined above, in which said plant is *Arabidopsis thaliana.*

In an embodiment, the invention relates to a process as defined above, for promoting the growth of an *Arabidopsis thaliana* plant, in which AtmiPEP164a1 is introduced into said *Arabidopsis thaliana* plant, said AtmiPEP164a1 also being naturally present in said *Arabidopsis thaliana* plant, said AtmiPEP164a1 introduced being a peptide comprising or consisting of a sequence identical to that of said AtmiPEP164a1 naturally present, where the AtmiPEP164a1 naturally present is a peptide of 4 to 100 amino acids the sequence of which is encoded by an open reading frame located at 5' on the primary transcript of the miR164a, said AtmiPEP164a1 being capable of increasing the accumulation of said miR164a, where said miR164a regulates the expression of at least one gene involved in the development of the vegetative or reproductive parts of *Arabidopsis thaliana,* the sum total of the quantity of said AtmiPEP164a1 introduced and that of said AtmiPEP164a1 naturally present being strictly greater than the quantity of said AtmiPEP164a1 naturally present.

In an embodiment, the invention relates to a process as defined above, for promoting the growth of an *Arabidopsis thaliana* plant, in which AtmiPEP319a1 is introduced into said *Arabidopsis thaliana* plant, said AtmiPEP319a1 also being naturally present in said *Arabidopsis thaliana* plant, said AtmiPEP319a1 introduced being a peptide comprising or consisting of a sequence identical to that of said AtmiPEP319a1 naturally present, where the AtmiPEP319a1 naturally present is a peptide of 4 to 100 amino acids the sequence of which is encoded by an open reading frame located at 5' on the primary transcript of the miR319a, said AtmiPEP319a1 being capable of increasing the accumulation of said miR319a, where miR319a regulates the expression of at least one gene involved in the development of the vegetative or reproductive parts of *Arabidopsis thaliana,* the sum total of the quantity of said AtmiPEP319a1 introduced and that of said AtmiPEP319a1 naturally present being strictly greater than the quantity of said AtmiPEP319a1 naturally present.

In an embodiment, the invention relates to a process as defined above, in which said miPEP is introduced into the plant externally, preferably by watering, by spraying or by adding a fertilizer, a compost, a culture substrate or an inert support.

In an embodiment, the invention relates to a process as defined above, in which said miPEP is administered to the plant in the form of a composition comprising $10^{-9}$ M to $10^{-4}$ M of said miPEP, in particular $10^{-9}$, $10^{-8}$, $10^{-7}$, $10^{-6}$, $10^{-5}$ or $10^{-4}$ M of said miPEP.

In an embodiment, the invention relates to a process as defined above, in which said miPEP is introduced into the plant by means of a nucleic acid encoding said miPEP, said nucleic acid being introduced into the plant.

In an embodiment, the invention relates to a process as defined above, in which the size of the stem is increased in the plant into which said miPEP has been introduced relative to the size of the stem of an identical plant of the same age into which no miPEP has been introduced, or relative to the size of the stem of an identical plant of the same age into which said miPEP has not been introduced.

In an embodiment, the invention relates to a process as defined above, in which the number of leaves is increased in the plant into which said miPEP has been introduced relative to the number of leaves of an identical plant of the same age into which no miPEP has been introduced, or relative to the number of leaves of an identical plant of the same age into which said miPEP has not been introduced.

In an embodiment, the invention relates to a process as defined above, in which the size of the leaves is increased in the plant into which said miPEP has been introduced relative to the size of the leaves of an identical plant of the same age into which no miPEP has been introduced, or relative to the size of the leaves of an identical plant of the same age into which said miPEP has not been introduced.

In an embodiment, the invention relates to a process as defined above, in which the number of roots is increased in the plant into which said miPEP has been introduced relative to the number of roots of an identical plant of the same age into which no miPEP has been introduced, or relative to the number of roots of an identical plant of the same age into which said miPEP has not been introduced.

In an embodiment, the invention relates to a process as defined above, in which the length of the roots is increased in the plant into which said miPEP has been introduced relative to the length of the roots of an identical plant of the same age into which no miPEP has been introduced, or relative to the length of the roots of an identical plant of the same age into which said miPEP has not been introduced.

In an embodiment, the invention relates to a process as defined above, in which the rate of nodulation is increased in the plant into which said miPEP has been introduced relative to the rate of nodulation of an identical plant of the same age into which no miPEP has been introduced, or relative to the rate of nodulation of an identical plant of the same age into which said miPEP has not been introduced.

In an embodiment, the invention relates to a process as defined above, in which the number of nodules is increased in the plant into which said miPEP has been introduced relative to the number of nodules of an identical plant of the same age into which no miPEP has been introduced, or relative to the number of nodules of an identical plant of the same age into which said miPEP has not been introduced.

In another aspect, the invention relates to a plant into which a miPEP has been introduced according to the use or the process for promoting the growth of a plant described above.

In another aspect, the invention relates to a process for producing a transgenic plant comprising:

a) a step of introducing a nucleic acid encoding a miPEP of 4 to 100 amino acids into a plant, or into at least one cell of said plant, under conditions allowing the expression of said miPEP, said miPEP also being naturally present in said plant, said miPEP naturally present being a peptide the sequence of which is encoded by an open reading frame located at 5' on the primary transcript of a miRNA, said miPEP being capable of modulating the accumulation of said miRNA in the plant, said miRNA regulating the expression of at least one gene involved in the development of the vegetative or reproductive parts of the plant, in particular the roots, stem, leaves or flowers, and b) a step of culturing the plant, or at least one cell of said plant, obtained in step a) under conditions allowing a transgenic plant to be obtained.

In an embodiment, the invention relates to a process for producing a transgenic plant as defined above, in which said transgenic plant obtained in step b) has improved growth relative to an identical plant in which said nucleic acid has not been introduced.

In an embodiment, the invention relates to a process for producing a transgenic plant as defined above, in which step a) is carried out using a vector containing said nucleic acid, preferably a plasmid.

In an embodiment, the invention relates to a process for producing a transgenic plant as defined above, in which the expression of said nucleic acid of step a) is placed under the control of a strong promoter, preferably a constitutive strong promoter such as the 35S promoter.

In an embodiment, the invention relates to a process for producing a transgenic plant as defined above, in which said gene involved in the development of the vegetative or reproductive parts of the plant is selected from the group consisting of: NAC1 (Accession No. AT1G56010.1), NAC4 (Accession No. AT5G07680.1), NAC5 (Accession No. AT5G61430.1), CUC1 (Accession No. AT3G15170.1), CUC2 (Accession No. AT5G53950.1), TCP3 (Accession No. AT1G53230.1) and TCP4 (Accession No. AT3G15030.1).

In an embodiment, the invention relates to a process for producing a transgenic plant as defined above, in which said miPEP has an amino acid sequence comprising or consisting of a sequence selected from the group consisting of SEQ ID NO: 1 to SEQ ID NO: 101 and SEQ ID NO: 375 to SEQ ID NO: 386.

In an embodiment, the invention relates to a process for producing a transgenic plant as defined above, in which said miRNA is miR164a, in particular in which said miR164a has a nucleotide sequence consisting of SEQ ID NO: 297.

In an embodiment, the invention relates to a process for producing a transgenic plant as defined above, in which said miPEP is AtmiPEP164a1, in particular in which said AtmiPEP164a1 has an amino acid sequence consisting of SEQ ID NO: 24.

In an embodiment, the invention relates to a process for producing a transgenic plant as defined above, in which said miRNA is miR319a, in particular in which said miR319a has a nucleotide sequence consisting of SEQ ID NO: 331.

In an embodiment, the invention relates to a process for producing a transgenic plant as defined above, in which said miPEP is AtmiPEP319a1, in particular in which said AtmiPEP319a1 has an amino acid sequence consisting of SEQ ID NO: 76.

In an embodiment, the invention relates to a process for producing a transgenic plant as defined above, in which said nucleic acid introduced in step a) comprises a nucleotide sequence selected from SEQ ID NO: 128 and SEQ ID NO: 180.

In an embodiment, the invention relates to a process for producing a transgenic plant as defined above, in which said plant is a crucifer such as *Arabidopsis thaliana*, a leguminous plant such as *Glycine max* (soya), *Medicago truncatula* and *Medicago sativa* (alfalfa) or a plant of the Solanaceae family such as *Nicotiana benthamiana* (tobacco), *Solanum tuberosum* (potato), *Solanum lycopersicum* (tomato) or *Solanum melongena* (aubergine).

In an embodiment, the invention relates to a process for producing a transgenic plant as defined above, in which said transgenic plant is a crucifer.

In an embodiment, the invention relates to a process for producing a transgenic plant as defined above, in which said transgenic plant is *Arabidopsis thaliana.*

In an embodiment, the invention relates to a process for producing a transgenic plant as defined above, comprising:

a) a step of introducing a nucleic acid containing the nucleotide sequence SEQ ID NO: 128, encoding AtmiPEP164a1 consisting of the amino acid sequence SEQ ID NO: 24, into an *Arabidopsis thaliana* plant, or into at least one cell of said *Arabidopsis thaliana* plant, under conditions allowing the expression of AtmiPEP164a1, said AtmiPEP164a1 also being naturally present in said *Arabidopsis thaliana* plant, said miPEP naturally present being a peptide the sequence of which is encoded by an open reading frame located at 5' on the primary transcript of miR164a, said AtmiPEP164a1 being capable of modulating the accumulation of said miR164, where miR164a controls the expression of at least one gene involved in the development of the vegetative or reproductive parts of *Arabidopsis thaliana*, and b) a step of culturing the plant, or at least one cell of said plant, obtained in step a) under conditions allowing a transgenic *Arabidopsis thaliana* plant to be obtained.

In an embodiment, the invention relates to a process for producing a transgenic plant as defined above, comprising:

a) a step of introducing a nucleic acid containing the nucleotide sequence SEQ ID NO: 180, encoding AtmiPEP319a1 consisting of the amino acid sequence SEQ ID NO: 76, into an *Arabidopsis thaliana* plant, or into at least one cell of said *Arabidopsis thaliana* plant, under conditions allowing the expression of AtmiPEP319a1, said AtmiPEP319a1 also being naturally present in said *Arabidopsis thaliana* plant, said miPEP naturally present being a peptide the sequence of which is encoded by an open reading frame located at 5' on the primary transcript of the miR319a, said AtmiPEP319a1 being capable of modulating the accumulation of said miR319, which miR319a regulates the expression of at least one gene involved in the development of the vegetative or reproductive parts of *Arabidopsis thaliana*, and b) a step of culturing the plant, or at least one cell of said plant, obtained in step a) under conditions allowing a transgenic *Arabidopsis thaliana* plant to be obtained.

In an embodiment, the invention relates to a process of production as defined above, in which said miPEP is introduced into the plant by means of a nucleic acid encoding said miPEP, said nucleic acid being introduced into the plant.

In an embodiment, the invention relates to a process for producing a transgenic plant as defined above, in which the size of the stem is increased in the plant into which said miPEP has been introduced relative to the size of the stem of an identical plant of the same age into which no miPEP has been introduced, or relative to the size of the stem of an identical plant of the same age into which said miPEP has not been introduced.

In an embodiment, the invention relates to a process for producing a transgenic plant as defined above, in which the number of leaves is increased in the plant into which said miPEP has been introduced relative to the number of leaves of an identical plant of the same age into which no miPEP has been introduced, or relative to the number of leaves of an identical plant of the same age into which said miPEP has not been introduced.

In an embodiment, the invention relates to a process for producing a transgenic plant as defined above, in which the size of the leaves is increased in the plant into which said miPEP has been introduced relative to the size of the leaves of an identical plant of the same age into which no miPEP has been introduced, or relative to the size of the leaves of an identical plant of the same age into which said miPEP has not been introduced.

In an embodiment, the invention relates to a process for producing a transgenic plant as defined above, in which the number of roots is increased in the plant into which said miPEP has been introduced relative to the number of roots of an identical plant of the same age into which no miPEP has been introduced, or relative to the number of roots of an identical plant of the same age into which said miPEP has not been introduced.

In an embodiment, the invention relates to a process for producing a transgenic plant as defined above, in which the length of the roots is increased in the plant into which said miPEP has been introduced relative to the length of the roots of an identical plant of the same age into which no miPEP has been introduced, or relative to the length of the roots of an identical plant of the same age into which said miPEP has not been introduced.

In an embodiment, the invention relates to a process for producing a transgenic plant as defined above, in which the rate of nodulation is increased in the plant into which said miPEP has been introduced relative to the rate of nodulation of an identical plant of the same age into which no miPEP has been introduced, or relative to the rate of nodulation of an identical plant of the same age into which said miPEP has not been introduced.

In an embodiment, the invention relates to a process for producing a transgenic plant as defined above, in which the number of nodules is increased in the plant into which said miPEP has been introduced relative to the number of nodules of an identical plant of the same age into which no miPEP has been introduced, or relative to the number of nodules of an identical plant of the same age into which said miPEP has not been introduced.

In an aspect, the invention also relates to a transgenic plant as obtained by the process of production as defined above.

In another aspect, the invention relates to a composition comprising, in combination, a quantity of seeds of a plant and a quantity of a peptide the sequence of which comprises or consists of a sequence identical to that of a miPEP naturally present in said plant.

In an embodiment, the invention relates to a composition comprising, in combination, a quantity of seeds of a plant, in particular *A. thaliana*, and a quantity of a peptide the sequence of which comprises or consists of a sequence identical to that of AtmiPEP164a1.

In an embodiment, the invention relates to a composition comprising, in combination, a quantity of seeds of a plant, in particular *A. thaliana*, and a quantity of a peptide the sequence of which comprises or consists of a sequence identical to that of AtmiPEP319a1.

In an embodiment, the invention relates to a composition comprising, in combination, a quantity of seeds of a plant, in particular *M. truncatula*, and a quantity of a peptide the sequence of which comprises or consists of a sequence identical to that of MtmiPEP171b.

In an embodiment, the invention relates to a composition as defined above, formulated so as to form a dressed seed.

Dressing may be carried out by the processes used conventionally in the agri-food industry and may be obtained using a material able to disaggregate in a solvent or in the ground, such as a binder or clay.

According to the invention, dressing may be used for example for conferring particular properties on a composition of miPEP, or on a composition of seeds in combination with a miPEP.

In an embodiment, the invention relates to a composition as defined above, formulated so as to form a dressed seed comprising MtmiPEP171b.

In an embodiment, the invention relates to a composition as defined above, formulated so as to form a dressed seed comprising AtmiPEP164a1.

In an embodiment, the invention relates to a composition as defined, above formulated so as to form a dressed seed comprising AtmiPEP319a1.

In another aspect, the invention relates to a composition comprising at least one:

miPEP as defined above nucleic acid encoding said miPEP, or vector containing said nucleic acid.

for use as a medicament, in particular for humans or for animals.

The use of the compositions of the invention is applicable in human medicine and in veterinary medicine.

In another aspect, the invention relates to a composition comprising at least one:

miPEP as defined above nucleic acid encoding said miPEP, or vector containing said nucleic acid, for use in the prevention and/or treatment of a disease involving deregulation of the expression of a gene of the patient, the expression of said gene being regulated by a microRNA the accumulation of which is modulated by said miPEP.

In an embodiment, the invention relates to the composition as defined above in which said disease is selected from cancer, diabetes, obesity, infectious diseases and neurodegenerative diseases.

In another aspect, the invention relates to a composition comprising at least one:

miPEP as defined above, nucleic acid encoding said miPEP, or vector containing said nucleic acid, for use in the prevention and/or treatment of an infection of an animal or of a human with a parasitic organism, said parasitic organism having a gene the expression of which is regulated by a microRNA the accumulation of which is modulated by said miPEP.

In another aspect, the invention relates to an antibody specifically recognizing a miPEP.

In particular, the invention relates to an antibody specifically recognizing AtmiPEP165a.

In particular, the invention relates to an antibody specifically recognizing MtmiPEP171b.

In particular, the invention relates to an antibody specifically recognizing AtmiPEP164a1. In particular, the invention relates to an antibody specifically recognizing AtmiPEP319a1.

Such an antibody may be obtained by a process known to a person skilled in the art, such as for example by injecting said miPEP into a non-human animal in order to trigger an immunization reaction and the production of antibodies by said animal.

In another aspect, the invention relates to a process of immunolocalization of a miPEP comprising a step of labelling a biological sample from a plant with an antibody specifically recognizing a miPEP.

In particular, the invention relates to a process of immunolocalization of AtmiPEP165a using an antibody specifically recognizing AtmiPEP165a.

In particular, the invention relates to a process of immunolocalization of MtmiPEP171b using an antibody specifically recognizing MtmiPEP171b.

In particular, the invention relates to a process of immunolocalization of AtmiPEP164a1 using an antibody specifically recognizing AtmiPEP164a1.

In particular, the invention relates to a process of immunolocalization of MtmiPEP319a1 using an antibody specifically recognizing AtmiPEP319a1.

In another aspect, the invention relates to a protocol for producing a recombinant peptide, the sequence of which comprises or consists of a sequence identical to that of a miPEP as defined above, comprising a step of transforming an organism with an expression vector encoding said recombinant peptide.

In an embodiment, said organism is selected from the group comprising bacteria, yeasts, fungi (other than yeasts), animal cells, plants and animals.

In an embodiment, said organism is *Escherichia coli.*

In particular, the invention relates to a protocol for producing a recombinant peptide as defined above, comprising the following steps:

binding the nucleic acid encoding said recombinant peptide to a nucleic acid encoding a tag, such as GST, introducing the expression vector containing said nucleic acid encoding said recombinant peptide into the bacterium *E. coli,* culturing the bacterium *E. coli* containing the expression vector in LB medium preferably up to an OD between 0.2 and 0.4, inducing production of the recombinant peptide with IPTG, preferably for 4 to 5 hours, centrifuging and lysing the *E. coli* bacteria, filtering the supernatant, purifying said recombinant peptide on a glutathione sepharose affinity column, if necessary, cleaving the GST with a protease.

All the sequences of the miPEPs, miORFs, miRNAs and primary transcripts of miRNAs are presented in Tables 1, 2, 3, 4, 5 and 6.

Table 7 presents an analysis of the polymorphism of the DNA sequence of the different regions of pri-miR171b (a haplotype is defined when it differs by at least one amino acid from the other haplotypes).

TABLE 1

List of potential miPEPs (miPEPs)

| miPEP (pI/size MW) | miRNA | Organism | Target genes of the miRNA | Sequence of the miPEP | SEQ ID |
|---|---|---|---|---|---|
| AtmiPEP156a1 (10.57 / 3824) | miR156a | *Arabidopsis thaliana* | SPL gene family, involved in development of the stem and flowering | MFCSIQCVARHLFPLHVREIKKATRAI KKGKTL | SEQ ID NO: 1 |
| AtmiPEP156a2 | miR156a | *Arabidopsis thaliana* | | MRRQTSVPFACKRDKESDKSHKER | SEQ ID NO: 2 |
| AtmiPEP156a3 | miR156a | *Arabidopsis thaliana* | | MVMFFLDLDKNPRFDLLKGLKWNLF SSHISPSLPPSL | SEQ ID NO: 3 |
| AtmiPEP156e1 (8.5 / 1359) | miR156c | *Arabidopsis thaliana* | | MKDNFPLLLRL | SEQ ID NO: 4 |
| AtmiPEP156e2 | miR156c | *Arabidopsis thaliana* | | MSDD | SEQ ID NO: 5 |
| AtmiPEP156e1 (4.03 / 1818) | miR156c | *Arabidopsis thaliana* | | MIYINKYGSISAVEDD | SEQ ID NO: 6 |
| AtmiPEP156f1 (9.5 / 520) | miR156f | *Arabidopsis thaliana* | | MSQR | SEQ ID NO: 7 |
| AlmiPEP159a | miR159a | *Arabidopsis lyrata* | MYB gene family, involved in germination and flowering | MTCPLLSLSFLLSKYI | SEQ ID NO: 8 |
| AtmiPEP159a1 (8.34 / 1898) | miR159a | *Arabidopsis thaliana* | | MTWPLLSLSFLLSKYV | SEQ ID NO: 9 |
| CrmiPEP159a | miR159a | *Capsella rubella* | | MTCTLSALSLSLNMFRVN | SEQ ID NO: 10 |
| AtmiPEP159b1 (5.27 / 659) | miR159b | *Arabidopsis thaliana* | | MFYLS | SEQ ID NO: 11 |
| AtmiPEP159b2 | miR159b | *Arabidopsis thaliana* | | MVNTSSFFISSFILPLVLSESNCLLFRTI YKFSMVLY | SEQ ID NO: 12 |
| AtmiPEP160a1 (8.02 / 2936) | miR160a | *Arabidopsis thaliana* | ARF gene family, involved in germination, development and flowering | MFCLLIPIFSFVFSPNRHLRLQEQ | SEQ ID NO: 13 |
| AtmiPEP160b1 (5.28 / 608) | miR160b | *Arabidopsis thaliana* | | MFSPQ | SEQ ID NO: 14 |
| AtmiPEP160b2 | miR160b | *Arabidopsis thaliana* | | MKYIHILILFKSRSTYKLSTNHI | SEQ ID NO: 15 |
| AtmiPEP161 (10/ 1199) | miR161 | *Arabidopsis thaliana* | PPR gene family | MKIPLFLPKL | SEQ ID NO: 16 |
| AtmiPEP162a1 (4.03 / 3045) | miR162a | *Arabidopsis thaliana* | DCL1 gene, involved in development | MVSGQEDSWLKLSSLCFLFLSLLDSLI | SEQ ID NO: 17 |
| AtmiPEP162b1 (5.71 /4114) | miR162b | *Arabidopsis thaliana* | | MFLLIFLRLIMICVCSSTDFLRSVNYFC LFIYDL | SEQ ID NO: 18 |
| AtmiPEP163-1 (6.5 / 1076) | miR163 | *Arabidopsis thaliana* | SAMT gene family, involved in the production of secondary metabolites | MSTTQEHRS | SEQ ID NO: 19 |
| AtmiPEP163-2 | miR163 | *Arabidopsis thaliana* | | MILKCWSSRFLRVSPYQNAHSLSLG | SEQ ID NO: 20 |
| AlmiPEP164a1 | miR164a | *Arabidopsis lyrata* | NAC gene family, involved in root, foliar and floral development | MPLAVIRQGIVWP | SEQ ID NO: 21 |
| AlmiPEP164a2 | miR164a | *Arabidopsis lyrata* | | MPSWHDMVLLPYVKHTHANTRHIT | SEQ ID NO: 22 |
| AlmiPEP164a3 | miR164a | *Arabidopsis lyrata* | | MTWFFCLT | SEQ ID NO: 23 |
| AtmiPEP164a1 (7.05 / 4256) | miR164a | *Arabidopsis thaliana* | | MPSWHGMVLLPYVKHTHASTHTHTH NIYGCACELVFH | SEQ ID NO: 24 |

TABLE 1-continued

List of potential miPEPs (miPEPs)

| miPEP (pI/size MW) | miRNA | Organism | Target genes of the miRNA | Sequence of the miPEP | SEQ ID |
|---|---|---|---|---|---|
| AtmiPEP164a2 | miR164a | *Arabidopsis thaliana* | | MAWYGSFALRKTHSRQHTHTHT | SEQ ID NO: 25 |
| AtmiPEP164a3 | miR164a | *Arabidopsis thaliana* | | MVWFFCLT | SEQ ID NO: 26 |
| BrmiPEP164a1 | miR164a | *Brassica rapa* | | MMIILWK | SEQ ID NO: 27 |
| BrmiPEP164a2 | miR164a | *Brassica rapa* | | MLWAKLVSFSTLHSLVFLLSPSFA | SEQ ID NO: 28 |
| BrmiPEP164a3 | miR164a | *Brassica rapa* | | MPSWHGIVILPFVKHTHANIHYSYSC VCI | SEQ ID NO: 29 |
| CpmiPEP164a1 | miR164a | *Carica papaya* | | MIACHPYLPFPLFLSLTFYSIFFSPSPPS PSLPL | SEQ ID NO: 30 |
| CpmiPEP164a2 | miR164a | *Carica papaya* | | MPSLLAFSPFPFSNILLNLLLPLPPFPLS AIITIIKPLSLSLPLSLSLSGFSV | SEQ ID NO: 31 |
| CrmiPEP164a1 | miR164a | *Capsella rubella* | | MELKGLRTWQLLDKV | SEQ ID NO: 32 |
| CrmiPEP164a2 | miR164a | *Capsella rubella* | | MPSWHGMACFYCLT | SEQ ID NO: 33 |
| CrmiPEP164a3 | miR164a | *Capsella rubella* | | MAWHGMFLLPYVKHTHANTYSLYM | SEQ ID NO: 34 |
| GrmiPEP164a1 | miR164a | *Gossypium raimondii* | | MMRSRILKFQYRFGMGIGGRKQLKN QLCQIQGRIS | SEQ ID NO: 35 |
| GrmiPEP164a2 | miR164a | *Gossypium raimondii* | | MSNSRSYQLK | SEQ ID NO: 36 |
| GrmiPEP164a3 | miR164a | *Gossypium raimondii* | | MNEDLEISTRKRTPQLC | SEQ ID NO: 37 |
| MtmiPEP164a1 | miR164a | *Medicago truncatula* | | MPKFDIFFYIFV | SEQ ID NO: 38 |
| MtmiPEP164a2 | miR164a | *Medicago truncatula* | | MSYISLSPKLLPINTKPFPWLVQFNFY FSSNTKCNKLHFLGEKLLVGEAGHVQ ILFLIHSLIMHINIFCTCSPSPTRLPHPSL | SEQ ID NO: 39 |
| OsmiPEP164a1 | miR164a | *Oryza sativa* | | MQTHSNTPQSTYSLSLSLSE | SEQ ID NO: 40 |
| OsmiPEP164a2 | miR164a | *Oryza sativa* | | MCVCDINMHSMLMLL | SEQ ID NO: 41 |
| AlmiPEP165a | miR165a | *Arabidopsis lyrata* | HD-ZIPIII gene family, involved in vascular, root, foliar and floral development, and nodulation | MRIKLFQLRGMLSGSRILYIYTCVC | SEQ ID NO: 42 |
| AtmiPEP165a (12.3 /2105) | miR165a | *Arabidopsis thaliana* | | MRVKLFQLRGMLSGSRIL | SEQ ID NO: 43 |
| BcmiPEP165a | miR165a | *Brassica carinata* | | MRMKLFQLRGMLSGSRILYIHKYVY MLIQVFDHICI | SEQ ID NO: 44 |
| BjmiPEP165a | miR165a | *Brassica juncea* | | MRMKLFQLRGMLSGSRILYIHKYVYI C | SEQ ID NO: 45 |
| BnmiPEP165a | miR165a | *Brassica napus* | | MRMKLFQLRGMLSGSRILYIHKYVY MIIQVFDHICI | SEQ ID NO: 46 |
| BomiPEP165a | miR165a | *Brassica oleracea* | | MRMKLFQLRGMLSGSRILYIHKYVY MLIQVFDHICI | SEQ ID NO: 47 |
| BrmiPEP165a | miR165a | *Brassica rapa* | | MRMKLFQLRGMLSGSRILYIHKYVYI C | SEQ ID NO: 48 |
| AtmiPEP166a (4.68 / 2372) | miR166a | *Arabidopsis thaliana* | | MLDLFRSNNRIEPSDFRFD | SEQ ID NO: 49 |
| AtmiPEP166b (9.35 / 576) | miR166b | *Arabidopsis thaliana* | | MRDR | SEQ ID NO: 50 |
| AtmiPEP167a (11 / 1148) | miR167a | *Arabidopsis thaliana* | ARF gene family, involved in root and floral development | MNRKISLSLS | SEQ ID NO: 51 |
| AtmiPEP167b1 | miR167b | *Arabidopsis thaliana* | | MMGCFVGF | SEQ ID NO: 52 |

TABLE 1-continued

List of potential miPEPs (miPEPs)

| miPEP (pI/size MW) | miRNA | Organism | Target genes of the miRNA | Sequence of the miPEP | SEQ ID |
|---|---|---|---|---|---|
| (5.27 / 891) | | | gene family of | | |
| AtmiPEP167b2 | miR167b | *Arabidopsis thaliana* | CCAAT-bing factor, | MQEETYEG | SEQ ID NO: 53 |
| AtmiPEP169c1 (9.3 / 7110) | miR169c | *Arabidopsis thaliana* | involved in nodulation, drought resistance, resistance | MPHTNLKDLFIFSPNVFFSFAIYLHNSWNKNYIHKRENFHNTSFALIFFSSIMSINYG | SEQ ID NO: 54 |
| AtmiPEP169c2 | miR169c | *Arabidopsis thaliana* | to nitrogen deficiency | MFFFRLLFISTILGTKTTFTNERIFTTPLLLSFFFFRPL | SEQ ID NO: 55 |
| AtmiPEP1691 (8.52 / 786) | miR1691 | *Arabidopsis thaliana* | | MRHKES | SEQ ID NO: 56 |
| AtmiPEP171a1 (11.05 / 4057) | miR171a | *Arabidopsis thaliana* | GRAS gene family, involved in floral, | MNLLKKERQRRRQRSIGSHCIASLVLKDGYMKKI | SEQ ID NO: 57 |
| AtmiPEP17 1b (8.5 / 995) | miR171b | *Arabidopsis thaliana* | foliar, and root development, | MVLSGKLTF | SEQ ID NO: 58 |
| MtmiPEP171b1 | miR171b | *Medicago truncatula* | mycorrhization, nodulation | MLLHRLSKFCKIERDIVYIS | SEQ ID NO: 59 |
| MtmiPEP171b2 | miR171b | *Medicago truncatula* | | MKIEE | SEQ ID NO: 60 |
| ZmmiPEP171b | miR171b | *Zea mays* | | MHLPSTPSRPPPQHTSLSFLGKEMTKGTTTACFG | SEQ ID NO: 61 |
| AtmiPEP171c1 (6.68 / 1187) | miR171c | *Arabidopsis thaliana* | | MLSLSHFHIC | SEQ ID NO: 62 |
| MtmiPEP171e | miR171e | *Medicago truncatula* | | MMVFGKPKKAMLVRFNPKTDLHV | SEQ ID NO: 63 |
| MtmiPEP171h | miR171h | *Medicago truncatula* | | MASAAKVYMA | SEQ ID NO: 64 |
| AtmiPEP172a1 (8.5 / 734) | miR172a | *Arabidopsis thaliana* | AP2 gene family, involved in floral | MASKIW | SEQ ID NO: 65 |
| AtmiPEP172a3 | miR172a | *Arabidopsis thaliana* | development | MVRFQLSIRD | SEQ ID NO: 66 |
| AtmiPEP172b1 (7.9 / 1621) | miR172b | *Arabidopsis thaliana* | | MCTYYYLINKYF | SEQ ID NO: 67 |
| AtmiPEP172c1 (7.98 / 1367) | miR172c | *Arabidopsis thaliana* | | MFPAKWCRLES | SEQ ID NO: 68 |
| AtmiPEP172e1 (8.35 / 2452) | miR172e | *Arabidopsis thaliana* | | MGSLSLFKSQLEILMLLLSLSK | SEQ ID NO: 69 |
| AtmiPEP172e2 | miR172e | *Arabidopsis thaliana* | | MSVYIHVPISLNCFSPKSSC | SEQ ID NO: 70 |
| AtmiPEP172e3 | miR172e | *Arabidopsis thaliana* | | MGVPNFRPRNR | SEQ ID NO: 71 |
| AcmiPEP319a1 | miR319a | *Arabidopsis cebennensis* | TCP gene family, | MRSRVSFFFFKIMLFRLLGYRSM | SEQ ID NO: 72 |
| AcmiPEP319a2 | miR319a | *Arabidopsis cebennensis* | involved in floral and foliar development | MHTYIHTISNISSIFFCSKRSFSPFTYIRIIVVIDPFRIALTFR | SEQ ID NO: 73 |
| AhmiPEP319a | miR319a | *Arabidopsis halleri* | | MRSRVSLFLSFSSNFAAYSPRS | SEQ ID NO: 74 |
| AlmiPEP319a | miR319a | *Arabidopsis lyrata* | | MHTYIPSSSFPISNISSVFFCYKRSFSPYTYIRIIVVIDPFRIALTFR | SEQ ID NO: 75 |
| AtmiPEP319a1 (6.56 / 5917) | miR319a | *Arabidopsis thaliana* | | MNIHTYHHLLFPSLVFHQSSDVPNALSLHIHTYEYIIVVIDPFRITLAFR | SEQ ID NO: 76 |
| AtmiPEP319a2 | miR319a | *Arabidopsis thaliana* | | MFQTLYLFIYIHTNILLLS | SEQ ID NO: 77 |
| BrmiPEP319a | miR319a | *Brassica rapa* | | MFKLYFSAILSTQYMHTYHHRIALIFLSILYPSTNYLMSPILNPT | SEQ ID NO: 78 |

TABLE 1-continued

List of potential miPEPs (miPEPs)

| miPEP (pI/size MW) | miRNA | Organism | Target genes of the miRNA | Sequence of the miPEP | SEQ ID |
|---|---|---|---|---|---|
| CpmiPEP319a | miR319a | *Carica papaya* | | MKIKLGFSLIKIIILLDKNS | SEQ ID NO: 79 |
| CrmiPEP319a | miR319a | *Capsella rubella* | | MHPHTYIHIPSSSFLISSFCL | SEQ ID NO: 80 |
| EgmiPEP319a | miR319a | *Eucalyptus grandis* | | MKHIQRWRYGETSGRQGDWKRLEIK VHSNPSLKVKKNTNNFSSSL | SEQ ID NO: 81 |
| GrmiPEP319a | miR319a | *Gossypium raimondii* | | MIHFNLSQWRAICMANFHLTYSFLFG VL | SEQ ID NO: 82 |
| MtmiPEP319a | miR319a | *Medicago truncatula* | | MHVYLELFMVIKGLGFLLLVK | SEQ ID NO: 83 |
| OsmiPEP319a | miR319a | *Oryza sativa* | | MEMIQRPCLILKFFFKLSTLYIP | SEQ ID NO: 84 |
| PpmiPEP319a | miR319a | *Physcomitrella patens* | | MFHRRRSSVLLPPFGQTQPNPRCLPDL RFPSCFTPCTA | SEQ ID NO: 85 |
| ThmiPEP319a1 | miR319a | *Thellungiella halophila* | | MTICKVSKACFYAGKIENSRLIKKIGIP KREGAPFSPIRENQ | SEQ ID NO: 86 |
| ThmiPEP319a2 | miR319a | *Thellungiella halophila* | | MEIQIKKKNLYIMNTQKLPNLYIYIYK YVFIKLMVVE | SEQ ID NO: 87 |
| AtmiPEP319b1 (8.04 / 5120) | miR319b | *Arabidopsis thaliana* | | MVPQINLWSSRVILKIRIDSSTHREED HCIQNHKHGLSFIFSF | SEQ ID NO: 88 |
| AtmiPEP394 al (9.7 / 1977) | miR394a | *Arabidopsis thaliana* | F-box gene family, involved in foliar development and drought resistance | MSLQFYERVSFKNTVK | SEQ ID NO: 89 |
| AtmiPEP395e1 (3.58 / 1429) | miR395c | *Arabidopsis thaliana* | Family of the APS and AST genes, involved | MTEQEEESQMST | SEQ ID NO: 90 |
| AtmiPEP395e1 (9.98 / 4700) | miR395e | *Arabidopsis thaliana* | in germination and sulphur metabolism | MYLQYIDNVISIYSNNRRVGRMFSRV PLSTSLEIQFFIK | SEQ ID NO: 91 |
| AtmiPEP397b1 (4.53 / 1418) | miR397b | *Arabidopsis thaliana* | Family of the genes of laccases, involved in copper metabolism, their overexpression improves growth | MSKEIFFSPGFE | SEQ ID NO: 92 |
| AtmiPEP398c1 | miR398c | *Arabidopsis thaliana* | CSD gene family, involved in copper metabolism, its overexpression improves growth | MIRTHEQSTAITTLRHCYSSRFMCSQV TPAELFLYRPCFINAVAR | SEQ ID NO: 93 |
| AtmiPEP399b (11 /678) | miR399b | *Arabidopsis thaliana* | PHO2 gene family, involved in | MKRNM | SEQ ID NO: 94 |
| AtmiPEP399d1 (4 / 622) | miR399d | *Arabidopsis thaliana* | phosphorus metabolism | MQCEI | SEQ ID NO: 95 |
| AtmiPEP403 (5.27470) | miR403 | *Arabidopsis thaliana* | AGO gene family | MFCA | SEQ ID NO: 96 |

TABLE 1-continued

| List of potential miPEPs (miPEPs) | | | | | |
|---|---|---|---|---|---|
| miPEP (pI/size MW) | miRNA | Organism | Target genes of the miRNA | Sequence of the miPEP | SEQ ID |
| AtmiPEP447a1 (6.69 / 724) | miR447a | *Arabidopsis thaliana* | Family of the genes of phosphoglycerate kinase | MVMAHH | SEQ ID NO: 97 |
| AtmiPEP447a2 | miR447a | *Arabidopsis thaliana* | | MMKPRWNCSLYGITEWTNNQNQKSKRKGRRKTQIWRIGDRLDTVECITLMLSAY | SEQ ID NO: 98 |
| AtmiPEP447b1 (4 / 1155) | miR447b | *Arabidopsis thaliana* | | MLLIIVELVL | SEQ ID NO: 99 |
| AtmiPEP447b2 | miR447b | *Arabidopsis thaliana* | | MLCFNFRCVRRFAE | SEQ ID NO: 100 |
| AtmiPEP447c | miR447c | *Arabidopsis thaliana* | | MYTYQLDNSFSWFLCTRFCLYRYFLFNFRCFRRFSE | SEQ ID NO: 101 |
| DmmiPEP1a | miR1 | *Drosophila melanogaster* | Muscular differentiation | MWREVCAQKSQTKRRNFITGNQRRNKTKANRKAETKQQKVYEFFVQARERCKTRKKHEKKTLKKTKKIQNRYRAVSENEWGKGFPSHI | SEQ ID NO: 102 |
| DmmiPEP1b | miR1 | *Drosophila melanogaster* | Muscular differentiation | MRTKKSNKKAQFYYGQPTTKQNKSQPKSRNKAAKSL | SEQ ID NO: 103 |
| DmmiPEP8 | miR8 | *Drosophila melanogaster* | Growth | MEPGFVFVLFPTHLSTQHTQREKSILVMGLNLQSAKQSDKQNSKERKKNTQINSQRIPYRQGGQCSKVLSP | SEQ ID NO: 104 |
| HsmiPEP155 | miR155 | *Homo sapiens* | inflammation | MEMALMVAQTRKGKSVV | SEQ ID NO: 355 |
| AtmiPEP157c (5.95 / 1776) | miR157c | *Arabidopsis thaliana* | SPL gene family, involved in development of the stem and flowering | MMLHITHRFESDVGC | SEQ ID NO: 375 |
| AtmiPEP157d (5.27 / 524) | miR157d | *Arabidopsis thaliana* | | MLYV | SEQ ID NO: 376 |
| AtmiPEP160c (9.98 / 1790) | miR160c | *Arabidopsis thaliana* | ARF gene family, involved in germination, development and flowering | MFMRRGLVYNNIYI | SEQ ID NO: 377 |
| AtmiPEP164b (4.72 / 1949) | miR164b | *Arabidopsis thaliana* | NACgene family, involved in root, foliar and floral development | MMKVCDEQDGEAGHVHY | SEQ ID NO: 378 |
| AtmiPEP166c (10.42 / 3407) | miR166c | *Arabidopsis thaliana* | HD-ZIPIII gene family, involved in vascular, root, foliar and floral development and nodulation | MKKRITRINLEEQIKKTLDDSRTRLHSP | SEQ ID NO: 379 |
| AtmiPEP166d (8.35 / 1125) | miR166d | *Arabidopsis thaliana* | | MKKIGSIDSF | SEQ ID NO: 380 |

TABLE 1-continued

| List of potential miPEPs (miPEPs) | | | | | |
|---|---|---|---|---|---|
| miPEP (pI/size MW) | miRNA | Organism | Target genes of the miRNA | Sequence of the miPEP | SEQ ID |
| AtmiPEP169a (9.5 / 784) | miR169a | *Arabidopsis thaliana* | Gene family of CCAAT-bing factor, involved in nodulation, drought resistance, resistance to nitrogen deficiency | MTCRFK | SEQ ID NO: 381 |
| AtmiPEP169h1 (5.28 / 349) | miR169h | *Arabidopsis thaliana* | | MVT | |
| AtmiPEP169h2 | miR169h | *Arabidopsis thaliana* | | MKNENLCGSQG | SEQ ID NO: 382 |
| AtmiPEP169n (8.96 /5315) | miR169n | *Arabidopsis thaliana* | | MKCMMKKRGLTWRKASCLVAKDDL PDLFRLHDSISNSCILDYYTF | SEQ ID NO: 383 |
| AtmiPEP170 (5.75 / 879) | miR170 | *Arabidopsis thaliana* | GRAS gene family, involved in floral, foliar, and root development, mycorrhization, nodulation | MFPRESL | SEQ ID NO: 384 |
| AtmiPEP396a (5.3 / 3636) | miR396a | *Arabidopsis thaliana* | Family of the GRF genes involved in root development and cellular proliferation, mycorrhization | MTLSVFFHSFLELQNFFRFFFFSFDISY A | SEQ ID NO: 385 |
| AtmiPEP399c (8.66/2703) | miR399c | *Arabidopsis thaliana* | PHO2 gene family, involved in phosphorus metabolism | MSLAKGELPCHCFRLNTVYNRFC | SEQ ID NO: 386 |

TABLE 2

| List of the miORFs | | | |
|---|---|---|---|
| miPEP | Organism | Sequence of the miORF | SEQ ID |
| AtmiPEP156a1 | *Arabidopsis thaliana* | ATGTTCTGTTCAATTCAATGCGTCGCCAGACATCTGTTCCCTTTGCATGTAAGAGAGATAAAGAAAGCGACAAGAGCCATAAAGAAAGGTAA | SEQ ID NO: 105 |
| AtmiPEP156a2 | *Arabidopsis thaliana* | ATGCGTCGCCAGACATCTGTTCCCTTTGCATGTAAGAGAGATAAAGAAAGCGACAAGAGCCATAAAGAAAGGTAA | SEQ ID NO: 106 |
| AtmiPEP156a3 | *Arabidopsis thaliana* | ATGGTTATGTTTTTTCTCGATTTAGACAAAAACCCTAGATTTGATCTTCTAAAGGGTCTCAAATGGAATCTCTTCTCTTCTCATATCTCTCCCTCTCTCCCTCCCTCTCTTTGA | SEQ ID NO: 107 |
| AtmiPEP156c1 | *Arabidopsis thaliana* | ATGAAGGACAACTTTCCTCTTCTCCTTCGGTTATAA | SEQ ID NO: 108 |
| AtmiPEP156c2 | *Arabidopsis thaliana* | ATGAGTGATGACTGA | SEQ ID NO: 109 |
| AtmiPEP156e1 | *Arabidopsis thaliana* | ATGATATATATAAATAAATATGGGTCGATATCGGCTGTGGAGGACGACTAG | SEQ ID NO: 110 |
| AtmiPEP156f1 | *Arabidopsis thaliana* | ATGAGCCAAAGATAA | SEQ ID NO: 111 |
| AlmiPEP159a | *Arabidopsis lyrata* | ATGACGTGTCCTCTTCTCTCTCTCTCTTTCCTTCTCTCTAAGTATATTTAG | SEQ ID NO: 112 |
| AtmiPEP159a1 | *Arabidopsis thaliana* | ATGACGTGGCCTCTTCTCTCTCTCTCTTTCCTTCTCTCTAAGTATGTTTAG | SEQ ID NO: 113 |
| CrmiPEP159a | *Capsella rubella* | ATGACGTGTACTCTCTCTGCTCTATCTCTCTCTCTAAATATGTTTAGGGTTAA | SEQ ID NO: 114 |
| AtmiPEP159b1 | *Arabidopsis thaliana* | ATGTTTTATCTTTCATAA | SEQ ID NO: 115 |
| AtmiPEP159b2 | *Arabidopsis thaliana* | ATGGTTAATACTAGTAGCTTTTTCATTTCAAGTTTTATCCTTCCATTGGTTCTTTCTGAGTCAAATTGTCTCCTGTTTCGAACCATATATAAGTTTTCAATGGTTTTGTATTAA | SEQ ID NO: 116 |
| AtmiPEP160a1 | *Arabidopsis thaliana* | ATGTTTTGTTTGTTGATTCCCATCTTCTCTTTTGTCTTTTCACCAAATCGTCATTTAAGGCTTCAAGAACAGTAA | SEQ ID NO: 117 |
| AtmiPEP160b1 | *Arabidopsis thaliana* | ATGTTTTCCCCTCAATGA | SEQ ID NO: 118 |
| AtmiPEP160b2 | *Arabidopsis thaliana* | ATGAAATACATACACATTTTGATTTTATTTAAATCAAGATCGACGTATAAGCTATCCACCAATCATATTTAA | SEQ ID NO: 119 |
| AtmiPEP161 | *Arabidopsis thaliana* | ATGAAAATTCCATTGTTTCTGCCGAAGCTTTGA | SEQ ID NO: 120 |
| AtmiPEP162a1 | *Arabidopsis thaliana* | ATGGTATCTGGTCAAGAAGATTCCTGGTTAAAACTTTCATCTCTCTGTTTCCTTTTTCTTTCTTTGTTGGATTCATTAATTTGA | SEQ ID NO: 121 |
| AtmiPEP162b1 | *Arabidopsis thaliana* | ATGTTTCTTTTAATCTTTTTGAGATTAATAATGATTTGTGTTTGTTCATCAACCGATTTTCTCAGATCTGTCAATTATTTTTGTTTATTTATTTATGATTTATGA | SEQ ID NO: 122 |
| AtmiPEP163-1 | *Arabidopsis thaliana* | ATGTCCACTACTCAAGAGCATAGGTCTTGA | SEQ ID NO: 123 |
| AtmiPEP163-2 | *Arabidopsis thaliana* | ATGATACTAAAGTGCTGGAGTTCCCGGTTCCTGAGAGTGAGTCCATATCAAAATGCGCATTCGTTATCACTTGGTTGA | SEQ ID NO: 124 |
| AlmiPEP164a1 | *Arabidopsis lyrata* | ATGCCCTTAGCAGTTATTAGACAAGGGATTGTTTGGCCCTAG | SEQ ID NO: 125 |
| AlmiPEP164a2 | *Arabidopsis lyrata* | ATGCCATCATGGCATGACATGGTTCTTTTGCCTTACGTAAAACACACTCACGCCAACACACGCCACATAACATAA | SEQ ID NO: 126 |
| AlmiPEP164a3 | *Arabidopsis lyrata* | ATGACATGGTTCTTTTGCCTTACGTAA | SEQ ID NO: 127 |
| AtmiPEP164a1 | *Arabidopsis thaliana* | ATGCCATCATGGCATGGTATGGTTCTTTTGCCTTACGTAAAACACACTCACGCCAGCACACACACACACACACACATAACATATACGGATGTGCGTGTGAGCTAGTCTTCCATTAA | SEQ ID NO: 128 |
| AtmiPEP164a2 | *Arabidopsis thaliana* | ATGGCATGGTATGGTTCTTTTGCCTTACGTAAAACACACTCACGCCAGCACACACACACACACACATAA | SEQ ID NO: 129 |
| AtmiPEP164a3 | *Arabidopsis thaliana* | ATGGTATGGTTCTTTTGCCTTACGTAA | SEQ ID NO: 130 |
| BrmiPEP164a1 | *Brassica rapa* | ATGATGATAATTTTGTGGAAATAA | SEQ ID NO: 131 |

TABLE 2-continued

List of the miORFs

| miPEP | Organism | Sequence of the miORF | SEQ ID |
|---|---|---|---|
| BrmiPEP164a2 | *Brassica rapa* | ATGCTTTGGGCCAAGCTAGTTTCTTTTAGCACTCTTCACTCACTAG TTTTTCTTCTCAGCCCTTCTTTTGCGTGA | SEQ ID NO: 132 |
| BrmiPEP164a3 | *Brassica rapa* | ATGCCATCATGGCATGGCATTGTCATTTTGCCTTTCGTAAAACAC ACTCACGCCAACATACATTATTCATATTCATGTGTATGTATATGA ATGCCATCATGGCATATGCCATCATGGCAT | SEQ ID NO: 133 |
| CpmiPEP164a1 | *Carica papaya* | ATGATTGCATGCCATCCCTACTTGCCTTTTCCCCTTTTCCTTTCTCT AACATTTTACTCAATCTTCTTCTCCCCCTCCCCCCCTTCCCCCTCTC TGCCATTATAA | SEQ ID NO: 134 |
| CpmiPEP164a2 | *Carica papaya* | ATGCCATCCCTACTTGCCTTTTCCCCTTTTCCTTTCTCTAACATTTT ACTCAATCTTCTTCTCCCCCTCCCCCCCTTCCCCCTCTCTGCCATTA TAACCATAATTAAACCTCTCTCCCTCTCTCTCCCTCTCTCTCTCTCT CTCTCTGGGTTCTCAGTATAA | SEQ ID NO: 135 |
| CrmiPEP164a1 | *Capsella rubella* | ATGGAATTAAAAGGTTTGAGAACTTGGCAGTTATTAGACAAGGTA TAG | SEQ ID NO: 136 |
| CrmiPEP164a2 | *Capsella rubella* | ATGCCATCATGGCATGGCATGGCATGTTTCTATTGCCTTACGTAA | SEQ ID NO: 137 |
| CrmiPEP164a3 | *Capsella rubella* | ATGGCATGGCATGTTTCTATTGCCTTACGTAAAACACACTCACGC CAACACATACTCACTATACATGTAAATAAGTATGTGCGCGTGTGA | SEQ ID NO: 138 |
| GrmiPEP164a1 | *Gossypium raimondii* | ATGATGAGATCAAGAATTTTAAAGTTTCAATATAGATTTGGCATG GGTATTGGCGGCAGAAAGCAATTAAAAAACCAGTTATGTCAAAT TCAAGGTCGTATCAGTTAA | SEQ ID NO: 139 |
| GrmiPEP164a2 | *Gossypium raimondii* | ATGTCAAATTCAAGGTCGTATCAGTTAAAATGA | SEQ ID NO: 140 |
| GrmiPEP164a3 | *Gossypium raimondii* | ATGAATGAAGATTTAGAAATTTCAACAAGGAAGAGGACCCCACA GCTTTGTTAA | SEQ ID NO: 141 |
| MtmiPEP164a1 | *Medicago truncatula* | ATGCCCAAATTTGATATTTTTTTTATATATTTGTATAG | SEQ ID NO: 142 |
| MtmiPEP164a2 | *Medicago truncatula* | ATGTCATATATCTCTCTCTCTCCTAAGTTGCTACCTATAAATACTA AGCCTTTCCCTTGGTTGGTTCAATTCAACTTCTACTTCTCATCAAA CACAAAGTGCAATAAGCTTCATTTCCTGGGTGAGAAGCTCCTTGT TGGAGAAGCAGGGCACGTGCAAATCCTCTTTCTGATTCATTCTCT CATAATGCATATCAATATCTTTTGCACGTGCTCCCCTTCTCCAACT AGG | SEQ ID NO: 143 |
| OsmiPEP164a1 | *Oryza saliva* | ATGCAAACCCACTCCAACACTCCACAATCCACATACTCTCTCTCT CTCTCTCTCTCTGAGTAG | SEQ ID NO: 144 |
| OsmiPEP164a2 | *Oryza saliva* | ATGTGTGTGTGTGATATCAATATGCATTCGATGTTGATGCTACTGT AG | SEQ ID NO: 145 |
| AlmiPEP165a | *Arabidopsis lyrata* | ATGAGAATTAAGCTATTTCAGTTGAGGGGAATGTTGTCTGGATCG AGGATATTATACATATATACATGTGTATGTTGA | SEQ ID NO: 146 |
| AtmiPEP165a | *Arabidopsis thaliana* | ATGAGGGTTAAGCTATTTCAGTTGAGGGGAATGTTGTCTGGATCG AGGATATTATAG | SEQ ID NO: 147 |
| BcmiPEP165a | *Brassica carinata* | ATGAGAATGAAGCTATTTCAGTTGAGGGGAATGTTGTCTGGATCG AGGATATTATATATACACAAATACGTATATATGTTAATACAAGTG TTTGATCATATATGTATATAG | SEQ ID NO: 148 |
| BjmiPEP165a | *Brassica juncea* | ATGAGAATGAAGCTATTTCAGTTGAGGGGAATGTTGTCTGGATCG AGGATATTATATATACACAAATATGTATATATATGTTAA | SEQ ID NO: 149 |
| BnmiPEP165a | *Brassica napus* | ATGAGAATGAAGCTATTTCAGTTGAGGGGAATGTTGTCTGGATCG AGGATATTATATATACACAAATACGTATATATGATAATACAAGTG TTTGATCATATATGTATATAG | SEQ ID NO: 150 |
| BomiPEP165a | *Brassica oleracea* | ATGAGAATGAAGCTATTTCAGTTGAGGGGAATGTTGTCTGGATCG AGGATATTATATATACACAAGTACGTATATATGTTAATACAAGTG TTTGATCATATATGTATATAG | SEQ ID NO: 151 |
| BrmiPEP165a | *Brassica rapa* | ATGAGAATGAAGCTATTTCAGTTGAGGGGAATGTTGTCTGGATCG AGGATATTATATATACACAAATATGTATATATATGTTAA | SEQ ID NO: 152 |
| AtmiPEP166a | *Arabidopsis thaliana* | ATGTTGGATCTCTTTCGATCTAACAATCGAATTGAACCTTCAGATT TCAGATTTGATTAG | SEQ ID NO: 153 |

TABLE 2-continued

List of the miORFs

| miPEP | Organism | Sequence of the miORF | SEQ ID |
|---|---|---|---|
| AtmiPEP166b | *Arabidopsis thaliana* | ATGAGAGATAGATAA | SEQ ID NO: 154 |
| AtmiPEP167a | *Arabidopsis thaliana* | ATGAACAGAAAAATCTCTCTTTCTCTTTCTTGA | SEQ ID NO: 155 |
| AtmiPEP167b1 | *Arabidopsis thaliana* | ATGATGGGTTGTTTTGTGGGATTTTAA | SEQ ID NO: 156 |
| AtmiPEP167b2 | *Arabidopsis thaliana* | ATGCAGGAGGAAACATATGAGGGGTGA | SEQ ID NO: 157 |
| AtmiPEP169c1 | *Arabidopsis thaliana* | ATGCCACATACAAACTTGAAAGATCTCTTCATCTTTTCTCCAAATG TTTTTTTTTCGTTTGCTATTTATCTCCACAATTCTTGGAACAAAAA CTACATTCACAAACGAGAGAATTTTCACAACACCTCTTTTGCTCTC ATTTTTTTTTTTTCGTCCATTATGAGTATTAATTATGGTTAG | SEQ ID NO: 158 |
| AtmiPEP169c2 | *Arabidopsis thaliana* | ATGTTTTTTTTTCGTTTGCTATTTATCTCCACAATTCTTGGAACAA AAACTACATTCACAAACGAGAGAATTTTCACAACACCTCTTTTGC TCTCATTTTTTTTTTTTCGTCCATTATGA | SEQ ID NO: 159 |
| AtmiPEP169l1 | *Arabidopsis thaliana* | ATGAGACATAAAGAGAGTTAA | SEQ ID NO: 160 |
| AtmiPEP171a1 | *Arabidopsis thaliana* | ATGAACCTCCTCAAGAAGGAAAGACAGAGGAGGAGACAAAGAA GTATAGGTTCACATTGCATAGCCAGTTTAGTTTTGAAGGATGGAT ATATGAAAAAAATATGA | SEQ ID NO: 161 |
| AtmiPEP171b | *Arabidopsis thaliana* | ATGGTTCTCTCCGGTAAATTAACATTTTAG | SEQ ID NO: 162 |
| MtmiPEP171b1 | *Medicago truncatula* | ATGCTTCTTCATAGGCTCTCCAAATTTTGCAAAATTGAAAGAGAC ATAGTATATATATCTTAG | SEQ ID NO: 163 |
| MtmiPEP171b2 | *Medicago truncatula* | ATGAAGATTGAAGAGTAA | SEQ ID NO: 164 |
| ZmmiPEP171b | *Zea mays* | ATGCATCTGCCTTCAACTCCCTCTCGCCCCCCACCCCAACACACAT CTCTCTCTTTTCTAGGGAAGGAAATGACGAAGGGGACGACGACG GCATGCTTCGGCTAG | SEQ ID NO: 165 |
| AtmiPEP171c1 | *Arabidopsis thaliana* | ATGTTGTCTCTTTCTCATTTTCATATCTGCTAA | SEQ ID NO: 166 |
| MtmiPEP171e | *Medicago truncatula* | ATGATGGTGTTTGGGAAGCCGAAAAAAGCGATGTTGGTGAGGTT CAATCCGAAGACGGATTTACATGTATAG | SEQ ID NO: 167 |
| MtmiPEP171h | *Medicago truncatula* | ATGGCTTCAGCTGCAAAAGTATACATGGCGTGA | SEQ ID NO: 168 |
| AtmiPEP172a1 | *Arabidopsis thaliana* | ATGGCTTCCAAGATCTGGTAA | SEQ ID NO: 169 |
| AtmiPEP172a3 | *Arabidopsis thaliana* | ATGGTTAGGTTCCAACTAAGTATACGAGATTAA | SEQ ID NO: 170 |
| AtmiPEP172b1 | *Arabidopsis thaliana* | ATGTGTACGTACTATTATCTCATAAATAAATATTTTTAA | SEQ ID NO: 171 |
| AtmiPEP172c1 | *Arabidopsis thaliana* | ATGTTTCCAGCAAAATGGTGCCGTCTTGAGTCTTGA | SEQ ID NO: 172 |
| AtmiPEP172e1 | *Arabidopsis thaliana* | ATGGGATCTCTCTCTTTATTTAAAAGTCAATTAGAGATCTTGATGC TACTTCTGTCCCTTTCCAAGTGA | SEQ ID NO: 173 |
| AtmiPEP172e2 | *Arabidopsis thaliana* | ATGAGTGTATATATTCATGTACCTATCTCTCTCAATTGCTTCTCAC CAAAATCATCTTGCTGA | SEQ ID NO: 174 |
| AtmiPEP172e3 | *Arabidopsis thaliana* | ATGGGAGTTCCCAACTTTAGACCTCGAAACCGATAA | SEQ ID NO: 175 |
| AcmiPEP319a1 | *Arabidopsis cebennensis* | ATGAGATCTAGGGTTTCTTTCTTTTTCTTCAAAATCATGCTTTTTC GCTTGCTAGGTTATAGATCCATGTAA | SEQ ID NO: 176 |
| AcmiPEP319a2 | *Arabidopsis cebennensis* | ATGCATACATACATACATACCATCTCTAATATTTCATCAATCTTCT TTTGTTCCAAACGCCTTTCTCTCCATTTACATACATACGAATCATT GTTGTCATAGATCCGTTTAGAATTGCTTTAACTTTTAGATGA | SEQ ID NO: 177 |
| AhmiPEP319a | *Arabidopsis halleri* | ATGAGATCTAGGGTTTCTTTGTTTCTTTCGTTTTCTTCAAATTTTGC TGCATATTCTCCAAGATCATGA | SEQ ID NO: 178 |
| AlmiPEP319a | *Arabidopsis lyrata* | ATGCATACATACATACCATCATCATCTTTTCCCATCTCTAATATTT CATCAGTCTTCTTTTGTTACAAACGCTCTTTCTCGCCATATACATA CATAAGAATCATTGTTGTCATAGATCCGTTTAGAATTGCTTTAACT TTTAGATGA | SEQ ID NO: 179 |
| AtmiPEP319a1 | *Arabidopsis thaliana* | ATGAATATACATACATACCATCATCTTCTTTTCCCATCTCTAGTTT TTCATCAATCTTCTGATGTTCCAAACGCTCTATCTCTTCATATACA TACATACGAATATATTATTGTTGTCATAGATCCATTTAGAATCACT TTAGCTTTTAGATGA | SEQ ID NO: 180 |

TABLE 2-continued

List of the miORFs

| miPEP | Organism | Sequence of the miORF | SEQ ID |
|---|---|---|---|
| AtmiPEP319a2 | *Arabidopsis thaliana* | ATGTTCCAAACGCTCTATCTCTTCATATACATACATACGAATATAT TATTGTTGTCATAG | SEQ ID NO: 181 |
| BrmiPEP319a | *Brassica rapa* | ATGTTTAAGCTCTACTTCTCAGCAATTCTCTCCACCCAATACATGC ATACATACCATCATCGTATCGCTCTAATTTTTCTATCAATCTTGTA TCCTTCCACAAATTATCTTATGTCTCCCATTTTAAATCCTACATAG | SEQ ID NO: 182 |
| CpmiPEP319a | *Carica papaya* | ATGAAGATTAAATTAGGTTTTAGTCTTATTAAGATTATTATATTAC TAGACAAAAACAGTTAA | SEQ ID NO: 183 |
| CrmiPEP319a | *Capsella rubella* | ATGCATCCACATACATACATACATATACCATCATCTTCTTTTCTCA TCTCTAGTTTTTGTTTATAA | SEQ ID NO: 184 |
| EgmiPEP319a | *Eucalyptus grandis* | ATGAAGCATATTCAAAGGTGGAGATATGGGGAGACTTCCGGAAG GCAAGGGGATTGGAAAAGGCTCGAGATCAAAGTGCATAGCAACC CTTCGCTAAAGGTGAAAAAGAATACGAATAACTTCAGTAGCTCAC TTTAA | SEQ ID NO: 185 |
| GrmiPEP319a | *Gossypium raimondii* | ATGATCCATTTCAACCTGTCACAGTGGAGAGCAATTTGTATGGCT AATTTCCATCTCACCTATTCTTTTCTGTTTGGGGTTCTCTAG | SEQ ID NO: 186 |
| MtmiPEP319a | *Medicago truncatula* | ATGCATGTATATCTTGAATTGTTTATGGTAATAAAGGGGTTAGGA TTTCTCCTTTTGGTGAAGTGA | SEQ ID NO: 187 |
| OsmiPEP319a | *Olyza sativa* | ATGGAAATGATACAAAGGCCGTGTTTAATTTTAAAATTTTTTTTCA AACTTTCAACACTTTACATCCCATAA | SEQ ID NO: 188 |
| PpmiPEP319a | *Physcomitrella patens* | ATGTTCCACCGTCGGAGATCCTCGGTGCTGCTACCCCCGTTCGGC CAAACCCAACCCAACCCTAGGTGTCTGCCGGACCTCCGCTTCCCC TCCTGCTTCACCCCCTGCACCGCTTAA | SEQ ID NO: 189 |
| ThmiPEP319a1 | *Thellungiella halophila* | ATGACGATATGTAAAGTAAGCAAGGCATGTTTTTATGCAGGGAA GATTGAAAATTCAAGATTAATCAAGAAAATTGGAATACCAAAAA GAGAGGGAGCTCCCTTCAGTCCAATCAGAGAGAATCAATGA | SEQ ID NO: 190 |
| ThmiPEP319a2 | *Thellungiella halophila* | ATGGAGATTCAAATTAAAAAGAAAAACTTATATATAATGAATAC ACAAAAGCTACCTAATCTGTATATATATATATATAAATATGTCTT CATTAAATTAATGGTCGTGGAATAG | SEQ ID NO: 191 |
| AtmiPEP319b1 | *Arabidopsis thaliana* | ATGGTACCTCAAATTAATCTATGGTCATCTAGGGTTATCTTGAAG ATTAGAATTGATTCTAGCACGCACAGAGAGGAAGATCATTGCATC CAGAATCACAAACATG[3]GCCTATCTTTTATCTTTTCTTTTTGA | SEQ ID NO: 192 |
| AtmiPEP394a1 | *Arabidopsis thaliana* | ATGTCTCTCCAATTTTATGAGAGGGTTTCCTTCAAGAACACAGTA AAATAG | SEQ ID NO: 193 |
| AtmiPEP395c1 | *Arabidopsis thaliana* | ATGACAGAGCAAGAAGAAGAAAGTCAAATGTCCACATGA | SEQ ID NO: 194 |
| AtmiPEP395e1 | *Arabidopsis thaliana* | ATGTATCTACAATATATTGATAATGTAATATCTATATATTCAAAC AATCGTCGTGTTGGTCGGATGTTTTCTAGAGTTCCTCTGAGCACTT CATTGGAGATACAATTTTTTATAAAATAG | SEQ ID NO: 195 |
| AtmiPEP397b1 | *Arabidopsis thaliana* | ATGAGCAAGGAGATATTTTTTTCCCCTGGGTTTGAATGA | SEQ ID NO: 196 |
| AtmiPEP398c1 | *Arabidopsis thaliana* | ATGAGAACACACGAGCAATCAACGGCTATAACGACGCTACGTCA TTGTTACAGCTCTCGTTTCATGTGTTCTCAGGTCACCCCTGCTGAG CTCTTTCTCTACCGTCCATGTTTTATCAACGCCGTGGCCCGTG | SEQ ID NO: 197 |
| AtmiPEP399b | *Arabidopsis thaliana* | ATGAAGAGAAACATGTAA | SEQ ID NO: 198 |
| AtmiPEP399d1 | *Arabidopsis thaliana* | ATGCAATGTGAAATATGA | SEQ ID NO: 199 |
| AtmiPEP403 | *Arabidopsis thaliana* | ATGTTTTGTGCTTGA | SEQ ID NO: 200 |
| AtmiPEP447a1 | *Arabidopsis thaliana* | ATGGTCATGGCTCATCATTAG | SEQ ID NO: 201 |
| AtmiPEP447a2 | *Arabidopsis thaliana* | ATGATGAAACCTCGATGGAACTGCTCTCTTTATGGAATCACGGAA TGGACAAATAATCAAAATCAGAAATCGAAGCGAAAAGGGAGGA GAAAAACGCAGATTTGGAGGATTGGGGACAGATTAGATACTGTT GAATGCATCACTCTAATGCTATCAGCCTATTAA | SEQ ID NO: 202 |

TABLE 2-continued

| List of the miORFs | | | |
|---|---|---|---|
| miPEP | Organism | Sequence of the miORF | SEQ ID |
| AtmiPEP447b1 | *Arabidopsis thaliana* | ATGCTGCTTATCATCGTGGAGTTGGTTCTGTAA | SEQ ID NO: 203 |
| AtmiPEP447b2 | *Arabidopsis thaliana* | ATGCTTTGTTTCAATTTCAGGTGCGTTAGAAGGTTTGCAGAGTAG | SEQ ID NO: 204 |
| AtmiPEP447c | *Arabidopsis thaliana* | ATGTACACCTACCAGCTTGATAACTCTTTTTCGTGGTTTCTGTGTA CTCGTTTCTGTTTGTACAGATACTTCTTGTTCAATTTCAGATGCTTT AGAAGGTTTTCGGAG | SEQ ID NO: 205 |
| dmmiPEP1a | *Drosophila melanogaster* | ATGTGGCGCGAAGTATGCGCACAAAAAAGTCAAACAAAAAGGCG CAATTTTATTACGGGCAACCAACGACGAAACAAAACAAAAGCCA ACCGAAAAGCAGAAACAAAGCAGCAAAAAGTTTATGAATTTTTT GTGCAGGCGCGTGAAAGATGCAAAACGAGAAAAAAACATGAAA AAAAAACATTAAAAAAAACAAAAAAAATCCAAAACAGATACCG AGCTGTATCCGAAAACGAGTGGGGAAAGGGGTTTCCCAGTCACA TATAA | SEQ ID NO: 206 |
| DmmiPEP1b | *Drosophila melanogaster* | ATGCGCACAAAAAAGTCAAACAAAAAGGCGCAATTTTATTACGG GCAACCAACGACGAAACAAAACAAAAGCCAACCGAAAAGCAGA AACAAAGCAGCAAAAAGTTTATGA | SEQ ID NO: 207 |
| DmmiPEP8 | *Drosophila melanogaster* | ATGGAGCCTGGCTTTGTTTTTGTTTTATTTCCAACCCACTTGAGCA CACAGCACACACAGAGAGAAAAATCAATACTCGTTATGGGATTA AATTTACAAAGCGCAAAGCAAAGCGACAAACAAAATTCAAAAGA AAGAAAAAAAAACACTCAAATAAACTCACAAAGAATTCCTTATC GCCAAGGGGGGCCAATGTTCTAAGGTTCTTTCGCCTTGA | SEQ ID NO: 208 |
| HsmiPEP155 | *Homo sapiens* | TGGAGATGGCTCTAATGGTGGCACAAACCAGGAAGGGGAAATCT GTGGTTTAA | SEQ ID NO: 356 |
| AtmiPEP157c | *Arabidopsis thaliana* | ATGATGTTGCATATCACACATAGGTTTGAGAGTGATGTTGGTTGT TGA | SEQ ID NO: 387 |
| AtmiPEP 157d | *Arabidopsis thaliana* | ATGCTGTATGTATAG | SEQ ID NO: 388 |
| AtmiPEP160c | *Arabidopsis thaliana* | ATGTTCATGCGTAGAGGTTTGGTATACAACAATATATACATATAA | SEQ ID NO: 389 |
| AtmiPEP164b | *Arabidopsis thaliana* | ATGATGAAGGTGTGTGATGAGCAAGATGGAGAAGCAGGGCACGT GCATTAC | SEQ ID NO: 390 TAG |
| AtmiPEP166c | *Arabidopsis thaliana* | ATGAAGAAGAGAATCACTCGAATTAATTTGGAAGAACAAATTAA GAAAACCCTAGATGATTCTCGGACCAGGCTTCATTCCCCCTAA | SEQ ID NO: 391 |
| AtmiPEP166d | *Arabidopsis thaliana* | ATGAAGAAGATCGGTAGIATTGATTCATTTTAA | SEQ ID NO: 392 |
| AtmiPEP169a | *Arabidopsis thaliana* | ATGACTTGCCGATTTAAATGA | SEQ ID NO: 393 |
| AtmiPEP169h1 | *Arabidopsis thaliana* | ATGGTGACATGA | SEQ ID NO: 394 |
| AtmiPEP169h2 | *Arabidopsis thaliana* | ATGAAGAATGAGAACTTGTGTGGTAGCCAAGGATGA | SEQ ID NO: 395 |
| AtmiPEP169n | *Arabidopsis thaliana* | ATGAAGTGTATGATGAAGAAGAGAGGTCTAACATGGCGGAAAGC GTCATGTTTAGTAGCCAAGGATGACTTGCCTGATCTTTTTCGCCTC CACGATTCAATTTCAAATTCATGCATTTTGGATTATTATACCTTTT AA | SEQ ID NO: 396 |
| AtmiPEP170 | *Arabidopsis thaliana* | ATGTTTCCGAGAGAGTCCCTCTGA | SEQ ID NO: 397 |
| AtmiPEP396a | *Arabidopsis thaliana* | ATGACCCTCTCTGTATTCTTCCACAGCTTTCTTGAACTGCAAAACT TCTTCAGATTTTTTTTTTTTTCTTTTGATATCTCTTACGCATAA | SEQ ID NO: 398 |
| AtmiPEP399c | *Arabidopsis thaliana* | ATGTCACTTGCCAAAGGAGAGTTGCCCTGTCACTGCTTCCGCTTA AACACAGTCTATAACCGGTTCTGCTAA | SEQ ID NO: 399 |

TABLE 3

| List of the primary transcripts (pri-miRNAs) | | | |
|---|---|---|---|
| miPEP | Organism | Sequence of the Pri-miRNA | SEQ ID |
| AtmiPEP156a1 AtmiPEP156a2 AtmiPEP156a3 | *Arabidopsis thaliana* | ATTCATTGTTCACTCTCAAATCTCAAGTTCATTGCCATTTTTAGGTCTCTC TATAAATTCAAATGTTCTGTTCAATTCAATGCGTCGCCAGACATCTGTTC CCTTTGCATGTAAGAGAGATAAAGAAAGCGACAAGAGCCATAAAGAAA GGTAAGACTCTTTGAAATAGAGAGAGATAAGGTTTTCTCTTATCTTCTTC | SEQ ID NO: 209 |

TABLE 3-continued

List of the primary transcripts (pri-miRNAs)

| miPEP | Organism | Sequence of the Pri-miRNA | SEQ ID |
|---|---|---|---|
| | | TCATCAGATCTTTGTTTCTTTACCCTCTTTCTTTCTTTTTTTTGCTTTTTATG<br>GTTATGTTTTTTCTCGATTTAGACAAAAACCCTAGATTTGATCTTCTAAAG<br>GGTCTCAAATGGAATCTCTTCTCTTCTCATATCTCTCCCTCTCTCCCTCCC<br>TCTCTTTGATTCTTTGTCTTCTCCAGTTAAAACTCAGATCTAACACAAAGC<br>TTAAAAGATTCTCATCGTTTCTTGTTTTCTTTGTTTCATCTTGTAGATCTCT<br>GAAGTTGGACTAATTGTGAATGAAAGAGTTGGGACAAGAGAAACGCAA<br>AGAAACTGACAGAAGAGAGTGAGCACACAAAGGCAATTTGCATATCATT<br>GCACTTGCTTCTCTTGCGTGCTCACTGCTCTTTCTGTCAGATTCCGGTGCT<br>GATCTCTTT | |
| AtmiPEP156c1<br>AtmiPEP156c2 | *Arabidopsis thaliana* | CTCTGCCTTTAGTTCTTTCTTTTTTGGTAATATATTTATTTTTCGTTACGAT<br>TTGGTCAAAACCCTAGATTTGTTTTCCAAAAGCATATCTGAAAATGAAGG<br>ACAACTTTCCTCTTCTCCTTCGGTTATAAATATTCTCTCCGGTTTTGCTTGT<br>TTAACCTAAAAGCCTCAGATCTAACTCCAACACCTTCAAAGTCTGCCTCC<br>TTTCCAATCTTCTTTCTTCTGTTCGATCTCTAATCTCAGAATTTGTGTCGGT<br>AAGGTAAAGGTGATAATGAGTGATGACTGATGAGGGAGTTTTGGGACAA<br>ATTTTAAGAGAAACGCATAGAAACTGACAGAAGAGAGTGAGCACACAA<br>AGGCACTTTGCATGTTCGATGCATTTGCTTCTCTTGCGTGCTCACTGCTCT<br>ATCTGTCAGATTCCGGCT | SEQ ID NO: 210 |
| AtmiPEP156e1 | *Arabidopsis thaliana* | TCCCACATCCAAAGATAGAAAGATGTAAGGTCTAGAGTCTTGTTCTTAAT<br>CCCCTAACAGAACAATGATATATATAAATAAATATGGGTCGATATCGGC<br>TGTGGAGGACGACTAGCTACGGTTTCGAGCCTGGTCACATGCGTAGAGT<br>GTGAAAGGTAATTAGGAGGTGACAGAAGAGAGTGAGCACACATGGTGG<br>TTTCTTGCATGCTTTTTTGATTAGGGTTTCATGCTTGAAGCTATGTGTGCT<br>TACTCTCTCTCTGTCACCCCT | SEQ ID NO: 211 |
| AtmiPEP156f1 | *Arabidopsis thaliana* | TCCCACAGCCAATGAGCCAAAGATAAAGAAACACCTATCCTATAATAAT<br>TTAGAGCAATATACCTCCATAATGGAACATCTATATATATAAAGGTATCC<br>GTATATCTCTATATATTATATTCATTGAGTTTAAAGTGGCTAGGGTTTATA<br>GATGTATGTGATATTAAGAGATATGAAACATATTTGTCGACGGTTTGAGT<br>GGTGAGGAATTGATGGTGACAGAAGAGAGTGAGCACACATGGTGGCTTT<br>CTTGCATATTTGAAGGTTCCATGCTTGAAGCTATGTGTGCTCACTCTCTAT<br>CCGTCACCCCCTTCTCTCCCTCTCCCTC | SEQ ID NO: 212 |
| AlmiPEP159a | *Arabidopsis lyrata* | AAAAAATGACGTGTCCTCTTCTCTCTCTCTCTTTCCTTCTCTCTAAGTATA<br>TTTAGGGTTAATTATTAGGGTTCTTTATCTCTTTCTTCAGTCTTTGAAGTTT<br>CTTCAATAGCTTTAATTGAAGTGATTTACCTCTCTGGGTGTTTTTAGTATA<br>TATATCATGTACATGATCGAATTTCTTTCTATCCAAGTTCTCATCAAACCT<br>TCTCATGTTTTGAAGAGTTAAAGGCTTTATAGTTTGCTTAGGTCAGATCC<br>ATAACATACTGTATTTGACAAGTTTCTTTGTCTCACGATAGATCTTGGTCT<br>GACCAAAATGATTTTCTCGAGAAAAAAAAAGATGGAAGTAGAGCTCCTT<br>GAAGTTCAAACGAGAGTTGAGCAGGGTAAAGAAAAGCTGCTAAGCTATG<br>GATCCCATAAGCCCTAATCCTTATAAAGAAAAAAAAAGGATTTGGTTATAT<br>GGCTTGCATATCTCAGGAGCTTTAACTTGCCCTTTAATGGCTTTTACTCTT<br>CTTTGGATTGAAGGGAGCTCTACATCTTCTTTCACCTTCTCTATTTTTCTTT<br>CTTTATTTTCTCCTCTACAGTAATTTATTTGGATT | SEQ ID NO: 213 |
| AtmiPEP159a1 | *Arabidopsis thaliana* | TTCCAAAACATGACGTGGCCTCTTCTCTCTCTCTCTTTCCTTCTCTCTAAG<br>TATGTTTAGGGTTAATAATTAGGGTTCCTCCTCTCTTTTGTTCTGTCTTTAT<br>ATCTCCTTCATAGCTCTAATGTAAGAGATTTACCTCTTTTGGTGTTTTTGT<br>TAATCCACGTTCTCATCAAAACTTTCTCATTGTTTTATGAAGAGTTAAAG<br>GTCTTTACAGTTTGCTTATGTCAGATCCATAATATATTTGACAAGATACTT<br>TGTTTTTCGATAGATCTTGATCTGACGATGGAAGTAGAGCTCCTTAAAGT<br>TCAAACATGAGTTGAGCAGGGTAAAGAAAAGCTGCTAAGCTATGGATCC<br>CATAAGCCCTAATCCTTGTAAAGTAAAAAAGGATTTGGTTATATGGATTG<br>CATATCTCAGGAGCTTTAACTTGCCCTTTAATGGCTTTTACTCTTCTTTGG<br>ATTGAAGGGAGCTCTACATCTTCTTTCACCTTCTCTATTTTTTATTTTTCTT<br>TATTTCTACTCAACAATTATTTATTCGGATTCATCTTTAATTTTCCGTTAT<br>AATTTCTTTTTGGTAAGGATTATTCGCTATAATTTGAGAAT | SEQ ID NO: 214 |
| CrmiPEP159a | *Capsella rubella* | TTCCAACGAATGACGTGTACTCTCTCTGCTCTATCTCTCTCTCTAAATATG<br>TTTAGGGTTAATTAGGGTTCTTCATCTGTCTCTCTCTCTCTCTCTCTTCAG<br>AGTCTTTATAGCTTCTTCCAAGATTTTTAATTGAAAGTAATTTACCTCTTT<br>TGGAGTTCTGTACATATAGAATATCAGGAGTCGTGTTTCTTTTTTATCAA<br>GGTTCTCATCTAACCTTTATAGTATTTTCATTAGTTGATAAAGGTCTTCAT<br>AGTTTGCTTAGATCAGATCTTGTCTTCGTCTTTTCGATAGATCTTGTTCTG<br>TCCAATATACAGTGATTTTATTTCGAGAGCAAAAAAGATGAGAGGTAGA<br>GCTCCTTGAAGTTCAAACGAGAGTTTAGCAGGGTAGAGAAAAGCTGCTA<br>AGCTATGGATCCCATAAGCCCTAATCCTTGTTAATGATAAAGGATTTGGT<br>TATATGGCTTGCATATCTCAGGAGCTTTAACTTGCCCTTTAATTGCTTTTA<br>CTCTTCTTTGGATTGAAGGGAGCTCTACATCTTCTTTGACTTCTCTCTCTA<br>TTAAGTCTTTCTTTATTTTCTTCTCTACAATAGTTGTTTTGGATCGGAAGA<br>TCTTTAAGTTTCCCTTA | SEQ ID NO: 215 |

TABLE 3-continued

List of the primary transcripts (pri-miRNAs)

| miPEP | Organism | Sequence of the Pri-miRNA | SEQ ID |
|---|---|---|---|
| AtmiPEP159b1<br>AtmiPEP159b2 | *Arabidopsis thaliana* | TTTCACTTTTGTTCTCCTCCTCCCTTTTTTTCTTTTCAGGATTCTTCTTTTCT<br>ATGTTTTATCTTTCATAATAGATCTGATAATTTTGATTTTTCACTATATAT<br>ATTATGGTTAATACTAGTAGCTTTTTCATTTCAAGTTTTATCCTTCCATTG<br>GTTCTTTCTGAGTCAAATTGTCTCCTGTTTCGAACCATATATAAGTTTTCA<br>ATGGTTTTGTATTAACTCAAGTATTCAACATTATGTCTCTCTTTTTCTTGC<br>TTGGATCTCTAATGCTGTTCATATTTTAAAGCATAGGTTTAGGTTAGATG<br>CATGTAACTGCCAATTAAAAGAAGGTCAAGAGTTTTTTGATTGTATGAAT<br>ATATGAGTTAGTCAAAGCAGATCCACACGATTATATAGAAAAACAAAGG<br>AAGAAGAAGAGGAAGAGCTCCTTGAAGTTCAATGGAGGGTTTAGCAGGG<br>TGAAGTAAAGCTGCTAAGCTATGGATCCCATAAGCCTTATCAAATTCAAT<br>ATAATTGATGATAAGGTTTTTTTATGGATGCCATATCTCAGGAGCTTTC<br>ACTTACCCCTTTAATGGCTTCACTCTTCTTTGGATTGAAGGGAGCTCTTCA<br>TCTCTC | SEQ ID NO: 216 |
| AtmiPEP160a1 | *Arabidopsis thaliana* | CATCCCACCCTTAATTGTTTTATATAAACCATTTCTCCTCCTCTCTCCATC<br>ACCTTCAATCTCTCTCGATCTCTCTCTGGATCCCCAATCTCACCTCCATGT<br>TTTGTTTGTTGATTCCCATCTTCTCTTTTGTCTTTTCACCAAATCGTCATTT<br>AAGGCTTCAAGAACAGTAACCCCAATTCCTCCACAAGAGGGAGAGAAAA<br>CAAAAGATCTTCCAATTCCATTCTCGTACATGCAAATCACAATCCATGCC<br>ATAGATTGTTTCTATTCCTCCTTATTTATTGCTTGTATCTGTTCATGCATG<br>GACCAGGTGGAGAGAGCATTACTTAAAAATAGAATTAGCTATCTGTTTTA<br>GGCGAATTAGTTTCCTTACATAACCATGTATATGTCATGACGCATATACA<br>TATGTAGATGTATATGTATTATATATGTATGCCTGGCTCCCTGTATGCCAT<br>ATGCTGAGCCCATCGAGTATCGATGACCTCCGTGGATGGCGTATGAGGA<br>GCCATGCATAT | SEQ ID NO: 217 |
| AtmiPEP160b1<br>AtmiPEP160b2 | *Arabidopsis thaliana* | ACTCATAACTCTCCCCAAATTCTTGACCAAAAATATCCGCCACTTTCTCTC<br>TGGTTCATGTTTTCCCCTCAATGAAATACATACACATTTTGATTTTATTTA<br>AATCAAGATCGACGTATAAGCTATCCACCAATCATATTTAAGGGTTCCCG<br>TATACATATATACTATATATATATATGGAATAATAGTCGTGCCTGGCTCC<br>CTGTATGCCACAAGAAAACATCGATTTAGTTTCAAAATCGATCACTAGTG<br>GCGTACAGAGTAGTCAAGCATGAC | SEQ ID NO: 218 |
| AtmiPEP161 | *Arabidopsis thaliana* | CTCTAACTCATCCTTCTCTTCTATGAAAATTCCATTGTTTCTGCCGAAGCT<br>TTGATCAGTACTTCTCTTTTGCTTGATCTCGGTTTTTGACCAGTTTATTGC<br>GTCGATCAATGCATTGAAAGTGACTACATCGGGGTTCCGATTTTTTTTGT<br>TCTTCATATGATGAAGCGGAAACAGTAATCAACCCTGGTTTAGTCACTTT<br>CACTGCATTAATCAATGCATTTGTAAAAAGAGGGAAAAGCA | SEQ ID NO: 219 |
| AtmiPEP162a1 | *Arabidopsis thaliana* | CTAGAAGAAAAAACCAGATCTATAAAGTTTGTTATTAAAAGATAGAGAG<br>AGAGGAGGGATGTAGTAGGCCAATAGGCAAATCAGAGAATCACAAATG<br>GTATCTGGTCAAGAAGATTCCTGGTTAAAACTTTCATCTCTCTGTTTCCTT<br>TTTCTTTCTTTGTTGGATTCATTAATTTGACATATCTCTATCATCACACTG<br>ATTCTCTTTCTCCCAGTTTGTCTGCAGATGCATGTGTGTAATCTAGGGTAT<br>ATGTTTTTGTCCATTTGGTTTCATAAGGCAATAAAGATCCAGCTATTTACT<br>ACTTGTGGTATAGATTTTGACTGTTGAATTTTCAGATCTGATGTGTTTCGT<br>TTGATCCGATTCGGAAAATTTATGTTTCGTTGACATTTTGGAGTTTAGTTG<br>GAAGAAGAGTGAGAGTCGCTGGAGGCAGCGGTTCATCGATCTCTTCCTG<br>TGAACACATTAAAAATGTAAAAGCATGAATAGATCGATAAACCTCTGCA<br>TCCAGCGTTTGCCTCTTGTATCTTTCTTATTGACTT | SEQ ID NO: 220 |
| AtmiPEP162b1 | *Arabidopsis thaliana* | CTGCATCTATCCACCTCTCTCTGTAAATTTATCTAAATGTTTCTTTTAATC<br>TTTTTGAGATTAATAATGATTTGTGTTTGTTCATCAACCGATTTTCTCAGA<br>TCTGTCAATTATTTTTGTTTATTTATTTATGATTTATGAATGAGGAAAGAG<br>TGAAGTCGCTGGAGGCAGCGGTTCATCGATCAATTCCTGTGAATATTTAT<br>TTTTGTTTACAAAAGCAAGAATCGATCGATAAACCTCTGCATCCAGCGCT<br>GCTTGCTC | SEQ ID NO: 221 |
| AtmiPEP163- 1<br>AtmiPEP163- 2 | *Arabidopsis thaliana* | TATCACAGTTCTCATCAAATATTTGAAAGTATCAAACAAAAAAAGGAGA<br>GTGAGAAAAATAAAGAGAGAGATAGAGAGAGATCATGTCCACTACTCA<br>AGAGCATAGGTCTTGATTGGTGGAAGACAAGTACCTTAGATAAACCGAC<br>CAAAACCCGGTGGATAAAATCGAGTTCCAACCTCTTCAACGACAACGAT<br>TTCAACACTCTCTTCCAGGAACAACTTCCTCCAGGCAGATGATACTAAAG<br>TGCTGGAGTTCCCGGTTCCTGAGAGTGAGTCCATATCAAAATGCGCATTC<br>GTTATCACTTGGTTGAACCCATTTGGGGATTTAAATTTGGAGGTGAAATG<br>GAACGCGTAATTGATGACTCCTACGTGGAACCTCTTCTTAGGAAGAGCAC<br>GGTCGAAGAAGTAACTGCGCAGTGCTTAAATCGTAGATGCTAAAGTCGT<br>TGAAGAGGACTTGGAACTTCGATATTATCCCCCGTGT | SEQ ID NO: 222 |
| AlmiPEP164a1<br>AlmiPEP164a2<br>AlmiPEP164a3 | *Arabidopsis lyrata* | AGTAGGGTTGGAAAATTTTTTTACATTTTTACTCTAAAATAGAATAGAGT<br>TGGAGATGCCCTTAGCAGTTATTAGACAAGGGATTGTTTGGCCCTAGCGA<br>TCCTCTCTTCACTCTCTCACTTTTGTAGTTCAACCCTTCTTTTGCGTGAGAT<br>GCCATCATGGCATGACATGGTTCTTTTGCCTTACGTAAAACACACTCACG<br>CCAACACACGCCACATAACATAAATAAATTATATATACATATACGTATGT<br>GCGTGTGAGTCTTCCATTAATGCAATCTTTGGGCCTATATATATATACAA<br>ACCTTCCATAACCAAAGTTATCATACTACAAAAGCTCTCTCGTACTTGGA | SEQ ID NO: 223 |

TABLE 3-continued

List of the primary transcripts (pri-miRNAs)

| miPEP | Organism | Sequence of the Pri-miRNA | SEQ ID |
|---|---|---|---|
| | | AATGCGGGTGAGAATCTCCATGTTGGAGAAGCAGGGCACGTGCAAACCA ACAAACACGAAATCCGTCTCATGTGTTTTGCACGTACTCCCCTTCTCCAA CATGAGCTCCTGACCCATTG | |
| AtmiPEP164a1 AtmiPEP164a2 AtmiPEP164a3 | *Arabidopsis thaliana* | AGACAAGCCCCCACACTAAAAAAACAGTAATATGGAATAAAAAAAAGC TTTCAAAACTTAGCAGTTATTAGACAAGGTATTGTTTGGCCCTAGCTAGC GATCGTTTAGCTCTCTTCACTCTCTCACTTTTTTAGTTCAACCCTTCTTTTG CGTGAGATGCCATCATGGCATGGTATGGTTCTTTTGCCTTACGTAAAACA CACTCACGCCAGCACACACACACACACACATAACATATACGGATGTGCG TGTGAGCTAGTCTTCCATTAATGCAATCTTTGGGCCTATATATACAAACC TTTCCATAACCAAAGTTCTCATACTACAAACGCCCCTCATGTGCTTGGAA ATGCGGGTGAGAATCTCCATGTTGGAGAAGCAGGGCACGTGCAAACCAA CAAACACGAAATCCGTCTCATTTGCTTATTTGCACGTACTTAACTTCTCCA ACATGAGCTCTTCACCC | SEQ ID NO: 224 |
| BrmiPEP164a1 BrmiPEP164a2 BrmiPEP164a3 | *Brassica rapa* | AGACAACCCCACGTTTTAAAATAAGAAATGATGATAATTTTGTGGAAAT AAAAGCTAGTATACTTTTGCAATAATTAGACAAGGTATTGATGCTTTGGG CCAAGCTAGTTTCTTTTAGCACTCTTCACTCACTAGTTTTTCTTCTCAGCC CTTCTTTTGCGTGAAATGCCATCATGGCATGGCATTGTCATTTTGCCTTTC GTAAAACACACTCACGCCAACATACATTATTCATATTCATGTGTATGTAT ATGAATGTTCCATTAATGCAATCTTTGGGGCCTATATATACGAAGCTTAC ATCACCAAAGCTCTCATATTACAAAAGCTCACATATATACTTGGAAATGT AGGTGAGAACCTCCATGTTGGAGAAGCAGGGCACGTGCAAACCAAAAA ACATGAAATCTGTTTCATATGCTTTGCACGTGCTCCCCTCCTCCAACATG A | SEQ ID NO: 225 |
| CpmiPEP164a1 CpmiPEP164a2 | *Carica papaya* | AGACAACACTCCTCTTTGTTCCCTTCCTCACGTATCCACTTTTGAAATTTG TAATTTGTGTGCACCACCATGATTGCATGCCATCCCTACTTGCCTTTTCCC CTTTTCCTTTCTCTAACATTTTACTCAATCTTCTTCTCCCCCTCCCCCCCTT CCCCCTCTCTGCCATTATAACCATAATTAAACCTCTCTCCCTCTCTCTCCC TCTCTCTCTCTCTCTCTCTGGGTTCTCAGTATAAATGCAGCTCTGCTTATA CTTCCACACCTATATATATATATACCTGACCCTTCTTCACCTCCTTCATCCAC CTCCTCCTTCTTCCCCAAAACTTTCTTAACTGTTCTCTGCATACATATATA TCCACATACATATATATATATATAGAGAGAGAGTGAGACAGAGAGGTTA CCGAGGCAATTGGGTGAGTAGCTCCCTGTTGGAGAAGCAGGGCACGTGC AAATTCTCCATGGCTTTCCCCTCTTTGCACGTGCTCCCCTTCTCCAACATG GGTTCC | SEQ ID NO: 226 |
| CrmiPEP164a1 CrmiPEP164a2 CrmiPEP164a3 | *Capsella rubella* | CGGCCACCCCCACATTTAACAAGAAAAAAACTGATGGAATTAAAAGGTT TGAGAACTTGGCAGTTATTAGACAAGGTATAGTTTGGCCCTAGCTTCTTT TAATTTAGCTCTCTCCACTCTCACACTTTTCAACTTTCACCCTTCTCTTGC GTGAGTCGCGAGATGCCATCATGGCATGGCATGGCATGTTTCTATTGCCT TACGTAAAACACACTCACGCCAACACATACTCACTATACATGTAAATAA GTATGTGCGCGTGTGAGTCTTCCATCCATCAATGCAATCTTTGGGGCTAT ATATATACAAACCTTTTCCATAACCAAAGCTCTCATATAAACTACAAAAG GCTCACTTOGGAAATGCOGGTGAGAATCTCCACGTTGGAGAAGCAGGGC ACGTGCAAACCAACAAACACGAAACCCTCCTCATGTGCTTTGCACGTACT CCCCTTCTCCAACATG | SEQ ID NO: 227 |
| GrmiPEP164a1 GrmiPEP164a2 GrmiPEP164a3 | *Gossypium raimondii* | GAAAACCCAAGTTCAGGCTAACAAGTTATCTGATGATGAGATCAAGAAT TTTAAAGTTTCAATATAGATTTGGCATGGGTATTGGCGGCAGAAAGCAAT TAAAAAACCAGTTATGTCAAATTCAAGGTCGTATCAGTTAAAATGAATG AAGATTTAGAAATTTCAACAAGGAAGAGGACCCCACAGCTTTGTTAAAT TAAGTGTGTGGTTTTTATAATTATCATCTCGAAAGTTTCATAATATCAATT AGATTAAAACATCTCTGAATTTCATAATTACAAACCAGATAGATAGATAC ATGAAAACTTAGACCCCAGAGATCTGTCTTTAAAGAATGCCCACTTCTAG ACTCAATCTCTATTACTCTCTTTTTTTCTCTCTCTCTCTCTTCGGAAAAACT TGTATATAAATAAATGACACTTTCTTTGCTTTCTGCACTCAACTCATGAAC TTGAAAAGCTTTACTTGGATGGGTTGGTTGGGGGTGAGTATCTCTTGTTG GAGAAGCAGGGCACGTGCAAGTTCCTATGTTTAAGTGAACTTTGCACGT GCTCCCCTTCTCCACCGTGAG | SEQ ID NO: 228 |
| MtmiPEP164a1 MtmiPEP164a2 | *Medicago truncatula* | GAAGAGAAAAAACCTAGTGTAAAATTTGATATACTCTTTATGTATAGTAC GAATGTTTTTTTAAAAATTATGTAAAAAATGATAAAATAATAACTAACTA AATTAACAGTAAAATTAGAAAAGTAAAATACTATGCCCAAATTTGATAT TTTTTTTTATATATTTGTATAGATTATTATTATTTGATATGTAAAGTCCAA TTAAAAATTTGTTTTAACTAAGATTTGAACTAGGTTTTCTTAAAAGACTC ATCTTTTACTTCAAATTTATTTATCATTTGAATTCAATCACTTTCTAATATT ATTATTATTATTTCCACCATACTCATTGCTTCTGCCACGTTACTTTAGTTA GATCTCTTATGTCATATATCTCTCTCTCTCCTAAGTTGCTACCTATAAATA CTAAGCCTTTCCCTTGGTTGGTTCAATTCAACTTCTACTTCTCATCAAACA CAAAGTGCAATAAGCTTCATTTCCTGGGTGAGAAGCTCCTTGTTGGAGAA GCAGGGCACGTGCAAATCCTCTTTCTGATTCATTCTCTCATAATGCATAT CAATATCTTTTGCACGTGCTCCCCTTCTCCAACTAGG | SEQ ID NO: 229 |

TABLE 3-continued

List of the primary transcripts (pri-miRNAs)

| miPEP | Organism | Sequence of the Pri-miRNA | SEQ ID |
|---|---|---|---|
| osmiPEP164a1 osmiPEP164a2 | *Oryza sativa* | ATGCAAACCCACTCCAACACTCCACAATCCACATACTCTCTCTCTCTCT CTCTCTGAGTAGGAGTACATGTGTGTGTGATATCAATATGCATTCGAT GTTGATGCTACTGTAGCCATCTTGTGGCTATATAAACCCAGCAGGCAGCA GCACAGCTTAGCTAGAGAGCCATATTGCATGCACACTCGCTAATCTCTTT TCTCTACTCTACTTGCATTACACCACCTCTGCATTGCACTTCAGTTCATTC ATTCCACTGATGCATGGATCGATGTTGCTACCTTCTTCTCTTCTCCTCATG CATCCATGCATCGATCTCACCTAGCTTCTTCCTCATCCTCTCTCGATCGAT TACAAGAGAAAAGTGTTTGCTGTTCTTGCTATCGATCTACAGGTGAGTAG GTTCTTGTTGGAGAAGCAGGGTACGTGCAAAATGCACACCGGTTGGTCG AGCTAATTAACAAGCTCTGACGACCATGGTGATCGAATGCACGTGCTCCC CTTCTCCACCATGGCCT | SEQ ID NO: 230 |
| AlmiPEP165a | *Arabidopsis lyrata* | CTAGGGTTTAGGAATGACGACTTGTTTCTGTTGTGTCTTATTAAAAGCCC ATCTTCGTCTCCGCCACTCATCATTCCCTCATCATAACACCATCATCACCA TTCACCAACCTCTCTCTCTTTCTCTCTCTCCTCTCGATCTACAACAAAATG TGAATCTGCTAAGATCGATTATCATGAGAATTAAGCTATTTCAGTTGAGG GGAATGTTGTCTGGATCGAGGATATTATACATATATACATGTGTATGTTG ATACATGTGATCATAGAGAGTATCCTCGGACCAGGCTTCATCCCCCCCAA CATGTTATTGCCTCTGATCACCATATATATGTCGTTACATTTCATGGTTAA TTACTTGCACAAATCACAAAAGCTTGGTTTGTAACTTTCTATGACCTTTTT TAATGACTTTGAATCTTTCATGCATGACTTCTTAAGAGTAGATTTACACA TTTGCGGATCCGTTTATGCTTTTTGCTTTTGTTTCGTTTATATATAT | SEQ ID NO: 231 |
| AtmiPEP165a | *Arabidopsis thaliana* | CTAGGGTTTAGGAATGACGACCTGTTTCTGTTGTGTCTTATTAAAAGCCC ATCTTCGTCTCCGCCACTCATCATTCCCTCATCATAACACCATCATCACCA TTCACCAACCTCTCTCTCTCTCCTCTATCACTCTCTACAACAAAAATTT GTGAATCTGCTAAGATCGATTATCATGAGGGTTAAGCTATTTCAGTTGAG GGGAATGTTGTCTGGATCGAGGATATTATAGATATATACATGTGTATGTT AATGATTCAAGTGATCATAGAGAGTATCCTCGGACCAGGCTTCATCCCCC CCAACATGTTATTGCCTCTGATCACCATTTATTGTTACATTTTTTTTTGTTA ATTACTTGCGCAAATTACAAAAGCTTGGTTTTTGTGATGACTTTGAATCTT TCTTGCATGGCTTCTTAAGAGTAGATTTACGGATCCGTCTATGCTTTTTGC TTTTTGTTTCGTTTATTTGTATTTAAAC | SEQ ID NO: 232 |
| BemiPEP165a | *Brassica carinata* | GAGATCAATGAAATTATCCTGCCAAATAAAACGTGTGACGTTTATTCAAA AATATATGCATTAGATGCTTTGATATTAAAATATTTCCTTTTAAAAGCTA GCTAGGGTTTAGGAATGACGAGTTGTGTCTTATTAAAAGCCCTTCTTCTC CTCCGCCACTCATCATTCCCTCATCATAACACCATCATCACCATTCACCC ACCTCTCCTCTTTCTCTCTCTCTCTCTCTCTCTCTCTCTAGAACAACAAG TGAGAATCTGCTAAAATATTGTGACTATTATCATGAGAATGAAGCTATTT CAGTTGAGGGGAATGTTGTCTGGATCGAGGATATTATATATACACAAAT ACGTATATATGTTAATACAAGTGTTTGATCATATATGTATATAGATTATT CTCGGACCAGGCTTCATCCCCCCTAACATGTTATTGCCTCTGATCACCAG ATTCTATCAACTCTTCGCTTATTATTTGTCACAAACAAGTAATAAGCTCA TAATTTTCTTTGAGTCTTTCAGCATCGTTTCATTATGTTTTTCGAATCCG | SEQ ID NO: 233 |
| BjmiPEP165a | *Brassica juncea* | GAGATCAATGAAATTATCCTGCCAAATAAAACGTGTGACGTTTATTCAAA AATATATGCATTAAATGCTTTGATATTAAAATATTTCCTTTTAAAAGCTA GCTAGGGTTTAGGAATGACGAGTTGTGTCTTATTAAAAGCCCTTCTTCTC CTCCGCCACTCATCATTCCCTCATCATAACACCATCATCACCATTCATCCA CCTCTTCTCTCCTCTCTCTCTCTCTCTCTCTCTCTCTCTCTCTCTCTCTCT AGAACAACAAGTGAGAATCTGCTAAAATATTGTGATTATTATCATGAGA ATGAAGCTATTTCAGTTGAGGGGAATGTTGTCTGGATCGAGGATATTATA TATACACAAATATGTATATATATGTTAATATCAGTGTTTGATCATATATA TGTATATAGATTATTCTCGGACCAGGCTTCATCCCCCCTAACATGTTATTG CCTCTGATCACCAGATTCTATCAACTCTTAGCTTATTATTTGTCACAAACA AGTAATAAGCTCAATAATGTCTTTGAGTCTTTCAGCATCGTTTCATATGTT TTCGAATCCG | SEQ ID NO: 234 |
| BnmiPEP165a | *Brassica napus* | GATATCAATGAAATTATCCTGCCAAATAAAACGTGTGACGTTTATTCAAA AATATATGCTTTAAATGCTTTCATATTAAAATATTTCCTTTTAAAAGCTAG CTAGGGTTTAGGAATGACGAGTTGTGTCTTATTAAAAGCCCTTCTTCTCC TCCGCCACTCATCATTCCCTCATCATAACACCATCATCACCATTCACCCA CCTCTCCTCTTTCTCTCTCTCTCTCTCTCTCTCTCTCTAGAACAACAAGT GAGAATCTGCTAAAATATTGTGACTATTATCATGAGAATGAAGCTATTTC AGTTGAGGGGAATGTTGTCTGGATCGAGGATATTATATATACACAAATA CGTATATATGATAATACAAGTGTTTGATCATATATGTATATAGATTATTC TCGGACCAGGCTTCATCCCCCCTAACATGTTATTGCCTCTGATCACCAGA TTCTATCAACTCTTCGCTTATTATTTGTCACAAACAAGTAATAAGCTCAAT AATGTCTTTGAGTCTTTCAGCATCGTTTCATATGTTTTCGAATCCG | SEQ ID NO: 235 |
| BomiPEP165a | *Brassica oleracea* | GGGATCAATGAAAATTATCCTGCCAAATAAAAACGTGTGACGTTTATCC AAAAATATATGCATTAAATGCTGTGATATGAAGTATTTCCTTTAAAAGCT AGCTAGGGTTTAGGAATTACGAGTTGTGTTTTATTAAAAGCCCTTCTTCT CCTCCGCCACTCATCATTCCCTCATCATAACACCATCATCACCATTCACCC ACCTCTCCTCTTTCTCTCTCTCTCTCTCTCTCTAGAACAACAAGTGAGA | SEQ ID NO: 236 |

TABLE 3-continued

List of the primary transcripts (pri-miRNAs)

| miPEP | Organism | Sequence of the Pri-miRNA | SEQ ID |
|---|---|---|---|
| | | ATCTGCTAAAATATTGTGACTATTATCATGAGAATGAAGCTATTTCAGTT<br>GAGGGGAATGTTGTCTGGATCGAGGATATTATATATACACAAGTACGTA<br>TATATGTTAATACAAGTGTTTGATCATATATGTATATAGATTATTCTCGG<br>ACCAGGCTTCATCCCCCCTAACATGTTATTGCCTCTGATCACCAGATTCT<br>ATCAACTCTTCGCTTATTATTTGTCACAAACAAGTAGTAAGCTCAATAAT<br>GTCTTTGAGCCTTTCAGCATCGTTTCATATGTTTTCGAATCCG | |
| BrmiPEP165a | *Brassica rapa* | GAGATCAATGAAATTATCCTGCCAAATAAAACGTGTGACGTTTATTCAAA<br>AATATATGCATTAAATGCTTTGATATTAAAATATTTCCTTTTAAAAGCTA<br>GCTAGGGTTTAGGAATGACGAGTTGTGTCTTATTAAAAGCCCTTCTTCTC<br>CTCCGCCACTCATCATTCCCTCATCATAACACCATCATCACCATTCATCCA<br>CCTCTTCTCTCCTCTCTCTCTCTCTCTCTCTCTCTCTCTCTCTCTCTCTCT<br>AGAACAACAAGTGAGAATCTGCTAAAATATTGTGATTATTATCATGAGA<br>ATGAAGCTATTTCAGTTGAGGGGAATGTTGTCTGGATCGAGGATATTATA<br>TATACACAAATATGTATATATATGTTAATATCAGTGTTTGATCATATATA<br>TGTATATAGATTATTCTCGGACCAGGCTTCATCCCCCCTAACATGTTATTG<br>CCTCTGATCACCAGATTCTATCAACTCTTAGCTTATTATTTGTCACAAACA<br>AGTAATAAGCTCAATAATGTCTTTGAGTCTTTCAGCATCGTTTCATATGTT<br>TTCGAATCCG | SEQ ID NO: 237 |
| AtmiPEP166a | *Arabidopsis thaliana* | CATCATCACCACTCACTTATCTTCTTCTCCATCTCTCTCTCTGCTTCTCCCT<br>TAATCTTAGCCGGGTCTCGTGGGGGACGAACATAGAAAGAGAGAGATAT<br>AAAGATATATATTCAGAAACCCTAGATTCTATAATTTCGACTGAAAAGA<br>AAAAGGGGCTTTCTCTTTTGAGGGGACTGTTGTCTGGCTCGAGGACTCTG<br>GCTCGCTCTATTCATGTTGGATCTCTTTCGATCTAACAATCGAATTGAACC<br>TTCAGATTTCAGATTTGATTAGGGTTTTAGCGTCTTCGGACCAGGCTTCAT<br>TCCCCCCAATTGTTGCTCCCTGTTTACTCCATATTTCTTCCTTCTTTTCAAA<br>TTAGGGTTTCAGATCCAGTGAATGAACCCTTGTTAAAGGTTTGATCTCTT<br>ACCTTACTTT | SEQ ID NO: 238 |
| AtmiPEP166b | *Arabidopsis thaliana* | TCTCATCATTCTCTTCATCATCACCACATTCATCTCTCTCTCTCTCTCTC<br>TCTCTCTCTTTCTCTTCCTTGATCTTAGCCGGATCTGTTGGGGGACGAACA<br>CATGAGAGATAGATAAAATATAAGAAATTTCTCGAAAAAACCTAATAGA<br>AAAAGGTCTGTTTCTTAAAGAAGAAGAAGAAGAGGATTTAAAGAGGGAT<br>TTTTCTTTTGAGGGGACTGTTGTCTGGCTCGAGGACTCTTATTCTAATACA<br>ATCTCATTTGAATACATTCAGATCTGATGATTGATTAGGGTTTTAGTGTC<br>GTCGGACCAGGCTTCATTCCCCCCAA | SEQ ID NO: 239 |
| AtmiPEP167a | *Arabidopsis thaliana* | TGATGAACAGAAAAATCTCTCTTTCTCTTTCTTGATCTGCTACGGTGAAG<br>TCTATGGTGCACCGGCATCTGATGAAGCTGCCAGCATGATCTAATTAGCT<br>TTCTTTATCCTTTGTTGTGTTTCATGACGATGGTTAAGAGATCAGTCTCGA<br>TTAGATCATGTTCGCAGTTTCACCCGTTGACTGTCGCACCC | SEQ ID NO: 240 |
| AtmiPEP167b1<br>AtmiPEP167b2 | *Arabidopsis thaliana* | AACCACAAAGTACCGCTGCTATTTTCTTTTTACGTCTTTGTATTTGCATCG<br>TCTAAGAGAATGATGGGTTGTTTTGTGGGATTTTAATGCAGGAGGAAAC<br>ATATGAGGGGTGATTAAGGCAAAAACCTTAAGATGTGGTCATTTAGATA<br>CATGGAGTCAAACTAAGAATGGACCTTGGCGAAAGCTTCTTCACGGTCA<br>AGATTTAAAATCAGGTACGACACTGTGTACGTGAGAGAGAGAGAGAGAG<br>AGAGAAAGAGATTATAGAAAGAAAGAGATGTATCACAATAAAGGAGTA<br>TATTTAGGGTCACAGGTGGTGGAGATATAGGTATGCAGGGCCAAGGCTC<br>TAATCTCTTCATAGCCCTATTGATTTTGTCCCTCTCTCTCTCTCTTTCTTCC<br>TCTCTTAGCTGTATGCATTATGATGCGTCTTTTAATTCACTGTTTCAGGCT<br>TCTTTAATTCGTGGTGTCTCTCTCCTTTTTACCCAACCATCTCTTAAAATTT<br>TTAACATCTGTTCCTCAAATCCTCTCTCATCTCTTTCTATAAGTATCTATA<br>GCGCCTCTTAAACCACAAAGCATCACCTCTGTCTTCTCTCATCTCCTTTCT<br>GTATTCTCTTTCATTGCCTTCACGTCTGTTGCAATTTCTCCACTTCTTGAG<br>CTTCCGTTTTTTACAATTATTGATCCGTCAAATATGTGAGATTTGCACAAC<br>TTGTTGCTCAGGTATTTTGAAGACAAGTCCACAAGGGAACAAGTGAAGC<br>TGCCAGCATGATCTATCTTTGGTTAAGAGATGAATGTGGAAACATATTGC<br>TTAAACCCAAGCTAGGTCATGCTCTGACAGCCTCACTCCTTCCT | SEQ ID NO: 241 |
| AtmiPEP169c1<br>AtmiPEP169c2 | *Arabidopsis thaliana* | GAGCAAGACAATGCCACATACAAACTTGAAAGATCTCTTCATCTTTTCTC<br>CAAATGTTTTTTTTTCGTTTGCTATTTATCTCCACAATTCTTGGAACAAAA<br>ACTACATTCACAAACGAGAGAATTTTCACAACACCTCTTTTGCTCTCATT<br>TTTTTTTTTTCGTCCATTATGAGTATTAATTATGGTTAGGGAATCTTACAG<br>AATGAAAATGAAGGTGTGAATGGATTGTCTCATCTAAAGCCTTGAATGT<br>GGGAAAAAGGCCATTGTTGTTCAGCCAAGGATGACTTGCCGGTAGCTTG<br>TATTATGATTACTCTATATTCGATTTATATTATGGAGATGATGGTTTATAT<br>ATATTTACTTATCTACATAGTTTTAGTTGATTTTTTTTCGTACGTAATATA<br>ATACGAAAAAGTATTTACTTATTTATATATGTGTGTTGGGGCAAGAAGTG<br>TAACCAAGCTAGCCCGGCAAGTCATCTATGGCTATGCAACTGTCTCTTCC<br>TCTCATTCTAGGCTTACGATGACACGTAAAAAATCCCAAATATCACTAAT<br>ATGATATGAATATGGATGA | SEQ ID NO: 242 |

TABLE 3-continued

List of the primary transcripts (pri-miRNAs)

| miPEP | Organism | Sequence of the Pri-miRNA | SEQ ID |
|---|---|---|---|
| AtmiPEP16911 | *Arabidopsis thaliana* | AGGCATGAGACATAAAGAGAGTTAAATATAATGAAGAAGAGAGGTCTA ATATGGCGAAAAGAGTCATGTTTAATAGCCAAGGATGACTTGCCTGATCT TTTTCACCTCCATGATTCAATTTTAAGTTCGTGGATTTTGGATTATTATGC GTTTAAAAGGTATAATAATTTGAGATCATGTTGAATCTTGCGGGTTAGGT TTCAGGCAGTCTCTTTGGCTATCTTGACATGCTTTCTTCATC | SEQ ID NO: 243 |
| AtmiPEP171a1 | *Arabidopsis thaliana* | GAATTTTGATTTATGAACCTCCTCAAGAAGGAAAGACAGAGGAGGAGAC AAAGAAGTATAGGTTCACATTGCATAGCCAGTTTAGTTTTGAAGGATGG ATATATGAAAAAAATATGAAGAGAGAGAAGAGAGAAGAAGAGGAGGAT TAAAGAGGGTGAGGCCAGCTTTTGTGCTTTGGTAGTAGATGAGGTTTAAA TGCTCCATACCTTCCATTTCCTTCTCTCTTACCCTAATTTAATTCTTCCTCT CCTTTATAACTCCCCACAGACATTCTCACTTCTCCTCCTCACACTTCACAT CAACACTTCTTTCTTGTTTTTTCATTTTACAATGTTTCCTTTGATATCCGCA CTTTAAGCATGAGAGAGTCCCTTTGATATTGGCCTGGTTCACTCAGATCT TACCTGACCACACACGTAGATATACATTATTCTCTCTAGATTATCTGATT GAGCCGCGCCAATATCTCAGTACTCTCTCGTCTCTATTTTGGACTTTGTGG TCTTGTAGATCGATTTGTATGTGTGTGTTGAAATGGAGACAAGTACTTGT AACTTCTTTGTTGTTATATTGTTTACCTATAGGCTGATGTCATAAACTCTT TTGATCTTGTTTCTAACTTCCAGATTCTTGAAAAATCAAGTCGTGTGTGTG TCTCCATGGAAGCCTTTTCCATTTCTTCCTTTCCA | SEQ ID NO: 244 |
| AtmiPEP171b | *Arabidopsis thaliana* | ACTCATAAACTTTGCTACTGGCCGCATTTCTATTTTCTCCTTCGATTCTTC TAATTCGTACTTTGGTTTCTGACGTCCCTAAAATTTTTAGACAGTAAGAG TTTCTCCAGGATCCGATGGTTCTCTCCGGTAAATTAACATTTTAGTGTCAA TAGTCATTTATACATATTTTTATTTCACTTTTTGTTTTGTTTATTGGTTTTC TGGAGCTAAGTGGAGATTATAGTCGAACAAGAGTGGTTTTATGCAAGGT AACGCGAGATATTAGTGCGGTTCAATCAAATAGTCGTCCTCTTAACTCAT GGAGAACGGTGTTGTTCGATTGAGCCGTGCCAATATCACGCGGTAAACC AAAAATGGCAAAGATAGTTATTATAACCTTAAAGGTATGTATCATTATCG TTTTATTGTTTCAATTTTGATTAATGGCTTTGATATTTCATTTTTTTTT | SEQ ID NO: 245 |
| MtmiPEP171b1 MtmiPEP171b2 | *Medicago truncatula* | ATTGGTCAAACATACATACAGTAGCACTAGCTGGTTTCATTATTCCACTA TGCTTCTTCATAGGCTCTCCAAATTTTGCAAAATTGAAAGAGACATAGTA TATATATCTTAGCAAGGAGAAATTCAGGATATTGAGGATGAAGATTGAA GAGTAATCAGTGATGAAGAAAGCAAGCAAGGTATTGGCGCGCCTCAATT TGAATACATGGCTATAAAAATGCATCATATCAGCCATGTAGTTTGATTGA GCCGCGTCAATATCTTGTTTCCATCTCCAAATTTACCAATCTCATCAAATC AAATTAACACCACAATCAAGGCTTTCATTTAATGCAGTCAAAATAGGTTG ACCTTATCATCGAAGAAATTGTTTTCTCATTCCTATCGAAGTTGGACTTGC CGAAAATGCTCGAAAGCATGTGTTTTAGTTCGACAGGCGAAAAAGTTAC CGAAGGACAATTTGGTTGTGGTTCGGATAAGATCAAGCAACGGATATTTT CAAGACACGTTCGAAATTCAAATCAAATGGATAAGTATCGTTAGTTTACT GCAGTTATAGTTTTAAATTCAAATCTAGGCAGTTGTTTCTATTTGTATAAA TAGTAGTTTTTCCCTAGGGAAAAGGGGTCGCAATTCAATCATACAAAAA ACTTACAATCAAATTATCCGCATGGAAGAGAGAAACGAGTCACAAGTTG CAATGTATGAACATGTGTACCAATTTACATTCAATCAGTACAATTTAAGT TCATTTCCATAAAAAAAAA | SEQ ID NO: 246 |
| ZmmiPEP171b | *Zea mays* | ACCAGGGTTAGGTATCCATCCACACAGCAATGCATCTGCCTTCAACTCCC TCTCGCCCCCCACCCCAACACACATCTCTCTCTTTTCTAGGGAAGGAAAT GACGAAGGGGACGACGACGGCATGCTTCGGCTAGCTCGTTGGTGCTAGG ACAAGGGCGGAGGTATTGGCGCGCCTCAATCCGAAGGCGTGGCTGATAG ATTGGCGCGGCAGCCATGTTCTTGGATTGAGCCGCGTCAATATCTCCCCT TGCCTGTCCCGTACCTAGCTAGCTTGCTTGCCTCACTGATCGATGTCGTCC CTATTTCATGGAGAAGCTGATGATTGATTATTCTCACAAGCAAGAACTGT CTGATCTGTTGCCTGCATCGATCAGGATCTATATGCTGGAGAGTTCACAA GAACATGGACAGAACTCGCTTCAACAACCGATCAATCGATTGATTAGGT ATGTACCTACCTCATATGCCTCAGCTCTTCGTTATGGATTTCTTCAACCGA AGGGTCAGTAAGCTCTTGGTTCCATGCCACTGCGTGAACTAAGCGTTCAC AAAATCCGTTCCMCGGCATGAACCAAGCACTCAAAATCGCATGCAGCAT CTTTCGTTTCAAAAAAAAATTGACTTYTGAAAACAATAGATGAATCAGTT TCAAACATATATGATTATCCATTTTCTCAACCGGGAATTTATATCTCGTTG GGATGCAAAACCGTTCAGTAGTAAAACTACTCCACGAGTATAAACTGTTT CAGTTATTTTACTATTAATTAGTTACCCGTATGCTGTTATGGTTTCTATAT ATCTATAAGTAAACCTTACTTAAATAAGATAGTTATACAAAAAAAAAAA AAAAA | SEQ ID NO: 247 |
| AtmiPEP171c1 | *Arabidopsis thaliana* | CAAGAAAAAACATTGAAATAGCTCATGTTGTCTCTTTCTCATTTTCATAT CTGCTAAAAAAAGAACCGTGTTTTCTAAACTGGTTTAACGGTAAGTACCT GTCTCTAGTAACTTACCTATCAATTTGTTCCAATCATTTACTTGCTTTGAC TTATTTGGTTTCCTTTTGTTTTGTTTTTCTTTAATATGTGGATGGAGTTTGG TGTAATAAGCAACTGAAGAGTCGATGAGCGCACTATCGGACATCAAATA CGAGATATTGGTGCGGTTCAATCAGAAAACCGTACTCTTTTGTTTTAAAG ATCGGTTTATTTGATTGAGCCGTGCCAATATCACGCGTTTAAATAGTTTA AAGATTCTATGTTAGTTGATGTGATCAATCAAGGTATGAATCTATATCAA TTCTCTTATGCATAGTTTTATATTTACAGAGATGAGGTATTATCAATGTCT | SEQ ID NO: 248 |

TABLE 3-continued

List of the primary transcripts (pri-miRNAs)

| miPEP | Organism | Sequence of the Pri-miRNA | SEQ ID |
|---|---|---|---|
| | | ATCGTCGAGGATCACGCTCTTACTTATGTTATATTTCTATATAATTTTATT AATTAGTTTTCTAAAAGAGAAGGACAATTTAAAATTATTTTAAAGAGTTT TTTTTAAGTAGTTTTGTTTTCATGTTTATCTTCTGCAGGCTCTGAAGTTAG GATAGTAACAAGAAAAAAGACAGAAAAAAAGAAGAAAATTCATATACA TTCGTGA | |
| MtmiPEP171e | *Medicago truncatula* | GAATAAGTGAATATTATCGATATTTATATCATATATCAACTTTTCTTCTGT GCTTGCTTGCAAATTTGCAATTAAGCTTTTTTGATCTTATGTAAGAGAAT ATTATTGATGATGGTGTTTGGGAAGCCGAAAAAAGCGATGTTGGTGAGG TTCAATCCGAAGACGGATTTACATGTATAGAGTTGTAAAATACGATCTCA GATTGAGCCGCGCCAATATCACTTT | SEQ ID NO: 249 |
| MtmiPEP171h | *Medicago truncatula* | CCACAAAACTATAACTAGCTAGAAGCTTTAATCGCCTTATTTATTATAAT AATAATAATAAATATGGCTTCAGCTGCAAAAGTATACATGGCGTGATATT GATCCGGCTCATCTATATCTTCAAGTTCAATCATCCATATTCATATCAATT TCAGACGAGCCGAATCAATATCACTCTTGTTTGCTTCATTGCATATTAATT ATATACTTCATTTATAAGTTATAGTTTGCCATATATATATTAGATTGATTC TGCAGAAGTAGACAGGAGTGGTGTTGTTTCTGCTCATCTTATTAAATAAT GAATGAATGAATGACATTTGCTTACTTATAAGACGAGCCGAATCAATATC ACTCCAGTACACCT | SEQ ID NO: 250 |
| AtmiPEP172a1 AtmiPEP172a3 | *Arabidopsis thaliana* | CTCTCTCTCTCTCTCTCTCTCATCTGTGTTCTAGATCTCACCAGGTCTTTCT CTGGTTAATATATGGCTTCCAAGATCTGGTAATATGTTATAAATACGTCA TACTTAAGCTTTTTTCAAATCAAAAATAGAAATTTGTGGGTTTGTCTCGTT TTACTATTTTAGCAGTATATATTAAGAAGTTCAGATGTTATTCGATCATCT GTTTTTGCTTCCCCTCTGCCATCTTTATCTTTTAGGGTTTCAATTCTTTTTC ACTTTTTTCTTCTGGTTTGGAGATGGTTAGGTTCCAACTAAGTATACGAG ATTAAATTTGACATCTTAGTTACTTCAAAATTCCTTCAATCAAAACAAGT CATCTCGACTATTCCGCCATGTTTGTATATACATATTTATATATTATATAT ATGAAGGTACGAGTTTCTAGTGTCTATAAATTAAGAAGGTTAAGTACCAT ATAGATGATATTTGTTAAGTAGTAAGTCACTCAAAGTTTGAGTTTGGGTT TGAGTTTGAGTTTGAGTTTGAGTTTGAGAGACAAAAGATTACTACAAGA AGATTGTTAAACAAAAATGGAAGACTAATTTCCGGAGCCACGGTCGTTG TTGGCTGCTGTGGCATCATCAAGATTCACATCTGTTGATGGACGGTGGTG ATTCACTCTCCACAAAGTTCTCTATGAAAATGAGAATCTTGATGATGCTG CATCGGC | SEQ ID NO: 251 |
| AtmiPEP172b1 | *Arabidopsis thaliana* | ACTTGCACCTCTCACTCCCTTTCTCTAACTAGTCTTGTGTGCACCCATTTA TGTGTACGTACTATTATCTCATAAATAAATATTTTTAAAATTAGATGCATT TATTGATATGAAAAAGTTACAAGATTAGTTTGTTGTGTGTGAGACTTTGG ATCGACAGATCGAAAAATTAACTAACCGGTCAGTATTGAATATCAACTA TTATATGCTCCATGCATTCGCTTATAGTTTCACACAATTTGTTTTCTTCAC GGTCTAAAATCAGAAGATTCCATATATTTTCTTATGACGTAAAAGGACCA CTTATAAGTTGACACGTCAGCCCTTGGATTCGTGAGGTTTTTCTCTCTACT TCACCTATCTACTTTTCCTCATATCCCACTGCTTTTCTCCTTCTTGTTCTTG TTTTTCTCGTTTTTTTCTTCTTCTTCTCCAAGAAAATAGAGATCGAAAAGA TTAGATCTATTTTGTGTAGCAAGAAATTATCATTTTCGTTTCTTCATTCAT ATATTGTTCTATTATGTTGTACAATAATAGATACTCGATCTCTTGTGCGTG CGTAAATTTTATACAAGTTGTCGGCGGATCCATGGAAGAAAGCTCATCTG TCGTTGTTTGTAGGCGCAGCACCATTAAGATTCACATGGAAATTGATAAA TACCCTAAATTAGGGTTTTGATATGTATATGAGAATCTTGATGATGCTGC ATCAAC | SEQ ID NO: 252 |
| AtmiPEP172c1 | *Arabidopsis thaliana* | TCACCAAATAGGCTCTTCTTTATCGCTTCATATATATAAAAGTCTACATCT ATCTCTTTCTAGGTCACTAGCTAGACTCTAGATTAAGGATTGAAATTAGG GTTTCATGTTTCCAGCAAAATGGTGCCGTCTTGAGTCTTGAAAAGATCCA AGACAAAACCAAATCACTACATACATCCCTATCATCAACCAGCTACTGTT CGCTGTTGGAGCATCATCAAGATTCACAAATCATCAAGTATTCGTGTAAA TAAACCCATTTATGATTAGATTTTTGATGTATGTATGAGAATCTTGATGA TGCTGCAGCTGCAATCAGTGGCT | SEQ ID NO: 253 |
| AtmiPEP172e1 AtmiPEP172c2 AtmiPEP172e3 | *Arabidopsis thaliana* | TGTCATATTGAGAACTCTTTAGCCTTTGGCTTCTGTTCCTGACACTTGTAT AGTGAAGTGGGCTTGTGTTATATAGATGGGATCTCTCTCTTATTTAAAA GTCAATTAGAGATCTTGATGCTACTTCTGTCCCTTTCCAAGTGATTTTACG TCGACCAACTAGCTTTTTTCATATGAGTGTATATATTCATGTACCTATCTC TCTCAATTGCTTCTCACCAAAATCATCTTGCTGATTCATTTGCTGTCTGAA TCCTCTTGCTTTCCTCTTTGCTTTTTCATTTGTTGATTTAAACCATGGGAGT TCCCAACTTTAGACCTCGAAACCGATAAGGATCTTTCTCTGCGGTTGAAA TAGCTAGGTTCTCGATGAATAGGCTAGCCTTTGGTGGATGTTATCAGCCA GTAGTCGCAGATGCAGCACCATTAAGATTCACAAGAGATGTGGTTCCCTT TGCTTTCGCCTCTCGATCCGCAGAAAAGGGTTCCTTATCGAGTGGGAATC TTGATGATGCTGCATCAGCAAATAC | SEQ ID NO: 254 |
| AcmiPEP319a1 AcmiPEP319a2 | *Arabidopsis cebennensis* | TTGTATCCATAGTGTATTTCCTCGCATCTACCATCCATTTTCTACGCCTCT CTCTCTCTCTTTCTCCATCAAATCTTGTTTTGTTCAAACTCTCTCTCTCATC AATTCTCTCCATACAATACATGCATACATACATACATACCATCTCTAATA | SEQ ID NO: 255 |

TABLE 3-continued

List of the primary transcripts (pri-miRNAs)

| miPEP | Organism | Sequence of the Pri-miRNA | SEQ ID |
|---|---|---|---|
| | | TTTCATCAATCTTCTTTTGTTCCAAACGCTCTTTCTCTCCATTTACATACAT<br>ACGAATCATTGTTGTCATAGATCCGTTTAGAATTGCTTTAACTTTTAGATG<br>AGATCTAGGGTTTCTTTCTTTTTCTTCAAAATCATGCTTTTTCGCTTGCTA<br>GGTTATAGATCCATGTAAGTTTAGAGTAGATGTACACACACACGCTCGG<br>ACACTTATTAAATACATGTTGATACACTTAATACTCGCTGTTTTGAATTG<br>ATGTTGTAGGAATATATAAATGTAGAGAGAGCTTCCTTGAGTCCATTCAC<br>AGGTCGGATATGATCCAATTAGCTTCCGACTCATTCATCCAAATACCGAG<br>TCGCCAAAATTCAAATTAGACTCGTTAAATGAATGAATGATGCGGTAGA<br>CAAATTGGATCATTGATTCTCTTTGATTGGACTGAAGGGAGCTCCCTCTC<br>TCTTCTGTATTCC | |
| AhmiPEP319a | *Arabidopsis halleri* | TTGTATCCATAGTGTATTTCCTCGCATCTACCATCCATTTTCTACGCCTCA<br>CTCTCTCTTTCTCCATCAAATCTTGTTTTGATCAAACTCTCTCTCTCTCT<br>CTCATCAATTGTCTCCATACAATACATACATACCATCATCTTTCCCATCTC<br>TAATATTTCATCAATCTTCTTTTGTTCAAACGCTCTTCCTCTCCATATACA<br>TATACATACATACGAATCACATTGGTGTCATAGATCCGTTTAGAATTGCT<br>TTAACTTTTAGATGAGATCTAGGGTTTCTTTGTTTCTTTCGTTTTCTTCAA<br>ATTTTGCTGCATATTCTCCAAGATCATGATTTTTCGCTTGCTAGGTTATAG<br>ATCCATGCAAATATAGAGTAGATTTACACACACACACGCTCGGACACTT<br>ATTACATACATGTTGATACACTTAATACTCGCTGTTTTTAATTGATGTTGT<br>AGGAATATATATATGTAGAGAGAGCTTCCTTGAGTCCATTCACAGGTCGT<br>GATATGATCCAATTAGCTTCCGACTCATTCATCCAAATACCGAGTCGCCA<br>AAATTCGAACTAGACTCGTTAAATGAATGAATGATGCGGTAGACAAATT<br>GGATCATTGATTCTCTTTGATTGGACTGAAGGGAGCTCCCTCTCTCTTCTG<br>TAT | SEQ ID NO: 256 |
| ALmiPEP319a | *Arabidopsis lyrata* | TTGTATCCATAGTGTATTTCCTCGCATCTACCATCCATTTTCTACGCCTCT<br>CTCTTTCTCCATCAAATCTTGTTTTGTTCCAACTCTCTCTCTCATCAATTCA<br>TTCCATACAATACATGCATACATACATACCATCATCATCTTTTCCCATCTC<br>TAATATTTCATCAGTCTTCTTTTGTTACAAACGCTCTTTCTCGCCATATAC<br>ATACATAAGAATCATTGTTGTCATAGATCCGTTTAGAATTGCTTTAACTTT<br>TAGATGAGATCTAGGGTTTCTTTCTTTTTCTTCAATTTTTGCTGCATATTCT<br>TCAAAATCATGATTTTTCGCTTGCTAGGTTATAGATCCATGCAAATATAG<br>AGTAGATGTACACACATTCACGCTCGGACACTTATTACATACATGTTGAT<br>ACACTTAATACTCGCTGTTTTGAATGGATGTTGTAGGAATATATATGTAG<br>AGAGAGCTTCCTTGAGTCCATTCACAGGTCGTGATATGATCCAATTAGCT<br>TCCGACTCATTCATCCAAATACCGAGTCGCCAAAATTCGAACTAGACTCG<br>TTAAATGAATGAATGATGCGGTAGACAAATTGGATCATTGATTCTCTTTG<br>ATTGGACTGAAGGGAGCTCCCTCT | SEQ ID NO: 257 |
| AtmiPEP319a1<br>AtmiPEP319a2 | *Arabidopsis thaliana* | TTGTATCCGCAGTGTATTTCCTCGCATCTACCATCCCTTTTCTACGCCTCT<br>CTCCCTCTCTCTCTTTCTCCATCAAATCTTGTTTTGTTCAAACTCTCTCTCT<br>CTCATCTATTCTCTCCATACAATACATGAATATACATACATACCATCATCT<br>TCTTTTCCCATCTCTAGTTTTTCATCAATCTTCTGATGTTCCAAACGCTCT<br>ATCTCTTCATATACATACATACGAATATATTATTGTTGTCATAGATCCATT<br>TAGAATCACTTTAGCTTTTAGATGAGATCTAGGGTTTCTTTGTTTTCTTTC<br>AAATTTTGTTGCATATTCTTCTAAATCATGGTTTTTCGCTTGCTAGGTTAT<br>AGATCCATGCAAATATGGAGTAGATGTACAAACACACGCTCGGACGCAT<br>ATTACACATGTTCATACACTTAATACTCGCTGTTTTGAATTGATGTTTTAG<br>GAATATATATGTAGAGAGAGCTTCCTTGAGTCCATTCACAGGTCGTGATA<br>TGATTCAATTAGCTTCCGACTCATTCATCCAAATACCGAGTCGCCAAAAT<br>TCAAACTAGACTCGTTAAATGAATGAATGATGCGGTAGACAAATTGGAT<br>CATTGATTCTCTTTGATTGGACTGAAGGGAGCTCCCTCT | SEQ ID NO: 258 |
| BrmiPEP319a | *Brassica rapa* | TTGTATCCATTGTGTATTTCCTTGCATCCATCAATAAATTTTATGTTACGC<br>CTCTCTATTATTTCTCTCTACATCACACTGTCTTATGTTTAAGCTCTACTTC<br>TCAGCAATTCTCTCCACCCAATACATGCATACATACCATCATCGTATCGC<br>TCTAATTTTTCTATCAATCTTGTATCCTTCCACAAATTATCTTATGTCTCCC<br>ATTTTAAATCCTACATAGATCCACACATACGAATTATTCTTGTCTGAAGA<br>TCCATCCATTTACGATTGCTTTAACTTTTACATGAGATCTAGGGCTTCTTT<br>ATTTTTCTTCAAATCTTGCTGCATATATTTCAAGATCATGCTTTTCGGCTT<br>GCTAGGGTTCTAGATCCATGGATGTATAGCGTACATACATACACGCACTA<br>ATTCATACCTGTAGTTTGTACGGAGAACATCATAAAATATCACTGTTTGG<br>AATTAATCGTGTAGGAAATATAGATAGGTAGGGAGCTTCCTTTAGTCCAT<br>TCACAGATCATGATATGATCCAATTAGCTTCCGACTCATTCATCCAAATA<br>CCGAGTCACGAAAATTTCAACTTAGACTCGTTAAATGAATGAATGATGC<br>GGTAAACAAATTGGATCATTGATTCTCTCTGATTGGACTGAAGGGAGCTC<br>CCTC | SEQ ID NO: 259 |
| CpmiPEP319a | *Carica papaya* | CTATATCCCTGTCAAATAGTACTTGGTTTTGTTTTAGCCACAAATCTTCTG<br>GTCTTGCAAAGTTCCTTCTGATCTCTCCCCCTTTCTCATTTTTTCCTCCTCT<br>TATATATGGATCATCAATTTGCTGTACACACACACACATTTACTGTAGTG<br>ATAATTAGCTAGCTAATTTGTTAGTATGTAAATTAGATCCCAAGTACCCT<br>GTTATATTTTTTTAGGCTTATCCTATGCATACCTGATAGTACAAGAACTTA<br>GTTTGTAATTAGGTACTTGGTAGTAGGGTTAGATTAATTACTGTCTTGAA<br>AGAGAACTTATCCAACAAATAGAGCTATGAAGATTAAATTAGGTTTTAG | SEQ ID NO: 260 |

TABLE 3-continued

| List of the primary transcripts (pri-miRNAs) | | | |
|---|---|---|---|
| miPEP | Organism | Sequence of the Pri-miRNA | SEQ ID |
| | | TCTTATTAAGATTATTATATTACTAGACAAAAACAGTTAAATTTTTTTAAT<br>TGGGTAATTAGGTACTTAGCAATAGGGTTAGATTAATTACTGTTTTGAAA<br>GAGAACCTACCTACAAATAGAGTTGAAATGATTATGTTTTAGTCTTACTA<br>AGATTGTCATATTTCTGGAAAAAAACAAATCTTGAAACAGATAATTCAG<br>ATAGTCATGATCAATGGAAAAAACATCATGGGTGTGTGCTTAATTAAGCT<br>AATATATATATATATGAAGATATAATGTTATGCACACTAGCTATGAATTT<br>GTAAGAATAATGAAGGATAAAGATGATATATTTAGATGTTATAAGTGTA<br>AGTAAGGTGGAATGGGTTGATGGGTAGTAGTAGTAGTAGTAGAGATGAT<br>TGGTGGAGAGAGCTTCCTTCAGCCCACTCATGGATGGGTATGAAGGGGT<br>AGAAGTAGCTGCCGACTCATTCATTCAGCCACTCAGTATGTAAACTCGTC<br>CCACTGTTGACTGTATGAATGATGCGGGAGATATTTTTACATCCATCTTT<br>CTCTGTGCTTGGACTGAAGGGAGCTCCTTCTT | |
| CrmiPEP319a | *Capsella rubella* | TTGTATCCATAGTGTATTTCCTCGCATCTACCATCTACTATTTTCTACGCC<br>TCTCTCTCTTTATCCCTCTATCTCTTTCTTCATCAAATCTTCTTTTGTTCAA<br>AGTCTCTCTCATCATTTTTCTCTATACACATACATGCATCCACATACATAC<br>ATACATATACCATCATCTTCTTTTCTCATCTCTAGTTTTTGTTTATAAATTT<br>TGTTCCAAGGATCTGTATCTCTCCAATAAAGATACATACAAATTATTGTT<br>GTCATAGATCTATTAGAATTGCTTTAACTTTTATATGAGATCTAGGATTTC<br>TTCCTTTTCTTTCAAAATTTGCTGCATATTTTTCAAAATCATGATTTATCG<br>CTTGCTAGGTTCTAGATCCATGCAAATTTAGAGTATTTTTACACACACAC<br>ACGCTTGGACACAAGTACATACATGTAGTTTTCTTTTATGTGGTGAAAAG<br>TACATAACATGTAGTTTATAGTTACTAGTCGCTATATAATTTAAAATTGA<br>TGTTATAGGAATATATGTACGGAGAGAGCTTCCTTGAGTCCATTCACAGG<br>TCGTGATATGATCCAATTAGCTTCCGACTCATTCATCCAAATACCGAGTC<br>TCACCAAAATTGGAACAAGACTTGTTAAATGAATGAATGATGCGGTAGA<br>CAAATTGGATCATTGATTCTCTTTGATTGGACTGAAGGGAGCTCC | SEQ ID NO: 261 |
| EgmiPEP319a | *Eucalyptus grandis* | TCGTTTCCCATCCCCATTTCATAGAATAATGCCACCAAACAAAGAAGCAT<br>TAGCTCAAAGACTAATTACCATCTGTTTTATTGATAGATACGTGCGAAAC<br>GGTGATTGTTTTTTCCCAAATAAGAAACCAAAATGAAGCATATTCAAAG<br>GTGGAGATATGGGGAGACTTCCGGAAGGCAAGGGGATTGGAAAAGGCT<br>CGAGATCAAAGTGCATAGCAACCCTTCGCTAAAGGTGAAAAAGAATACG<br>AATAACTTCAGTAGCTCACTTTAAATTCCGAAACATTAAACAAATCAAAT<br>CTCCCTCGCCCTCCTTGCCTCCTCTCTTTACCTATATAAAGCCACCGCCCC<br>TTCAATGAAATCCACGAGTGGAAGGTCACAGTATAGTAGGGTCCTGCAA<br>AGGGAGAGCGAGAGCGGCTCCACTGTCTACCTATAAGCAGTTCCTTTCTT<br>TTGTTTACATGTCTGTTGCACCTCACCGAGTTTTTCTATTCTCTTTCCTCTG<br>GTTGGTTAGCAGATTTCTCAGGGGACTTCCCTCCTCCCTTGAGGATCCTTC<br>TCTTGAAGCGATATGTCTCGAATGGGTAAGAGAGAGAGAGGAAGGGAGC<br>TTTCTTCAGTCCACCCATGGGACGTGTTGGGTTTTAATTAGCTGCCGACTC<br>ATTCATCCAAATACCGAGCGAGAGCAAGTAACAGAGCTCCGTAAATGAA<br>TGGATGATGCGGGAGTCTTGTTGATTCCCAAGCTTTCCGTGATTGGACTG<br>AAGGGAGCTCCCTCTATCT | SEQ ID NO: 262 |
| GrmiPEP319a | *Gossypium raimondii* | GCGTATCCTTCCACTTACGGATTCACCATAGCTGCTATAGCCCGAGTTTG<br>CTTGTCATAATAGAAATAAACTAAGGGAGAAAAAAGCTCTCCACTCTCG<br>CCTTTTTCTTCTTCGAGTCTCTCTCTTTGACTGGCCTTTGTGCAAAGATCTT<br>CCTTTTTTAAACAGTCGCTTTCTTTACTCTCCCTTTCCCTTCTTTCTCTTAA<br>TTGCTAAAGCAGCTTCCACTTCCACTCACTTTAACCCATGATCCATTTCAA<br>CCTGTCACAGTGGAGAGCAATTTGTATGGCTAATTTCCATCTCACCTATT<br>CTTTTCTGTTTGGGGTTCTCTAGTCTAGGGTTGCATGACATGAGAGACAT<br>GGCTCTTTTTTTTTTTTTTCAGTTCACAGGTGTTTATATATGTTGTTGTGTT<br>ATTTTGTCTTAAAGCTTTGTGATTGATGATCTGATAGGTAAGAGAGAGCT<br>TTCTTCAGTCCACTCATGGGATGGGGATGGGGTTTAATTAGCTGCCGACT<br>CATTCATCCAAATACTGTGTTACAAAACCCAGTAAATGAGTGAATGATGC<br>GGGAGACAAATTGAATCCTAATCTTCCTGTGCTTGGACTGAAGGGAGCTC<br>CCTCCC | SEQ ID NO: 263 |
| MtmiPEP319a | *Medicago truncatula* | ATTTATCCAATCATGTTGCTCTCACTTCTTTTCAGCAGTTCTGTTGATATC<br>ACCCTTTTAGTTGAAGCTTTGGATTCATGACTTTATGAGATGGTAAATCTT<br>TAAATTAAGTTTAAGTATGCACTTGATTTGTTTATATAATTTGTTTATTTA<br>GATTTTAAACCCTAAGTTGACTTTTTTAATTTGATTTAAATTATGATATGA<br>TTGTTATTTGGCTTACCATGGTCATAATTTAGGGTTTAGAAGATGCATGT<br>ATATCTTGAATTGTTTATGGTAATAAAGGGGTTAGGATTTCTCCTTTTGGT<br>GAAGTGAGAAAATCTCATAATTTTGTTCTGAAGGTAGTTTTTAAGATTTA<br>GGGTTATGGGTTCTTTGTTTGAATGCTTTTTCAAGTCTTTTTCAATGATAT<br>TTGCCTAGATCTGTTTTAATTTTGAATTAAAATTCTGGGTTTGGATTAATA<br>TTATTGAAGATTATTATTAATTAATTTATTAGAAATAGATGAAGAGAGCT<br>TCCTTCAGTCCACTCATGGAAGGGTAAGGGGTTTGAATTTACCTGCTGAC<br>TCATTGATTCAAACACAATAGACAATTATGGGGTTATGCTATTGTGAATT<br>GTGTGAATGATGCAGGAGGTGAATTTCTTCCTTTTCTTCTTTGCTTGGACT<br>GAAGGGAGTCTCCCTTT | SEQ ID NO: 264 |

TABLE 3-continued

List of the primary transcripts (pri-miRNAs)

| miPEP | Organism | Sequence of the Pri-miRNA | SEQ ID |
|---|---|---|---|
| OsmiPEP319a | *Oryza sattva* | TTATATCTGACGCGTTGTAATCCTGTTTAATTAGGGCTTTGCCCATTTCTT<br>TTGACCCCTTCCGGACATTCGCTAGTTGGAACCTTGTTTTACTCCTAGCAG<br>TGTACTGTGTAGTACTTATTACGAGCAAACGTAAAAATAAATAAATGGA<br>AATGATACAAAGGCCGTGTTTAATTTTAAAATTTTTTTTCAAACTTTCAAC<br>ACTTTACATCCCATAAAAAGCTTACTATACATACAAACTTCCAACCTTTT<br>CGTCACATCGTATCTAATTTCAACTAAACTTTTAATTTTAGCGTGAACTA<br>AACACAGCCGAAGCCCGGCCACATTCTCACTATTTTTATTCATTTTATCAT<br>GCCTGTGATGTCACGCCTTGGCCCTATTTAATAGGCCTTCTCCATTTCTCT<br>CCATATGATGTCTTCTCTTCTCTATCCCTCTTGCCATCTTCTATCTTCCCTC<br>TTGCACCCATCTTTGTGATAACTTCTACTAGCTCCTCTCCTACTACCAGTC<br>ATACCACTCTCACAAATCCTCCAAGATCCGCATGGGGAGAAGCTCCAAA<br>AGTTTCGTGGTTAGTTTAATTTCATGCTTGTTTGCTGCCGTTTTTCATGTT<br>GATCTGATCTTAATATATGTAGACTGCTGTTAACATATTCTTTTAATTTGA<br>TGGAAGAAGCGATCGATGGATGGAAGAGAGCGATCCTTCAGTCCACTCA<br>TGGGCGGTGCTAGGGTCGAATTAGCTGCCGACTCATTCACCCACAATGCC<br>AAGCAAGAAACGCTTGAGATAGCGAAGCTTAGCAGATGAGTGAATGAA<br>GCGGGAGAGTAACGTTCCGATCTCGCGCCGTCTTTGCTTGGACTGAAGGG<br>TGCTCCCTCCT | SEQ ID NO: 265 |
| PpmiPEP319a | *Physcomitrella patens* | TGGGATCCACACGAGTAATTATTCCCTCTCTCATGCATCACAACTTGGAC<br>TTGCCCAGCTTTTACCTCTCTCCATGTTCCACCGTCGGAGATCCTCGGTGC<br>TGCTACCCCCGTTCGGCCAAACCCAACCCAACCCTAGGTGTCTGCCGGAC<br>CTCCGCTTCCCCTCCTGCTTCACCCCCTGCACCGCTTAAATTTGCACCTCG<br>TAGTATTTATCTATGCCCCATTTCAGATGACTTGCATGACACCCATCTGG<br>ATTCGTCTCCAGGCGCCTTGTCGTATCTATTCGCTATCAGTCTTTCTTTCA<br>GTCTGTCTTTCTGCCAAGCACACCGTGCTGGTGGTGGTGCTATCAGTCGA<br>AGCAGTCGCCGAAGGGTCCTTGTATCCAGCCCTCACCGGAGACAGTTCG<br>CTTCGGGGTGGGGAGAACTGTTGAGACCGTCGATGTTGCATGCAGCAGC<br>ACTGGCGAAGGTGCTTCTGATACTGGGTATTCCAGCCTCGCCGCTCGGTG<br>CACTGCAGGTACGTGGTTACATGACACTACTGTGTGGGTAGTCTGGGCAC<br>AAGTAGATCGACATGCCAGATTTGGCCCGTATGCGTGTATGTGCGGTTAT<br>GTTCCCGTTTCGATTGCGGATACCTTGATTGTGGAGCTCCGTTTCGGTCCA<br>ATAGTGGCTGCGACGGAAGGTGGTCCCGCTGCCGAATCACACGTCCGGG<br>TTGCTTATCGGGGCAGGGCCCCGATACGGTATCCGAACGTTTGTCCCGGG<br>AACTGGTCGACCTTCCGCCCGGCGTCTCTTGGACTGAAGGGAGCTCCACT | SEQ ID NO: 266 |
| ThmiPEP319a1<br>ThmiPEP319a2 | *Thellungiella halophila* | TTTTATACAAATAATGTTCGATAACACTAAACCCTAGCCATCCAACTAAT<br>AGACAAAACCCTACTTGTAATTTACAACCGCAAATTCCCAGAGAACAGA<br>GTAACTACGAGAGAGAGATGGAGATTCAAATTAAAAGAAAAACTTATA<br>TATAATGAATACACAAAAGCTACCTAATCTGTATATATATATATATATAAAT<br>ATGTCTTCATTAAATTAATGGTCGTGGAATAGAAAAAGGAAAACCTAAT<br>TTGATCGCTAGGGCTTATCAGAGTAAAGATGGTTAACCTTCAAAAGATG<br>ACTAATTAACCGGGGAGATAATTAAAAGATTAAATACGCCAACAGAGAG<br>TTAAGAGATACCAGATTTAAATTCCACAATTTGGTCATGTTCTTCTTCAC<br>GTATTCATGACGATGTCTGAATTATAGAGAAACCCAAAATATAAAATGTT<br>AATTTTACCAGACATTTACATACCAATAACTCTATGACGATATGTAAAGT<br>AAGCAAGGCATGTTTTTATGCAGGGAAGATTGAAAATTCAAGATTAATC<br>AAGAAAATTGGAATACCAAAAAGAGAGGGAGCTCCCTTCAGTCCAATCA<br>GAGAGAATCAATGACCCAATTTGTCTACCGCATCATTCATTCATTTAACA<br>AGTCTAGCTCGAATTCTTGGTGACTCGGTATTTGGATGAATGAGTCGGAA<br>GCTAATTGGATCATATCACGACCTATGAATGGACTCAAGGAAGCTCTCTA<br>CAAATGTATTCCTACCACATCAACCCAAATATAGTGATTACAGATGCTGT<br>TCTCACTGTAGACTACATTTACGTTT | SEQ ID NO: 267 |
| AtmiPEP319b1 | *Arabidopsis thaliana* | AGACATCTCTTCTTCTCTCATCTCTCTTTTCTTCTCTCTTTTCCTCACATAA<br>ACTCTCTTTTTTTACTATTAAATCCATATGGTACCTCAAATTAATCTATGG<br>TCATCTAGGGTTATCTTGAAGATTAGAATTGATTCTAGCACGCACAGAGA<br>GGAAGATCATTGCATCCAGAATCACAAACATGGCCTATCTTTTATCTTTT<br>CTTTTTGATCTAAGTCACTGTTITATGCTATATATAGTATAATCAAATTCT<br>TTACATGTGCTTGTATGTATGCGTATATATAGTAACGGAATTGTTAATAT<br>GCTTATAGATGTTGAGTTGGTGGAGGAAGAGAGCTTTCTTCGGTCCACTC<br>ATGGAGTAATATGTGAGATTTAATTGACTCTCGACTCATTCATCCAAATA<br>CCAAATGAAAGAATTTGTTCTCATATGGTAAATGAATGAATGATGCGAG<br>AGACAAATTGAGTCTTCACTTCTCTATGCTTGGACTGAAGGGAGCTCCCT | SEQ ID NO: 268 |
| AtmiPEP394a1 | *Arabidopsis thaliana* | TCTTATTCCATCACAATCATCTAGGGTTTTAAGCCAAGCTTATATAGCCC<br>GTCATAAAGAGAACTCATCTGCCTCTCTCTCAATACCAATAAATATCACC<br>ACCGTCCTTCTCTCCTATCACTATTCAATCTATCGCAAACTCCTTTATGTC<br>TCTCCAATTTTATGAGAGGGTTTCCTTCAAGAACACAGTAAAATAGATTG<br>GATCTTTAAACTTTTGTTCCTTTTCATGAGGGTTTGACAAAGATTTTCTTA<br>CAGTCATCTTTGGCATTCTGTCCACCTCCTTCTATACATATATGCATGTGT<br>ATATATATATGCGTTTCGTGTGAAAGAAGGAGGTGGGTATACTGCCAAT<br>AGAGATCTGTTAG | SEQ ID NO: 269 |

TABLE 3-continued

List of the primary transcripts (pri-miRNAs)

| miPEP | Organism | Sequence of the Pri-miRNA | SEQ ID |
|---|---|---|---|
| AtmiPEP395c1 | *Arabidopsis thaliana* | TTGTATCATGACAGAGCAAGAAGAAGAAAGTCAAATGTCCACATGAGTT<br>CCCTTTAACGCTTCATTGTTGAATACTCAAAGCCACATTGGTTTGTATATA<br>ACACTGAAGTGTTTGGGGGGACTCTTGGTGTCAT | SEQ ID NO: 270 |
| AtmiPEP395e1 | *Arabidopsis thaliana* | TTTCAAACCCTAACACTCTTATAAACCGATTCGCCAAAATGTATCTACAA<br>TATATTGATAATGTAATATCTATATATTCAAACAATCGTCGTGTTGGTCG<br>GATGTTTTCTAGAGTTCCTCTGAGCACTTCATTGGAGATACAATTTTTTAT<br>AAAATAGTTTTCTACTGAAGTGTTTGGGGGAACTCCCGGGCTGATTCGGT<br>ATTTTAAATTCAGTAGACTAGCTAGCTG | SEQ ID NO: 271 |
| AtmiPEP397b1 | *Arabidopsis thaliana* | TGGTAATAGAAATGAGCAAGGAGATATTTTTTTCCCCTGGGTTTGAATGA<br>ACATCATTGAGTGCATCGTTGATGTAATTTTACTTATTTTATTCCATTGTT<br>GAATTAATTAAAGAAGTATATATCAGCGTTGCATTCAATTATGTTTTTCT<br>AATTTTCAGGAAATACAAAAAAAATGAAAAAAAAAAATCACTTAAAAG<br>ACCTTGAGAGTTCTTTTGACT | SEQ ID NO: 272 |
| AtmiPEP398c1 | *Arabidopsis thaliana* | GGATATCGAAACTCAAACTGTAACAGTCCTTTTATTACTGGTTTAGAAGA<br>TAGATAAATATTGTTAAGGTAGTGGATCTCGACAGGGTTGATATGAGAA<br>CACACGAGCAATCAACGGCTATAACGACGCTACGTCATTGTTACAGCTCT<br>CGTTTCATGTGTTCTCAGGTCACCCCTGCTGAGCTCTTTCTCTACCGTCCA<br>TGTTTTATCAACGCCGTGGCCCGTG | SEQ ID NO: 273 |
| AtmiPEP399b | *Arabidopsis thaliana* | TCTTATAGAGATGAAGAGAAACATGTAAACTCACTAGTTTTAGGGCGCCT<br>CTCCATTGGCAGGTCCTTTACTTCCAAATATACACATACATATATGAATA<br>TCGAAAATTTCCGATGATCGATTTATAAATGACCTGCCAAAGGAGAGTTG<br>CCCTGAAACTGGTTC | SEQ ID NO: 274 |
| AtmiPEP399d1 | *Arabidopsis thaliana* | CAATAACTCAAAATGCAATGTGAAATATGAAGAATATATTAAATAGTAG<br>TGAAGATGCATGTTTATGAAGACAGAGAGATAATGTATGGTTGGATTAC<br>TGGGCGAATACTCCTATGGCAGATCGCATTGGCTAGATATGCAAGTAAA<br>ATGCTTCTCTGCCAAAGGAGATTTGCCCCGCAATTCATCC | SEQ ID NO: 275 |
| AtmiPEP403 | *Arabidopsis thaliana* | ATTTAGGTCTCTCTTCTTCTTCTTCTTTTTCTTCTTGAGCGCCGGCGAAAA<br>AAGTCTCTGTGAGAAAAAGATACGACGATTGTCATTAGAAGAGTCGTAT<br>TACATGTTTTGTGCTTGAATCTAATTCAACAGGCTTTATGTAAGAGATTCT<br>TTAACAATTCCTATAATCTTTGTTGTTGGATTAGATTCACGCACAAACTC<br>GTAATCTGTCTTTTCGATTTTTACCAGATCTGTC | SEQ ID NO: 276 |
| AtmiPEP447a1<br>AtmiPEP447a2 | *Arabidopsis thaliana* | AATTATATCCATGGTCATGGCTCATCATTAGTCGCACTGCTCTCCTTTTCT<br>CAAAGTTTAAATTCGACATTTGGTAAAATGATGAAACCTCGATGGAACT<br>GCTCTCTTTATGGAATCACGGAATGGACAAATAATCAAAATCAGAAATC<br>GAAGCGAAAAGGGAGGAGAAAAACGCAGATTTGGAGGATTGGGGACAG<br>ATTAGATACTGTTGAATGCATCACTCTAATGCTATCAGCCTATTAATAGC<br>GTCCTATATTTTCGAAGACTTTTAATGTTTAGGGTTATGGATTTTTCGAGC<br>GAAGCATGGAGAGATGTTGAATTGGATACTATAGGATTTGGTACAACAC<br>ATACATATGTTCTGCTTCTGCAAAACTAACATATCAAGTTCAGAGAAACC<br>AGTAAGTCGTTGAATATTTTATTATCCATTCAACGCTTTCTTCTTTTGGAT<br>CATGTCTTGTTTGCTTGACCACTTCTTCTTGCTTAAGAGGATGGACAATAT<br>ATAAAAACTGGAGCCTTCTTTTTCTATGAATGCTTATCATCGCGGAGTTG<br>ATCTGTTCAATTCACCTGCCATTGGATGCTTTTTTTATATATACTTCACTG<br>TTCAATTTCAGATGCTTTAGAAGGTTTGCGGAGTAGCTAGAGAATCTGGT<br>ATCTTCAGTTCTTCAATTTCAGCTACTTGGTATCAGCTTCGTCATTGTATA<br>TCAACACATTCTTAATATATAATACTACTTTTTCATCCATTAAACCCCTTA<br>CAATGTCGAGTAAACGAAGCATCTGTCCCCTGGTATTGTCTTCGAGCTTG<br>GTGTTTTTTTCTAGCCAACTCCAAGTTCTCGAGTTGATCATTGTTTGTATT<br>CTTGAGACATTATTTGGGGACGAGATGTTTTGTTGACTCGATATAAGAAG<br>GGGCTTTATGGAAGAAATTGTAGTATTATATATCGAGAGTG | SEQ ID NO: 277 |
| AtmiPEP447b1<br>AtmiPEP447b2 | *Arabidopsis thaliana* | CTATAAATGCTGCTTATCATCGTGGAGTTGGTTCTGTAAACATTTGAAAA<br>TTCTGAACAGTTTCACCTGCCATTGGATGCTTTGTTTCAATTTCAGGTGCG<br>TTAGAAGGTTTGCAGAGTAGCTAGAGAATCTCGTATCTTCACTTTCTGCT<br>ACTTGGTATCAGCTTCGTCACTTTATATCAACACATTCTTAATATACAATA<br>CTACTTTTTCATCCATTAATCCCCTTACAATGTCGAGTAAACGAAGCATC<br>TGTCCCCTGGTATTGTCTTCGAGCTTGGTGTGTTTTTCTAGCCAGCCCCAA<br>GTTCTCGAGTTGATCATTGTTTGTATTCTGACACATTATTTGGGGACGAG<br>ATGTTTTGTTGACTCGATATAAGAAGGGGCTTTATGGAAGAAATTGTAGT<br>ATTATATATTGAGAATG | SEQ ID NO: 278 |
| AtmiPEP447c | *Arabidopsis thaliana* | TAGTATAACCGCTGATGTACACCTACCAGCTTGATAACTCTTTTTCGTGG<br>TTTCTGTGTACTCGTTTCTGTTTGTACAGATACTTCTTGTTCAATTTCAGA<br>TGCTTTAGAAGGTTTTCGGAGTGGCTAGAGATCTGTTATCTGTATGAACA<br>GCTACTTGGTATCAGCTTCGTCATTTTATCAACACATTCTTAATATACAAT<br>ACTTCTTTTTCATGCATTAAGCCCCTTACAATGTCGAGTAAACAAAGCAT<br>GTGTCCGCTAATATTGTCTTCGAGCTTGGTATTTTTGTATTCTGATACGGT<br>ATTTGGGGACGACATCTTTTGTTGACTCGATATAAGAAGGGGGTTTGTGG<br>AAGAAATTGTAGTATTATATATCAAGAATG | SEQ ID NO: 279 |

TABLE 3-continued

List of the primary transcripts (pri-miRNAs)

| miPEP | Organism | Sequence of the Pri-miRNA | SEQ ID |
|---|---|---|---|
| DmmiPEP1a<br>DmmiPEP1b | *Drosophila melanogaster* | TTTGTGGAACACATTCGACCCACTGAAAAATTGATATAATTTAATGAAAG<br>TGCATAAAAATGGTGGACAGTGCATTAAACTGAGCATTGAACACAAAGG<br>CCGCTCAGCAAATTGCTAATTAAAATTCACGATTGCCATTTCACCTGACA<br>CGTTGACGATTTTCATTACAATTCGATTATGTTTCGTTGCAGGGAATTTTA<br>AATGTTAATTGCCAAGAATGTTTCAACAAATTCATTTCTCATTAATGTGT<br>CTTTTCATTTAATTTTATGTTGTATGAGCTGCACGAGAAATGAGTTGTACT<br>TTTAGTTCGACGGCAGAGTCATGAATGTTCGGCAAAGAATGTAATAATA<br>ACTATCCTCTTTAGACAAATATAGATACAAATCTATCAGATTCTAAAAGT<br>AGAATAATCAATTAATCAGAAAGCTAAAAATAAATAGGCATATTTATAT<br>TTTAATGCGGATTTTTGAAGTTCAACGGGAGAAATGAATCCTTTTTACCA<br>GCCACAGGCGCAATTTGCAACAGAAAGTGTAGCAGAAGTACTCCTCGAA<br>TATTTCCCTGCTCCAGGAGTCATCCATGTGGTTTCGAGGCACACATTTGA<br>CAAACTCATGCCCCGCTATTTGTTGTAAAAACACAATCGCACACATGGCC<br>GCATTTCGGCGACTTCCAGAGAGCGGTACACTTAAGGCGGCCTGGGAAA<br>CGCCTGCAATCTGCTGGTCGCGAACTGCAGATTGCATCCATGTGCCAGGC<br>GACCATGCGACCATGTGACCATGTGCCCGCCCGACGCCTCGCAGCCCAC<br>ATCCTGCCCATCGAGGGCACAACTCAGCGTGGGTATTGCCGCTCCGGCTG<br>CTTCAAGTAGGTAAAAACCGAGAAGATTGAGGATGAATGTATGAGTATG<br>AGAAAATACTCGGCGGAACATATGCTGCCGGGCTTGACCTGACCCTGCC<br>TCATGTGTGGGTCTCCGATTTAATTTTAGGCACCTATATAAACGCGTGTTT<br>ACACTGCAGCCAGAACACAGTCGCCGTCTTCAGTTCGCGCCGTCAACTCC<br>TCGATCGATCGATCGCATCGTCTCGGATCGAATAGAGCTGGGCTTCTGCT<br>CCGGAGCTACATCGCCGTACTTGTCGGACGAGTGTGGTGATGAAAAGTC<br>GCTTAGTCCGGGATTCCTGCCAGATCTCTAAGGGATGAGCTGGCATCCCA<br>GGCTGGCCATGTGGCGCGAAGTATGCGCACAAAAAAGTCAAACAAAAA<br>GGCGCAATTTTATTACGGGCAACCAACGACGAAACAAAACAAAAGCCAA<br>CCGAAAAGCAGAAACAAAGCAGCAAAAAGTTTATGAATTTTTTGTGCAG<br>GCGCGTGAAAGATGCAAAACGAGAAAAAAACATGAAAAAAAAACATTA<br>AAAAAAACAAAAAAAATCCAAAACAGATACCGAGCTGTATCCGAAAAC<br>GAGTGGGGAAAGGGGTTTCCCAGTCACATATAAACACACTTCAGTGCGC<br>TTAAAAATTGCTTTATTGCAGTTGGACTATAAAAACGCACGGCAGCGAA<br>CACCGCACAACAAAAAGGACGAGCAGAAGTGGGCAAATAAAACGAAAG<br>CTCTTAAACGAAAAACAGGAAAATTTGCATGCCACAAAAATAAGCATAA<br>GGATTTGCCGCGCACAAAGTAGAAGCAAAAAGGAATTGCCCAAATGCAG<br>CCACAAAAGACTGTGGCAAATGTTTTGCAGCTTGCCCCTTTTTCCCTGCA<br>ATTACCGTCAGTCGTTGTCATTATTCAGCAGATTATATGGTTTTGCTTATT<br>CCGGACCACCATCATCATCATCATTATCATCATCTTCGGTAAGTTAGACA<br>ATCCCATAAAAAACTGTCCAAGTGAGTAGTGCCACCAAAAGTTAGCCGC<br>GTTGTGGAAAATCCAAAACAAAGACCATCCCATATTCAGCCTTTGAGAG<br>TTCCATGCTTCCTTGCATTCAATAGTTATATTCAAGCATATGGAATGTAA<br>AGAAGTATGGAGCGAAATCTGGCGAGACATCGGAGTTGAAACTAAAACT<br>GAAATTTGATTGAAACAGAAGTAGAACCGTAATGAAATGAATGAAATAT<br>TAACCCGTTTCTACAATCCCTGAATAAAATTATTAATTAATTATAGAGCG<br>GGCTAATTTTACAATATATATTGATTTTTTTTTGAAG | SEQ ID NO: 280 |
| DmmiPEP8 | *Drosophila melanogaster* | ATTCTTTTTTGGTGCTCGATCGTGACGGTTTGCTCGCGCTCTCCGCTGCGC<br>CGCTCTTTCCGTTGCATATGTGTGCGGGCGTTATTGTGCATGTTTCCGGTG<br>GCCGAAAAAAAATAGTAAAATAAAATATAGAAAACAGAAACCAAGAAT<br>AATAACAGCCATACGATAAACAGTGTGCCAATGTGTGTGTCTGTGTGTGT<br>GTGCATCTCGCGTAACAACAATAATTGCATTTATCGGATGGCGCCAGCTT<br>CAATTTAATTATAAATAACATGTTCAACTTTTTATACTATTTTCCCTGCGT<br>CAAAGTGGGCGTTGCAACTGCCCCCGGAAAATCACGCGCCCCGGTTCAA<br>AGTTAAAGTTTGCTGGGTAACGCACACACACACACACACAATCACTCAC<br>ACGCGGTCACACGCACATTTCAATAAACTAATG[1]GAGCCTGGCTTTGTTTT<br>TGTTTTATTTCCAACCCACTTGAGCACACAGCACACACAGAGAGAAAAA<br>TCAATACTCGTTATGGGATTAAATTTACAAAGCGCAAAGCAAAGCGACA<br>AACAAAATTCAAAAGAAAGAAAAAAAAACACTCAAATAAACTCACAAA<br>GAATTCCTTATCGCCAAGGGGGCCAATGTTCTAAGGTTCTTTCGCCTTGA[1]<br>GAACTTTGAGCTTCCTCTGGCAAAGGAGATTATAATGTACAAATAATGTT<br>GCAATAACCAGTTGAAACCAATGGAATACCGAATCTTGCTAATTAGCAA<br>GGACATCTGTTCACATCTTACCGGGCAGCATTAGATCCTTTTTATAACTCT<br>AATACTGTCAGGTAAAGATGTCGTCCGTGTCCTTAACCTTCAGTACCACC<br>AACAGCAGCAGCAGCACCAAAAAAAAAAAAAAAAAAATGCGTAAAAAT<br>CCAAACAAATCATAAAAGTCGAAGGA | SEQ ID NO: 281 |
| HsmiPEP155 | *Homo sapiens* | GCCGAGCCCGGGCCCAGCGCCGCCTGCAGCCTCGGGAAGGGAGCGGATA<br>GCGGAGCCCCGAGCCGCCCGCAGAGCAAGCGCGGGGAACCAAGGAGAC<br>GCTCCTGGCACTGCAGATAACTTGTCTGCATTTCAAGAACAACCTACCAG<br>AGACCTTACCTGTCACCTTGGCTCTCCCACCCAATGGAGATGGCTCTAAT<br>GGTGGCACAAACCAGGAAGGGGAAATCTGTGGTTTAAATTCTTTATGCCT<br>CATCCTCTGAGTGCTGAAGGCTTGCTGTAGGCTGTATGCTGTTAATGCTA<br>ATCGTGATAGGGGTTTTTGCCTCCAACTGACTCCTACATATTAGCATTAA<br>CAGTGTATGATGCCTGTTACTAGCATTCACATGGAACAAATTGCTGCCGT<br>GGGAGGATGACAAAGAAGCATGAGTCACCCTGCTGGATAAACTTAGACT<br>TCAGGCTTTATCATTTTTCAATCTGTTAATCATAATCTGGTCACTGGGATG | SEQ ID NO: 357 |

TABLE 3-continued

| List of the primary transcripts (pri-miRNAs) | | | |
|---|---|---|---|
| miPEP | Organism | Sequence of the Pri-miRNA | SEQ ID |
| | | TTCAACCTTAAACTAAGTTTTGAAAGTAAGGTTATTTAAAAGATTTATCA GTAGTATCCTAAATGCAAACATTTTCATTTAAATGTCAAGCCCATGTTTG TTTTTATCATTAACAGAAAATATATTCATGTCATTCTTAATTGCAGGTTTT GGCTTGTTCATTATAATGTTCATAAACACCTTTGATTCAACTGTTAGAAA TGTGGGCTAAACACAAATTTCTATAATATTTTTGTAGTTAAAAATTAGAA GGACTACTAACCTCCAGTTATATCATGGATTGTCTGGCAACGTTTTTTAA AAGATTTAGAAACTGGTACTTTCCCCCAGGTAACGATTTTCTGTTCAGGC AACTTCAGTTTAAAATTAATACTTTTATTTGACTCTTAAAGGGAAACTGA AAGGCTATGAAGCTGAATTTTTTTAATGAAATATTTTTAACAGTTAGCAG GGTAAATAACATCTGACAGCTAATGAGATATTTTTTCCATACAAGATAAA AAGATTTAATCAAAAAATTTCATATTTGAAATGAAGTCCCAAATCTAGGT TCAAGTTCAATAGCTTAGCCACATAATACGGTTGTGCGAGCAGAGAATCT ACCTTTCCACTTCTAAGCCTGTTTCTTCCTCCATATGGGGATAATACTTTA CAAGGTTGTTGTGAGGCTTAGATGAGATAGAGAATTATTCCATAAGATA ATCAAGTGCTACATTAATGTTATAGTTAGATTAATCCAAGAACTAGTCAC CCTACTTTATTAGAGAAGAGAAAAGCTAATGATTTGATTTGCAGAATATT TAAGGTTTGGATTTCTATGCAGTTTTTCTAAATAACCATCACTTACAAAT ATGTAACCAAACGTAATTGTTAGTATATTTAATGTAAACTTGTTTTAACA ACTCTTCTCAACATTTTGTCCAGGTTATTCACTGTAACCAAATAAATCTCA TGAGTCTTTAGTTGATTTAAAATAAAAAAAAAAAAAAAAAAAAAAAAAAA AA | |
| AtmiPEP157c | *Arabidopsis thaliana* | CTTTGTCACTTCATACACTCCCTATTGTCTATATATATATATATACTTACA CATATTCAAACATTATAATACTTAATTACACATACATACTTTATGATGTT GCATATCACACATAGGTTTGAGAGTGATGTTGGTTGTTGACAGAAGATA GAGAGCACTAAGGATGACATGCAAGTACATACATACATATATATCATCACACC GCATGTGGATGATAAAATATGTATAACAAATTCAAAGAAAGAGAGGGAG AGAAAGAGAGAGAACCTGCATCTCTACTCTTTTGTGCTCTCTATACTTCT GTCACCACCTTTATCTCTTCTTCTCTCTAACCT | SEQ ID NO: 400 |
| AtmiPEP157d | *Arabidopsis thaliana* | ATTTACTCTTCACCGCCCTCTCTCTATATATAGTCTCTATCCTCACATATT ATATATCAAACCGCAAGAATGCTGTATGTATAGTGGAGGGTGATAGTGT GGTTGCTGACAGAAGATAGAGAGCACTAAGGATGCTATGCAAAACAGAC ACAGATATGTGTTTCTAATTGTATTTCATACTTTAACCTCAAAGTTGATAT AAAAAAAGAAAGAAAGATAGAAGAGCTAGAAGACTATCTGCATCTCTAT TCCTATGTGCTCTCTATGCTTCTGTCATCACCTTTCTTTCTCTATTTCTCTC TAC | SEQ ID NO: 401 |
| AtmiPEP160c | *Arabidopsis thaliana* | AACCAAAACTCTTCAACATTTCTCTCTGACTACTTCATTTCCTCTTCCCAA CAGTTAAAAAAAGTTCTGATTCGATTCAAGCCAAGATCCACGTATAAAG ATATGTTCATGCGTAGAGGTTTGGTATACAACAATATATACATATAATAG TTTGTCGTTATGCCTGGCTCCCTGTATGCCACGAGTGGATACCGATTTTG GTTTTAAAATCGGCTGCCGGTGGCGTACAAGGAGTCAAGCATGAC | SEQ ID NO: 402 |
| AtmiPEP164b | *Arabidopsis thaliana* | ATACATTCTCTCTTTCTCTCTCTCTCTCTCTCATCCCGGCCCAGTTATGT GGTCGGAGAGAATGATGAAGGTGTGTGATGAGCAAGATGGAGAAGCAG GGCACGTGCATTACTAGCTCATATATACACTCTCACCACAAATGCGTGTA TATATGCGGAATTTTGTGATATAGATGTGTGTGTGTGTTGAGTGTGATGA TATGGATGAGTTAGTTCTTCATGTGCCCATCTTCACCATC | SEQ ID NO: 403 |
| AtmiPEP166c | *Arabidopsis thaliana* | TCACACATACCTTTCTTTCTCTTCTTCTTCTTACGAAAAGTTTCATCACAT TCACATTATCTTTAACTTTGGTCTCTTTCTTTTTGTCTCTTTTCTCTTCTT GATAACGTGGTTCTAGTCTTGATTAATTCATTGTTGTGCGATTTAGTGTTG AGAGGATTGTTGTCTGGCTCGAGGTCATGAAGAAGAGAATCACTCGAAT TAATTTGGAAGAACAAATTAAGAAAACCCTAGATGATTCTCGGACCAGG CTTCATTCCCCCTAACCTACTTATCGC | SEQ ID NO: 404 |
| AtmiPEP166d | *Arabidopsis thaliana* | ATTTAGCTTCTTCTTCTTCTTCTTCTTCTGTCTACTTACATAAAGTTATCCTt GCTTTGGTTTAGGGTTGAGAGGAATATTGTCTGGCTCGAGGTCATGAAGA AGATCGGTAGtATTGATTCATTTTAAAGAGTGAAATCCCTAAATGATTCTC GGACCAGGCTTCATTCCCCCCAACC | SEQ ID NO: 405 |
| AtmiPEP169a | *Arabidopsis thaliana* | TAGTATTCATAAGCACCAAAACAAATATGTAGAGATCTCCTCTTCCATTC TCTATTGTTACTTTCGAGAAGAAACATACAAAACACATACATTTTTCTTTT GTTTGTGGTTTTCATATATACAAGTGGGTATAGCTAGTGAAACGCGAATG TGACGAAAGTAGTGTGCAGCCAAGGATGACTTGCCGATTTAAATGATCTT TCTTTATACTCTATTAAGACAATTTAGTTTCAAACTTTTTTTTTTTTTTTT TTTGAAGGATTCAGGAAGAAATTAGGATATATTATTCCGTATAAAATACA AGATATATAAAACCAAAAAGAAAAAGTAACATGATCGGCAAGTTGTCCT TGGCTACACGTTACTTTGTGTCGC | SEQ ID NO: 406 |
| AtmiPEP169h1 AtmiPEP169h2 | *Arabidopsis thaliana* | ACTCATCAACAACCTCTTCATAAATACATAAATCATATAAGAGAAAATG GTGACATGAAGAATGAGAACTTGTGTGG | SEQ ID NO: 407 |

TABLE 3-continued

List of the primary transcripts (pri-miRNAs)

| miPEP | Organism | Sequence of the Pri-miRNA | SEQ ID |
|---|---|---|---|
| AtmiPEP169n | *Arabidopsis thaliana* | AGGCAAAAACATATAGAGAGTAATGAAGTGTATGATGAAGAAGAGAGG TCTAACATGGCGGAAAGCGTCATGTTTAGTAGCCAAGGATGACTTGCCTG ATCTTTTTCGCCTCCACGATTCAATTTCAAATTCATGCATTTTGGATTATT ATACCTTTTAAAGTATAATAGGTCAAATATCATGTTGAATCTTGCGGGTT AGGTTTCAGGCAGTCTCTTTGGCTATCTTGACATGCTTTTTCCATCCAT | SEQ ID NO: 408 |
| AtmiPEP170 | *Arabidopsis thaliana* | ATTCACTCCCTTCTTCTTCTTAATCTCCTTACAGTTACAGACATTCTCTCA CTTGCGTTCTTGTTTCTTTTACAAAACAGATACACTATGTTTCCGAGAGA GTCCCTCTGATATTGGCCTGGTTCACTCAGATTCTCTTTTACTAACTCATC TGATTGAGCCGTGTCAATATCTCAGTCCTCTCTCG | SEQ ID NO: 409 |
| AtmiPEP396a | *Arabidopsis thaliana* | TCTCACAACTTCAACTTCCCTCTTTCTCTATATTACGCTTTTGCCCCTCACT CCCTCTTTCCACAATTAGGGTTTCGTCTGCTCTACATGACCCTCTCTGTAT TCTTCCACAGCTTTCTTGAACTGCAAAACTTCTTCAGATTTTTTTTTTTTC TTTTGATATCTCTTACGCATAAAATAGTGATTTTCTTCATATCTCTGCTCG ATTGATTTGCGGTTCAATAAAGCTGTGGGAAGATACAGAC | SEQ ID NO: 410 |
| AtmiPEP399c | *Arabidopsis thaliana* | GAATAACCAACCAGCCTTCTCTCAAAGCAAACCAAAAAGAAAAACCAAC ATTGAAAGAGGAAGTTACGATAAGCGGAGCAGTAATAGGGCATCTTTCT ATTGGCAGGCGACTTGGCTATTTGTATCTTTTGTGTTCTTGACTATTGGCT ATGTCACTTGCCAAAGGAGAGTTGCCCTGTCACTGCTTCCGCTTAAACAC AGTCTATAACCGGTTCTGCTAATATCAATCCTTCTTTTGGACATGTCCAA AGCCGAGATTGATTGATAGAGAATTGGTCTCTCTGGCTACAAAACTAGTG CGGTTCTCTCGATTTAAGTTTTAATAGCATTCACTTTGCACATTGCATCTT TCACATCAAATTTCCATTTCATCAACCATCTAAACCTCTTTGTTAGCTTTG ATATAAGCAACGATCTAAAGTCTAAAAACCATTAATCCTCTGAAAAAAA AGACAATTTCGATGGTTCTATTATGTTTCTCCAATGCAGAAATTGTATCG TCTGAATTATAGTAGATTTTTTCTAGACTAAAGTGTAAACCAAGACGAAT CTGCACTAACAAGACACACCAATAGACTTTACAGAGAAAGGTTACGAGT TTTGAAAATATTAACGGACCATAGTCATCGCG | SEQ ID NO: 411 |

TABLE 4

List of the microRNAs (miRNAs)

| miPEP | Organism | Sequence of the miRNA | SEQ ID |
|---|---|---|---|
| AtmiPEP156a1 AtmiPEP156a2 AtmiPEP156a3 | *Arabidopsis thaliana* | ugacagaagagagugagcac | SEQ ID NO: 282 |
| AtmiPEP156c1 AtmiPEP156c2 | *Arabidopsis thaliana* | ugacagaagagagugagcac | SEQ ID NO: 283 |
| AtmiPEP156e1 | *Arabidopsis thaliana* | ugacagaagagagugagcac | SEQ ID NO: 284 |
| AtmiPEP156f1 | *Arabidopsis thaliana* | ugacagaagagagugagcac | SEQ ID NO: 285 |
| AlmiPEP159a | *Arabidopsis lyrata* | uuuggauugaagggagcucua | SEQ ID NO: 286 |
| AtmiPEP159a1 | *Arabidopsis thaliana* | uuuggauugaagggagcucua | SEQ ID NO: 287 |
| CrmiPEP159a | *Capsella rubella* | uuuggauugaagggagcucua | SEQ ID NO: 288 |
| AtmiPEP159b1 AtmiPEP159b2 | *Arabidopsis thaliana* | uuuggauugaagggagcucuu | SEQ ID NO: 289 |
| AtmiPEP160a1 | *Arabidopsis thaliana* | ugccuggcucccuguaugcca | SEQ ID NO: 290 |
| AtmiPEP160b1 AtmiPEP160b2 | *Arabidopsis thaliana* | ugccuggcucccuguaugcca | SEQ ID NO: 291 |
| AtmiPEP161 | *Arabidopsis thaliana* | ucaaugcauugaaagugacua | SEQ ID NO: 292 |
| AtmiPEP162a1 | *Arabidopsis thaliana* | ucgauaaaccucugcauccag | SEQ ID NO: 293 |
| AtmiPEP162b1 | *Arabidopsis thaliana* | ucgauaaaccucugcauccag | SEQ ID NO: 294 |
| AtmiPEP163-1 AtmiPEP163-2 | *Arabidopsis thaliana* | uugaagaggacuuggaacuucgau | SEQ ID NO: 295 |

TABLE 4-continued

List of the microRNAs (miRNAs)

| miPEP | Organism | Sequence of the miRNA | SEQ ID |
|---|---|---|---|
| AlmiPEP164a1<br>AlmiPEP164a2<br>AlmiPEP164a3 | *Arabidopsis lyrata* | uggagaagcagggcacgugca | SEQ ID NO: 296 |
| AtmiPEP164a1<br>AtmiPEP164a2<br>AtmiPEP164a3 | *Arabidopsis thaliana* | uggagaagcagggcacgugca | SEQ ID NO: 297 |
| BrmiPEP164a1<br>BrmiPEP164a2<br>BrmiPEP164a3 | *Brassica rapa* | uggagaagcagggcacgugca | SEQ ID NO: 298 |
| CpmiPEP164a1<br>CpmiPEP164a2 | *Carica papaya* | uggagaagcagggcacgugca | SEQ ID NO: 299 |
| CrmiPEP164a1<br>CrmiPEP164a2<br>CrmiPEP164a3 | *Capsella rubella* | uggagaagcagggcacgugca | SEQ ID NO: 300 |
| GrmiPEP164a1<br>GrmiPEP164a2<br>GrmiPEP164a3 | *Gossypium raimondii* | uggagaagcagggcacgugca | SEQ ID NO: 301 |
| MtmiPEP164a1<br>MtmiPEP164a2 | *Aledicago truncatula* | uggagaagcagggcacgugca | SEQ ID NO: 302 |
| OsmiPEP164a1<br>OsmiPEP164a2 | *Oryza sativa* | uggagaagcaggguacgugca | SEQ ID NO: 303 |
| AlmiPEP165a | *Arabidopsis lyrata* | ucggaccaggcuucauccccc | SEQ ID NO: 304 |
| AtmiPEP165a | *Arabidopsis thaliana* | ucggaccaggcuucauccccc | SEQ ID NO: 305 |
| BcmiPEP165a | *Brassica carinata* | ucggaccaggcuucauccccc | SEQ ID NO: 306 |
| BjmiPEP165a | *Brassica juncea* | ucggaccaggcuucauccccc | SEQ ID NO: 307 |
| BnmiPEP165a | *Brassica napus* | ucggaccaggcuucauccccc | SEQ ID NO: 308 |
| BomiPEP165a | *Brassica oleracea* | ucggaccaggcuucauccccc | SEQ ID NO: 309 |
| BrmiPEP165a | *Brassica rapa* | ucggaccaggcuucauccccc | SEQ ID NO: 310 |
| AtmiPEP166a | *Arabidopsis thaliana* | ucggaccaggcuucauucccc | SEQ ID NO: 311 |
| AtmiPEP166b | *Arabidopsis thaliana* | ucggaccaggcuucauucccc | SEQ ID NO: 312 |
| AtmiPEP167a | *Arabidopsis thaliana* | ugaagcugccagcaugaucua | SEQ ID NO: 313 |
| AtmiPEP167b1<br>AtmiPEP167b2 | *Arabidopsis thaliana* | ugaagcugccagcaugaucua | SEQ ID NO: 314 |
| AtmiPEP169c1<br>AtmiPEP169c2 | *Arabidopsis thaliana* | cagccaaggaugacuugccgg | SEQ ID NO: 315 |
| AtmiPEP169l1 | *Arabidopsis thaliana* | uagccaaggaugacuugccug | SEQ ID NO: 316 |
| AtmiPEP171a1 | *Arabidopsis thaliana* | ugauugagccgcgccaauauc | SEQ ID NO: 317 |
| AtmiPEP171b | *Arabidopsis thaliana* | uugagccgugccaauaucacg | SEQ ID NO: 318 |
| MtmiPEP171b1<br>MtmiPEP171b2 | *Medicago truncatula* | ugauugagccgcgucaauauc | SEQ ID NO: 319 |
| ZmmiPEP171b | *Zea mays* | ggauugagccgcgucaauauc | SEQ ID NO: 320 |
| AtmiPEP171c1 | *Arabidopsis thaliana* | uugagccgugccaauaucacg | SEQ ID NO: 321 |
| MtmiPEP171e | *Medicago truncatula* | agauugagccgcgccaauauc | SEQ ID NO: 322 |
| MtmiPEP171h | *Medicago truncatula* | cgagccgaaucaauaucacuc | SEQ ID NO: 323 |
| AtmiPEP172a1<br>AtmiPEP172a3 | *Arabidopsis thaliana* | agaaucuugaugaugcugcau | SEQ ID NO: 324 |

TABLE 4-continued

| List of the microRNAs (miRNAs) | | | |
|---|---|---|---|
| miPEP | Organism | Sequence of the miRNA | SEQ ID |
| AtmiPEP172b1 | *Arabidopsis thaliana* | gcagcaccauuaagauucac | SEQ ID NO: 325 |
| AtmiPEP172c1 | *Arabidopsis thaliana* | agaaucuugaugaugcugcag | SEQ ID NO: 326 |
| AtmiPEP172e1<br>AtmiPEP172e2<br>AtmiPEP172e3 | *Arabidopsis thaliana* | ggaaucuugaugaugcugcau | SEQ ID NO: 327 |
| AcmiPEP319a1<br>AcmiPEP319a2 | *Arabidopsis cebennensis* | uuggacugaagggagcucccu | SEQ ID NO: 328 |
| AhmiPEP319a | *Arabidopsis halleri* | uuggacugaagggagcucccu | SEQ ID NO: 329 |
| AlmiPEP319a | *Arabidopsis lyrata* | uuggacugaagggagcucccu | SEQ ID NO: 330 |
| AtmiPEP319a1<br>AtmiPEP319a2 | *Arabidopsis thaliana* | uuggacugaagggagcucccu | SEQ ID NO: 331 |
| BrmiPEP319a | *Brassica rapa* | uuggacugaagggagcucccu | SEQ ID NO: 332 |
| CpmiPEP319a | *Carica papaya* | uuggacugaagggagcucccuu | SEQ ID NO: 333 |
| CrmiPEP319a | *Capsella rubella* | uuggacugaagggagcucc | SEQ ID NO: 334 |
| EgmiPEP319a | *Eucalyptus grandis* | uuggacugaagggagcucccu | SEQ ID NO: 335 |
| GrmiPEP319a | *Gossypium raimondii* | uuggacugaagggagcucccu | SEQ ID NO: 336 |
| MtmiPEP319a | *Medicago truncatula* | uuggacugaagggagucucccu | SEQ ID NO: 337 |
| OsmiPEP319a | *Oryza sativa* | uuggacugaagggugcucccu | SEQ ID NO: 338 |
| PpmiPEP319a | *Physcomitrella patens* | cuuggacugaagggagcucc | SEQ ID NO: 339 |
| ThmiPEP319a1<br>ThmiPEP319a2 | *Thellungiella halophila* | uggacucaaggaagcucucu | SEQ ID NO: 340 |
| AtmiPEP319b1 | *Arabidopsis thaliana* | uuggacugaagggagcucccu | SEQ ID NO: 341 |
| AtmiPEP394a1 | *Arabidopsis thaliana* | uuggcauucuguccaccucc | SEQ ID NO: 342 |
| AtmiPEP395c1 | *Arabidopsis thaliana* | cugaaguguuugggggacuc | SEQ ID NO: 343 |
| AtmiPEP395e1 | *Arabidopsis thaliana* | cugaaguguuugggggaacuc | SEQ ID NO: 344 |
| AtmiPEP397b1 | *Arabidopsis thaliana* | ucauugagugcaucguugaug | SEQ ID NO: 345 |
| AtmiPEP398c1 | *Arabidopsis thaliana* | uguguucucaggucaccccug | SEQ ID NO: 346 |
| AtmiPEP399b | *Arabidopsis thaliana* | ugccaaaggagaguugcccug | SEQ ID NO: 347 |
| AtmiPEP399d1 | *Arabidopsis thaliana* | ugccaaaggagauuugccccg | SEQ ID NO: 348 |
| AtmiPEP403 | *Arabidopsis thaliana* | uuagauucacgcacaaacucg | SEQ ID NO: 349 |
| AtmiPEP447a1<br>AtmiPEP447a2 | *Arabidopsis thaliana*<br>*Arabidopsis thaliana* | uuggggacgagauguuuuguug<br>uuggggacgagauguuuuguug | SEQ ID NO: 350 |
| AtmiPEP447b1<br>AtmiPEP447b2 | *Arabidopsis thaliana*<br>*Arabidopsis thaliana* | uuggggacgagauguuuuguug<br>uuggggacgagauguuuuguug | SEQ ID NO: 351 |
| AtmiPEP447c | *Arabidopsis thaliana* | ccccuuacaaugucgaguaaa | SEQ ID NO: 352 |
| DmmiPEP1a<br>DmmiPEP1b | *Drosophila melanogaster* | uggaauguaaagaaguauggag | SEQ ID NO: 353 |
| DmmiPEP8 | *Drosophila melanogaster* | uaauacugucagguaaagauguc | SEQ ID NO: 354 |
| HsmiPEP155 | *Homo sapiens* | uuaaugcuaaucgugauaggggu | SEQ ID NO: 358 |
| AtmiPEP157c | *Arabidopsis thaliana* | uugacagaagauagagagcac | SEQ ID NO: 412 |
| AtmiPEP157d | *Arabidopsis thaliana* | ugacagaagauagagagcac | SEQ ID NO: 413 |

TABLE 4-continued

| List of the microRNAs (miRNAs) | | | |
|---|---|---|---|
| miPEP | Organism | Sequence of the miRNA | SEQ ID |
| AtmiPEP160c | *Arabidopsis thaliana* | ugccuggcucccuguaugcca | SEQ ID NO: 414 |
| AtmiPEP164b | *Arabidopsis thaliana* | uggagaagcagggcacgugca | SEQ ID NO: 415 |
| AtmiPEP166c | *Arabidopsis thaliana* | ucggaccaggcuucauucccc | SEQ ID NO: 416 |
| AtmiPEP166d | *Arabidopsis thaliana* | ucggaccaggcuucauucccc | SEQ ID NO: 417 |
| AtmiPEP169a | *Arabidopsis thaliana* | cagccaaggaugacuugccga | SEQ ID NO: 418 |
| AtmiPEP169h | *Arabidopsis thaliana* | uagccaaggaugacuugccug | SEQ ID NO: 419 |
| AtmiPEP169n | *Arabidopsis thaliana* | uagccaaggaugacuugccug | SEQ ID NO: 420 |
| AtmiPEP170 | *Arabidopsis thaliana* | ugauugagccgugucaauauc | SEQ ID NO: 421 |
| AtmiPEP396a | *Arabidopsis thaliana* | uuccacagcuuucuugaacug | SEQ ID NO: 422 |
| AtmiPEP399c | *Arabidopsis thaliana* | ugccaaaggagaguugcccug | SEQ ID NO: 423 |

TABLE 5

| List of the control Pre-miRNAs | | | |
|---|---|---|---|
| Pre-miRNA | Organism | Sequence of the Pre-miRNA | SEQ ID |
| Pre-miR169 | *Medicago truncatula* | TTAGGGTTTTCAGCTCATGGTAATA AAAATGTCATCTAATGTCTTGCATG TGGGAATGAGGTCATATATGCAGCC AAGGATGACTTGCCGGCGAGCCTCT TTCGATACTTTTATGACATAATTAA TCATGTGGATAGCCAAGGTACTAAA CTCACTTTGCACTAAAACAAATATT TTTGCTTTAGTGCAAACTTAGTTTA GGCGCTTCGCAACGGCTAGTCAAAT GTCCTAGTTCCAATGTGATTGGTTG TCCGGCAAGTCGTCTCTGGCTACGT AAAGGCCTCCTTTTTTCATGCTAGA TTTTTGATGATTTGATATAGCCACA CATATTTTGGAA | SEQ ID NO: 359 |
| Pre-miR169a | *Medicago truncatula* | AAGAGGCAGAGAGAGTAATGCAGCC AAGGATGACTTGCCGACAACATTGG CGAATGTTCATGTGATTTCTGCCTC ATTGTGCCGGCAAGTTGTCCTTGGC TATGTTAGTCTCTCATCTTCT | SEQ ID NO: 360 |
| Pre-miR171a MI 0001753 | *Medicago truncatula* | TGAATTCCCCTCCGCTTTTTGATGT TGGCTTGTCTCAATCAAATCAAAGT TCTTGAAATTTGAGTTCTTTAGTCT GATTGAGTCGTGCCAATATCATATT AAGCGATAAAAGTC | SEQ ID NO: 361 |
| Pre-miR171h | *Medicago truncatula* | CCACAAAACTATAACTAGCTAGAAG CTTTAATCGCCTTATTTATTATAAT AATAATAATAAATATGGCTTCAGCT GCAAAAGTATACATGGCGTGATATT GATCCGGCTCATCTATATCTTCAAG TTCAATCATCCATATTCATATCAAT TTCAGACGAGCCGAATCAATATCAC TCTTGTTTGCTTCATTGCATATTAA TTATATACTTCATTTATAAGTTATA GTTTGCCATATATATATTAGATTGA TTCTGCAGAAGTAGACAGGAGTGGT GTTGTTTCTGCTCATCTTATTAAAT AATGAATGAATGAATGACATTTGCT TACTTATAAGACGAGCCGAATCAAT ATCACTCCAGTACACCT | SEQ ID NO: 362 |
| Pre-miR393a | *Medicago truncatula* | AACTGCAACTTGAGGAGGCATCCAA AGGGATCGCATTGATCCTATAATAT TTCAACTTTAGTCACTTTAATTTTC TCTCATATAATACTTAATTGGGATC ATGCCATCCCTTTGGATTTCTCCTT TAGTAGCTAC | SEQ ID NO: 363 |
| Pre-miR393b | *Medicago truncatula* | AGGCATCCAAAGGGATCGCATTGAT CCCAAATCTAATTAAGTCCCTAGCT CATTAATTAACAACTTAATTTCCTT AATATCTCATAATATTTGGGATCAT GCTATCCCTTTGGATTCAT | SEQ ID NO: 364 |
| Pre-miR396a | *Medicago truncatula* | TGCTTTTCCACAGCTTTCTTGAACT TCTTTCGTATCTTAAATCTGTTTTC AAGATTAAAAGTCCTAGAAGCTCAA GAAAGCTGTGGGAGAATA | SEQ ID NO: 365 |
| Pre-miR396b | *Medicago truncatula* | TATTCTTCCACAGCTTTCTTGAACT GCATCCAAATTGAGTTCCTTTGCAT TGCCATGGCCATTGTTTTGCGGTTC AATAAAGCTGTGGGAAGATA | SEQ ID NO: 366 |

TABLE 6

| List of the control miRNAs | | | |
|---|---|---|---|
| miRNA | Organism | Sequence of the miRNA | SEQ ID |
| miR169 | *Medicago truncatula* | CAGCCAAGGAUGACUUGCCGG | SEQ ID NO: 367 |
| miR169a | *Medicago truncatula* | CAGCCAAGGAUGACUUGCCGA | SEQ ID NO: 368 |
| miR171a | *Medicago truncatula* | UGAUUGAGUCGUGCCAAUAUC | SEQ ID NO: 369 |
| miR171h | *Medicago truncatula* | GAGCCGAAUCAAUAUCACUC | SEQ ID NO: 370 |
| miR393a | *Medicago truncatula* | UCCAAAGGGAUCGCAUUGAUC | SEQ ID NO: 371 |
| miR393b | *Medicago truncatula* | UCCAAAGGGAUCGCAUUGAUC | SEQ ID NO: 372 |

TABLE 6-continued

| List of the control miRNAs | | | |
|---|---|---|---|
| miRNA | Organism | Sequence of the miRNA | SEQ ID |
| miR396a | *Medicago truncatula* | UUCCACAGCUUUCUUGAACUU | SEQ ID NO: 373 |
| miR396b | *Medicago truncatula* | UUCCACAGCUUUCUUGAACUG | SEQ ID NO: 374 |

TABLE 7

| Polymorphism of the DNA sequence of the different regions of pri-miR171b | | | | | |
|---|---|---|---|---|---|
| | Size | # SNPs | # mutations | % SNP | # haplotypes |
| pri-mir171b | 1127 | 91 | 100 | 8.07 | 161 |
| 5' pri-miR171b | 129 | 4 | 4 | 3.1 | 5 |
| miPEP171b | 62 | 2 | 2 | 3.22 | 3 |
| Pre-miR171b | 118 | 1 | 1 | 0.85 | 2 |
| miR171b + miR171b* | 42 | 0 | 0 | 0 | 1 |
| 3' pri-miR171b | 259 | 39 | 42 | 15.06 | 89 |

EXAMPLES

A: Analysis of the miPEPS in Plants

Example 1—Characterization in the Model Plant *Medicago truncatula* a) Identification and Characterization of MtmiPEP171b1 (miPEP171b1 Identified in *Medicago truncatula*)

Figure 1:
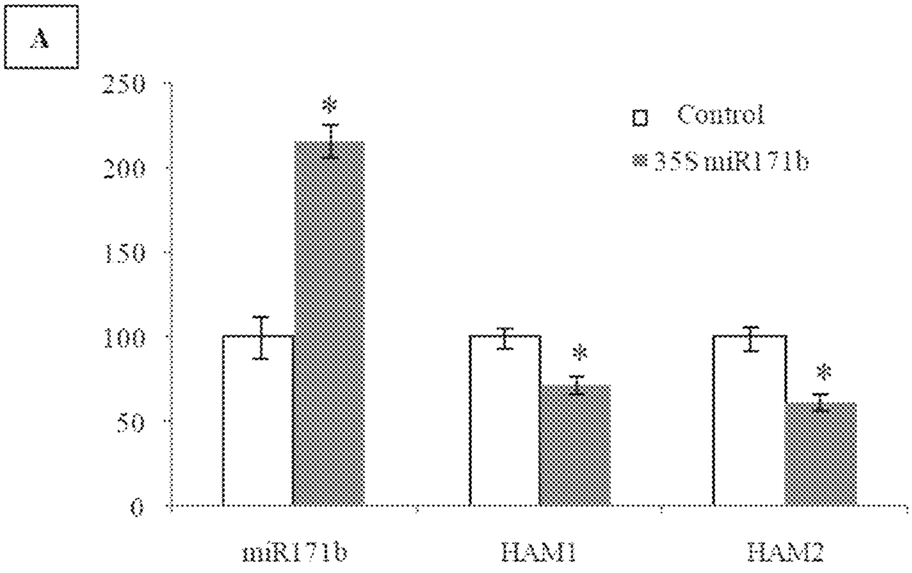
FIG. 1. Effects of overexpression of MtmiR171b (miR171b identified in *Medicago truncatula*) on the expression of the HAM1 and HAM2 genes (A) or on the number of lateral roots (B) in *M. truncatula.*
Figure 1:
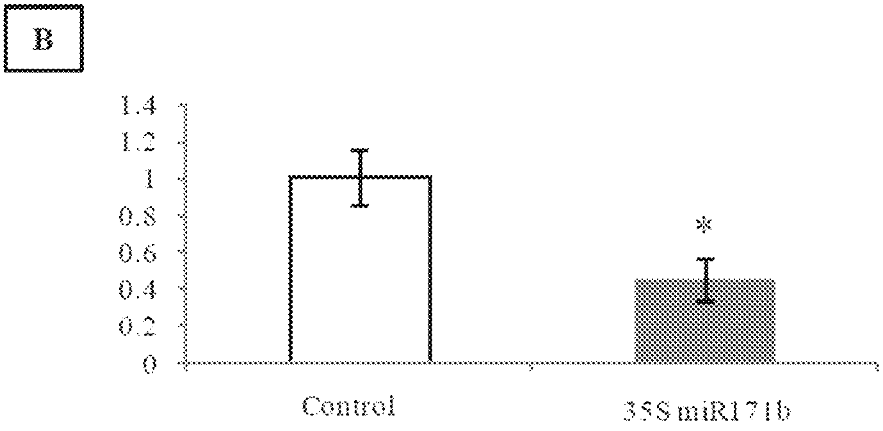

This microRNA is expressed in the meristematic region of the roots. The overexpression of this microRNA in particular leads to a reduction in the expression of the genes HAM1 (Accession No. MtGI9-TC114268) and HAM2 (Accession No. MtGI9-TC120850) (FIG. 1A), as well as to a reduction in the number of lateral roots (FIG. 1B).

The sequence of the primary transcript of MtmiR171b was determined using the RACE-PCR technique. Analysis of the sequence of the primary transcript made it possible to identify the presence of several completely unexpected small open reading frames (sORFs). These sORFs were called miORFs for "microRNA ORFs". These miORFs potentially encode short peptides, from about 4 to 100 amino acids. No significant homology relating to these miORFS was found in the databases.

The overexpression of the first miORF, called MtmiORF171b, leads to an increase in the accumulation of MtmiR171b and a reduction in the expression of the HAM1 and HAM2 genes (see FIG. 2A), as well as to a reduction in the number of lateral roots (FIG. 2B), as was already observed in the overexpression of MtmiR171b.

In order to determine whether MtmiORF171b leads to the real production of a peptide and whether the regulatory function observed above is indeed carried by said peptide, a synthetic peptide, the sequence of which is identical to that potentially encoded by MtmiORF171b, was applied on the roots of *Medicago truncatula*. Application of this peptide leads to the phenotype already observed above in the overexpression of MtmiORF171b, i.e. it leads to an increase in the accumulation of MtmiR171b and a reduction in the expression of the HAM1 and HAM2 genes (see FIG. 3A), as well as a reduction in the number of lateral roots (FIG. 3B).

The results of these experiments demonstrate that MtmiORF171b encodes a peptide capable of modulating the accumulation of MtmiR171b, and the expression of the target genes of MtmiR171b: HAM1 and HAM2. Said peptide has been called MtmiPEP171b1 ("miPEP" corresponding to microRNA encoded PEPtide).

Moreover, MtPEP171b1 leads to an increase in the accumulation of MtmiR171b (FIG. 4A) and of pre-MtmiR171b (FIG. 4B).

b) Specificity of miPEP171b1

The expression of different microRNA precursors of *Medicago truncatula* (MtmiR171b SEQ ID NO: 319, MtmiR169 SEQ ID NO: 367, MtmiR169a SEQ ID NO: 368, MtmiR171a SEQ ID NO: 369, MtmiR171h SEQ ID NO: 370, MtmiR393a SEQ ID NO: 371, MtmiR393b SEQ ID NO: 372, MtmiR396a SEQ ID NO: 373 and MtmiR396b SEQ ID NO: 374) was determined and compared between control plants and plants in which MtmiORF171b encoding MtmiPEP171b1 was overexpressed (FIG. 5A), or between control plants and plants grown on culture medium containing MtmiPEP171b1 (FIG. 5B).

The results obtained indicate that MtmiPEP171b1 only leads to an increase in the accumulation of MtmiR171b and not of the other miRNAs, which indicates that a miPEP only has an effect on the microRNA from which it is derived.

c) Localization of miPEP171b1

Moreover, the immunolocalization of miPEP171b1 in the roots of *M. truncatula* reveals the presence of miPEP171b1 in the lateral root initiation sites, showing a co-localization between the microRNA and the corresponding miPEP (FIG. 28).

Example 2—Characterization in the Model Plant of Tobacco a) Conservation of the Mechanism in Tobacco In order to determine whether the mechanism of regulation of the microRNAs is conserved in other plant species, the regulation of MtmiR171b by MtmiPEP171b1 was tested in a different cellular model. For this, MtmiR171b and MtmiPEP171b1 were introduced into tobacco leaves.

The accumulation of MtmiR171b was measured in tobacco leaves transformed in order to express MtmiR171b of *Medicago truncatula* starting from wild-type pri-miRNA capable of producing MtmiPEP171b1, or starting from a mutated version of pri-miRNA incapable of producing MtmiPEP171b1 (in which the start codon ATG of MtmiORF171b has been replaced with ATT) (FIG. 6 and FIG. 20). Absence of translation of MtmiPEP171b1 leads to a marked decrease in the accumulation of MtmiR171b.

The accumulation of pre-MtmiR171b was measured in tobacco leaves transformed in order to express MtmiR171b of *Medicago truncatula* alone (control), or additionally expressing the wild-type MtmiORF171b of *Medicago truncatula* (35SmiPEP171b1 ATG), or a mutated version of MtmiORF171b in which the start codon ATG has been replaced with ATT (35SmiPEP171b1 ATT) (FIG. 7 and FIG. 21). The expression of MtmiORF171b leads to an increase in the accumulation of pre-miR171b, and this accumulation of pre-miR171b depends on the translation of MtmiORF171b to micropeptide.

Moreover, in the tobacco leaves transformed in order to express MtmiR171b of *Medicago truncatula*, untreated or treated by spraying with MtmiPEP171b1 (0.1 μM) for the first time 12 h before sampling and then a second time 30 minutes before sampling, it was observed that MtmiPEP171b1 may be used directly in peptide form by foliar sprayings (FIG. 8). Moreover, it was observed in tobacco (as in *Medicago truncatula*) that the MtmiPEP171b1 leads to an increase in the accumulation of MtmiR171b (FIG. 9A) and of pre-MtmiR171b (FIG. 9B), but reduces the accumulation of pri-MtmiR171b (FIG. 9C).

Taken together, these results indicate that the mechanism of regulation of the microRNAs and of their target genes under the control of miPEPs is conserved between the species.

b) Intracellular Localization of MtmiPEP171b1

Tobacco leaves were transformed in order to overexpress MtmiPEP171b1 of *Medicago truncatula* fused with a fluorescent protein (GFP) (FIG. 10). The results obtained indicate that the miPEP is localized in small nuclear bodies.

c) Identification of miPEPS from Databases

Genomic databases of plants were searched for the presence of open reading frames within primary transcripts of 70 miRNAs, and 101 miORFs capable of encoding a miPEP were identified.

At present, AtmiPEP165a and AtmiPEP319a2, identified in *Arabidopsis thaliana*, have already been characterized. The experiments conducted in the model plant of tobacco made it possible to demonstrate that the overexpression of AtmiORF165a or of AtmiORF319a leads to an increase in the accumulation of AtmiR165a or of AtmiR319a respectively (FIG. 11).

miR165a regulates transcription factors such as Revoluta, Phavoluta and Phabulosa. miR319 regulates genes of the TCP family.

Example 3—Characterization in the *Arabidopsis thaliana* Model Plant

Example 3A—AtmiPEP165a

Regarding AtmiPEP165a, it has been demonstrated in vivo in *Arabidopsis thaliana* that treatment with AtmiPEP165a leads to a phenotype with greatly accelerated root growth (FIG. 12).

Moreover, treatment of plants with higher and higher concentrations of miPEP165a shows a dose-dependent effect on the accumulation of miR165a and the negative regulation of its target genes (PHAVOLUTA: PHV, PHABOLUSA: PHB and REVOLUTA: REV) as a function of the amount of miPEP165A (see FIG. 22).

Example 3B—AtmiPEP164a

Regarding AtmiPEP164a, this was synthesized and was used for investigating an increase in the accumulation of miR164a in roots of *A. thaliana* treated with the synthetic peptide.

Northern blot analyses indicate that treatment of the plant with the peptide miPEP164a leads to an increase in the accumulation of miR164a (FIG. 23).

It has also been demonstrated in vivo in *Arabidopsis thaliana* that treatment of the plant with AtmiPEP164a increases plant growth significantly (FIG. 24).

Example 3C—AtmiPEP165a

Regarding AtmiPEP165a, this was synthesized and was used for investigating an increase in the accumulation of miR165a in roots of *A. thaliana* treated with the synthetic peptide.

Northern blot analyses indicate that treatment of the plant with the peptide miPEP165a leads to an increase in the accumulation of miR165a (FIG. 25).

Example 4C—AtmiPEP319a1

Regarding AtmiPEP319a1, this was also synthesized and was used for investigating an increase in the accumulation of miR319a in roots of *A. thaliana* treated with the synthetic peptide.

Analyses by qRT-PCR show that the overexpression of AtmiPEP319a1 leads to an increase in the accumulation of miR319a (FIG. 26).

It was also demonstrated in vivo in *Arabidopsis thaliana* that treatment of the plant with AtmiPEP319a1 increases plant growth significantly (FIG. 27).

Material and Methods

Biological Material

The surface of seeds of *M. truncatula* was sterilized and they were left to germinate on agar plates for 5 days at 4° C. in the dark. The young shoots were then grown on 12-cm square plates filled with Fahraeus medium without nitrogen and containing 7.5 UM phosphate (Laressergues et al., *Plant J.,* 72(3): 512-22, 2012). The lateral roots were counted every day. In pots, the plants were watered every other day with modified Long Ashton medium with low phosphorus content (Balzergue et al., *Journal of Experimental Botany*, (62)1049-1060, 2011).

The peptides were synthesized by Eurogentec or Smartox-Biotech. MtmiPEP171b1 was resuspended in a solution of 40% water/50% acetonitrile/10% acetic acid (v/v/v), and the other peptides were resuspended in water.

The leaves were watered by spraying with the peptides using peptide solutions at different concentrations (0.01, 0.1, 1 μM), firstly 12 h before sampling and then a second time 30 min before sampling.

Reverse Transcription of the microRNAs

The RNA was extracted using the reagent Tri-Reagent (MRC) according to the manufacturer's instructions, except for precipitation of the RNA, which was carried out with 3 volumes of ethanol. The reverse transcription of the RNA was carried out using the specific stem-loop primer RTprimer171b in combination with hexamers for performing the reverse transcription of RNA of high molecular weight.

In brief, 1 μg of RNA was added to the stem-loop primer MIR171b (0.2 μM), the hexamer (500 ng), the buffer RT (1×), the enzyme SuperScript Reverse transcriptase (SSIII) (one unit), the dNTPs (0.2 mM each), DTT (0.8 mM) in a final reaction mixture of 25 μl. In order to carry out the reverse transcription, a reaction of pulsed reverse transcription was performed (40 repetitions of the following cycle: 16° C. for 2 minutes, 42° C. for one minute and 50° C. for one second, followed by a final inactivation of the reverse transcription at 85° C. for 5 minutes).

Analyses by Quantitative RT-PCR (qRT-PCR)

The total RNA was extracted from roots of *M. truncatula* or from tobacco leaves using the extraction kit RNeasy Plant Mini Kit (Qiagen). The reverse transcription was performed using the reverse transcriptase SuperScript II (Invitrogen) starting from 500 ng of total RNA. Three repetitions (n=3) were carried out, each with two technical repetitions. Each experiment was repeated from two to three times. The amplifications by qPCR were carried out using a LightCycler 480 System thermocycler (Roche Diagnostics) by the method described in Lauressergues et al. (*Plant J.,* 72(3): 512-22, 2012).

Statistical Analyses

The mean values of the relative expression of the genes or of the production of lateral roots were analysed using the Student test or the Kruskal-Wallis test. The error bars represent the SEM (Standard Error of the Mean). The asterisks indicate a significant difference ($p<0.05$).

Plasmid Constructs

The DNA fragments of interest were amplified with Pfu polymerase (Promega). The DNA fragments were cloned using the XhoI and NotI enzymes into a pPEX-DsRED plasmid for an overexpression under the control of the constitutive strong promoter 35S, and using the KpnI-NcoI enzymes into a pPEX GUS plasmid for the reporter genes, by the method described in Combier et al. (*Genes & Dev,* 22: 1549-1559, 2008).

For the miPEPs 165a and 319a, the corresponding miORFs were cloned into pBIN19 by the method described in Combier et al. (*Genes & Dev,* 22: 1549-1559, 2008).

Transformation of the Plants

The composite plants having roots transformed with *Agrobacterium rhizogenes* were obtained by the method described in Boisson-Dernier et al. (*Mol Plant-Microbe Interact,* 18: 1269-1276, 2005). The transformed roots were verified and selected by observations of DsRED with a binocular fluorescence magnifier. The control roots correspond to roots transformed with *A. rhizogenes* not containing the pPEX-DsRED vector. Transformation of the tobacco leaves was carried out by the method described in Combier et al. (*Genes & Dev,* 22: 1549-1559, 2008).

Northern Blot

Northern blot analysis was carried out according to the protocol described in Lauressergues et al. *Plant J,* 72(3): 512-22, 2012.

The biological samples were homogenized in a buffer containing 0.1 M of NaCl, 2% of SDS, 50 mM of Tris-HCl (pH 9), 10 mM of EDTA (pH 8) and 20 mM of mercaptoethanol, and the RNA was extracted twice with a phenol/chloroform mixture and was precipitated with ethanol.

The RNA was loaded on PAGE 15% gel and transferred to a nylon membrane (HybondNX, Amersham). RNA was hybridized with a radioactive oligonucleotide probe labelled at its end, in order to detect the RNA U6 or for miR164a.

The hybridizations were carried out at 55° C. The hybridization signals were quantified using a phosphorimager (Fuji) and normalized with the signal of the specific probe of RNA U6.

Histochemical Labelling

Labelling with GUS was carried out by the method described in Combier et al., (*Genes & Dev,* 22: 1549-1559, 2008). The samples were observed with a microscope (axiozoom).

Immunolocalization

Roots or plantlets of tissues of *Medicago* were fixed for 2 hours in 4% formol (v/v) with 50 mM of phosphate buffer (pH 7.2), and then embedded in agarose LMP 5% in water (with a low melting point). Thin sections (100 μm) were obtained and were placed in Pbi (phosphate buffer for immunology) on Teflon-coated slides, blocked in Pbi, 2% Tween and 1% of bovine serum albumin for 2 hours (PbiT-BSA), then labelled overnight (12 h) at 4° C. with the primary antibody diluted in BSA-PbiT. The sections were washed with PBiT and incubated at ambient temperature for 2 h with a secondary antibody diluted in PbiT-BSA. The slides were then washed in Pbi for 30 min and mounted in Citifluor (mounting medium). The primary antibodies and the dilutions were as follows: 1716a (1:500, v/v). The secondary antibody was a goat anti-rabbit IgG antibody coupled to the Alexa Fluor 633 fluorescent probe (Molecular Probes), and was used at a dilution of 1:1000 (v/v).

B: Analysis of the miPEPs in Animals

Example 4—Identification of Candidate miPEPs in *Drosophila*

A first study carried out by RACE-PCR in the model animal *Drosophila melanogaster* shows the existence of miRNAs that are expressed during embryogenesis, miR1 and miR8.

As in the plants, miORFs were identified in each of the two miRNAs studied. For example, miR8, known for its role in the regulation of growth in insects, has a miORF potentially encoding miPEP8.

Regarding DmmiR1 (identified in *Drosophila melanogaster*), it has two DmmiORFs potentially encoding DmmiPEP1a and DmmiPEP1b.

A phylogenetic analysis shows evolutionary conservation of the presence of the miORFs among the dozen *Drosophila* species analysed, i.e. since their divergence more than 60 million years ago (FIG. 13).

Moreover, the miPEPs identified in *Drosophila* have several similarities with the plant miPEPs. If their primary sequence and therefore their size evolve rapidly between species, a reduced size (from 32 to 104 AA) is found, as well as strong conservation for a basic overall charge (pHi from 9.5 to 12) (FIG. 14).

Taken together, these results therefore indicate the existence of regulatory miPEPs, encoded by the primary transcript of the microRNAs, over a broad spectrum of eukaryotic species. These discovered peptides represent an as yet unexplored reservoir of natural molecules that may regulate a variety of fundamental biological functions, both in plants and in animals.

Cells of *Drosophila melanogaster*

S2 cells are cultured in a T75 flask in 12 mL of Schneider's medium (GIBCO), containing 1% of penicillin 100 U/mL and streptavidin 100 mg/mL (Sigma) and 10% of decomplemented foetal calf serum (30 min at 56° C.).

The transient transfections are carried out using the FuGENE® HD transfection kit (Roche), according to the recommendations. Conventionally, 1.5 million S2 cells, previously seeded in 6-well plates (3 ml of medium per well), are transfected with 250 ng of total plasmid DNA. The DNA is brought into contact with the Fugene (3 μl) in 100 μl of OPTIMEM (GIBCO). After 20 minutes, the transfection reagent formed is brought into contact with the cells in the culture medium. The RNA of the cells is extracted 66 h after transfection.

C: Characterization of miPEPs in Humans

Example 5—Characterization of HsmiPEP155

The DNA fragments of interest (HsmiPEP155 and the mutated miPEP) were synthesized or amplified by PCR using specific primers, and then cloned using the enzymes XhoI and NotI into a pUAS plasmid permitting their overexpression by means of the GAL4 transcription factor, the expression of which is controlled by a constitutive strong promoter.

The different constructs were produced either by PCR amplification on genomic DNA of HeLa cells, or by RT-PCR on total RNAs of L428 human cells. The amplified PCR fragments are digested with the HindIII/EcoRI restriction enzymes and then cloned into the vector pcDNA3.1. The DH5α strain of *Escherichia coli* is electroporated and then cultured on a solid medium (2YT+agar+ampicillin). The plasmid DNA from different clones is then prepared and sequenced for verification. The constructs are then prepared using the QIAfilter Plasmid Midi kit (QIAGEN) and stored at −20° C.

The Hela cells (established tumour line, ATCC CCL-2.2) are cultured in a 6-well plate in complete medium [(DMEM (1×)+Glutamax+4.5 g/L glucose without pyruvate+1× penicillin/streptomycin+1 mM Na-pyruvate+10% calf serum] and placed in an incubator at 37° C. and 5% $CO_2$.

The cells are transfected when they are at 50% confluence. At the start of the experiment, the complete medium containing the antibiotics is replaced with complete medium without antibiotics.

For each well, a mix A [250 μl of Optimem (+Glutamax) (Gibco)+2 μg of DNA] and a mix B [250 μl of Optimem+4 μl of Lipofectamine 2000 (Invitrogen)] is prepared, and left for 5 min at ambient temperature. Then mix B is mixed dropwise into mix A, and left to incubate for 25 min at ambient temperature. The mixture is then deposited dropwise into the well. 4-5 hours later, the medium is changed and replaced with complete medium with antibiotics. 48 hours after transfection, the cells are stopped. The medium is aspirated and discarded; the cells are rinsed with PBS 1×. It is then possible to store the cells at −20° C. or extract the total RNAs directly.

For each well, the RNAs are extracted by depositing 1 ml of Tri-Reagent (Euromedex) on the cells. The Tri-reagent is aspirated and returned several times so that the cells are lysed correctly, and then it is transferred into a 1.5-ml tube. 0.2 ml of water-saturated chloroform is added. It is mixed by vortexing, then left for 2 to 3 minutes at ambient temperature. It is centrifuged for 5 minutes at 15300 rpm and at 4° C. The aqueous phase is precipitated from 0.5 ml of isopropanol after incubation for 10 minutes at ambient temperature and centrifugation for 15 minutes at 15300 rpm and at 4° C. The supernatant is discarded and the pellet is rinsed with 1 ml of 70% ethanol, with centrifugation for 5 minutes at 15300 rpm at 4° C. The supernatant is again discarded and the pellet is dried for a few minutes in the air.

For best-possible removal of the genomic DNA potentially remaining, the RNAs are treated with DNase. For this, the pellet is resuspended in 170 μl of ultra-pure water, 20 μl of DNase buffer 10× and 10 μl of RQ1 RNase-free DNase and held at 37° C. for 30 minutes. Then 20 μl of SDS10% and 5 μl of proteinase K (20 mg/ml) are added over 20 minutes at 37° C.

A last phenol extraction is carried out with 225 μl of a phenol/$H_2O$/chloroform mixture, and centrifuged for 5 minutes at 15300 rpm at 4° C.

The aqueous phase is then precipitated from 20 μl of 3M sodium acetate and 600 μl of 100% ethanol for 20 minutes at −80° C. Then it is centrifuged for 15 min at 4° C. at 15300 rpm. The supernatant is discarded. The pellet is rinsed in 1 ml of 70% ethanol, centrifuged for 5 min at 15300 rpm at 4° C., the supernatant is discarded again and the pellet is left to dry for some minutes in the air.

The pellet is then taken up in 15-20 μl of ultra-pure water and the RNAs are assayed.

10-15 μg of total RNAs is then analysed by Northern blot on 15% acrylamide gel [solution of acrylamide/40% bis-acrylamide, ratio 19:1], 7M urea in TBE 1×. Migration is carried out at 400V, in TBE1× as migration buffer, after preheating the gel. The RNAs are then electro-transferred onto a Biodyne Plus 0.45 μm nylon membrane, for 2 hours, at 1V and 4° C. in a transfer tank. At the end of transfer, the membrane is irradiated with UV at 0.124 $J/cm^2$. The membrane is then pre-hybridized in a buffer 5×SSPE, 1×Denhardt's, 1% SDS and 150 μg/ml of yeast tRNA, for 1 hour at 50° C. in a hybridization oven. Then the nucleotide probe is added, labelled at 5' with γ-$^{32}$P-ATP (0.5 to 1.106 cpm/ml of hybridization buffer) and is hybridized overnight at 50° C. The membrane is then washed twice in 0.1×SSPE/0.1% SDS at ambient temperature and exposed in an autoradiography cassette containing a BioMax HE screen (Kodak) and a BioMax MS film (Kodak), in order to detect a microRNA, for 24-48 hours, at −80° C.

The invention claimed is:

1. A process comprising:

a) identifying an open reading frame (ORF) from 12 to 303 nucleotides in length contained in the 5' or 3' portion of the primary transcript sequence of a microRNA (miRNA);

b1) exogenously contacting a first plant cell expressing the miRNA with a peptide encoded by the ORF or a nucleotide encoding the peptide; and b2) comparing between:

i) a phenotype in the first plant cell expressing the miRNA in the presence of the peptide encoded by the ORF, the peptide being present in the first plant cell independently of transcription of the primary transcript of the miRNA, and ii) the phenotype in a second plant cell of the same type as the first plant cell expressing the miRNA that has not been exogenously contacted with the peptide encoded by the ORF or the nucleotide encoding the peptide, wherein a change of the phenotype in the presence of the peptide relative to the phenotype in the absence of the peptide indicates that the ORF encodes a miPEP that modulates the amount of the miRNA; and c) synthesizing (i) the miPEP that modulates the amount of the miRNA, or (ii) a nucleic acid sequence encoding the miPEP that modulates the amount of the miRNA and that does not comprise mature miRNA.

2. The process of claim 1, wherein the nucleic acid sequence encoding the miPEP that modulates the amount of the miRNA and that does not comprise the mature miRNA is operably linked to a heterologous promoter.

3. The process of claim 1, wherein the synthesis in step c) is chemical synthesis or synthesis in a cell that transgenically expresses the miPEP that modulates the amount of the miRNA or the nucleic acid sequence encoding the miPEP that modulates the amount of the miRNA and that does not comprise the mature miRNA.

4. The process of claim 3, further comprising the step d) of isolating the miPEP from the cell that transgenically expresses the miPEP.

5. The process of claim 4, further comprising the step e) of formulating the miPEP isolated in step d) for administration to a plant or part thereof.

6. A process comprising synthesizing (i) a miPEP that modulates the amount of a microRNA (miRNA), or (ii) a nucleic acid sequence encoding the miPEP that modulates the amount of the miRNA and that does not comprise mature miRNA, wherein said miPEP encoded by an open reading frame (ORF) from 12 to 303 nucleotides in length contained in the 5' or 3' portion of the primary transcript sequence of the miRNA, and wherein said miPEP has an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 375, SEQ ID NO: 376, SEQ ID NO: 377, SEQ ID NO: 378, SEQ ID NO: 379, SEQ ID NO: 380, SEQ ID NO: 381, SEQ ID NO: 382, SEQ ID NO: 383, SEQ ID NO: 384, SEQ ID NO: 385 and SEQ ID NO: 386, and wherein said miPEP was identified by:

a) exogenously contacting a first plant cell expressing the miRNA with a peptide encoded by the ORF or a nucleotide encoding the peptide; and b) comparing between:

i) a phenotype in the first plant cell expressing the miRNA in the presence of the peptide encoded by the ORF, the peptide having been present in the first plant cell independently of transcription of the primary transcript of the miRNA, and ii) the phenotype in a second plant cell of the same type as the first plant cell expressing the miRNA that had not been exogenously contacted with the peptide encoded by the ORF or the nucleotide encoding the peptide, wherein a change of the phenotype in the presence of the peptide relative to the phenotype in the absence of the peptide indicated that the ORF encodes the miPEP that modulates the amount of the miRNA.

7. The process of claim 4, wherein the nucleic acid sequence encoding the miPEP that modulates the amount of the miRNA and that does not comprise the mature miRNA is operably linked to a heterologous promoter.

8. The process of claim 4, wherein the synthesizing is chemical synthesis or synthesis in a cell that transgenically expresses the miPEP that modulates the amount of the miRNA or the nucleic acid sequence encoding the miPEP that modulates the amount of the miRNA and that does not comprise the mature miRNA.

9. The process of claim 8, further comprising the step d) of isolating the miPEP from the cell that transgenically expresses the miPEP.

10. The process of claim 9, further comprising the step e) of formulating the miPEP isolated in step d) for administration to a plant or part thereof.

* * * * *

SEQUENCE LISTING

```
Sequence total quantity: 423
SEQ ID NO: 1            moltype = AA  length = 33
FEATURE                 Location/Qualifiers
source                  1..33
                        mol_type = protein
                        organism = Arabidopsis thaliana
SEQUENCE: 1
MFCSIQCVAR HLFPLHVREI KKATRAIKKG KTL                          33

SEQ ID NO: 2            moltype = AA  length = 24
FEATURE                 Location/Qualifiers
source                  1..24
                        mol_type = protein
                        organism = Arabidopsis thaliana
SEQUENCE: 2
MRRQTSVPFA CKRDKESDKS HKER                                    24

SEQ ID NO: 3            moltype = AA  length = 37
FEATURE                 Location/Qualifiers
source                  1..37
                        mol_type = protein
                        organism = Arabidopsis thaliana
SEQUENCE: 3
MVMFFLDLDK NPRFDLLKGL KWNLFSSHIS PSLPPSL                      37
```

```
SEQ ID NO: 4            moltype = AA  length = 11
FEATURE                 Location/Qualifiers
source                  1..11
                        mol_type = protein
                        organism = Arabidopsis thaliana
SEQUENCE: 4
MKDNFPLLLR L                                                        11

SEQ ID NO: 5            moltype = AA  length = 4
FEATURE                 Location/Qualifiers
source                  1..4
                        mol_type = protein
                        organism = Arabidopsis thaliana
SEQUENCE: 5
MSDD                                                                4

SEQ ID NO: 6            moltype = AA  length = 16
FEATURE                 Location/Qualifiers
source                  1..16
                        mol_type = protein
                        organism = Arabidopsis thaliana
SEQUENCE: 6
MIYINKYGSI SAVEDD                                                   16

SEQ ID NO: 7            moltype = AA  length = 4
FEATURE                 Location/Qualifiers
source                  1..4
                        mol_type = protein
                        organism = Arabidopsis thaliana
SEQUENCE: 7
MSQR                                                                4

SEQ ID NO: 8            moltype = AA  length = 16
FEATURE                 Location/Qualifiers
source                  1..16
                        mol_type = protein
                        organism = Arabidopsis lyrata
SEQUENCE: 8
MTCPLLSLSF LLSKYI                                                   16

SEQ ID NO: 9            moltype = AA  length = 16
FEATURE                 Location/Qualifiers
source                  1..16
                        mol_type = protein
                        organism = Arabidopsis thaliana
SEQUENCE: 9
MTWPLLSLSF LLSKYV                                                   16

SEQ ID NO: 10           moltype = AA  length = 18
FEATURE                 Location/Qualifiers
source                  1..18
                        mol_type = protein
                        organism = Capsella rubella
SEQUENCE: 10
MTCTLSALSL SLNMFRVN                                                 18

SEQ ID NO: 11           moltype = AA  length = 5
FEATURE                 Location/Qualifiers
source                  1..5
                        mol_type = protein
                        organism = Arabidopsis thaliana
SEQUENCE: 11
MFYLS                                                               5

SEQ ID NO: 12           moltype = AA  length = 37
FEATURE                 Location/Qualifiers
source                  1..37
                        mol_type = protein
                        organism = Arabidopsis thaliana
SEQUENCE: 12
MVNTSSFFIS SFILPLVLSE SNCLLFRTIY KFSMVLY                            37

SEQ ID NO: 13           moltype = AA  length = 24
FEATURE                 Location/Qualifiers
source                  1..24
                        mol_type = protein
                        organism = Arabidopsis thaliana
SEQUENCE: 13
MFCLLIPIFS FVFSPNRHLR LQEQ                                          24
```

```
SEQ ID NO: 14          moltype = AA  length = 5
FEATURE                Location/Qualifiers
source                 1..5
                       mol_type = protein
                       organism = Arabidopsis thaliana
SEQUENCE: 14
MFSPQ                                                                  5

SEQ ID NO: 15          moltype = AA  length = 23
FEATURE                Location/Qualifiers
source                 1..23
                       mol_type = protein
                       organism = Arabidopsis thaliana
SEQUENCE: 15
MKYIHILILF KSRSTYKLST NHI                                             23

SEQ ID NO: 16          moltype = AA  length = 10
FEATURE                Location/Qualifiers
source                 1..10
                       mol_type = protein
                       organism = Arabidopsis thaliana
SEQUENCE: 16
MKIPLFLPKL                                                            10

SEQ ID NO: 17          moltype = AA  length = 27
FEATURE                Location/Qualifiers
source                 1..27
                       mol_type = protein
                       organism = Arabidopsis thaliana
SEQUENCE: 17
MVSGQEDSWL KLSSLCFLFL SLLDSLI                                         27

SEQ ID NO: 18          moltype = AA  length = 34
FEATURE                Location/Qualifiers
source                 1..34
                       mol_type = protein
                       organism = Arabidopsis thaliana
SEQUENCE: 18
MFLLIFLRLI MICVCSSTDF LRSVNYFCLF IYDL                                 34

SEQ ID NO: 19          moltype = AA  length = 9
FEATURE                Location/Qualifiers
source                 1..9
                       mol_type = protein
                       organism = Arabidopsis thaliana
SEQUENCE: 19
MSTTQEHRS                                                              9

SEQ ID NO: 20          moltype = AA  length = 25
FEATURE                Location/Qualifiers
source                 1..25
                       mol_type = protein
                       organism = Arabidopsis thaliana
SEQUENCE: 20
MILKCWSSRF LRVSPYQNAH SLSLG                                           25

SEQ ID NO: 21          moltype = AA  length = 13
FEATURE                Location/Qualifiers
source                 1..13
                       mol_type = protein
                       organism = Arabidopsis lyrata
SEQUENCE: 21
MPLAVIRQGI VWP                                                        13

SEQ ID NO: 22          moltype = AA  length = 24
FEATURE                Location/Qualifiers
source                 1..24
                       mol_type = protein
                       organism = Arabidopsis lyrata
SEQUENCE: 22
MPSWHDMVLL PYVKHTHANT RHIT                                            24

SEQ ID NO: 23          moltype = AA  length = 8
FEATURE                Location/Qualifiers
source                 1..8
                       mol_type = protein
                       organism = Arabidopsis lyrata
SEQUENCE: 23
```

```
MTWFFCLT                                                              8

SEQ ID NO: 24           moltype = AA  length = 37
FEATURE                 Location/Qualifiers
source                  1..37
                        mol_type = protein
                        organism = Arabidopsis thaliana
SEQUENCE: 24
MPSWHGMVLL PYVKHTHAST HTHTHNIYGC ACELVFH                              37

SEQ ID NO: 25           moltype = AA  length = 22
FEATURE                 Location/Qualifiers
source                  1..22
                        mol_type = protein
                        organism = Arabidopsis thaliana
SEQUENCE: 25
MAWYGSFALR KTHSRQHTHT HT                                              22

SEQ ID NO: 26           moltype = AA  length = 8
FEATURE                 Location/Qualifiers
source                  1..8
                        mol_type = protein
                        organism = Arabidopsis thaliana
SEQUENCE: 26
MVWFFCLT                                                              8

SEQ ID NO: 27           moltype = AA  length = 7
FEATURE                 Location/Qualifiers
source                  1..7
                        mol_type = protein
                        organism = Brassica rapa
SEQUENCE: 27
MMIILWK                                                               7

SEQ ID NO: 28           moltype = AA  length = 24
FEATURE                 Location/Qualifiers
source                  1..24
                        mol_type = protein
                        organism = Brassica rapa
SEQUENCE: 28
MLWAKLVSFS TLHSLVFLLS PSFA                                            24

SEQ ID NO: 29           moltype = AA  length = 29
FEATURE                 Location/Qualifiers
source                  1..29
                        mol_type = protein
                        organism = Brassica rapa
SEQUENCE: 29
MPSWHGIVIL PFVKHTHANI HYSYSCVCI                                       29

SEQ ID NO: 30           moltype = AA  length = 34
FEATURE                 Location/Qualifiers
source                  1..34
                        mol_type = protein
                        organism = Carica papaya
SEQUENCE: 30
MIACHPYLPF PLFLSLTFYS IFFSPSPPSP SLPL                                 34

SEQ ID NO: 31           moltype = AA  length = 53
FEATURE                 Location/Qualifiers
source                  1..53
                        mol_type = protein
                        organism = Carica papaya
SEQUENCE: 31
MPSLLAFSPF PFSNILLNLL LPLPPFPLSA IITIIKPLSL SLPLSLSLSG FSV             53

SEQ ID NO: 32           moltype = AA  length = 15
FEATURE                 Location/Qualifiers
source                  1..15
                        mol_type = protein
                        organism = Capsella rubella
SEQUENCE: 32
MELKGLRTWQ LLDKV                                                      15

SEQ ID NO: 33           moltype = AA  length = 14
FEATURE                 Location/Qualifiers
source                  1..14
                        mol_type = protein
                        organism = Capsella rubella
```

```
SEQUENCE: 33
MPSWHGMACF YCLT                                                   14

SEQ ID NO: 34          moltype = AA  length = 24
FEATURE                Location/Qualifiers
source                 1..24
                       mol_type = protein
                       organism = Capsella rubella
SEQUENCE: 34
MAWHGMFLLP YVKHTHANTY SLYM                                        24

SEQ ID NO: 35          moltype = AA  length = 35
FEATURE                Location/Qualifiers
source                 1..35
                       mol_type = protein
                       organism = Gossypium raimondii
SEQUENCE: 35
MMRSRILKFQ YRFGMGIGGR KQLKNQLCQI QGRIS                            35

SEQ ID NO: 36          moltype = AA  length = 10
FEATURE                Location/Qualifiers
source                 1..10
                       mol_type = protein
                       organism = Gossypium raimondii
SEQUENCE: 36
MSNSRSYQLK                                                        10

SEQ ID NO: 37          moltype = AA  length = 17
FEATURE                Location/Qualifiers
source                 1..17
                       mol_type = protein
                       organism = Gossypium raimondii
SEQUENCE: 37
MNEDLEISTR KRTPQLC                                                17

SEQ ID NO: 38          moltype = AA  length = 12
FEATURE                Location/Qualifiers
source                 1..12
                       mol_type = protein
                       organism = Medicago truncatula
SEQUENCE: 38
MPKFDIFFYI FV                                                     12

SEQ ID NO: 39          moltype = AA  length = 83
FEATURE                Location/Qualifiers
source                 1..83
                       mol_type = protein
                       organism = Medicago truncatula
SEQUENCE: 39
MSYISLSPKL LPINTKPFPW LVQFNFYFSS NTKCNKLHFL GEKLLVGEAG HVQILFLIHS  60
LIMHINIFCT CSPSPTRLPH PSL                                         83

SEQ ID NO: 40          moltype = AA  length = 20
FEATURE                Location/Qualifiers
source                 1..20
                       mol_type = protein
                       organism = Oryza sativa
SEQUENCE: 40
MQTHSNTPQS TYSLSLSLSE                                             20

SEQ ID NO: 41          moltype = AA  length = 15
FEATURE                Location/Qualifiers
source                 1..15
                       mol_type = protein
                       organism = Oryza sativa
SEQUENCE: 41
MCVCDINMHS MLMLL                                                  15

SEQ ID NO: 42          moltype = AA  length = 25
FEATURE                Location/Qualifiers
source                 1..25
                       mol_type = protein
                       organism = Arabidopsis lyrata
SEQUENCE: 42
MRIKLFQLRG MLSGSRILYI YTCVC                                       25

SEQ ID NO: 43          moltype = AA  length = 18
FEATURE                Location/Qualifiers
source                 1..18
```

```
                        mol_type = protein
                        organism = Arabidopsis thaliana
SEQUENCE: 43
MRVKLFQLRG MLSGSRIL                                                  18

SEQ ID NO: 44           moltype = AA  length = 36
FEATURE                 Location/Qualifiers
source                  1..36
                        mol_type = protein
                        organism = Brassica carinata
SEQUENCE: 44
MRMKLFQLRG MLSGSRILYI HKYVYMLIQV FDHICI                              36

SEQ ID NO: 45           moltype = AA  length = 27
FEATURE                 Location/Qualifiers
source                  1..27
                        mol_type = protein
                        organism = Brassica juncea
SEQUENCE: 45
MRMKLFQLRG MLSGSRILYI HKYVYIC                                        27

SEQ ID NO: 46           moltype = AA  length = 36
FEATURE                 Location/Qualifiers
source                  1..36
                        mol_type = protein
                        organism = Brassica napus
SEQUENCE: 46
MRMKLFQLRG MLSGSRILYI HKYVYMIIQV FDHICI                              36

SEQ ID NO: 47           moltype = AA  length = 36
FEATURE                 Location/Qualifiers
source                  1..36
                        mol_type = protein
                        organism = Brassica oleracea
SEQUENCE: 47
MRMKLFQLRG MLSGSRILYI HKYVYMLIQV FDHICI                              36

SEQ ID NO: 48           moltype = AA  length = 27
FEATURE                 Location/Qualifiers
source                  1..27
                        mol_type = protein
                        organism = Brassica rapa
SEQUENCE: 48
MRMKLFQLRG MLSGSRILYI HKYVYIC                                        27

SEQ ID NO: 49           moltype = AA  length = 19
FEATURE                 Location/Qualifiers
source                  1..19
                        mol_type = protein
                        organism = Arabidopsis thaliana
SEQUENCE: 49
MLDLFRSNNR IEPSDFRFD                                                 19

SEQ ID NO: 50           moltype = AA  length = 4
FEATURE                 Location/Qualifiers
source                  1..4
                        mol_type = protein
                        organism = Arabidopsis thaliana
SEQUENCE: 50
MRDR                                                                 4

SEQ ID NO: 51           moltype = AA  length = 10
FEATURE                 Location/Qualifiers
source                  1..10
                        mol_type = protein
                        organism = Arabidopsis thaliana
SEQUENCE: 51
MNRKISLSLS                                                           10

SEQ ID NO: 52           moltype = AA  length = 8
FEATURE                 Location/Qualifiers
source                  1..8
                        mol_type = protein
                        organism = Arabidopsis thaliana
SEQUENCE: 52
MMGCFVGF                                                             8

SEQ ID NO: 53           moltype = AA  length = 8
FEATURE                 Location/Qualifiers
```

```
source                  1..8
                        mol_type = protein
                        organism = Arabidopsis thaliana
SEQUENCE: 53
MQEETYEG                                                                  8

SEQ ID NO: 54           moltype = AA  length = 59
FEATURE                 Location/Qualifiers
source                  1..59
                        mol_type = protein
                        organism = Arabidopsis thaliana
SEQUENCE: 54
MPHTNLKDLF IFSPNVFFSF AIYLHNSWNK NYIHKRENFH NTSFALIFFF SSIMSINYG   59

SEQ ID NO: 55           moltype = AA  length = 39
FEATURE                 Location/Qualifiers
source                  1..39
                        mol_type = protein
                        organism = Arabidopsis thaliana
SEQUENCE: 55
MFFFRLLFIS TILGTKTTFT NERIFTTPLL LSFFFFRPL                         39

SEQ ID NO: 56           moltype = AA  length = 6
FEATURE                 Location/Qualifiers
source                  1..6
                        mol_type = protein
                        organism = Arabidopsis thaliana
SEQUENCE: 56
MRHKES                                                                    6

SEQ ID NO: 57           moltype = AA  length = 34
FEATURE                 Location/Qualifiers
source                  1..34
                        mol_type = protein
                        organism = Arabidopsis thaliana
SEQUENCE: 57
MNLLKKERQR RRQRSIGSHC IASLVLKDGY MKKI                              34

SEQ ID NO: 58           moltype = AA  length = 9
FEATURE                 Location/Qualifiers
source                  1..9
                        mol_type = protein
                        organism = Arabidopsis thaliana
SEQUENCE: 58
MVLSGKLTF                                                                 9

SEQ ID NO: 59           moltype = AA  length = 20
FEATURE                 Location/Qualifiers
source                  1..20
                        mol_type = protein
                        organism = Medicago truncatula
SEQUENCE: 59
MLLHRLSKFC KIERDIVYIS                                              20

SEQ ID NO: 60           moltype = AA  length = 5
FEATURE                 Location/Qualifiers
source                  1..5
                        mol_type = protein
                        organism = Medicago truncatula
SEQUENCE: 60
MKIEE                                                                     5

SEQ ID NO: 61           moltype = AA  length = 34
FEATURE                 Location/Qualifiers
source                  1..34
                        mol_type = protein
                        organism = Zea mays
SEQUENCE: 61
MHLPSTPSRP PPQHTSLSFL GKEMTKGTTT ACFG                              34

SEQ ID NO: 62           moltype = AA  length = 10
FEATURE                 Location/Qualifiers
source                  1..10
                        mol_type = protein
                        organism = Arabidopsis thaliana
SEQUENCE: 62
MLSLSHFHIC                                                         10

SEQ ID NO: 63           moltype = AA  length = 23
```

```
FEATURE                Location/Qualifiers
source                 1..23
                       mol_type = protein
                       organism = Medicago truncatula
SEQUENCE: 63
MMVFGKPKKA MLVRFNPKTD LHV                                          23

SEQ ID NO: 64          moltype = AA  length = 10
FEATURE                Location/Qualifiers
source                 1..10
                       mol_type = protein
                       organism = Medicago truncatula
SEQUENCE: 64
MASAAKVYMA                                                         10

SEQ ID NO: 65          moltype = AA  length = 6
FEATURE                Location/Qualifiers
source                 1..6
                       mol_type = protein
                       organism = Arabidopsis thaliana
SEQUENCE: 65
MASKIW                                                             6

SEQ ID NO: 66          moltype = AA  length = 10
FEATURE                Location/Qualifiers
source                 1..10
                       mol_type = protein
                       organism = Arabidopsis thaliana
SEQUENCE: 66
MVRFQLSIRD                                                         10

SEQ ID NO: 67          moltype = AA  length = 12
FEATURE                Location/Qualifiers
source                 1..12
                       mol_type = protein
                       organism = Arabidopsis thaliana
SEQUENCE: 67
MCTYYYLINK YF                                                      12

SEQ ID NO: 68          moltype = AA  length = 11
FEATURE                Location/Qualifiers
source                 1..11
                       mol_type = protein
                       organism = Arabidopsis thaliana
SEQUENCE: 68
MFPAKWCRLE S                                                       11

SEQ ID NO: 69          moltype = AA  length = 22
FEATURE                Location/Qualifiers
source                 1..22
                       mol_type = protein
                       organism = Arabidopsis thaliana
SEQUENCE: 69
MGSLSLFKSQ LEILMLLLSL SK                                           22

SEQ ID NO: 70          moltype = AA  length = 20
FEATURE                Location/Qualifiers
source                 1..20
                       mol_type = protein
                       organism = Arabidopsis thaliana
SEQUENCE: 70
MSVYIHVPIS LNCFSPKSSC                                              20

SEQ ID NO: 71          moltype = AA  length = 11
FEATURE                Location/Qualifiers
source                 1..11
                       mol_type = protein
                       organism = Arabidopsis thaliana
SEQUENCE: 71
MGVPNFRPRN R                                                       11

SEQ ID NO: 72          moltype = AA  length = 23
FEATURE                Location/Qualifiers
source                 1..23
                       mol_type = protein
                       organism = Arabidopsis cebennensis
SEQUENCE: 72
MRSRVSFFFF KIMLFRLLGY RSM                                          23
```

```
SEQ ID NO: 73          moltype = AA  length = 44
FEATURE                Location/Qualifiers
source                 1..44
                       mol_type = protein
                       organism = Arabidopsis cebennensis
SEQUENCE: 73
MHTYIHTISN ISSIFFCSKR SFSPFTYIRI IVVIDPFRIA LTFR                  44

SEQ ID NO: 74          moltype = AA  length = 22
FEATURE                Location/Qualifiers
source                 1..22
                       mol_type = protein
                       organism = Arabidopsis halleri
SEQUENCE: 74
MRSRVSLFLS FSSNFAAYSP RS                                          22

SEQ ID NO: 75          moltype = AA  length = 48
FEATURE                Location/Qualifiers
source                 1..48
                       mol_type = protein
                       organism = Arabidospis lyrata
SEQUENCE: 75
MHTYIPSSSF PISNISSVFF CYKRSFSPYT YIRIIVVIDP FRIALTFR              48

SEQ ID NO: 76          moltype = AA  length = 50
FEATURE                Location/Qualifiers
source                 1..50
                       mol_type = protein
                       organism = Arabidopsis thaliana
SEQUENCE: 76
MNIHTYHHLL FPSLVFHQSS DVPNALSLHI HTYEYIIVVI DPFRITLAFR            50

SEQ ID NO: 77          moltype = AA  length = 19
FEATURE                Location/Qualifiers
source                 1..19
                       mol_type = protein
                       organism = Arabidopsis thaliana
SEQUENCE: 77
MFQTLYLFIY IHTNILLLS                                              19

SEQ ID NO: 78          moltype = AA  length = 45
FEATURE                Location/Qualifiers
source                 1..45
                       mol_type = protein
                       organism = Brassica rapa
SEQUENCE: 78
MFKLYFSAIL STQYMHTYHH RIALIFLSIL YPSTNYLMSP ILNPT                 45

SEQ ID NO: 79          moltype = AA  length = 20
FEATURE                Location/Qualifiers
source                 1..20
                       mol_type = protein
                       organism = Carica papaya
SEQUENCE: 79
MKIKLGFSLI KIIILLDKNS                                             20

SEQ ID NO: 80          moltype = AA  length = 21
FEATURE                Location/Qualifiers
source                 1..21
                       mol_type = protein
                       organism = Capsella rubella
SEQUENCE: 80
MHPHTYIHIP SSSFLISSFC L                                           21

SEQ ID NO: 81          moltype = AA  length = 45
FEATURE                Location/Qualifiers
source                 1..45
                       mol_type = protein
                       organism = Eucalyptus grandis
SEQUENCE: 81
MKHIQRWRYG ETSGRQGDWK RLEIKVHSNP SLKVKKNTNN FSSSL                 45

SEQ ID NO: 82          moltype = AA  length = 28
FEATURE                Location/Qualifiers
source                 1..28
                       mol_type = protein
                       organism = Gossypium raimondii
SEQUENCE: 82
MIHFNLSQWR AICMANFHLT YSFLFGVL                                    28
```

```
SEQ ID NO: 83          moltype = AA  length = 21
FEATURE                Location/Qualifiers
source                 1..21
                       mol_type = protein
                       organism = Medicago truncatula
SEQUENCE: 83
MHVYLELFMV IKGLGFLLLV K                                      21

SEQ ID NO: 84          moltype = AA  length = 23
FEATURE                Location/Qualifiers
source                 1..23
                       mol_type = protein
                       organism = Oryza sativa
SEQUENCE: 84
MEMIQRPCLI LKFFFKLSTL YIP                                    23

SEQ ID NO: 85          moltype = AA  length = 38
FEATURE                Location/Qualifiers
source                 1..38
                       mol_type = protein
                       organism = Physcomitrella patens
SEQUENCE: 85
MFHRRRSSVL LPPFGQTQPN PRCLPDLRFP SCFTPCTA                    38

SEQ ID NO: 86          moltype = AA  length = 42
FEATURE                Location/Qualifiers
source                 1..42
                       mol_type = protein
                       organism = Thellungiella halophila
SEQUENCE: 86
MTICKVSKAC FYAGKIENSR LIKKIGIPKR EGAPFSPIRE NQ               42

SEQ ID NO: 87          moltype = AA  length = 37
FEATURE                Location/Qualifiers
source                 1..37
                       mol_type = protein
                       organism = Thellungiella halophila
SEQUENCE: 87
MEIQIKKKNL YIMNTQKLPN LYIYIYKYVF IKLMVVE                     37

SEQ ID NO: 88          moltype = AA  length = 43
FEATURE                Location/Qualifiers
source                 1..43
                       mol_type = protein
                       organism = Arabidopsis thaliana
SEQUENCE: 88
MVPQINLWSS RVILKIRIDS STHREEDHCI QNHKHGLSFI FSF              43

SEQ ID NO: 89          moltype = AA  length = 16
FEATURE                Location/Qualifiers
source                 1..16
                       mol_type = protein
                       organism = Arabidopsis thaliana
SEQUENCE: 89
MSLQFYERVS FKNTVK                                            16

SEQ ID NO: 90          moltype = AA  length = 12
FEATURE                Location/Qualifiers
source                 1..12
                       mol_type = protein
                       organism = Arabidopsis thaliana
SEQUENCE: 90
MTEQEEESQM ST                                                12

SEQ ID NO: 91          moltype = AA  length = 39
FEATURE                Location/Qualifiers
source                 1..39
                       mol_type = protein
                       organism = Arabidopsis thaliana
SEQUENCE: 91
MYLQYIDNVI SIYSNNRRVG RMFSRVPLST SLEIQFFIK                   39

SEQ ID NO: 92          moltype = AA  length = 12
FEATURE                Location/Qualifiers
source                 1..12
                       mol_type = protein
                       organism = Arabidopsis thaliana
SEQUENCE: 92
```

```
MSKEIFFSPG FE                                                    12

SEQ ID NO: 93           moltype = AA  length = 44
FEATURE                 Location/Qualifiers
source                  1..44
                        mol_type = protein
                        organism = Arabidopsis thaliana
SEQUENCE: 93
MRTHEQSTAI TTLRHCYSSR FMCSQVTPAE LFLYRPCFIN AVAR                 44

SEQ ID NO: 94           moltype = AA  length = 5
FEATURE                 Location/Qualifiers
source                  1..5
                        mol_type = protein
                        organism = Arabidopsis thaliana
SEQUENCE: 94
MKRNM                                                            5

SEQ ID NO: 95           moltype = AA  length = 5
FEATURE                 Location/Qualifiers
source                  1..5
                        mol_type = protein
                        organism = Arabidopsis thaliana
SEQUENCE: 95
MQCEI                                                            5

SEQ ID NO: 96           moltype = AA  length = 4
FEATURE                 Location/Qualifiers
source                  1..4
                        mol_type = protein
                        organism = Arabidopsis thaliana
SEQUENCE: 96
MFCA                                                             4

SEQ ID NO: 97           moltype = AA  length = 6
FEATURE                 Location/Qualifiers
source                  1..6
                        mol_type = protein
                        organism = Arabidopsis thaliana
SEQUENCE: 97
MVMAHH                                                           6

SEQ ID NO: 98           moltype = AA  length = 54
FEATURE                 Location/Qualifiers
source                  1..54
                        mol_type = protein
                        organism = Arabidopsis thaliana
SEQUENCE: 98
MMKPRWNCSL YGITEWTNNQ NQKSKRKGRR KTQIWRIGDR LDTVECITLM LSAY      54

SEQ ID NO: 99           moltype = AA  length = 10
FEATURE                 Location/Qualifiers
source                  1..10
                        mol_type = protein
                        organism = Arabidopsis thaliana
SEQUENCE: 99
MLLIIVELVL                                                       10

SEQ ID NO: 100          moltype = AA  length = 14
FEATURE                 Location/Qualifiers
source                  1..14
                        mol_type = protein
                        organism = Arabidopsis thaliana
SEQUENCE: 100
MLCFNFRCVR RFAE                                                  14

SEQ ID NO: 101          moltype = AA  length = 36
FEATURE                 Location/Qualifiers
source                  1..36
                        mol_type = protein
                        organism = Arabidopsis thaliana
SEQUENCE: 101
MYTYQLDNSF SWFLCTRFCL YRYFLFNFRC FRRFSE                          36

SEQ ID NO: 102          moltype = AA  length = 88
FEATURE                 Location/Qualifiers
source                  1..88
                        mol_type = protein
                        organism = Drosophila melanogaster
```

```
SEQUENCE: 102
MWREVCAQKS QTKRRNFITG NQRRNKTKAN RKAETKQQKV YEFFVQARER CKTRKKHEKK  60
TLKKTKKIQN RYRAVSENEW GKGFPSHI                                    88

SEQ ID NO: 103         moltype = AA  length = 36
FEATURE                Location/Qualifiers
source                 1..36
                       mol_type = protein
                       organism = Drosophila melanogaster
SEQUENCE: 103
MRTKKSNKKA QFYYGQPTTK QNKSQPKSRN KAAKSL                            36

SEQ ID NO: 104         moltype = AA  length = 71
FEATURE                Location/Qualifiers
source                 1..71
                       mol_type = protein
                       organism = Drosophila melanogaster
SEQUENCE: 104
MEPGFVFVLF PTHLSTQHTQ REKSILVMGL NLQSAKQSDK QNSKERKKNT QINSQRIPYR  60
QGGQCSKVLS P                                                       71

SEQ ID NO: 105         moltype = DNA  length = 92
FEATURE                Location/Qualifiers
source                 1..92
                       mol_type = unassigned DNA
                       organism = Arabidopsis thaliana
SEQUENCE: 105
atgttctgtt caattcaatg cgtcgccaga catctgttcc ctttgcatgt aagagagata  60
aagaaagcga caagagccat aaagaaaggt aa                                92

SEQ ID NO: 106         moltype = DNA  length = 75
FEATURE                Location/Qualifiers
source                 1..75
                       mol_type = unassigned DNA
                       organism = Arabidopsis thaliana
SEQUENCE: 106
atgcgtcgcc agacatctgt tccctttgca tgtaagagag ataaagaaag cgacaagagc  60
cataaagaaa ggtaa                                                   75

SEQ ID NO: 107         moltype = DNA  length = 114
FEATURE                Location/Qualifiers
source                 1..114
                       mol_type = unassigned DNA
                       organism = Arabidopsis thaliana
SEQUENCE: 107
atggttatgt tttttctcga tttagacaaa aaccctagat ttgatcttct aaagggtctc  60
aaatggaatc tcttctcttc tcatatctct ccctctctcc ctccctctct ttga        114

SEQ ID NO: 108         moltype = DNA  length = 36
FEATURE                Location/Qualifiers
source                 1..36
                       mol_type = unassigned DNA
                       organism = Arabidopsis thaliana
SEQUENCE: 108
atgaaggaca actttcctct tctccttcgg ttataa                            36

SEQ ID NO: 109         moltype = DNA  length = 15
FEATURE                Location/Qualifiers
source                 1..15
                       mol_type = unassigned DNA
                       organism = Arabidopsis thaliana
SEQUENCE: 109
atgagtgatg actga                                                   15

SEQ ID NO: 110         moltype = DNA  length = 51
FEATURE                Location/Qualifiers
source                 1..51
                       mol_type = unassigned DNA
                       organism = Arabidopsis thaliana
SEQUENCE: 110
atgatatata taaataaata tgggtcgata tcggctgtgg aggacgacta g           51

SEQ ID NO: 111         moltype = DNA  length = 15
FEATURE                Location/Qualifiers
source                 1..15
                       mol_type = unassigned DNA
                       organism = Arabidopsis thaliana
SEQUENCE: 111
atgagccaaa gataa                                                   15
```

```
SEQ ID NO: 112          moltype = DNA  length = 51
FEATURE                 Location/Qualifiers
source                  1..51
                        mol_type = unassigned DNA
                        organism = Arabidopsis lyrata
SEQUENCE: 112
atgacgtgtc ctcttctctc tctctctttc cttctctcta agtatattta g          51

SEQ ID NO: 113          moltype = DNA  length = 51
FEATURE                 Location/Qualifiers
source                  1..51
                        mol_type = unassigned DNA
                        organism = Arabidopsis thaliana
SEQUENCE: 113
atgacgtggc ctcttctctc tctctctttc cttctctcta agtatgttta g          51

SEQ ID NO: 114          moltype = DNA  length = 53
FEATURE                 Location/Qualifiers
source                  1..53
                        mol_type = unassigned DNA
                        organism = Capsella rubella
SEQUENCE: 114
atgacgtgta ctctctctgc tctatctctc tctctaaata tgtttagggt taa        53

SEQ ID NO: 115          moltype = DNA  length = 18
FEATURE                 Location/Qualifiers
source                  1..18
                        mol_type = unassigned DNA
                        organism = Arabidopsis thaliana
SEQUENCE: 115
atgttttatc tttcataa                                               18

SEQ ID NO: 116          moltype = DNA  length = 114
FEATURE                 Location/Qualifiers
source                  1..114
                        mol_type = unassigned DNA
                        organism = Arabidopsis thaliana
SEQUENCE: 116
atggttaata ctagtagctt tttcatttca agttttatcc ttccattggt tctttctgag  60
tcaaattgtc tcctgtttcg aaccatatat aagttttcaa tggttttgta ttaa        114

SEQ ID NO: 117          moltype = DNA  length = 75
FEATURE                 Location/Qualifiers
source                  1..75
                        mol_type = unassigned DNA
                        organism = Arabidopsis thaliana
SEQUENCE: 117
atgttttgtt tgttgattcc catcttctct tttgtctttt caccaaatcg tcatttaagg  60
cttcaagaac agtaa                                                  75

SEQ ID NO: 118          moltype = DNA  length = 18
FEATURE                 Location/Qualifiers
source                  1..18
                        mol_type = unassigned DNA
                        organism = Arabidopsis thaliana
SEQUENCE: 118
atgttttccc ctcaatga                                               18

SEQ ID NO: 119          moltype = DNA  length = 72
FEATURE                 Location/Qualifiers
source                  1..72
                        mol_type = unassigned DNA
                        organism = Arabidopsis thaliana
SEQUENCE: 119
atgaaataca tacacatttt gattttattt aaatcaagat cgacgtataa gctatccacc  60
aatcatattt aa                                                     72

SEQ ID NO: 120          moltype = DNA  length = 33
FEATURE                 Location/Qualifiers
source                  1..33
                        mol_type = unassigned DNA
                        organism = Arabidopsis thaliana
SEQUENCE: 120
atgaaaattc cattgtttct gccgaagctt tga                              33

SEQ ID NO: 121          moltype = DNA  length = 84
FEATURE                 Location/Qualifiers
source                  1..84
```

```
                        mol_type = unassigned DNA
                        organism = Arabidopsis thaliana
SEQUENCE: 121
atggtatctg gtcaagaaga ttcctggtta aaactttcat ctctctgttt cctttttctt  60
tctttgttgg attcattaat ttga                                          84

SEQ ID NO: 122          moltype = DNA  length = 105
FEATURE                 Location/Qualifiers
source                  1..105
                        mol_type = unassigned DNA
                        organism = Arabidopsis thaliana
SEQUENCE: 122
atgtttcttt taatcttttt gagattaata atgatttgtg tttgttcatc aaccgatttt  60
ctcagatctg tcaattattt ttgtttattt atttatgatt tatga                   105

SEQ ID NO: 123          moltype = DNA  length = 30
FEATURE                 Location/Qualifiers
source                  1..30
                        mol_type = unassigned DNA
                        organism = Arabidopsis thaliana
SEQUENCE: 123
atgtccacta ctcaagagca taggtcttga                                    30

SEQ ID NO: 124          moltype = DNA  length = 78
FEATURE                 Location/Qualifiers
source                  1..78
                        mol_type = unassigned DNA
                        organism = Arabidopsis thaliana
SEQUENCE: 124
atgatactaa agtgctggag ttcccggttc ctgagagtga gtccatatca aaatgcgcat  60
tcgttatcac ttggttga                                                 78

SEQ ID NO: 125          moltype = DNA  length = 42
FEATURE                 Location/Qualifiers
source                  1..42
                        mol_type = unassigned DNA
                        organism = Arabidopsis lyrata
SEQUENCE: 125
atgcccttag cagttattag acaagggatt gtttggccct ag                      42

SEQ ID NO: 126          moltype = DNA  length = 75
FEATURE                 Location/Qualifiers
source                  1..75
                        mol_type = unassigned DNA
                        organism = Arabidopsis lyrata
SEQUENCE: 126
atgccatcat ggcatgacat ggttcttttg ccttacgtaa aacacactca cgccaacaca  60
cgccacataa cataa                                                    75

SEQ ID NO: 127          moltype = DNA  length = 27
FEATURE                 Location/Qualifiers
source                  1..27
                        mol_type = unassigned DNA
                        organism = Arabidopsis lyrata
SEQUENCE: 127
atgacatggt tcttttgcct tacgtaa                                       27

SEQ ID NO: 128          moltype = DNA  length = 114
FEATURE                 Location/Qualifiers
source                  1..114
                        mol_type = unassigned DNA
                        organism = Arabidopsis thaliana
SEQUENCE: 128
atgccatcat ggcatggtat ggttcttttg ccttacgtaa aacacactca cgccagcaca  60
cacacacaca cacataacat atacggatgt gcgtgtgagc tagtcttcca ttaa         114

SEQ ID NO: 129          moltype = DNA  length = 69
FEATURE                 Location/Qualifiers
source                  1..69
                        mol_type = unassigned DNA
                        organism = Arabidopsis thaliana
SEQUENCE: 129
atggcatggt atggttcttt tgccttacgt aaaacacact cacgccagca cacacacaca  60
cacacataa                                                           69

SEQ ID NO: 130          moltype = DNA  length = 27
FEATURE                 Location/Qualifiers
source                  1..27
                        mol_type = unassigned DNA
```

```
                        organism = Arabidopsis thaliana
SEQUENCE: 130
atggtatggt tcttttgcct tacgtaa                                     27

SEQ ID NO: 131          moltype = DNA  length = 24
FEATURE                 Location/Qualifiers
source                  1..24
                        mol_type = unassigned DNA
                        organism = Brassica rapa
SEQUENCE: 131
atgatgataa ttttgtggaa ataa                                        24

SEQ ID NO: 132          moltype = DNA  length = 75
FEATURE                 Location/Qualifiers
source                  1..75
                        mol_type = unassigned DNA
                        organism = Brassica rapa
SEQUENCE: 132
atgctttggg ccaagctagt ttcttttagc actcttcact cactagtttt tcttctcagc  60
ccttcttttg cgtga                                                  75

SEQ ID NO: 133          moltype = DNA  length = 120
FEATURE                 Location/Qualifiers
source                  1..120
                        mol_type = unassigned DNA
                        organism = Brassica rapa
SEQUENCE: 133
atgccatcat ggcatggcat tgtcattttg cctttcgtaa aacacactca cgccaacata  60
cattattcat attcatgtgt atgtatatga atgccatcat ggcatatgcc atcatggcat  120

SEQ ID NO: 134          moltype = DNA  length = 105
FEATURE                 Location/Qualifiers
source                  1..105
                        mol_type = unassigned DNA
                        organism = Carica papaya
SEQUENCE: 134
atgattgcat gccatcccta cttgcctttt cccctttttcc tttctctaac attttactca  60
atcttcttct ccccctcccc cccttccccc tctctgccat tataa                 105

SEQ ID NO: 135          moltype = DNA  length = 162
FEATURE                 Location/Qualifiers
source                  1..162
                        mol_type = unassigned DNA
                        organism = Carica papaya
SEQUENCE: 135
atgccatccc tacttgcctt ttccccttttt cctttctcta acattttact caatcttctt  60
ctccccctcc ccccttccc cctctctgcc attataacca taattaaacc tctctccctc  120
tctctccctc tctctctctc tctctctggg ttctcagtat aa                    162

SEQ ID NO: 136          moltype = DNA  length = 48
FEATURE                 Location/Qualifiers
source                  1..48
                        mol_type = unassigned DNA
                        organism = Capsella rubella
SEQUENCE: 136
atggaattaa aaggtttgag aacttggcag ttattagaca aggtatag              48

SEQ ID NO: 137          moltype = DNA  length = 45
FEATURE                 Location/Qualifiers
source                  1..45
                        mol_type = unassigned DNA
                        organism = Capsella rubella
SEQUENCE: 137
atgccatcat ggcatggcat ggcatgtttc tattgcctta cgtaa                 45

SEQ ID NO: 138          moltype = DNA  length = 90
FEATURE                 Location/Qualifiers
source                  1..90
                        mol_type = unassigned DNA
                        organism = Capsella rubella
SEQUENCE: 138
atggcatggc atgtttctat tgccttacgt aaaacacact cacgccaaca catactcact  60
atacatgtaa ataagtatgt gcgcgtgtga                                  90

SEQ ID NO: 139          moltype = DNA  length = 108
FEATURE                 Location/Qualifiers
source                  1..108
                        mol_type = unassigned DNA
                        organism = Gossypium raimondii
```

```
SEQUENCE: 139
atgatgagat caagaatttt aaagtttcaa tatagatttg gcatgggtat tggcggcaga  60
aagcaattaa aaaaccagtt atgtcaaatt caaggtcgta tcagttaa              108

SEQ ID NO: 140         moltype = DNA  length = 33
FEATURE                Location/Qualifiers
source                 1..33
                       mol_type = unassigned DNA
                       organism = Gossypium raimondii
SEQUENCE: 140
atgtcaaatt caaggtcgta tcagttaaaa tga                              33

SEQ ID NO: 141         moltype = DNA  length = 54
FEATURE                Location/Qualifiers
source                 1..54
                       mol_type = unassigned DNA
                       organism = Gossypium raimondii
SEQUENCE: 141
atgaatgaag atttagaaat ttcaacaagg aagaggaccc cacagctttg ttaa        54

SEQ ID NO: 142         moltype = DNA  length = 39
FEATURE                Location/Qualifiers
source                 1..39
                       mol_type = unassigned DNA
                       organism = Medicago truncatula
SEQUENCE: 142
atgcccaaat ttgatatttt tttttatata tttgtatag                        39

SEQ ID NO: 143         moltype = DNA  length = 231
FEATURE                Location/Qualifiers
source                 1..231
                       mol_type = unassigned DNA
                       organism = Medicago truncatula
SEQUENCE: 143
atgtcatata tctctctctc tcctaagttg ctacctataa atactaagcc tttcccttgg  60
ttggttcaat tcaacttcta cttctcatca aacacaaagt gcaataagct tcatttcctg  120
ggtgagaagc tccttgttgg agaagcaggg cacgtgcaaa tcctctttct gattcattct  180
ctcataatgc atatcaatat cttttgcacg tgctcccctt ctccaactag g          231

SEQ ID NO: 144         moltype = DNA  length = 63
FEATURE                Location/Qualifiers
source                 1..63
                       mol_type = unassigned DNA
                       organism = Oryza sativa
SEQUENCE: 144
atgcaaaccc actccaacac tccacaatcc acatactctc tctctctctc tctctctgag  60
tag                                                               63

SEQ ID NO: 145         moltype = DNA  length = 48
FEATURE                Location/Qualifiers
source                 1..48
                       mol_type = unassigned DNA
                       organism = Oryza sativa
SEQUENCE: 145
atgtgtgtgt gtgatatcaa tatgcattcg atgttgatgc tactgtag              48

SEQ ID NO: 146         moltype = DNA  length = 78
FEATURE                Location/Qualifiers
source                 1..78
                       mol_type = unassigned DNA
                       organism = Arabidopsis lyrata
SEQUENCE: 146
atgagaatta agctatttca gttgaggga atgttgtctg gatcgaggat attatacata  60
tatacatgtg tatgttga                                               78

SEQ ID NO: 147         moltype = DNA  length = 57
FEATURE                Location/Qualifiers
source                 1..57
                       mol_type = unassigned DNA
                       organism = Arabidopsis thaliana
SEQUENCE: 147
atgagggtta agctatttca gttgagggga atgttgtctg gatcgaggat attatag     57

SEQ ID NO: 148         moltype = DNA  length = 111
FEATURE                Location/Qualifiers
source                 1..111
                       mol_type = unassigned DNA
                       organism = Brassica carinata
SEQUENCE: 148
```

```
atgagaatga agctatttca gttgagggga atgttgtctg gatcgaggat attatatata  60
cacaaatacg tatatatgtt aatacaagtg tttgatcata tatgtatata g           111

SEQ ID NO: 149         moltype = DNA  length = 84
FEATURE                Location/Qualifiers
source                 1..84
                       mol_type = unassigned DNA
                       organism = Brassica juncea
SEQUENCE: 149
atgagaatga agctatttca gttgagggga atgttgtctg gatcgaggat attatatata  60
cacaaatatg tatatatatg ttaa                                         84

SEQ ID NO: 150         moltype = DNA  length = 111
FEATURE                Location/Qualifiers
source                 1..111
                       mol_type = unassigned DNA
                       organism = Brassica napus
SEQUENCE: 150
atgagaatga agctatttca gttgagggga atgttgtctg gatcgaggat attatatata  60
cacaaatacg tatatatgat aatacaagtg tttgatcata tatgtatata g           111

SEQ ID NO: 151         moltype = DNA  length = 111
FEATURE                Location/Qualifiers
source                 1..111
                       mol_type = unassigned DNA
                       organism = Brassica oleracea
SEQUENCE: 151
atgagaatga agctatttca gttgagggga atgttgtctg gatcgaggat attatatata  60
cacaagtacg tatatatgtt aatacaagtg tttgatcata tatgtatata g           111

SEQ ID NO: 152         moltype = DNA  length = 84
FEATURE                Location/Qualifiers
source                 1..84
                       mol_type = unassigned DNA
                       organism = Brassica rapa
SEQUENCE: 152
atgagaatga agctatttca gttgagggga atgttgtctg gatcgaggat attatatata  60
cacaaatatg tatatatatg ttaa                                         84

SEQ ID NO: 153         moltype = DNA  length = 60
FEATURE                Location/Qualifiers
source                 1..60
                       mol_type = unassigned DNA
                       organism = Arabidopsis thaliana
SEQUENCE: 153
atgttggatc tctttcgatc taacaatcga attgaacctt cagatttcag atttgattag  60

SEQ ID NO: 154         moltype = DNA  length = 15
FEATURE                Location/Qualifiers
source                 1..15
                       mol_type = unassigned DNA
                       organism = Arabidopsis thaliana
SEQUENCE: 154
atgagagata gataa                                                   15

SEQ ID NO: 155         moltype = DNA  length = 33
FEATURE                Location/Qualifiers
source                 1..33
                       mol_type = unassigned DNA
                       organism = Arabidopsis thaliana
SEQUENCE: 155
atgaacagaa aaatctctct ttctctttct tga                               33

SEQ ID NO: 156         moltype = DNA  length = 27
FEATURE                Location/Qualifiers
source                 1..27
                       mol_type = unassigned DNA
                       organism = Arabidopsis thaliana
SEQUENCE: 156
atgatgggtt gttttgtggg attttaa                                      27

SEQ ID NO: 157         moltype = DNA  length = 27
FEATURE                Location/Qualifiers
source                 1..27
                       mol_type = unassigned DNA
                       organism = Arabidopsis thaliana
SEQUENCE: 157
atgcaggagg aaacatatga ggggtga                                      27
```

```
SEQ ID NO: 158         moltype = DNA  length = 180
FEATURE                Location/Qualifiers
source                 1..180
                       mol_type = unassigned DNA
                       organism = Arabidopsis thaliana
SEQUENCE: 158
atgccacata caaacttgaa agatctcttc atcttttctc caaatgtttt tttttcgttt  60
gctatttatc tccacaattc ttggaacaaa aactacattc acaaacgaga gaattttcac  120
aacacctctt ttgctctcat ttttttttt tcgtccatta tgagtattaa ttatggttag  180

SEQ ID NO: 159         moltype = DNA  length = 120
FEATURE                Location/Qualifiers
source                 1..120
                       mol_type = unassigned DNA
                       organism = Arabidopsis thaliana
SEQUENCE: 159
atgttttttt ttcgtttgct atttatctcc acaattcttg gaacaaaaac tacattcaca  60
aacgagagaa ttttcacaac acctcttttg ctctcatttt ttttttttcg tccattatga  120

SEQ ID NO: 160         moltype = DNA  length = 21
FEATURE                Location/Qualifiers
source                 1..21
                       mol_type = unassigned DNA
                       organism = Arabidopsis thaliana
SEQUENCE: 160
atgagacata aagagagtta a                                           21

SEQ ID NO: 161         moltype = DNA  length = 105
FEATURE                Location/Qualifiers
source                 1..105
                       mol_type = unassigned DNA
                       organism = Arabidopsis thaliana
SEQUENCE: 161
atgaacctcc tcaagaagga aagacagagg aggagacaaa gaagtatagg ttcacattgc  60
atagccagtt tagttttgaa ggatggatat atgaaaaaaa tatga                 105

SEQ ID NO: 162         moltype = DNA  length = 30
FEATURE                Location/Qualifiers
source                 1..30
                       mol_type = unassigned DNA
                       organism = Arabidopsis thaliana
SEQUENCE: 162
atggttctct ccggtaaatt aacattttag                                  30

SEQ ID NO: 163         moltype = DNA  length = 63
FEATURE                Location/Qualifiers
source                 1..63
                       mol_type = unassigned DNA
                       organism = Medicago truncatula
SEQUENCE: 163
atgcttcttc ataggctctc caaattttgc aaaattgaaa gagacatagt atatatatct  60
tag                                                               63

SEQ ID NO: 164         moltype = DNA  length = 18
FEATURE                Location/Qualifiers
source                 1..18
                       mol_type = unassigned DNA
                       organism = Medicago truncatula
SEQUENCE: 164
atgaagattg aagagtaa                                               18

SEQ ID NO: 165         moltype = DNA  length = 105
FEATURE                Location/Qualifiers
source                 1..105
                       mol_type = unassigned DNA
                       organism = Zea mays
SEQUENCE: 165
atgcatctgc cttcaactcc ctctcgcccc ccaccccaac acacatctct ctcttttcta  60
gggaaggaaa tgacgaaggg gacgacgacg gcatgcttcg gctag                 105

SEQ ID NO: 166         moltype = DNA  length = 33
FEATURE                Location/Qualifiers
source                 1..33
                       mol_type = unassigned DNA
                       organism = Arabidopsis thaliana
SEQUENCE: 166
atgttgtctc tttctcattt tcatatctgc taa                              33

SEQ ID NO: 167         moltype = DNA  length = 72
```

```
FEATURE                Location/Qualifiers
source                 1..72
                       mol_type = unassigned DNA
                       organism = Medicago truncatula
SEQUENCE: 167
atgatggtgt ttgggaagcc gaaaaaagcg atgttggtga ggttcaatcc gaagacggat  60
ttacatgtat ag                                                      72

SEQ ID NO: 168         moltype = DNA  length = 33
FEATURE                Location/Qualifiers
source                 1..33
                       mol_type = unassigned DNA
                       organism = Medicago truncatula
SEQUENCE: 168
atggcttcag ctgcaaaagt atacatggcg tga                               33

SEQ ID NO: 169         moltype = DNA  length = 21
FEATURE                Location/Qualifiers
source                 1..21
                       mol_type = unassigned DNA
                       organism = Arabidopsis thaliana
SEQUENCE: 169
atggcttcca agatctggta a                                            21

SEQ ID NO: 170         moltype = DNA  length = 33
FEATURE                Location/Qualifiers
source                 1..33
                       mol_type = unassigned DNA
                       organism = Arabidopsis thaliana
SEQUENCE: 170
atggttaggt tccaactaag tatacgagat taa                               33

SEQ ID NO: 171         moltype = DNA  length = 39
FEATURE                Location/Qualifiers
source                 1..39
                       mol_type = unassigned DNA
                       organism = Arabidopsis thaliana
SEQUENCE: 171
atgtgtacgt actattatct cataaataaa tatttttaa                         39

SEQ ID NO: 172         moltype = DNA  length = 36
FEATURE                Location/Qualifiers
source                 1..36
                       mol_type = unassigned DNA
                       organism = Arabidopsis thaliana
SEQUENCE: 172
atgtttccag caaaatggtg ccgtcttgag tcttga                            36

SEQ ID NO: 173         moltype = DNA  length = 69
FEATURE                Location/Qualifiers
source                 1..69
                       mol_type = unassigned DNA
                       organism = Arabidopsis thaliana
SEQUENCE: 173
atgggatctc tctctttatt taaaagtcaa ttagagatct tgatgctact tctgtccctt  60
tccaagtga                                                          69

SEQ ID NO: 174         moltype = DNA  length = 63
FEATURE                Location/Qualifiers
source                 1..63
                       mol_type = unassigned DNA
                       organism = Arabidopsis thaliana
SEQUENCE: 174
atgagtgtat atattcatgt acctatctct ctcaattgct tctcaccaaa atcatcttgc  60
tga                                                                63

SEQ ID NO: 175         moltype = DNA  length = 36
FEATURE                Location/Qualifiers
source                 1..36
                       mol_type = unassigned DNA
                       organism = Arabidopsis thaliana
SEQUENCE: 175
atgggagttc ccaactttag acctcgaaac cgataa                            36

SEQ ID NO: 176         moltype = DNA  length = 72
FEATURE                Location/Qualifiers
source                 1..72
                       mol_type = unassigned DNA
                       organism = Arabidopsis cebennensis
```

```
SEQUENCE: 176
atgagatcta gggtttcttt ctttttcttc aaaatcatgc tttttcgctt gctaggttat  60
agatccatgt aa                                                       72

SEQ ID NO: 177         moltype = DNA  length = 134
FEATURE                Location/Qualifiers
source                 1..134
                       mol_type = unassigned DNA
                       organism = Arabidopsis cebennensis
SEQUENCE: 177
atgcatacat acatacatac catctctaat atttcatcaa tcttcttttg ttccaaacgc  60
ctttctctcc atttacatac atacgaatca ttgttgtcat agatccgttt agaattgctt  120
taacttttag atga                                                     134

SEQ ID NO: 178         moltype = DNA  length = 69
FEATURE                Location/Qualifiers
source                 1..69
                       mol_type = unassigned DNA
                       organism = Arabidopsis halleri
SEQUENCE: 178
atgagatcta gggtttcttt gtttctttcg ttttcttcaa attttgctgc atattctcca  60
agatcatga                                                           69

SEQ ID NO: 179         moltype = DNA  length = 147
FEATURE                Location/Qualifiers
source                 1..147
                       mol_type = unassigned DNA
                       organism = Arabidospis lyrata
SEQUENCE: 179
atgcatacat acataccatc atcatctttt cccatctcta atatttcatc agtcttcttt  60
tgttacaaac gctctttctc gccatataca tacataagaa tcattgttgt catagatccg  120
tttagaattg ctttaacttt tagatga                                       147

SEQ ID NO: 180         moltype = DNA  length = 153
FEATURE                Location/Qualifiers
source                 1..153
                       mol_type = unassigned DNA
                       organism = Arabidopsis thaliana
SEQUENCE: 180
atgaatatac atacatacca tcatcttctt ttcccatctc tagtttttca tcaatcttct  60
gatgttccaa acgctctatc tcttcatata catacatacg aatatattat tgttgtcata  120
gatccattta gaatcacttt agcttttaga tga                                153

SEQ ID NO: 181         moltype = DNA  length = 60
FEATURE                Location/Qualifiers
source                 1..60
                       mol_type = unassigned DNA
                       organism = Arabidopsis thaliana
SEQUENCE: 181
atgttccaaa cgctctatct cttcatatac atacatacga atatattatt gttgtcatag  60

SEQ ID NO: 182         moltype = DNA  length = 138
FEATURE                Location/Qualifiers
source                 1..138
                       mol_type = unassigned DNA
                       organism = Brassica rapa
SEQUENCE: 182
atgtttaagc tctacttctc agcaattctc tccacccaat acatgcatac ataccatcat  60
cgtatcgctc taatttttct atcaatcttg tatccttcca caaattatct tatgtctccc  120
attttaaatc ctacatag                                                 138

SEQ ID NO: 183         moltype = DNA  length = 63
FEATURE                Location/Qualifiers
source                 1..63
                       mol_type = unassigned DNA
                       organism = Carica papaya
SEQUENCE: 183
atgaagatta aattaggttt tagtcttatt aagattatta tattactaga caaaaacagt  60
taa                                                                 63

SEQ ID NO: 184         moltype = DNA  length = 66
FEATURE                Location/Qualifiers
source                 1..66
                       mol_type = unassigned DNA
                       organism = Capsella rubella
SEQUENCE: 184
atgcatccac atacatacat acatatacca tcatcttctt ttctcatctc tagtttttgt  60
ttataa                                                              66
```

```
SEQ ID NO: 185          moltype = DNA  length = 138
FEATURE                 Location/Qualifiers
source                  1..138
                        mol_type = unassigned DNA
                        organism = Eucalyptus grandis
SEQUENCE: 185
atgaagcata ttcaaaggtg gagatatggg gagacttccg gaaggcaagg ggattggaaa  60
aggctcgaga tcaaagtgca tagcaaccct tcgctaaagg tgaaaaagaa tacgaataac  120
ttcagtagct cactttaa                                                138

SEQ ID NO: 186          moltype = DNA  length = 87
FEATURE                 Location/Qualifiers
source                  1..87
                        mol_type = unassigned DNA
                        organism = Gossypium raimondii
SEQUENCE: 186
atgatccatt tcaacctgtc acagtggaga gcaatttgta tggctaattt ccatctcacc  60
tattcttttc tgtttggggt tctctag                                      87

SEQ ID NO: 187          moltype = DNA  length = 66
FEATURE                 Location/Qualifiers
source                  1..66
                        mol_type = unassigned DNA
                        organism = Medicago truncatula
SEQUENCE: 187
atgcatgtat atcttgaatt gtttatggta ataaaggggt taggatttct ccttttggtg  60
aagtga                                                             66

SEQ ID NO: 188          moltype = DNA  length = 72
FEATURE                 Location/Qualifiers
source                  1..72
                        mol_type = unassigned DNA
                        organism = Oryza sativa
SEQUENCE: 188
atggaaatga tacaaaggcc gtgtttaatt ttaaaatttt ttttcaaact ttcaacactt  60
tacatcccat aa                                                      72

SEQ ID NO: 189          moltype = DNA  length = 117
FEATURE                 Location/Qualifiers
source                  1..117
                        mol_type = unassigned DNA
                        organism = Physcomitrella patens
SEQUENCE: 189
atgttccacc gtcggagatc ctcggtgctg ctacccccgt tcggccaaac ccaacccaac  60
cctaggtgtc tgccggacct ccgcttcccc tcctgcttca ccccctgcac cgcttaa     117

SEQ ID NO: 190          moltype = DNA  length = 129
FEATURE                 Location/Qualifiers
source                  1..129
                        mol_type = unassigned DNA
                        organism = Thellungiella halophila
SEQUENCE: 190
atgacgatat gtaaagtaag caaggcatgt ttttatgcag ggaagattga aaattcaaga  60
ttaatcaaga aaattggaat accaaaaaga gagggagctc ccttcagtcc aatcagagag  120
aatcaatga                                                          129

SEQ ID NO: 191          moltype = DNA  length = 114
FEATURE                 Location/Qualifiers
source                  1..114
                        mol_type = unassigned DNA
                        organism = Thellungiella halophila
SEQUENCE: 191
atggagattc aaattaaaaa gaaaaactta tatataatga atacacaaaa gctacctaat  60
ctgtatatat atatatataa atatgtcttc attaaattaa tggtcgtgga atag        114

SEQ ID NO: 192          moltype = DNA  length = 132
FEATURE                 Location/Qualifiers
source                  1..132
                        mol_type = unassigned DNA
                        organism = Arabidopsis thaliana
SEQUENCE: 192
atggtacctc aaattaatct atggtcatct agggttatct tgaagattag aattgattct  60
agcacgcaca gagaggaaga tcattgcatc cagaatcaca aacatggcct atcttttatc  120
ttttcttttt ga                                                      132

SEQ ID NO: 193          moltype = DNA  length = 51
FEATURE                 Location/Qualifiers
source                  1..51
                        mol_type = unassigned DNA
```

```
                        organism = Arabidopsis thaliana
SEQUENCE: 193
atgtctctcc aattttatga gagggtttcc ttcaagaaca cagtaaaata g           51

SEQ ID NO: 194          moltype = DNA  length = 39
FEATURE                 Location/Qualifiers
source                  1..39
                        mol_type = unassigned DNA
                        organism = Arabidopsis thaliana
SEQUENCE: 194
atgacagagc aagaagaaga aagtcaaatg tccacatga                         39

SEQ ID NO: 195          moltype = DNA  length = 120
FEATURE                 Location/Qualifiers
source                  1..120
                        mol_type = unassigned DNA
                        organism = Arabidopsis thaliana
SEQUENCE: 195
atgtatctac aatatattga taatgtaata tctatatatt caaacaatcg tcgtgttggt  60
cggatgtttt ctagagttcc tctgagcact tcattggaga tacaattttt tataaaatag  120

SEQ ID NO: 196          moltype = DNA  length = 39
FEATURE                 Location/Qualifiers
source                  1..39
                        mol_type = unassigned DNA
                        organism = Arabidopsis thaliana
SEQUENCE: 196
atgagcaagg agatattttt ttcccctggg tttgaatga                         39

SEQ ID NO: 197          moltype = DNA  length = 133
FEATURE                 Location/Qualifiers
source                  1..133
                        mol_type = unassigned DNA
                        organism = Arabidopsis thaliana
SEQUENCE: 197
atgagaacac acgagcaatc aacggctata acgacgctac gtcattgtta cagctctcgt  60
ttcatgtgtt ctcaggtcac ccctgctgag ctctttctct accgtccatg ttttatcaac  120
gccgtggccc gtg                                                     133

SEQ ID NO: 198          moltype = DNA  length = 18
FEATURE                 Location/Qualifiers
source                  1..18
                        mol_type = unassigned DNA
                        organism = Arabidopsis thaliana
SEQUENCE: 198
atgaagagaa acatgtaa                                                18

SEQ ID NO: 199          moltype = DNA  length = 18
FEATURE                 Location/Qualifiers
source                  1..18
                        mol_type = unassigned DNA
                        organism = Arabidopsis thaliana
SEQUENCE: 199
atgcaatgtg aaatatga                                                18

SEQ ID NO: 200          moltype = DNA  length = 15
FEATURE                 Location/Qualifiers
source                  1..15
                        mol_type = unassigned DNA
                        organism = Arabidopsis thaliana
SEQUENCE: 200
atgttttgtg cttga                                                   15

SEQ ID NO: 201          moltype = DNA  length = 21
FEATURE                 Location/Qualifiers
source                  1..21
                        mol_type = unassigned DNA
                        organism = Arabidopsis thaliana
SEQUENCE: 201
atggtcatgg ctcatcatta g                                            21

SEQ ID NO: 202          moltype = DNA  length = 165
FEATURE                 Location/Qualifiers
source                  1..165
                        mol_type = unassigned DNA
                        organism = Arabidopsis thaliana
SEQUENCE: 202
atgatgaaac ctcgatggaa ctgctctctt tatggaatca cggaatggac aaataatcaa  60
aatcagaaat cgaagcgaaa agggaggaga aaaacgcaga tttggaggat tggggacaga  120
```

```
ttagatactg ttgaatgcat cactctaatg ctatcagcct attaa                  165

SEQ ID NO: 203          moltype = DNA  length = 33
FEATURE                 Location/Qualifiers
source                  1..33
                        mol_type = unassigned DNA
                        organism = Arabidopsis thaliana
SEQUENCE: 203
atgctgctta tcatcgtgga gttggttctg taa                               33

SEQ ID NO: 204          moltype = DNA  length = 45
FEATURE                 Location/Qualifiers
source                  1..45
                        mol_type = unassigned DNA
                        organism = Arabidopsis thaliana
SEQUENCE: 204
atgctttgtt tcaatttcag gtgcgttaga aggtttgcag agtag                  45

SEQ ID NO: 205          moltype = DNA  length = 108
FEATURE                 Location/Qualifiers
source                  1..108
                        mol_type = unassigned DNA
                        organism = Arabidopsis thaliana
SEQUENCE: 205
atgtacacct accagcttga taactctttt tcgtggtttc tgtgtactcg tttctgtttg  60
tacagatact tcttgttcaa tttcagatgc tttagaaggt tttcggag               108

SEQ ID NO: 206          moltype = DNA  length = 267
FEATURE                 Location/Qualifiers
source                  1..267
                        mol_type = unassigned DNA
                        organism = Drosophila melanogaster
SEQUENCE: 206
atgtggcgcg aagtatgcgc acaaaaaagt caaacaaaaa ggcgcaattt tattacgggc  60
aaccaacgac gaaacaaaac aaaagccaac cgaaaagcag aaacaaagca gcaaaaagtt  120
tatgaatttt ttgtgcaggc gcgtgaaaga tgcaaaacga gaaaaaaaca tgaaaaaaaa  180
acattaaaaa aaacaaaaaa aatccaaaac agataccgag ctgtatccga aaacgagtgg  240
ggaaaggggt ttcccagtca catataa                                      267

SEQ ID NO: 207          moltype = DNA  length = 111
FEATURE                 Location/Qualifiers
source                  1..111
                        mol_type = unassigned DNA
                        organism = Drosophila melanogaster
SEQUENCE: 207
atgcgcacaa aaaagtcaaa caaaaaggcg caattttatt acgggcaacc aacgacgaaa  60
caaaacaaaa gccaaccgaa aagcagaaac aaagcagcaa aaagtttatg a           111

SEQ ID NO: 208          moltype = DNA  length = 216
FEATURE                 Location/Qualifiers
source                  1..216
                        mol_type = unassigned DNA
                        organism = Drosophila melanogaster
SEQUENCE: 208
atggagcctg gctttgtttt tgttttattt ccaacccact tgagcacaca gcacacacag  60
agagaaaaat caatactcgt tatgggatta aatttacaaa gcgcaaagca aagcgacaaa  120
caaaattcaa aagaaagaaa aaaaaacact caaataaact cacaaagaat tccttatcgc  180
caagggggcc aatgttctaa ggttctttcg ccttga                            216

SEQ ID NO: 209          moltype = DNA  length = 614
FEATURE                 Location/Qualifiers
source                  1..614
                        mol_type = unassigned DNA
                        organism = Arabidopsis thaliana
SEQUENCE: 209
attcattgtt cactctcaaa tctcaagttc attgccattt ttaggtctct ctataaattc  60
aaatgttctg ttcaattcaa tgcgtcgcca gacatctgtt ccctttgcat gtaagagaga  120
taaagaaagc gacaagagcc ataaagaaag gtaagactct ttgaaataga gagagataag  180
gttttctctt atcttcttct catcagatct ttgtttcttt accctctttc tttctttttt  240
ttgcttttta tggttatgtt ttttctcgat ttagacaaaa accctagatt tgatcttcta  300
aagggtctca aatggaatct cttctcttct catatctctc cctctctccc tccctctctt  360
tgattctttg tcttctccag ttaaaactca gatctaacac aaagcttaaa agattctcat  420
cgtttcttgt tttctttgtt tcatcttgta gatctctgaa gttggactaa ttgtgaatga  480
aagagttggg acaagagaaa cgcaaagaaa ctgacagaag agagtgagca cacaaaggca  540
atttgcatat cattgcactt gcttctcttg cgtgctcact gctctttctg tcagattccg  600
gtgctgatct cttt                                                    614

SEQ ID NO: 210          moltype = DNA  length = 422
FEATURE                 Location/Qualifiers
```

```
source                 1..422
                       mol_type = unassigned DNA
                       organism = Arabidopsis thaliana
SEQUENCE: 210
ctctgccttt agttctttct tttttggtaa tatatttatt tttcgttacg atttggtcaa  60
aaccctagat ttgttttcca aaagcatatc tgaaaatgaa ggacaacttt cctcttctcc  120
ttcggttata aatattctct ccggttttgc ttgtttaacc taaaagcctc agatctaact  180
ccaacacctt caaagtctgc ctcctttcca atcttctttc ttctgttcga tctctaatct  240
cagaatttgt gtcggtaagg taaaggtgat aatgagtgat gactgatgag ggagttttgg  300
gacaaatttt aagagaaacg catagaaact gacagaagag agtgagcaca caaaggcact  360
ttgcatgttc gatgcatttg cttctcttgc gtgctcactg ctctatctgt cagattccgg  420
ct                                                                 422

SEQ ID NO: 211         moltype = DNA  length = 268
FEATURE                Location/Qualifiers
source                 1..268
                       mol_type = unassigned DNA
                       organism = Arabidopsis thaliana
SEQUENCE: 211
tcccacatcc aaagatagaa agatgtaagg tctagagtct tgttcttaat ccccctaacag  60
aacaatgata tatataaata aatatgggtc gatatcggct gtggaggacg actagctacg  120
gtttcgagcc tggtcacatg cgtagagtgt gaaaggtaat taggaggtga cagaagagag  180
tgagcacaca tggtggtttc ttgcatgctt ttttgattag ggtttcatgc ttgaagctat  240
gtgtgcttac tctctctctg tcacccct                                     268

SEQ ID NO: 212         moltype = DNA  length = 328
FEATURE                Location/Qualifiers
source                 1..328
                       mol_type = unassigned DNA
                       organism = Arabidopsis thaliana
SEQUENCE: 212
tcccacagcc aatgagccaa agataaagaa acacctatcc tataataatt tagagcaata  60
tacctccata atggaacatc tatatatata aaggtatccg tatatctcta tatattatat  120
tcattgagtt taaagtggct agggtttata gatgtatgtg atattaagag atatgaaaca  180
tatttgtcga cggtttgagt ggtgaggaat tgatggtgac agaagagagt gagcacacat  240
ggtggctttc ttgcatattt gaaggttcca tgcttgaagc tatgtgtgct cactctctat  300
ccgtcacccc cttctctccc tctccctc                                     328

SEQ ID NO: 213         moltype = DNA  length = 592
FEATURE                Location/Qualifiers
source                 1..592
                       mol_type = unassigned DNA
                       organism = Arabidopsis lyrata
SEQUENCE: 213
aaaaaatgac gtgtcctctt ctctctctct ctttccttct ctctaagtat atttagggtt  60
aattattagg gttctttatc tctttcttca gtctttgaag tttcttcaat agctttaatt  120
gaagtgattt acctctctgg gtgtttttag tatatatatc atgtacatga tcgaatttct  180
ttctatccaa gttctcatca aaccttctca tgttttgaag agttaaaggc tttatagttt  240
gcttaggtca gatccataac atactgtatt tgacaagttt ctttgtctca cgatagatct  300
tggtctgacc aaaatgattt tctcgagaaa aaaaaagatg gaagtagagc tccttgaagt  360
tcaaacgaga gttgagcagg gtaaagaaaa gctgctaagc tatggatccc ataagcccta  420
atccttataa agaaaaaaaa ggatttggtt atatggcttg catatctcag gagctttaac  480
ttgcccttta atggctttta ctcttctttg gattgaaggg agctctacat cttctttcac  540
cttctctatt tttctttctt tattttctcc tctacagtaa tttatttgga tt          592

SEQ ID NO: 214         moltype = DNA  length = 599
FEATURE                Location/Qualifiers
source                 1..599
                       mol_type = unassigned DNA
                       organism = Arabidopsis thaliana
SEQUENCE: 214
ttccaaaaca tgacgtggcc tcttctctct ctctctttcc ttctctctaa gtatgtttag  60
ggttaataat tagggttcct cctctctttt gttctgtctt tatatctcct tcatagctct  120
aatgtaagag atttacctct tttggtgttt ttgttaatcc acgttctcat caaaactttc  180
tcattgtttt atgaagagtt aaaggtcttt acagtttgct tatgtcagat ccataatata  240
tttgacaaga tactttgttt ttcgatagat cttgatctga cgatggaagt agagctcctt  300
aaagttcaaa catgagttga gcagggtaaa gaaaagctgc taagctatgg atcccataag  360
ccctaatcct tgtaaagtaa aaaaggattt ggttatatgg attgcatatc tcaggagctt  420
taacttgccc tttaatggct tttactcttc tttggattga agggagctct acatcttctt  480
tcaccttctc tattttttat ttttctttat ttctactcaa caattattta ttcggattca  540
tctttaattt tccgttataa tttctttttg gtaaggatta ttcgctataa tttgagaat   599

SEQ ID NO: 215         moltype = DNA  length = 623
FEATURE                Location/Qualifiers
source                 1..623
                       mol_type = unassigned DNA
                       organism = Capsella rubella
SEQUENCE: 215
ttccaacgaa tgacgtgtac tctctctgct ctatctctct ctctaaatat gtttagggtt  60
```

```
aattagggtt cttcatctgt ctctctctct ctctctcttc agagtcttta tagcttcttc  120
caagattttt aattgaaagt aatttacctc ttttggagtt ctgtacatat agaatatcag  180
gagtcgtgtt tcttttttat caaggttctc atctaacctt tatagtattt tcattagttg  240
ataaaggtct tcatagtttg cttagatcag atcttgtctt cgtcttttcg atagatcttg  300
ttctgtccaa tatacagtga ttttatttcg agagcaaaaa agatgagagg tagagctcct  360
tgaagttcaa acgagagttt agcagggtag agaaaagctg ctaagctatg gatcccataa  420
gccctaatcc ttgttaatga taaaggattt ggttatatgg cttgcatatc tcaggagctt  480
taacttgccc tttaattgct tttactcttc tttggattga agggagctct acatcttctt  540
tgacttctct ctctattaag tctttcttta ttttcttctc tacaatagtt gttttggatc  600
ggaagatctt taagtttccc tta                                           623

SEQ ID NO: 216         moltype = DNA  length = 612
FEATURE                Location/Qualifiers
source                 1..612
                       mol_type = unassigned DNA
                       organism = Arabidopsis thaliana
SEQUENCE: 216
tttcactttt gttctcctcc tccctttttt tcttttcagg attcttcttt tctatgtttt  60
atctttcata atagatctga taattttgat ttttcactat atatattatg gttaatacta  120
gtagcttttt catttcaagt tttatccttc cattggttct ttctgagtca aattgtctcc  180
tgtttcgaac catatataag ttttcaatgg ttttgtatta actcaagtat tcaacattat  240
gtctctcttt ttcttgcttg gatctctaat gctgttcata ttttaaagca taggtttagg  300
ttagatgcat gtaactgcca attaaaagaa ggtcaagagt tttttgattg tatgaatata  360
tgagttagtc aaagcagatc cacacgatta tatagaaaaa caaaggaaga agaagaggaa  420
gagctccttg aagttcaatg gagggtttag cagggtgaag taaagctgct aagctatgga  480
tcccataagc cttatcaaat tcaatataat tgatgataag gtttttttta tggatgccat  540
atctcaggag ctttcactta ccccttttaat ggcttcactc ttctttggat tgaagggagc  600
tcttcatctc tc                                                       612

SEQ ID NO: 217         moltype = DNA  length = 515
FEATURE                Location/Qualifiers
source                 1..515
                       mol_type = unassigned DNA
                       organism = Arabidopsis thaliana
SEQUENCE: 217
catcccaccc ttaattgttt tatataaacc atttctcctc ctctctccat caccttcaat  60
ctctctcgat ctctctctgg atccccaatc tcacctccat gttttgtttg ttgattccca  120
tcttctcttt tgtcttttca ccaaatcgtc atttaaggct tcaagaacag taaccccaat  180
tcctccacaa gagggagaga aaacaaaaga tcttccaatt ccattctcgt acatgcaaat  240
cacaatccat gccatagatt gtttctattc ctccttattt attgcttgta tctgttcatg  300
catggaccag gtggagagag cattacttaa aaatagaatt agctatctgt tttaggcgaa  360
ttagtttcct tacataacca tgtatatgtc atgacgcata tacatatgta gatgtatatg  420
tattatatat gtatgcctgg ctccctgtat gccatatgct gagcccatcg agtatcgatg  480
acctccgtgg atggcgtatg aggagccatg catat                              515

SEQ ID NO: 218         moltype = DNA  length = 276
FEATURE                Location/Qualifiers
source                 1..276
                       mol_type = unassigned DNA
                       organism = Arabidopsis thaliana
SEQUENCE: 218
actcataact ctccccaaat tcttgaccaa aaatatccgc cactttctct ctggttcatg  60
ttttcccctc aatgaaatac atacacattt tgattttatt taaatcaaga tcgacgtata  120
agctatccac caatcatatt taagggttcc cgtatacata tatactatat atatatatgg  180
aataatagtc gtgcctggct ccctgtatgc cacaagaaaa catcgattta gtttcaaaat  240
cgatcactag tggcgtacag agtagtcaag catgac                             276

SEQ ID NO: 219         moltype = DNA  length = 243
FEATURE                Location/Qualifiers
source                 1..243
                       mol_type = unassigned DNA
                       organism = Arabidopsis thaliana
SEQUENCE: 219
ctctaactca tccttctctt ctatgaaaat tccattgttt ctgccgaagc tttgatcagt  60
acttctcttt tgcttgatct cggtttttga ccagtttatt gcgtcgatca atgcattgaa  120
agtgactaca tcggggttcc gattttttttt gttcttcata tgatgaagcg gaaacagtaa  180
tcaaccctgg tttagtcact ttcactgcat taatcaatgc atttgtaaaa agagggaaaa  240
gca                                                                 243

SEQ ID NO: 220         moltype = DNA  length = 537
FEATURE                Location/Qualifiers
source                 1..537
                       mol_type = unassigned DNA
                       organism = Arabidopsis thaliana
SEQUENCE: 220
ctagaagaaa aaaccagatc tataaagttt gttattaaaa gatagagaga gaggagggat  60
gtagtaggcc aataggcaaa tcagagaatc acaaatggta tctggtcaag aagattcctg  120
gttaaaactt tcatctctct gtttcctttt tctttctttg ttggattcat taatttgaca  180
tatctctatc atcacactga ttctctttct cccagtttgt ctgcagatgc atgtgtgtaa  240
```

```
tctagggtat atgtttttgt ccatttggtt tcataaggca ataaagatcc agctatttac  300
tacttgtggt atagattttg actgttgaat tttcagatct gatgtgtttc gtttgatccg  360
attcggaaaa tttatgtttc gttgacattt tggagtttag ttggaagaag agtgagagtc  420
gctggaggca gcggttcatc gatctcttcc tgtgaacaca ttaaaaatgt aaaagcatga  480
atagatcgat aaacctctgc atccagcgtt tgcctcttgt atctttctta ttgactt     537

SEQ ID NO: 221         moltype = DNA  length = 261
FEATURE                Location/Qualifiers
source                 1..261
                       mol_type = unassigned DNA
                       organism = Arabidopsis thaliana
SEQUENCE: 221
ctgcatctat ccacctctct ctgtaaattt atctaaatgt ttcttttaat ctttttgaga  60
ttaataatga tttgtgtttg ttcatcaacc gattttctca gatctgtcaa ttatttttgt  120
ttatttattt atgatttatg aatgaggaaa gagtgaagtc gctggaggca gcggttcatc  180
gatcaattcc tgtgaatatt tatttttgtt tacaaaagca agaatcgatc gataaacctc  240
tgcatccagc gctgcttgct c                                            261

SEQ ID NO: 222         moltype = DNA  length = 481
FEATURE                Location/Qualifiers
source                 1..481
                       mol_type = unassigned DNA
                       organism = Arabidopsis thaliana
SEQUENCE: 222
tatcacagtt ctcatcaaat atttgaaagt atcaaacaaa aaaaggagag tgagaaaaat  60
aaagagagag atagagagag atcatgtcca ctactcaaga gcataggtct tgattggtgg  120
aagacaagta ccttagataa accgaccaaa acccggtgga taaaatcgag ttccaacctc  180
ttcaacgaca acgatttcaa cactctcttc caggaacaac ttcctccagg cagatgatac  240
taaagtgctg gagttcccgg ttcctgagag tgagtccata tcaaaatgcg cattcgttat  300
cacttggttg aacccatttg gggatttaaa tttggaggtg aaatggaacg cgtaattgat  360
gactcctacg tggaacctct tcttaggaag agcacggtcg aagaagtaac tgcgcagtgc  420
ttaaatcgta gatgctaaag tcgttgaaga ggacttggaa cttcgatatt atcccccgtg  480
t                                                                  481

SEQ ID NO: 223         moltype = DNA  length = 471
FEATURE                Location/Qualifiers
source                 1..471
                       mol_type = unassigned DNA
                       organism = Arabidopsis lyrata
SEQUENCE: 223
agtagggttg gaaaattttt ttacattttt actctaaaat agaatagagt tggagatgcc  60
cttagcagtt attagacaag ggattgtttg gccctagcga tcctctcttc actctctcac  120
ttttgtagtt caacccttct tttgcgtgag atgccatcat ggcatgacat ggttcttttg  180
ccttacgtaa aacacactca cgccaacaca cgccacataa cataaataaa ttatatatac  240
atatacgtat gtgcgtgtga gtcttccatt aatgcaatct ttgggcctat atatatatac  300
aaaccttcca taaccaaagt tatcatacta caaaagctct ctcgtacttg gaaatgcggg  360
tgagaatctc catgttggag aagcagggca cgtgcaaacc aacaaacacg aaatccgtct  420
catgtgtttt gcacgtactc cccttctcca acatgagctc ctgacccatt g           471

SEQ ID NO: 224         moltype = DNA  length = 466
FEATURE                Location/Qualifiers
source                 1..466
                       mol_type = unassigned DNA
                       organism = Arabidopsis thaliana
SEQUENCE: 224
agacaagccc ccacactaaa aaaacagtaa tatggaataa aaaaaagctt tcaaaactta  60
gcagttatta gacaaggtat tgtttggccc tagctagcga tcgtttagct ctcttcactc  120
tctcactttt ttagttcaac ccttcttttg cgtgagatgc catcatggca tggtatggtt  180
cttttgcctt acgtaaaaca cactcacgcc agcacacaca cacacacaca taacatatac  240
ggatgtgcgt gtgagctagt cttccattaa tgcaatcttt gggcctatat atacaaacct  300
ttccataacc aaagttctca tactacaaac gcccctcatg tgcttggaaa tgcgggtgag  360
aatctccatg ttggagaagc agggcacgtg caaaccaaca aacacgaaat ccgtctcatt  420
tgcttatttg cacgtactta acttctccaa catgagctct tcaccc                 466

SEQ ID NO: 225         moltype = DNA  length = 450
FEATURE                Location/Qualifiers
source                 1..450
                       mol_type = unassigned DNA
                       organism = Brassica rapa
SEQUENCE: 225
agacaacccc acgttttaaa ataagaaatg atgataattt tgtggaaata aaagctagta  60
tacttttgca ataattagac aaggtattga tgctttgggc caagctagtt tcttttagca  120
ctcttcactc actagttttt cttctcagcc cttcttttgc gtgaaatgcc atcatggcat  180
ggcattgtca ttttgccttt cgtaaaacac actcacgcca acatacatta ttcatattca  240
tgtgtatgta tatgaatgtt ccattaatgc aatctttggg gcctatatat acgaagctta  300
catcaccaaa gctctcatat tacaaaagct cacatatata cttggaaatg taggtgagaa  360
cctccatgtt ggagaagcag ggcacgtgca aaccaaaaaa catgaaatct gtttcatatg  420
ctttgcacgt gctcccctcc tccaacatga                                   450
```

```
SEQ ID NO: 226          moltype = DNA  length = 513
FEATURE                 Location/Qualifiers
source                  1..513
                        mol_type = unassigned DNA
                        organism = Carica papaya
SEQUENCE: 226
agacaacact cctctttgtt cccttcctca cgtatccact tttgaaattt gtaatttgtg  60
tgcaccacca tgattgcatg ccatccctac ttgccttttc cccttttcct ttctctaaca  120
ttttactcaa tcttcttctc cccctccccc ccttcccccct ctctgccatt ataaccataa  180
ttaaacctct ctccctctct ctccctctct ctctctctct ctctgggttc tcagtataaa  240
tgcagctctg cttatacttc cacacctata tatatatacc tgacccttct tcacctcctt  300
catccacctc ctccttcttc cccaaaactt tcttaactgt tctctgcata catatatatc  360
cacatacata tatatatata tagagagaga gtgagacaga gaggttaccg aggcaattgg  420
gtgagtagct ccctgttgga gaagcagggc acgtgcaaat tctccatggc tttcccctct  480
ttgcacgtgc tccccttctc caacatgggt tcc                                513

SEQ ID NO: 227          moltype = DNA  length = 464
FEATURE                 Location/Qualifiers
source                  1..464
                        mol_type = unassigned DNA
                        organism = Capsella rubella
SEQUENCE: 227
cggccacccc cacatttaac aagaaaaaaa ctgatggaat taaaaggttt gagaacttgg  60
cagttattag acaaggtata gtttggccct agcttctttt aatttagctc tctccactct  120
cacacttttc aactttcacc cttctcttgc gtgagtcgcg agatgccatc atggcatggc  180
atggcatgtt tctattgcct tacgtaaaac acactcacgc caacacatac tcactataca  240
tgtaaataag tatgtgcgcg tgtgagtctt ccatccatca atgcaatctt tggggctata  300
tatatacaaa ccttttccat aaccaaagct ctcatataaa ctacaaaagg ctcacttggg  360
aaatgcgggt gagaatctcc acgttggaga agcagggcac gtgcaaacca acaaacacga  420
aaccctcctc atgtgctttg cacgtactcc ccttctccaa catg                    464

SEQ ID NO: 228          moltype = DNA  length = 571
FEATURE                 Location/Qualifiers
source                  1..571
                        mol_type = unassigned DNA
                        organism = Gossypium raimondii
SEQUENCE: 228
gaaaacccaa gttcaggcta acaagttatc tgatgatgag atcaagaatt ttaaagtttc  60
aatatagatt tggcatgggt attggcggca gaaagcaatt aaaaaaccag ttatgtcaaa  120
ttcaaggtcg tatcagttaa aatgaatgaa gatttagaaa tttcaacaag gaagaggacc  180
ccacagcttt gttaaattaa gtgtgtggtt tttataatta tcatctcgaa agtttcataa  240
tatcaattag attaaaacat ctctgaattt cataattaca aaccagatag atagatacat  300
gaaaacttag accccagaga tctgtcttta aagaatgccc acttctagac tcaatctcta  360
ttactctctt tttttctctc tctctctctt cggaaaaact tgtatataaa taaatgacac  420
tttctttgct ttctgcactc aactcatgaa cttgaaaagc tttacttgga tgggttggtt  480
gggggtgagt atctcttgtt ggagaagcag ggcacgtgca agttcctatg tttaagtgaa  540
ctttgcacgt gctccccttc tccaccgtga g                                  571

SEQ ID NO: 229          moltype = DNA  length = 592
FEATURE                 Location/Qualifiers
source                  1..592
                        mol_type = unassigned DNA
                        organism = Medicago truncatula
SEQUENCE: 229
gaagagaaaa aacctagtgt aaaatttgat atactcttta tgtatagtac gaatgttttt  60
ttaaaaatta tgtaaaaaat gataaaataa taactaacta aattaacagt aaaattagaa  120
aagtaaaata ctatgcccaa atttgatatt ttttttata tatttgtata gattattatt  180
atttgatatg taaagtccaa ttaaaaattt gttttaacta agatttgaac taggttttct  240
taaaagactc atcttttact tcaaatttat ttatcatttg aattcaatca ctttctaata  300
ttattattat tatttccacc atactcattg cttctgccac gttactttag ttagatctct  360
tatgtcatat atctctctct ctcctaagtt gctacctata aatactaagc ctttcccttg  420
gttggttcaa ttcaacttct acttctcatc aaacacaaag tgcaataagc ttcatttcct  480
gggtgagaag ctccttgttg gagaagcagg gcacgtgcaa atcctctttc tgattcattc  540
tctcataatg catatcaata tcttttgcac gtgctcccct tctccaacta gg           592

SEQ ID NO: 230          moltype = DNA  length = 520
FEATURE                 Location/Qualifiers
source                  1..520
                        mol_type = unassigned DNA
                        organism = Oryza sativa
SEQUENCE: 230
atgcaaaccc actccaacac tccacaatcc acatactctc tctctctctc tctctctgag  60
taggagtaca tgtgtgtgtg tgatatcaat atgcattcga tgttgatgct actgtagcca  120
tcttgtggct atataaaccc agcaggcagc agcacagctt agctagagag ccatattgca  180
tgcacactcg ctaatctctt ttctctactc tacttgcatt acaccacctc tgcattgcac  240
ttcagttcat tcattccact gatgcatgga tcgatgttgc taccttcttc tcttctcctc  300
atgcatccat gcatcgatct cacctagctt cttcctcatc ctctctcgat cgattacaag  360
agaaaagtgt ttgctgttct tgctatcgat ctacaggtga gtaggttctt gttggagaag  420
cagggtacgt gcaaaatgca caccggttgg tcgagctaat taacaagctc tgacgaccat  480
```

```
ggtgatcgaa tgcacgtgct ccccttctcc accatggcct                      520

SEQ ID NO: 231         moltype = DNA  length = 501
FEATURE                Location/Qualifiers
source                 1..501
                       mol_type = unassigned DNA
                       organism = Arabidopsis lyrata
SEQUENCE: 231
ctagggttta ggaatgacga cttgtttctg ttgtgtctta ttaaaagccc atcttcgtct  60
ccgccactca tcattccctc atcataacac catcatcacc attcaccaac ctctctctct  120
ttctctctct cctctcgatc tacaacaaaa tgtgaatctg ctaagatcga ttatcatgag  180
aattaagcta tttcagttga ggggaatgtt gtctggatcg aggatattat acatatatac  240
atgtgtatgt tgatacatgt gatcatagag agtatcctcg gaccaggctt catccccccc  300
aacatgttat tgcctctgat caccatatat atgtcgttac atttcatggt taattacttg  360
cacaaatcac aaaagcttgg tttgtaactt tctatgacct tttttaatga ctttgaatct  420
ttcatgcatg acttcttaag agtagattta cacatttgcg gatccgttta tgctttttgc  480
ttttgtttcg tttatatata t                                          501

SEQ ID NO: 232         moltype = DNA  length = 484
FEATURE                Location/Qualifiers
source                 1..484
                       mol_type = unassigned DNA
                       organism = Arabidopsis thaliana
SEQUENCE: 232
ctagggttta ggaatgacga cctgtttctg ttgtgtctta ttaaaagccc atcttcgtct  60
ccgccactca tcattccctc atcataacac catcatcacc attcaccaac ctctctctct  120
ctctcctcta tcactctcta caacaaaaat ttgtgaatct gctaagatcg attatcatga  180
gggttaagct atttcagttg aggggaatgt tgtctggatc gaggatatta tagatatata  240
catgtgtatg ttaatgattc aagtgatcat agagagtatc ctcggaccag gcttcatccc  300
ccccaacatg ttattgcctc tgatcaccat ttattgttac attttttttt gttaattact  360
tgcgcaaatt acaaaagctt ggtttttgtg atgactttga atctttcttg catggcttct  420
taagagtaga tttacggatc cgtctatgct ttttgctttt tgtttcgttt atttgtattt  480
aaac                                                             484

SEQ ID NO: 233         moltype = DNA  length = 552
FEATURE                Location/Qualifiers
source                 1..552
                       mol_type = unassigned DNA
                       organism = Brassica carinata
SEQUENCE: 233
gagatcaatg aaattatcct gccaaataaa acgtgtgacg tttattcaaa aatatatgca  60
ttagatgctt tgatattaaa atatttcctt ttaaaagcta gctagggttt aggaatgacg  120
agttgtgtct tattaaaagc ccttcttctc ctccgccact catcattccc tcatcataac  180
accatcatca ccattcaccc acctctcctc tttctctctc tctctctctc tctctctctc  240
tagaacaaca agtgagaatc tgctaaaata ttgtgactat tatcatgaga atgaagctat  300
ttcagttgag gggaatgttg tctggatcga ggatattata tatacacaaa tacgtatata  360
tgttaataca agtgtttgat catatatgta tatagattat tctcggacca ggcttcatcc  420
cccctaacat gttattgcct ctgatcacca gattctatca actcttcgct tattattttg  480
tcacaaacaa gtaataagct cataattttc tttgagtctt tcagcatcgt ttcattatgt  540
ttttcgaatc cg                                                    552

SEQ ID NO: 234         moltype = DNA  length = 566
FEATURE                Location/Qualifiers
source                 1..566
                       mol_type = unassigned DNA
                       organism = Brassica juncea
SEQUENCE: 234
gagatcaatg aaattatcct gccaaataaa acgtgtgacg tttattcaaa aatatatgca  60
ttaaatgctt tgatattaaa atatttcctt ttaaaagcta gctagggttt aggaatgacg  120
agttgtgtct tattaaaagc ccttcttctc ctccgccact catcattccc tcatcataac  180
accatcatca ccattcatcc acctcttctc tcctctctct ctctctctct ctctctctct  240
ctctctctct ctctagaaca acaagtgaga atctgctaaa atattgtgat tattatcatg  300
agaatgaagc tatttcagtt gaggggaatg ttgtctggat cgaggatatt atatatacac  360
aaatatgtat atatatgtta atatcagtgt ttgatcatat atatgtatat agattattct  420
cggaccaggc ttcatccccc ctaacatgtt attgcctctg atcaccagat tctatcaact  480
cttagcttat tatttgtcac aaacaagtaa taagctcaat aatgtctttg agtctttcag  540
catcgtttca tatgttttcg aatccg                                     566

SEQ ID NO: 235         moltype = DNA  length = 549
FEATURE                Location/Qualifiers
source                 1..549
                       mol_type = unassigned DNA
                       organism = Brassica napus
SEQUENCE: 235
gatatcaatg aaattatcct gccaaataaa acgtgtgacg tttattcaaa aatatatgct  60
ttaaatgctt tcatattaaa atatttcctt ttaaaagcta gctagggttt aggaatgacg  120
agttgtgtct tattaaaagc ccttcttctc ctccgccact catcattccc tcatcataac  180
accatcatca ccattcaccc acctctcctc tttctctctc tctctctctc tctctctctc  240
tagaacaaca agtgagaatc tgctaaaata ttgtgactat tatcatgaga atgaagctat  300
```

```
ttcagttgag gggaatgttg tctggatcga ggatattata tatacacaaa tacgtatata  360
tgataataca agtgtttgat catatatgta tatagattat tctcggacca ggcttcatcc  420
cccctaacat gttattgcct ctgatcacca gattctatca actcttcgct tattatttgt  480
cacaaacaag taataagctc aataatgtct ttgagtcttt cagcatcgtt tcatatgttt  540
tcgaatccg                                                          549

SEQ ID NO: 236          moltype = DNA  length = 543
FEATURE                 Location/Qualifiers
source                  1..543
                        mol_type = unassigned DNA
                        organism = Brassica oleracea
SEQUENCE: 236
gggatcaatg aaaattatcc tgccaaataa aaacgtgtga cgtttatcca aaaatatatg  60
cattaaatgc tgtgatatga agtatttcct ttaaaagcta gctagggttt aggaattacg  120
agttgtgttt tattaaaagc ccttcttctc ctccgccact catcattccc tcatcataac  180
accatcatca ccattcaccc acctctcctc tttctctctc tctctctctc tctctagaac  240
aacaagtgag aatctgctaa aatattgtga ctattatcat gagaatgaag ctatttcagt  300
tgaggggaat gttgtctgga tcgaggatat tatatataca caagtacgta tatatgttaa  360
tacaagtgtt tgatcatata tgtatataga ttattctcgg accaggcttc atcccccta   420
acatgttatt gcctctgatc accagattct atcaactctt cgcttattat ttgtcacaaa  480
caagtagtaa gctcaataat gtctttgagc ctttcagcat cgtttcatat gttttcgaat  540
ccg                                                                543

SEQ ID NO: 237          moltype = DNA  length = 566
FEATURE                 Location/Qualifiers
source                  1..566
                        mol_type = unassigned DNA
                        organism = Brassica rapa
SEQUENCE: 237
gagatcaatg aaattatcct gccaaataaa acgtgtgacg tttattcaaa aatatatgca  60
ttaaatgctt tgatattaaa atatttcctt ttaaaagcta gctagggttt aggaatgacg  120
agttgtgtct tattaaaagc ccttcttctc ctccgccact catcattccc tcatcataac  180
accatcatca ccattcatcc acctcttctc tcctctctct ctctctctct ctctctctct  240
ctctctctct ctctagaaca acaagtgaga atctgctaaa atattgtgat tattatcatg  300
agaatgaagc tatttcagtt gaggggaatg ttgtctggat cgaggatatt atatatacac  360
aaatatgtat atatatgtta atatcagtgt ttgatcatat atatgtatat agattattct  420
cggaccaggc ttcatccccc ctaacatgtt attgcctctg atcaccagat tctatcaact  480
cttagcttat tatttgtcac aaacaagtaa taagctcaat aatgtctttg agtctttcag  540
catcgtttca tatgttttcg aatccg                                       566

SEQ ID NO: 238          moltype = DNA  length = 414
FEATURE                 Location/Qualifiers
source                  1..414
                        mol_type = unassigned DNA
                        organism = Arabidopsis thaliana
SEQUENCE: 238
catcatcacc actcacttat cttcttctcc atctctctct ctgcttctcc cttaatctta  60
gccgggtctc gtgggggacg aacatagaaa gagagagata taaagatata tattcagaaa  120
ccctagattc tataatttcg actgaaaaga aaaaggggct ttctcttttg aggggactgt  180
tgtctggctc gaggactctg gctcgctcta ttcatgttgg atctctttcg atctaacaat  240
cgaattgaac cttcagattt cagatttgat tagggtttta gcgtcttcgg accaggcttc  300
attcccccca attgttgctc cctgtttact ccatatttct tccttctttt caaattaggg  360
tttcagatcc agtgaatgaa cccttgttaa aggtttgatc tcttacctta cttt        414

SEQ ID NO: 239          moltype = DNA  length = 328
FEATURE                 Location/Qualifiers
source                  1..328
                        mol_type = unassigned DNA
                        organism = Arabidopsis thaliana
SEQUENCE: 239
tctcatcatt ctcttcatca tcaccacatt catctctctc tctctctctc tctctctctc  60
tttctcttcc ttgatcttag ccggatctgt tgggggacga acacatgaga gatagataaa  120
atataagaaa tttctcgaaa aaacctaata gaaaaaggtc tgtttcttaa agaagaagaa  180
gaagaggatt taaagaggga tttttctttt gaggggactg ttgtctggct cgaggactct  240
tattctaata caatctcatt tgaatacatt cagatctgat gattgattag ggttttagtg  300
tcgtcggacc aggcttcatt ccccccaa                                     328

SEQ ID NO: 240          moltype = DNA  length = 192
FEATURE                 Location/Qualifiers
source                  1..192
                        mol_type = unassigned DNA
                        organism = Arabidopsis thaliana
SEQUENCE: 240
tgatgaacag aaaaatctct ctttctcttt cttgatctgc tacggtgaag tctatggtgc  60
accggcatct gatgaagctg ccagcatgat ctaattagct ttctttatcc tttgttgtgt  120
ttcatgacga tggttaagag atcagtctcg attagatcat gttcgcagtt tcacccgttg  180
actgtcgcac cc                                                      192

SEQ ID NO: 241          moltype = DNA  length = 846
```

```
FEATURE                 Location/Qualifiers
source                  1..846
                        mol_type = unassigned DNA
                        organism = Arabidopsis thaliana
SEQUENCE: 241
aaccacaaag taccgctgct atttttcttt tacgtctttg tatttgcatc gtctaagaga  60
atgatgggtt gttttgtggg attttaatgc aggaggaaac atatgagggg tgattaaggc  120
aaaaacctta agatgtggtc atttagatac atggagtcaa actaagaatg gaccttggcg  180
aaagcttctt cacggtcaag atttaaaatc aggtacgaca ctgtgtacgt gagagagaga  240
gagagagaga gaaagagatt atagaaagaa agagatgtat cacaataaag gagtatattt  300
agggtcacag gtggtggaga tataggtatg cagggccaag gctctaatct cttcatagcc  360
ctattgattt tgtccctctc tctctctctt tcttcctctc ttagctgtat gcattatgat  420
gcgtctttta attcactgtt tcaggcttct ttaattcgtg gtgtctctct cctttttacc  480
caaccatctc ttaaaatttt taacatctgt tcctcaaatc ctctctcatc tctttctata  540
agtatctata gcgcctctta aaccacaaag catcacctct gtcttctctc atctcctttc  600
tgtattctct ttcattgcct tcacgtctgt tgcaatttct ccacttcttg agcttccgtt  660
ttttacaatt attgatccgt caaatatgtg agatttgcac aacttgttgc tcaggtattt  720
tgaagacaag tccacaaggg aacaagtgaa gctgccagca tgatctatct ttggttaaga  780
gatgaatgtg gaaacatatt gcttaaaccc aagctaggtc atgctctgac agcctcactc  840
cttcct                                                             846

SEQ ID NO: 242          moltype = DNA  length = 571
FEATURE                 Location/Qualifiers
source                  1..571
                        mol_type = unassigned DNA
                        organism = Arabidopsis thaliana
SEQUENCE: 242
gagcaagaca atgccacata caaacttgaa agatctcttc atctttttctc caaatgtttt  60
tttttcgttt gctatttatc tccacaattc ttggaacaaa aactacattc acaaacgaga  120
gaattttcac aacacctctt ttgctctcat tttttttttt tcgtccatta tgagtattaa  180
ttatggttag ggaatcttac agaatgaaaa tgaaggtgtg aatggattgt ctcatctaaa  240
gccttgaatg tgggaaaaag gccattgttg ttcagccaag gatgacttgc cggtagcttg  300
tattatgatt actctatatt cgatttatat tatggagatg atggtttata tatatttact  360
tatctacata gttttagttg attttttttc gtacgtaata taatacgaaa aagtatttac  420
ttatttatat atgtgtgttg gggcaagaag tgtaaccaag ctagcccggc aagtcatcta  480
tggctatgca actgtctctt cctctcattc taggcttacg atgacacgta aaaaatccca  540
aatatcacta atatgatatg aatatggatg a                                 571

SEQ ID NO: 243          moltype = DNA  length = 241
FEATURE                 Location/Qualifiers
source                  1..241
                        mol_type = unassigned DNA
                        organism = Arabidopsis thaliana
SEQUENCE: 243
aggcatgaga cataaagaga gttaaatata atgaagaaga gaggtctaat atggcgaaaa  60
gagtcatgtt taatagccaa ggatgacttg cctgatcttt ttcacctcca tgattcaatt  120
ttaagttcgt ggattttgga ttattatgcg tttaaaaggt ataataattt gagatcatgt  180
tgaatcttgc gggttaggtt tcaggcagtc tctttggcta tcttgacatg ctttcttcat  240
c                                                                  241

SEQ ID NO: 244          moltype = DNA  length = 689
FEATURE                 Location/Qualifiers
source                  1..689
                        mol_type = unassigned DNA
                        organism = Arabidopsis thaliana
SEQUENCE: 244
gaattttgat ttatgaacct cctcaagaag gaaagacaga ggaggagaca aagaagtata  60
ggttcacatt gcatagccag tttagttttg aaggatggat atatgaaaaa aatatgaaga  120
gagagaagag agaagaagag gaggattaaa gagggtgagg ccagcttttg tgctttggta  180
gtagatgagg tttaaatgct ccataccttc catttccttc tctcttaccc taatttaatt  240
cttcctctcc tttataactc cccacagaca ttctcacttc tcctcctcac acttcacatc  300
aacacttctt tcttgttttt tcattttaca atgtttcctt tgatatccgc actttaagca  360
tgagagagtc cctttgatat tggcctggtt cactcagatc ttacctgacc acacacgtag  420
atatacatta ttctctctag attatctgat tgagccgcgc caatatctca gtactctctc  480
gtctctattt tggactttgt ggtcttgtag atcgatttgt atgtgtgtgt tgaaatggag  540
acaagtactt gtaacttctt tgttgttata ttgtttacct ataggctgat gtcataaact  600
cttttgatct tgtttctaac ttccagattc ttgaaaaatc aagtcgtgtg tgtgtctcca  660
tggaagcctt ttccatttct tcctttcca                                    689

SEQ ID NO: 245          moltype = DNA  length = 452
FEATURE                 Location/Qualifiers
source                  1..452
                        mol_type = unassigned DNA
                        organism = Arabidopsis thaliana
SEQUENCE: 245
actcataaac tttgctactg gccgcatttc tattttctcc ttcgattctt ctaattcgta  60
ctttggtttc tgacgtccct aaaattttta gacagtaaga gtttctccag gatccgatgg  120
ttctctccgg taaattaaca ttttagtgtc aatagtcatt tatacatatt tttatttcac  180
tttttgtttt gtttattggt tttctggagc taagtggaga ttatagtcga acaagagtgg  240
```

```
ttttatgcaa ggtaacgcga gatattagtg cggttcaatc aaatagtcgt cctcttaact  300
catggagaac ggtgttgttc gattgagccg tgccaatatc acgcggtaaa ccaaaaatgg  360
caaagatagt tattataacc ttaaaggtat gtatcattat cgttttattg tttcaatttt  420
gattaatggc tttgatattt catttttttt tt                                452

SEQ ID NO: 246          moltype = DNA  length = 767
FEATURE                 Location/Qualifiers
source                  1..767
                        mol_type = unassigned DNA
                        organism = Medicago truncatula
SEQUENCE: 246
attggtcaaa catacataca gtagcactag ctggtttcat tattccacta tgcttcttca  60
taggctctcc aaattttgca aaattgaaag agacatagta tatatatctt agcaaggaga  120
aattcaggat attgaggatg aagattgaag agtaatcagt gatgaagaaa gcaagcaagg  180
tattggcgcg cctcaatttg aatacatggc tataaaaatg catcatatca gccatgtagt  240
ttgattgagc cgcgtcaata tcttgtttcc atctccaaat ttaccaatct catcaaatca  300
aattaacacc acaatcaagg ctttcattta atgcagtcaa aataggttga ccttatcatc  360
gaagaaattg ttttctcatt cctatcgaag ttggacttgc cgaaaatgct cgaaagcatg  420
tgttttagtt cgacaggcga aaaagttacc gaaggacaat ttggttgtgg ttcggataag  480
atcaagcaac ggatattttc aagacacgtt cgaaattcaa atcaaatgga taagtatcgt  540
tagtttactg cagttatagt tttaaattca aatctaggca gttgtttcta tttgtataaa  600
tagtagtttt tccctaggga aaaggggtcg caattcaatc atacaaaaaa cttacaatca  660
aattatccgc atggaagaga gaaacgagtc acaagttgca atgtatgaac atgtgtacca  720
atttacattc aatcagtaca atttaagttc atttccataa aaaaaaa                767

SEQ ID NO: 247          moltype = DNA  length = 854
FEATURE                 Location/Qualifiers
source                  1..854
                        mol_type = unassigned DNA
                        organism = Zea mays
SEQUENCE: 247
accagggtta ggtatccatc cacacagcaa tgcatctgcc ttcaactccc tctcgccccc  60
caccccaaca cacatctctc tcttttctag ggaaggaaat gacgaagggg acgacgacgg  120
catgcttcgg ctagctcgtt ggtgctagga caagggcgga ggtattggcg cgcctcaatc  180
cgaaggcgtg gctgatagat tggcgcggca gccatgttct tggattgagc cgcgtcaata  240
tctccccttg cctgtcccgt acctagctag cttgcttgcc tcactgatcg atgtcgtccc  300
tatttcatgg agaagctgat gattgattat tctcacaagc aagaactgtc tgatctgttg  360
cctgcatcga tcaggatcta tatgctggag agttcacaag aacatggaca gaactcgctt  420
caacaaccga tcaatcgatt gattaggtat gtacctacct catatgcctc agctcttcgt  480
tatggatttc ttcaaccgaa gggtcagtaa gctcttggtt ccatgccact gcgtgaacta  540
agcgttcaca aaatccgttc cmcggcatga accaagcact caaaatcgca tgcagcatct  600
ttcgtttcaa aaaaaaattg acttytgaaa acaatagatg aatcagtttc aaacatatat  660
gattatccat tttctcaacc gggaatttat atctcgttgg gatgcaaaac cgttcagtag  720
taaaactact ccacgagtat aaactgtttc agttatttta ctattaatta gttacccgta  780
tgctgttatg gtttctatat atctataagt aaaccttact taaataagat agttatacaa  840
aaaaaaaaaa aaaa                                                    854

SEQ ID NO: 248          moltype = DNA  length = 660
FEATURE                 Location/Qualifiers
source                  1..660
                        mol_type = unassigned DNA
                        organism = Arabidopsis thaliana
SEQUENCE: 248
caagaaaaaa cattgaaata gctcatgttg tctctttctc attttcatat ctgctaaaaa  60
aagaaccgtg ttttctaaac tggtttaacg gtaagtacct gtctctagta acttacctat  120
caatttgttc caatcattta cttgctttga cttatttggt ttccttttgt tttgtttttc  180
tttaatatgt ggatggagtt tggtgtaata agcaactgaa gagtcgatga gcgcactatc  240
ggacatcaaa tacgagatat tggtgcggtt caatcagaaa accgtactct tttgttttaa  300
agatcggttt atttgattga gccgtgccaa tatcacgcgt ttaaatagtt taaagattct  360
atgttagttg atgtgatcaa tcaaggtatg aatctatatc aattctctta tgcatagttt  420
tatatttaca gagatgaggt attatcaatg tctatcgtcg aggatcacgc tcttacttat  480
gttatatttc tatataattt tattaattag ttttctaaaa gagaaggaca atttaaaatt  540
attttaaaga gtttttttta agtagttttg ttttcatgtt tatcttctgc aggctctgaa  600
gttaggatag taacaagaaa aaagacagaa aaaaagaaga aaattcatat acattcgtga  660

SEQ ID NO: 249          moltype = DNA  length = 225
FEATURE                 Location/Qualifiers
source                  1..225
                        mol_type = unassigned DNA
                        organism = Medicago truncatula
SEQUENCE: 249
gaataagtga atattatcga tatttatatc atatatcaac ttttcttctg tgcttgcttg  60
caaatttgca attaagcttt tttgatctta tgtaagagaa tattattgat gatggtgttt  120
gggaagccga aaaaagcgat gttggtgagg ttcaatccga agacggattt acatgtatag  180
agttgtaaaa tacgatctca gattgagccg cgccaatatc acttt                  225

SEQ ID NO: 250          moltype = DNA  length = 367
FEATURE                 Location/Qualifiers
source                  1..367
```

```
                         mol_type = unassigned DNA
                         organism = Medicago truncatula
SEQUENCE: 250
ccacaaaact ataactagct agaagcttta atcgccttat ttattataat aataataata  60
aatatggctt cagctgcaaa agtatacatg gcgtgatatt gatccggctc atctatatct  120
tcaagttcaa tcatccatat tcatatcaat ttcagacgag ccgaatcaat atcactcttg  180
tttgcttcat tgcatattaa ttatatactt catttataag ttatagtttg ccatatatat  240
attagattga ttctgcagaa gtagacagga gtggtgttgt ttctgctcat cttattaaat  300
aatgaatgaa tgaatgacat ttgcttactt ataagacgag ccgaatcaat atcactccag  360
tacacct                                                            367

SEQ ID NO: 251           moltype = DNA  length = 712
FEATURE                  Location/Qualifiers
source                   1..712
                         mol_type = unassigned DNA
                         organism = Arabidopsis thaliana
SEQUENCE: 251
ctctctctct ctctctctct catctgtgtt ctagatctca ccaggtcttt ctctggttaa  60
tatatggctt ccaagatctg gtaatatgtt ataaatacgt catacttaag ctttttttcaa  120
atcaaaaata gaaatttgtg ggtttgtctc gttttactat tttagcagta tatattaaga  180
agttcagatg ttattcgatc atctgttttt gcttcccctc tgccatcttt atcttttagg  240
gtttcaattc tttttcactt ttttcttctg gtttggagat ggttaggttc caactaagta  300
tacgagatta aatttgacat cttagttact tcaaaattcc ttcaatcaaa acaagtcatc  360
tcgactattc cgccatgttt gtatatacat atttatatat tatatatatg aaggtacgag  420
tttctagtgt ctataaatta agaaggttaa gtaccatata gatgatattt gttaagtagt  480
aagtcactca aagtttgagt ttgggtttga gtttgagttt gagtttgagt ttgagagaca  540
aaagattact acaagaagat tgttaaacaa aaatggaaga ctaatttccg gagccacggt  600
cgttgttggc tgctgtggca tcatcaagat tcacatctgt tgatggacgg tggtgattca  660
ctctccacaa agttctctat gaaaatgaga atcttgatga tgctgcatcg gc          712

SEQ ID NO: 252           moltype = DNA  length = 714
FEATURE                  Location/Qualifiers
source                   1..714
                         mol_type = unassigned DNA
                         organism = Arabidopsis thaliana
SEQUENCE: 252
acttgcacct ctcactccct ttctctaact agtcttgtgt gcacccattt atgtgtacgt  60
actattatct cataaataaa tatttttaaa attagatgca tttattgata tgaaaaagtt  120
acaagattag tttgttgtgt gtgagacttt ggatcgacag atcgaaaaat taactaaccg  180
gtcagtattg aatatcaact attatatgct ccatgcattc gcttatagtt tcacacaatt  240
tgttttcttc acggtctaaa atcagaagat tccatatatt ttcttatgac gtaaaaggac  300
cacttataag ttgacacgtc agcccttgga ttcgtgaggt ttttctctct acttcaccta  360
tctacttttc ctcatatccc actgcttttc tccttcttgt tcttgttttt ctcgtttttt  420
tcttcttctt ctccaagaaa atagagatcg aaaagattag atctattttg tgtagcaaga  480
aattatcatt ttcgtttctt cattcatata ttgttctatt atgttgtaca ataatagata  540
ctcgatctct tgtgcgtgcg taaattttat acaagttgtc ggcggatcca tggaagaaag  600
ctcatctgtc gttgtttgta ggcgcagcac cattaagatt cacatggaaa ttgataaata  660
ccctaaatta gggttttgat atgtatatga gaatcttgat gatgctgcat caac        714

SEQ ID NO: 253           moltype = DNA  length = 324
FEATURE                  Location/Qualifiers
source                   1..324
                         mol_type = unassigned DNA
                         organism = Arabidopsis thaliana
SEQUENCE: 253
tcaccaaata ggctcttctt tatcgcttca tatatataaa agtctacatc tatctctttc  60
taggtcacta gctagactct agattaagga ttgaaattag ggtttcatgt ttccagcaaa  120
atggtgccgt cttgagtctt gaaaagatcc aagacaaaac caaatcacta catacatccc  180
tatcatcaac cagctactgt tcgctgttgg agcatcatca agattcacaa atcatcaagt  240
attcgtgtaa ataaacccat ttatgattag atttttgatg tatgtatgag aatcttgatg  300
atgctgcagc tgcaatcagt ggct                                         324

SEQ ID NO: 254           moltype = DNA  length = 531
FEATURE                  Location/Qualifiers
source                   1..531
                         mol_type = unassigned DNA
                         organism = Arabidopsis thaliana
SEQUENCE: 254
tgtcatattg agaactcttt agcctttggc ttctgttcct gacacttgta tagtgaagtg  60
ggcttgtgtt atatagatgg gatctctctc tttatttaaa agtcaattag agatcttgat  120
gctacttctg tccctttcca agtgatttta cgtcgaccaa ctagcttttt tcatatgagt  180
gtatatattc atgtacctat ctctctcaat tgcttctcac caaaatcatc ttgctgattc  240
atttgctgtc tgaatcctct tgctttcctc tttgcttttt catttgttga tttaaaccat  300
gggagttccc aactttagac ctcgaaaccg ataaggatct ttctctgcgg ttgaaatagc  360
taggttctcg atgaataggc tagcctttgg tggatgttat cagccagtag tcgcagatgc  420
agcaccatta agattcacaa gagatgtggt tccctttgct ttcgcctctc gatccgcaga  480
aaagggttcc ttatcgagtg ggaatcttga tgatgctgca tcagcaaata c           531

SEQ ID NO: 255           moltype = DNA  length = 618
```

```
FEATURE                Location/Qualifiers
source                 1..618
                       mol_type = unassigned DNA
                       organism = Arabidopsis cebennensis
SEQUENCE: 255
ttgtatccat agtgtatttc ctcgcatcta ccatccattt tctacgcctc tctctctctc  60
tttctccatc aaatcttgtt ttgttcaaac tctctctctc atcaattctc tccatacaat  120
acatgcatac atacatacat accatctcta atatttcatc aatcttcttt tgttccaaac  180
gctctttctc tccatttaca tacatacgaa tcattgttgt catagatccg tttagaattg  240
ctttaacttt tagatgagat ctagggtttc tttcttttc ttcaaaatca tgctttttcg  300
cttgctaggt tatagatcca tgtaagttta gagtagatgt acacacacac gctcggacac  360
ttattaaata catgttgata cacttaatac tcgctgtttt gaattgatgt tgtaggaata  420
tataaatgta gagagagctt ccttgagtcc attcacaggt cggatatgat ccaattagct  480
tccgactcat tcatccaaat accgagtcgc caaaattcaa attagactcg ttaaatgaat  540
gaatgatgcg gtagacaaat tggatcattg attctctttg attggactga agggagctcc  600
ctctctcttc tgtattcc                                               618

SEQ ID NO: 256         moltype = DNA  length = 660
FEATURE                Location/Qualifiers
source                 1..660
                       mol_type = unassigned DNA
                       organism = Arabidopsis halleri
SEQUENCE: 256
ttgtatccat agtgtatttc ctcgcatcta ccatccattt tctacgcctc actctctctt  60
tctccatcaa atcttgtttt gatcaaactc tctctctctc tctctcatca attgtctcca  120
tacaatacat acataccatc atctttccca tctctaatat ttcatcaatc ttcttttgtt  180
caaacgctct tcctctccat atacatatac atacatacga atcacattgg tgtcatagat  240
ccgtttagaa ttgctttaac ttttagatga gatctagggt ttctttgttt ctttcgtttt  300
cttcaaattt tgctgcatat tctccaagat catgattttt cgcttgctag gttatagatc  360
catgcaaata tagagtagat ttacacacac acacgctcgg acacttatta catacatgtt  420
gatacactta atactcgctg tttttaattg atgttgtagg aatatatata tgtagagaga  480
gcttccttga gtccattcac aggtcgtgat atgatccaat tagcttccga ctcattcatc  540
caaataccga gtcgccaaaa ttcgaactag actcgttaaa tgaatgaatg atgcggtaga  600
caaattggat cattgattct ctttgattgg actgaaggga gctccctctc tcttctgtat  660

SEQ ID NO: 257         moltype = DNA  length = 632
FEATURE                Location/Qualifiers
source                 1..632
                       mol_type = unassigned DNA
                       organism = Arabidospis lyrata
SEQUENCE: 257
ttgtatccat agtgtatttc ctcgcatcta ccatccattt tctacgcctc tctctttctc  60
catcaaatct tgttttgttc caactctctc tctcatcaat tcattccata caatacatgc  120
atacatacat accatcatca tcttttccca tctctaatat ttcatcagtc ttcttttgtt  180
acaaacgctc tttctcgcca tatacataca taagaatcat tgttgtcata gatccgttta  240
gaattgcttt aacttttaga tgagatctag ggtttctttc tttttcttca atttttgctg  300
catattcttc aaaatcatga tttttcgctt gctaggttat agatccatgc aaatatagag  360
tagatgtaca cacattcacg ctcggacact tattacatac atgttgatac acttaatact  420
cgctgttttg aatggatgtt gtaggaatat atatgtagag agagcttcct tgagtccatt  480
cacaggtcgt gatatgatcc aattagcttc cgactcattc atccaaatac cgagtcgcca  540
aaattcgaac tagactcgtt aaatgaatga atgatgcggt agacaaattg gatcattgat  600
tctctttgat tggactgaag ggagctccct ct                               632

SEQ ID NO: 258         moltype = DNA  length = 646
FEATURE                Location/Qualifiers
source                 1..646
                       mol_type = unassigned DNA
                       organism = Arabidopsis thaliana
SEQUENCE: 258
ttgtatccgc agtgtatttc ctcgcatcta ccatcccttt tctacgcctc tctccctctc  60
tctctttctc catcaaatct tgttttgttc aaactctctc tctctcatct attctctcca  120
tacaatacat gaatatacat acataccatc atcttctttt cccatctcta gtttttcatc  180
aatcttctga tgttccaaac gctctatctc ttcatataca tacatacgaa tatattattg  240
ttgtcataga tccatttaga atcactttag cttttagatg agatctaggg tttctttgtt  300
ttctttcaaa ttttgttgca tattcttcta aatcatggtt tttcgcttgc taggttatag  360
atccatgcaa atatggagta gatgtacaaa cacacgctcg gacgcatatt acacatgttc  420
atacacttaa tactcgctgt tttgaattga tgttttagga atatatatgt agagagagct  480
tccttgagtc cattcacagg tcgtgatatg attcaattag cttccgactc attcatccaa  540
ataccgagtc gccaaaattc aaactagact cgttaaatga atgaatgatg cggtagacaa  600
attggatcat tgattctctt tgattggact gaagggagct ccctct                646

SEQ ID NO: 259         moltype = DNA  length = 660
FEATURE                Location/Qualifiers
source                 1..660
                       mol_type = unassigned DNA
                       organism = Brassica rapa
SEQUENCE: 259
ttgtatccat tgtgtatttc cttgcatcca tcaataaatt ttatgttacg cctctctatt  60
atttctctct acatcacact gtcttatgtt taagctctac ttctcagcaa ttctctccac  120
```

```
ccaatacatg catacatacc atcatcgtat cgctctaatt tttctatcaa tcttgtatcc  180
ttccacaaat tatcttatgt ctcccatttt aaatcctaca tagatccaca catacgaatt  240
attcttgtct gaagatccat ccatttacga ttgctttaac ttttacatga gatctagggc  300
ttctttattt ttcttcaaat cttgctgcat atatttcaag atcatgcttt tcggcttgct  360
agggttctag atccatggat gtatagcgta catacataca cgcactaatt catacctgta  420
gtttgtacgg agaacatcat aaaatatcac tgtttggaat taatcgtgta ggaaatatag  480
ataggtaggg agcttccttt agtccattca cagatcatga tatgatccaa ttagcttccg  540
actcattcat ccaaataccg agtcacgaaa atttcaactt agactcgtta aatgaatgaa  600
tgatgcggta aacaaattgg atcattgatt ctctctgatt ggactgaagg gagctccctc  660

SEQ ID NO: 260         moltype = DNA  length = 932
FEATURE                Location/Qualifiers
source                 1..932
                       mol_type = unassigned DNA
                       organism = Carica papaya
SEQUENCE: 260
ctatatccct gtcaaatagt acttggtttt gttttagcca caaatcttct ggtcttgcaa  60
agttccttct gatctctccc cctttctcat tttttcctcc tcttatatat ggatcatcaa  120
tttgctgtac acacacacac atttactgta gtgataatta gctagctaat ttgttagtat  180
gtaaattaga tcccaagtac cctgttatat ttttttaggc ttatcctatg catacctgat  240
agtacaagaa cttagtttgt aattaggtac ttggtagtag ggttagatta attactgtct  300
tgaaagagaa cttatccaac aaatagagct atgaagatta aattaggttt tagtcttatt  360
aagattatta tattactaga caaaaacagt taaatttttt taattgggta attaggtact  420
tagcaatagg gttagattaa ttactgtttt gaaagagaac ctacctacaa atagagttga  480
aatgattatg ttttagtctt actaagattg tcatatttct ggaaaaaaac aaatcttgaa  540
acagataatt cagatagtca tgatcaatgg aaaaaacatc atgggtgtgt gcttaattaa  600
gctaatatat atatatatga agatataatg ttatgcacac tagctatgaa tttgtaagaa  660
taatgaagga taaagatgat atatttagat gttataagtg taagtaaggt ggaatgggtt  720
gatgggtagt agtagtagta gtagagatga ttggtggaga gagcttcctt cagcccactc  780
atggatgggt atgaaggggt agaagtagct gccgactcat tcattcagcc actcagtatg  840
taaactcgtc ccactgttga ctgtatgaat gatgcgggag atatttttac atccatcttt  900
ctctgtgctt ggactgaagg gagctccttc tt                                932

SEQ ID NO: 261         moltype = DNA  length = 702
FEATURE                Location/Qualifiers
source                 1..702
                       mol_type = unassigned DNA
                       organism = Capsella rubella
SEQUENCE: 261
ttgtatccat agtgtatttc ctcgcatcta ccatctacta ttttctacgc ctctctctct  60
ttatccctct atctctttct tcatcaaatc ttcttttgtt caaagtctct ctcatcattt  120
ttctctatac acatacatgc atccacatac atacatacat ataccatcat cttcttttct  180
catctctagt ttttgtttat aaattttgtt ccaaggatct gtatctctcc aataaagata  240
catacaaatt attgttgtca tagatctatt agaattgctt taacttttat atgagatcta  300
ggatttcttc cttttctttc aaaatttgct gcatattttt caaaatcatg atttatcgct  360
tgctaggttc tagatccatg caaatttaga gtatttttac acacacacac gcttggacac  420
aagtacatac atgtagtttt cttttatgtg gtgaaaagta cataacatgt agtttatagt  480
tactagtcgc tatataattt aaaattgatg ttataggaat atatgtacgg agagagcttc  540
cttgagtcca ttcacaggtc gtgatatgat ccaattagct tccgactcat tcatccaaat  600
accgagtctc accaaaattg gaacaagact tgttaaatga atgaatgatg cggtagacaa  660
attggatcat tgattctctt tgattggact gaagggagct cc                     702

SEQ ID NO: 262         moltype = DNA  length = 767
FEATURE                Location/Qualifiers
source                 1..767
                       mol_type = unassigned DNA
                       organism = Eucalyptus grandis
SEQUENCE: 262
tcgtttccca tccccatttc atagaataat gccaccaaac aaagaagcat tagctcaaag  60
actaattacc atctgtttta ttgatagata cgtgcgaaac ggtgattgtt ttttcccaaa  120
taagaaacca aaatgaagca tattcaaagg tggagatatg gggagacttc cggaaggcaa  180
ggggattgga aaaggctcga gatcaaagtg catagcaacc cttcgctaaa ggtgaaaaag  240
aatacgaata acttcagtag ctcactttaa attccgaaac attaaacaaa tcaaatctcc  300
ctcgccctcc ttgcctcctc tctttaccta tataaagcca ccgccccttc aatgaaatcc  360
acgagtggaa ggtcacagta tagtagggtc ctgcaaaggg agagcgagag cggctccact  420
gtctacctat aagcagttcc tttcttttgt ttacatgtct gttgcacctc accgagtttt  480
tctattctct ttcctctggt tggttagcag atttctcagg ggacttccct cctcccttga  540
ggatccttct cttgaagcga tatgtctcga atgggtaaga gagagagagg aagggagctt  600
tcttcagtcc acccatggga cgtgttgggt tttaattagc tgccgactca ttcatccaaa  660
taccgagcga gagcaagtaa cagagctccg taaatgaatg gatgatgcgg gagtcttgtt  720
gattcccaag ctttccgtga ttggactgaa gggagctccc tctatct                767

SEQ ID NO: 263         moltype = DNA  length = 612
FEATURE                Location/Qualifiers
source                 1..612
                       mol_type = unassigned DNA
                       organism = Gossypium raimondii
SEQUENCE: 263
gcgtatcctt ccacttacgg attcaccata gctgctatag cccgagtttg cttgtcataa  60
```

```
tagaaataaa ctaagggaga aaaaagctct ccactctcgc ctttttcttc ttcgagtctc  120
tctctttgac tggcctttgt gcaaagatct tcctttttta aacagtcgct ttctttactc  180
tccctttccc ttctttctct taattgctaa agcagcttcc acttccactc actttaaccc  240
atgatccatt tcaacctgtc acagtggaga gcaatttgta tggctaattt ccatctcacc  300
tattcttttc tgtttggggt tctctagtct agggttgcat gacatgagag acatggctct  360
ttttttttt tttcagttca caggtgttta tatatgttgt tgtgttattt tgtcttaaag  420
ctttgtgatt gatgatctga taggtaagag agagctttct tcagtccact catgggatgg  480
ggatggggtt taattagctg ccgactcatt catccaaata ctgtgttaca aaacccagta  540
aatgagtgaa tgatgcggga gacaaattga atcctaatct tcctgtgctt ggactgaagg  600
gagctccctc cc                                                       612

SEQ ID NO: 264          moltype = DNA  length = 675
FEATURE                 Location/Qualifiers
source                  1..675
                        mol_type = unassigned DNA
                        organism = Medicago truncatula
SEQUENCE: 264
atttatccaa tcatgttgct ctcacttctt ttcagcagtt ctgttgatat caccctttta  60
gttgaagctt tggattcatg actttatgag atggtaaatc tttaaattaa gtttaagtat  120
gcacttgatt tgtttatata atttgtttat ttagatttta aaccctaagt tgactttttt  180
aatttgattt aaattatgat atgattgtta tttggcttac catggtcata atttagggtt  240
tagaagatgc atgtatatct tgaattgttt atggtaataa aggggttagg atttctcctt  300
ttggtgaagt gagaaaatct cataattttg ttctgaaggt agtttttaag atttagggtt  360
atgggttctt tgtttgaatg ctttttcaag tctttttcaa tgatatttgc ctagatctgt  420
tttaattttg aattaaaatt ctgggtttgg attaatatta ttgaagatta ttattaatta  480
atttattaga aatagatgaa gagagcttcc ttcagtccac tcatggaagg gtaaggggtt  540
tgaatttacc tgctgactca ttgattcaaa cacaatagac aattatgggg ttatgctatt  600
gtgaattgtg tgaatgatgc aggaggtgaa tttcttcctt ttcttctttg cttggactga  660
agggagtctc ccttt                                                    675

SEQ ID NO: 265          moltype = DNA  length = 866
FEATURE                 Location/Qualifiers
source                  1..866
                        mol_type = unassigned DNA
                        organism = Oryza sativa
SEQUENCE: 265
ttatatctga cgcgttgtaa tcctgtttaa ttagggcttt gcccatttct tttgacccct  60
tccggacatt cgctagttgg aaccttgttt tactcctagc agtgtactgt gtagtactta  120
ttacgagcaa acgtaaaaat aaataaatgg aaatgataca aaggccgtgt ttaattttaa  180
aattttttt caaactttca acactttaca tcccataaaa agcttactat acatacaaac  240
ttccaacctt ttcgtcacat cgtatctaat ttcaactaaa cttttaattt tagcgtgaac  300
taaacacagc cgaagcccgg ccacattctc actattttta ttcattttat catgcctgtg  360
atgtcacgcc ttggccctat ttaataggcc ttctccattt ctctccatat gatgtcttct  420
cttctctatc cctcttgcca tcttctatct tccctcttgc acccatcttt gtgataactt  480
ctactagctc ctctcctact accagtcata ccactctcac aaatcctcca agatccgcat  540
ggggagaagc tccaaaagtt tcgtggttag tttaatttca tgcttgtttg ctgccgtttt  600
tcatgttgat ctgatcttaa tatatgtaga ctgctgttaa catattcttt taatttgatg  660
gaagaagcga tcgatggatg gaagagagcg atccttcagt ccactcatgg gcggtgctag  720
ggtcgaatta gctgccgact cattcaccca caatgccaag caagaaacgc ttgagatagc  780
gaagcttagc agatgagtga atgaagcggg agagtaacgt tccgatctcg cgccgtcttt  840
gcttggactg aagggtgctc cctcct                                        866

SEQ ID NO: 266          moltype = DNA  length = 801
FEATURE                 Location/Qualifiers
source                  1..801
                        mol_type = unassigned DNA
                        organism = Physcomitrella patens
SEQUENCE: 266
tgggatccac acgagtaatt attccctctc tcatgcatca caacttggac ttgcccagct  60
tttacctctc tccatgttcc accgtcggag atcctcggtg ctgctacccc cgttcggcca  120
aacccaaccc aaccctaggt gtctgccgga cctccgcttc ccctcctgct tcaccccctg  180
caccgcttaa atttgcacct cgtagtattt atctatgccc catttcagat gacttgcatg  240
acacccatct ggattcgtct ccaggcgcct tgtcgtatct attcgctatc agtctttctt  300
tcagtctgtc tttctgccaa gcacaccgtg ctggtggtgg tgctatcagt cgaagcagtc  360
gccgaagggt ccttgtatcc agccctcacc ggagacagtt cgcttcgggg tggggagaac  420
tgttgagacc gtcgatgttg catgcagcag cactggcgaa ggtgcttctg atactgggta  480
ttccagcctc gccgctcggt gcactgcagg tacgtggtta catgacacta ctgtgtgggt  540
agtctgggca caagtagatc gacatgccag atttggcccg tatgcgtgta tgtgcggtta  600
tgttcccgtt tcgattgcgg ataccttgat tgtggagctc cgtttcggtc caatagtggc  660
tgcgacggaa ggtggtcccg ctgccgaatc acacgtccgg gttgcttatc ggggcagggc  720
cccgatacgg tatccgaacg tttgtcccgg gaactggtcg accttccgcc cggcgtctct  780
tggactgaag ggagctccac t                                             801

SEQ ID NO: 267          moltype = DNA  length = 819
FEATURE                 Location/Qualifiers
source                  1..819
                        mol_type = unassigned DNA
                        organism = Thellungiella halophila
SEQUENCE: 267
```

```
ttttatacaa ataatgttcg ataacactaa accctagcca tccaactaat agacaaaacc  60
ctacttgtaa tttacaaccg caaattccca gagaacagag taactacgag agagagatgg  120
agattcaaat taaaaagaaa aacttatata taatgaatac acaaaagcta cctaatctgt  180
atatatatat atataaatat gtcttcatta aattaatggt cgtggaatag aaaaaggaaa  240
acctaatttg atcgctaggg cttatcagag taaagatggt taaccttcaa aagatgacta  300
attaaccggg gagataatta aaagattaaa tacgccaaca gagagttaag agataccaga  360
tttaaattcc acaatttggt catgttcttc ttcacgtatt catgacgatg tctgaattat  420
agagaaaccc aaaatataaa atgttaattt taccagacat ttacatacca ataactctat  480
gacgatatgt aaagtaagca aggcatgttt ttatgcaggg aagattgaaa attcaagatt  540
aatcaagaaa attggaatac caaaaagaga gggagctccc ttcagtccaa tcagagagaa  600
tcaatgaccc aatttgtcta ccgcatcatt cattcattta acaagtctag ctcgaattct  660
tggtgactcg gtatttggat gaatgagtcg gaagctaatt ggatcatatc acgacctatg  720
aatggactca aggaagctct ctacaaatgt attcctacca catcaaccca aatatagtga  780
ttacagatgc tgttctcact gtagactaca tttacgttt                         819

SEQ ID NO: 268         moltype = DNA  length = 503
FEATURE                Location/Qualifiers
source                 1..503
                       mol_type = unassigned DNA
                       organism = Arabidopsis thaliana
SEQUENCE: 268
agacatctct tcttctctca tctctctttt cttctctctt ttcctcacat aaactctctt  60
tttttactat taaatccata tggtacctca aattaatcta tggtcatcta gggttatctt  120
gaagattaga attgattcta gcacgcacag agaggaagat cattgcatcc agaatcacaa  180
acatggccta tcttttatct tttctttttg atctaagtca ctgttttatg ctatatatag  240
tataatcaaa ttctttacat gtgcttgtat gtatgcgtat atatagtaac ggaattgtta  300
atatgcttat agatgttgag ttggtggagg aagagagctt tcttcggtcc actcatggag  360
taatatgtga gatttaattg actctcgact cattcatcca aataccaaat gaaagaattt  420
gttctcatat ggtaaatgaa tgaatgatgc gagagacaaa ttgagtcttc acttctctat  480
gcttggactg aagggagctc cct                                          503

SEQ ID NO: 269         moltype = DNA  length = 365
FEATURE                Location/Qualifiers
source                 1..365
                       mol_type = unassigned DNA
                       organism = Arabidopsis thaliana
SEQUENCE: 269
tcttattcca tcacaatcat ctagggtttt aagccaagct tatatagccc gtcataaaga  60
gaactcatct gcctctctct caataccaat aaatatcacc accgtccttc tctcctatca  120
ctattcaatc tatcgcaaac tcctttatgt ctctccaatt ttatgagagg gtttccttca  180
agaacacagt aaaatagatt ggatctttaa acttttgttc cttttcatga gggtttgaca  240
aagattttct tacagtcatc tttggcattc tgtccacctc cttctataca tatatgcatg  300
tgtatatata tatgcgtttc gtgtgaaaga aggaggtggg tatactgcca atagagatct  360
gttag                                                              365

SEQ ID NO: 270         moltype = DNA  length = 134
FEATURE                Location/Qualifiers
source                 1..134
                       mol_type = unassigned DNA
                       organism = Arabidopsis thaliana
SEQUENCE: 270
ttgtatcatg acagagcaag aagaagaaag tcaaatgtcc acatgagttc cctttaacgc  60
ttcattgttg aatactcaaa gccacattgg tttgtatata acactgaagt gtttgggggg  120
actcttggtg tcat                                                    134

SEQ ID NO: 271         moltype = DNA  length = 229
FEATURE                Location/Qualifiers
source                 1..229
                       mol_type = unassigned DNA
                       organism = Arabidopsis thaliana
SEQUENCE: 271
tttcaaaccc taacactctt ataaaccgat tcgccaaaat gtatctacaa tatattgata  60
atgtaatatc tatatattca aacaatcgtc gtgttggtcg gatgttttct agagttcctc  120
tgagcacttc attggagata caatttttta taaaatagtt ttctactgaa gtgtttgggg  180
gaactcccgg gctgattcgg tattttaaat tcagtagact agctagctg              229

SEQ ID NO: 272         moltype = DNA  length = 220
FEATURE                Location/Qualifiers
source                 1..220
                       mol_type = unassigned DNA
                       organism = Arabidopsis thaliana
SEQUENCE: 272
tggtaataga aatgagcaag gagatatttt tttcccctgg gtttgaatga acatcattga  60
gtgcatcgtt gatgtaattt tacttatttt attccattgt tgaattaatt aaagaagtat  120
atatcagcgt tgcattcaat tatgtttttc taattttcag gaaatacaaa aaaaatgaaa  180
aaaaaaaatc acttaaaaga ccttgagagt tcttttgact                        220

SEQ ID NO: 273         moltype = DNA  length = 225
FEATURE                Location/Qualifiers
```

```
source                  1..225
                        mol_type = unassigned DNA
                        organism = Arabidopsis thaliana
SEQUENCE: 273
ggatatcgaa actcaaactg taacagtcct tttattactg gtttagaaga tagataaata  60
ttgttaaggt agtggatctc gacagggttg atatgagaac acacgagcaa tcaacggcta  120
taacgacgct acgtcattgt tacagctctc gtttcatgtg ttctcaggtc acccctgctg  180
agctctttct ctaccgtcca tgttttatca acgccgtggc ccgtg                  225

SEQ ID NO: 274          moltype = DNA  length = 165
FEATURE                 Location/Qualifiers
source                  1..165
                        mol_type = unassigned DNA
                        organism = Arabidopsis thaliana
SEQUENCE: 274
tcttatagag atgaagagaa acatgtaaac tcactagttt tagggcgcct ctccattggc  60
aggtccttta cttccaaata tacacataca tatatgaata tcgaaaattt ccgatgatcg  120
atttataaat gacctgccaa aggagagttg ccctgaaact ggttc                  165

SEQ ID NO: 275          moltype = DNA  length = 187
FEATURE                 Location/Qualifiers
source                  1..187
                        mol_type = unassigned DNA
                        organism = Arabidopsis thaliana
SEQUENCE: 275
caataactca aaatgcaatg tgaaatatga agaatatatt aaatagtagt gaagatgcat  60
gtttatgaag acagagagat aatgtatggt tggattactg ggcgaatact cctatggcag  120
atcgcattgg ctagatatgc aagtaaaatg cttctctgcc aaaggagatt tgccccgcaa  180
ttcatcc                                                            187

SEQ ID NO: 276          moltype = DNA  length = 235
FEATURE                 Location/Qualifiers
source                  1..235
                        mol_type = unassigned DNA
                        organism = Arabidopsis thaliana
SEQUENCE: 276
atttaggtct ctcttcttct tcttcttttt cttcttgagc gccggcgaaa aaagtctctg  60
tgagaaaaag atacgacgat tgtcattaga agagtcgtat tacatgtttt gtgcttgaat  120
ctaattcaac aggctttatg taagagattc tttaacaatt cctataatct ttgttgttgg  180
attagattca cgcacaaact cgtaatctgt cttttcgatt tttaccagat ctgtc       235

SEQ ID NO: 277          moltype = DNA  length = 944
FEATURE                 Location/Qualifiers
source                  1..944
                        mol_type = unassigned DNA
                        organism = Arabidopsis thaliana
SEQUENCE: 277
aattatatcc atggtcatgg ctcatcatta gtcgcactgc tctccttttc tcaaagttta  60
aattcgacat ttggtaaaat gatgaaacct cgatggaact gctctcttta tggaatcacg  120
gaatggacaa ataatcaaaa tcagaaatcg aagcgaaaag ggaggagaaa aacgcagatt  180
tggaggattg gggacagatt agatactgtt gaatgcatca ctctaatgct atcagcctat  240
taatagcgtc ctatattttc gaagactttt aatgtttagg gttatggatt tttcgagcga  300
agcatggaga gatgttgaat tggatactat aggatttggt acaacacata catatgttct  360
gcttctgcaa aactaacata tcaagttcag agaaaccagt aagtcgttga atattttatt  420
atccattcaa cgctttcttc ttttggatca tgtcttgttt gcttgaccac ttcttcttgc  480
ttaagaggat ggacaatata taaaaactgg agccttcttt ttctatgaat gcttatcatc  540
gcggagttga tctgttcaat tcacctgcca ttggatgctt tttttatata tacttcactg  600
ttcaatttca gatgctttag aaggtttgcg gagtagctag agaatctggt atcttcagtt  660
cttcaatttc agctacttgg tatcagcttc gtcattgtat atcaacacat tcttaatata  720
taatactact ttttcatcca ttaaacccct tacaatgtcg agtaaacgaa gcatctgtcc  780
cctggtattg tcttcgagct tggtgttttt ttctagccaa ctccaagttc tcgagttgat  840
cattgtttgt attcttgaga cattatttgg ggacgagatg ttttgttgac tcgatataag  900
aaggggcttt atggaagaaa ttgtagtatt atatatcgag agtg                   944

SEQ ID NO: 278          moltype = DNA  length = 420
FEATURE                 Location/Qualifiers
source                  1..420
                        mol_type = unassigned DNA
                        organism = Arabidopsis thaliana
SEQUENCE: 278
ctataaatgc tgcttatcat cgtggagttg gttctgtaaa catttgaaaa ttctgaacag  60
tttcacctgc cattggatgc tttgtttcaa tttcaggtgc gttagaaggt ttgcagagta  120
gctagagaat ctcgtatctt cactttctgc tacttggtat cagcttcgtc actttatatc  180
aacacattct taatatacaa tactactttt tcatccatta atccccttac aatgtcgagt  240
aaacgaagca tctgtcccct ggtattgtct tcgagcttgg tgtgtttttc tagccagccc  300
caagttctcg agttgatcat tgtttgtatt ctgacacatt atttggggac gagatgtttt  360
gttgactcga tataagaagg ggctttatgg aagaaattgt agtattatat attgagaatg  420

SEQ ID NO: 279          moltype = DNA  length = 383
```

```
FEATURE                 Location/Qualifiers
source                  1..383
                        mol_type = unassigned DNA
                        organism = Arabidopsis thaliana
SEQUENCE: 279
tagtataacc gctgatgtac acctaccagc ttgataactc tttttcgtgg tttctgtgta  60
ctcgtttctg tttgtacaga tacttcttgt tcaatttcag atgctttaga aggttttcgg  120
agtggctaga gatctgttat ctgtatgaac agctacttgg tatcagcttc gtcattttat  180
caacacattc ttaatataca atacttcttt ttcatgcatt aagcccctta caatgtcgag  240
taaacaaagc atgtgtccgc taatattgtc ttcgagcttg gtatttttgt attctgatac  300
ggtatttggg gacgacatct tttgttgact cgatataaga agggggtttg tggaagaaat  360
tgtagtatta tatatcaaga atg                                          383

SEQ ID NO: 280          moltype = DNA  length = 2164
FEATURE                 Location/Qualifiers
source                  1..2164
                        mol_type = unassigned DNA
                        organism = Drosophila melanogaster
SEQUENCE: 280
tttgtggaac acattcgacc cactgaaaaa ttgatataat ttaatgaaag tgcataaaaa  60
tggtggacag tgcattaaac tgagcattga acacaaaggc cgctcagcaa attgctaatt  120
aaaattcacg attgccattt cacctgacac gttgacgatt ttcattacaa ttcgattatg  180
tttcgttgca gggaatttta aatgttaatt gccaagaatg tttcaacaaa ttcatttctc  240
attaatgtgt cttttcattt aattttatgt tgtatgagct gcacgagaaa tgagttgtac  300
ttttagttcg acggcagagt catgaatgtt cggcaaagaa tgtaataata actatcctct  360
ttagacaaat atagatacaa atctatcaga ttctaaaagt agaataatca attaatcaga  420
aagctaaaaa taaataggca tatttatatt ttaatgcgga tttttgaagt tcaacgggag  480
aaatgaatcc tttttaccag ccacaggcgc aatttgcaac agaaagtgta gcagaagtac  540
tcctcgaata tttccctgct ccaggagtca tccatgtggt ttcgaggcac acatttgaca  600
aactcatgcc ccgctatttg ttgtaaaaac acaatcgcac acatggccgc atttcggcga  660
cttccagaga gcggtacact taaggcggcc tgggaaacgc ctgcaatctg ctggtcgcga  720
actgcagatt gcatccatgt gccaggcgac catgcgacca tgtgaccatg tgcccgcccg  780
acgcctcgca gcccacatcc tgcccatcga gggcacaact cagcgtgggt attgccgctc  840
cggctgcttc aagtaggtaa aaaccgagaa gattgaggat gaatgtatga gtatgagaaa  900
atactcggcg gaacatatgc tgccgggctt gacctgaccc tgcctcatgt gtgggtctcc  960
gatttaattt taggcaccta tataaacgcg tgtttacact gcagccagaa cacagtcgcc  1020
gtcttcagtt cgcgccgtca actcctcgat cgatcgatcg catcgtctcg gatcgaatag  1080
agctgggctt ctgctccgga gctacatcgc cgtacttgtc ggacgagtgt ggtgatgaaa  1140
agtcgcttag tccgggattc ctgccagatc tctaagggat gagctggcat cccaggctgg  1200
ccatgtggcg cgaagtatgc gcacaaaaaa gtcaaacaaa aaggcgcaat tttattacgg  1260
gcaaccaacg acgaaacaaa acaaaagcca accgaaaagc agaaacaaag cagcaaaaag  1320
tttatgaatt ttttgtgcag gcgcgtgaaa gatgcaaaac gagaaaaaaa catgaaaaaa  1380
aaacattaaa aaaaacaaaa aaaatccaaa acagataccg agctgtatcc gaaaacgagt  1440
ggggaaaggg gtttcccagt cacatataaa cacacttcag tgcgcttaaa aattgcttta  1500
ttgcagttgg actataaaaa cgcacggcag cgaacaccgc acaacaaaaa ggacgagcag  1560
aagtgggcaa ataaaacgaa agctcttaaa cgaaaaacag gaaaatttgc atgccacaaa  1620
aataagcata aggatttgcc gcgcacaaag tagaagcaaa aaggaattgc ccaaatgcag  1680
ccacaaaaga ctgtggcaaa tgttttgcag cttgcccctt tttccctgca attaccgtca  1740
gtcgttgtca ttattcagca gattatatgg ttttgcttat tccggaccac catcatcatc  1800
atcattatca tcatcttcgg taagttagac aatcccataa aaaactgtcc aagtgagtag  1860
tgccaccaaa agttagccgc gttgtggaaa atccaaaaca aagaccatcc catattcagc  1920
ctttgagagt tccatgcttc cttgcattca atagttatat tcaagcatat ggaatgtaaa  1980
gaagtatgga gcgaaatctg gcgagacatc ggagttgaaa ctaaaactga aatttgattg  2040
aaacagaagt agaaccgtaa tgaaatgaat gaaatattaa cccgtttcta caatccctga  2100
ataaaattat taattaatta tagagcgggc taattttaca atatatattg attttttttt  2160
gaag                                                               2164

SEQ ID NO: 281          moltype = DNA  length = 919
FEATURE                 Location/Qualifiers
source                  1..919
                        mol_type = unassigned DNA
                        organism = Drosophila melanogaster
SEQUENCE: 281
attctttttt ggtgctcgat cgtgacggtt tgctcgcgct ctccgctgcg ccgctctttc  60
cgttgcatat gtgtgcgggc gttattgtgc atgtttccgg tggccgaaaa aaaatagtaa  120
aataaaatat agaaaacaga aaccaagaat aataacagcc atacgataaa cagtgtgcca  180
atgtgtgtgt ctgtgtgtgt gtgcatctcg cgtaacaaca ataattgcat ttatcggatg  240
gcgccagctt caatttaatt ataaataaca tgttcaactt tttatactat tttccctgcg  300
tcaaagtggg cgttgcaact gcccccggaa aatcacgcgc cccggttcaa agttaaagtt  360
tgctgggtaa cgcacacaca cacacacaca atcactcaca cgcggtcaca cgcacatttc  420
aataaactaa tggagcctgg ctttgttttt gttttatttc caacccactt gagcacacag  480
cacacacaga gagaaaaatc aatactcgtt atgggattaa atttacaaag cgcaaagcaa  540
agcgacaaac aaaattcaaa agaaagaaaa aaaaacactc aaataaactc acaaagaatt  600
ccttatcgcc aagggggcca atgttctaag gttctttcgc cttgagaact ttgagcttcc  660
tctggcaaag gagattataa tgtacaaata atgttgcaat aaccagttga aaccaatgga  720
ataccgaatc ttgctaatta gcaaggacat ctgttcacat cttaccgggc agcattagat  780
cctttttata actctaatac tgtcaggtaa agatgtcgtc cgtgtcctta accttcagta  840
ccaccaacag cagcagcagc accaaaaaaa aaaaaaaaaa aatgcgtaaa aatccaaaca  900
aatcataaaa gtcgaagga                                               919
```

```
SEQ ID NO: 282          moltype = RNA  length = 20
FEATURE                 Location/Qualifiers
source                  1..20
                        mol_type = unassigned RNA
                        organism = Arabidopsis thaliana
SEQUENCE: 282
tgacagaaga gagtgagcac                                              20

SEQ ID NO: 283          moltype = RNA  length = 20
FEATURE                 Location/Qualifiers
source                  1..20
                        mol_type = unassigned RNA
                        organism = Arabidopsis thaliana
SEQUENCE: 283
tgacagaaga gagtgagcac                                              20

SEQ ID NO: 284          moltype = RNA  length = 20
FEATURE                 Location/Qualifiers
source                  1..20
                        mol_type = unassigned RNA
                        organism = Arabidopsis thaliana
SEQUENCE: 284
tgacagaaga gagtgagcac                                              20

SEQ ID NO: 285          moltype = RNA  length = 20
FEATURE                 Location/Qualifiers
source                  1..20
                        mol_type = unassigned RNA
                        organism = Arabidopsis thaliana
SEQUENCE: 285
tgacagaaga gagtgagcac                                              20

SEQ ID NO: 286          moltype = RNA  length = 21
FEATURE                 Location/Qualifiers
source                  1..21
                        mol_type = unassigned RNA
                        organism = Arabidopsis lyrata
SEQUENCE: 286
tttggattga agggagctct a                                            21

SEQ ID NO: 287          moltype = RNA  length = 21
FEATURE                 Location/Qualifiers
source                  1..21
                        mol_type = unassigned RNA
                        organism = Arabidopsis thaliana
SEQUENCE: 287
tttggattga agggagctct a                                            21

SEQ ID NO: 288          moltype = RNA  length = 21
FEATURE                 Location/Qualifiers
source                  1..21
                        mol_type = unassigned RNA
                        organism = Capsella rubella
SEQUENCE: 288
tttggattga agggagctct a                                            21

SEQ ID NO: 289          moltype = RNA  length = 21
FEATURE                 Location/Qualifiers
source                  1..21
                        mol_type = unassigned RNA
                        organism = Arabidopsis thaliana
SEQUENCE: 289
tttggattga agggagctct t                                            21

SEQ ID NO: 290          moltype = RNA  length = 21
FEATURE                 Location/Qualifiers
source                  1..21
                        mol_type = unassigned RNA
                        organism = Arabidopsis thaliana
SEQUENCE: 290
tgcctggctc cctgtatgcc a                                            21

SEQ ID NO: 291          moltype = RNA  length = 21
FEATURE                 Location/Qualifiers
source                  1..21
                        mol_type = unassigned RNA
                        organism = Arabidopsis thaliana
SEQUENCE: 291
```

```
tgcctggctc cctgtatgcc a                                              21

SEQ ID NO: 292          moltype = RNA  length = 21
FEATURE                 Location/Qualifiers
source                  1..21
                        mol_type = unassigned RNA
                        organism = Arabidopsis thaliana
SEQUENCE: 292
tcaatgcatt gaaagtgact a                                              21

SEQ ID NO: 293          moltype = RNA  length = 21
FEATURE                 Location/Qualifiers
source                  1..21
                        mol_type = unassigned RNA
                        organism = Arabidopsis thaliana
SEQUENCE: 293
tcgataaacc tctgcatcca g                                              21

SEQ ID NO: 294          moltype = RNA  length = 21
FEATURE                 Location/Qualifiers
source                  1..21
                        mol_type = unassigned RNA
                        organism = Arabidopsis thaliana
SEQUENCE: 294
tcgataaacc tctgcatcca g                                              21

SEQ ID NO: 295          moltype = RNA  length = 24
FEATURE                 Location/Qualifiers
source                  1..24
                        mol_type = unassigned RNA
                        organism = Arabidopsis thaliana
SEQUENCE: 295
ttgaagagga cttggaactt cgat                                           24

SEQ ID NO: 296          moltype = RNA  length = 21
FEATURE                 Location/Qualifiers
source                  1..21
                        mol_type = unassigned RNA
                        organism = Arabidopsis lyrata
SEQUENCE: 296
tggagaagca gggcacgtgc a                                              21

SEQ ID NO: 297          moltype = RNA  length = 21
FEATURE                 Location/Qualifiers
source                  1..21
                        mol_type = unassigned RNA
                        organism = Arabidopsis thaliana
SEQUENCE: 297
tggagaagca gggcacgtgc a                                              21

SEQ ID NO: 298          moltype = RNA  length = 21
FEATURE                 Location/Qualifiers
source                  1..21
                        mol_type = unassigned RNA
                        organism = Brassica rapa
SEQUENCE: 298
tggagaagca gggcacgtgc a                                              21

SEQ ID NO: 299          moltype = RNA  length = 21
FEATURE                 Location/Qualifiers
source                  1..21
                        mol_type = unassigned RNA
                        organism = Carica papaya
SEQUENCE: 299
tggagaagca gggcacgtgc a                                              21

SEQ ID NO: 300          moltype = RNA  length = 21
FEATURE                 Location/Qualifiers
source                  1..21
                        mol_type = unassigned RNA
                        organism = Capsella rubella
SEQUENCE: 300
tggagaagca gggcacgtgc a                                              21

SEQ ID NO: 301          moltype = RNA  length = 21
FEATURE                 Location/Qualifiers
source                  1..21
                        mol_type = unassigned RNA
                        organism = Gossypium raimondii
```

```
SEQUENCE: 301
tggagaagca gggcacgtgc a                                            21

SEQ ID NO: 302         moltype = RNA  length = 21
FEATURE                Location/Qualifiers
source                 1..21
                       mol_type = unassigned RNA
                       organism = Medicago truncatula
SEQUENCE: 302
tggagaagca gggcacgtgc a                                            21

SEQ ID NO: 303         moltype = RNA  length = 21
FEATURE                Location/Qualifiers
source                 1..21
                       mol_type = unassigned RNA
                       organism = Oryza sativa
SEQUENCE: 303
tggagaagca gggtacgtgc a                                            21

SEQ ID NO: 304         moltype = RNA  length = 21
FEATURE                Location/Qualifiers
source                 1..21
                       mol_type = unassigned RNA
                       organism = Arabidopsis lyrata
SEQUENCE: 304
tcggaccagg cttcatcccc c                                            21

SEQ ID NO: 305         moltype = RNA  length = 21
FEATURE                Location/Qualifiers
source                 1..21
                       mol_type = unassigned RNA
                       organism = Arabidopsis thaliana
SEQUENCE: 305
tcggaccagg cttcatcccc c                                            21

SEQ ID NO: 306         moltype = RNA  length = 21
FEATURE                Location/Qualifiers
source                 1..21
                       mol_type = unassigned RNA
                       organism = Brassica carinata
SEQUENCE: 306
tcggaccagg cttcatcccc c                                            21

SEQ ID NO: 307         moltype = RNA  length = 21
FEATURE                Location/Qualifiers
source                 1..21
                       mol_type = unassigned RNA
                       organism = Brassica juncea
SEQUENCE: 307
tcggaccagg cttcatcccc c                                            21

SEQ ID NO: 308         moltype = RNA  length = 21
FEATURE                Location/Qualifiers
source                 1..21
                       mol_type = unassigned RNA
                       organism = Brassica napus
SEQUENCE: 308
tcggaccagg cttcatcccc c                                            21

SEQ ID NO: 309         moltype = RNA  length = 21
FEATURE                Location/Qualifiers
source                 1..21
                       mol_type = unassigned RNA
                       organism = Brassica oleracea
SEQUENCE: 309
tcggaccagg cttcatcccc c                                            21

SEQ ID NO: 310         moltype = RNA  length = 21
FEATURE                Location/Qualifiers
source                 1..21
                       mol_type = unassigned RNA
                       organism = Brassica rapa
SEQUENCE: 310
tcggaccagg cttcatcccc c                                            21

SEQ ID NO: 311         moltype = RNA  length = 21
FEATURE                Location/Qualifiers
source                 1..21
                       mol_type = unassigned RNA
```

```
                        organism = Arabidopsis thaliana
SEQUENCE: 311
tcggaccagg cttcattccc c                                              21

SEQ ID NO: 312          moltype = RNA  length = 21
FEATURE                 Location/Qualifiers
source                  1..21
                        mol_type = unassigned RNA
                        organism = Arabidopsis thaliana
SEQUENCE: 312
tcggaccagg cttcattccc c                                              21

SEQ ID NO: 313          moltype = RNA  length = 21
FEATURE                 Location/Qualifiers
source                  1..21
                        mol_type = unassigned RNA
                        organism = Arabidopsis thaliana
SEQUENCE: 313
tgaagctgcc agcatgatct a                                              21

SEQ ID NO: 314          moltype = RNA  length = 21
FEATURE                 Location/Qualifiers
source                  1..21
                        mol_type = unassigned RNA
                        organism = Arabidopsis thaliana
SEQUENCE: 314
tgaagctgcc agcatgatct a                                              21

SEQ ID NO: 315          moltype = RNA  length = 21
FEATURE                 Location/Qualifiers
source                  1..21
                        mol_type = unassigned RNA
                        organism = Arabidopsis thaliana
SEQUENCE: 315
cagccaagga tgacttgccg g                                              21

SEQ ID NO: 316          moltype = RNA  length = 21
FEATURE                 Location/Qualifiers
source                  1..21
                        mol_type = unassigned RNA
                        organism = Arabidopsis thaliana
SEQUENCE: 316
tagccaagga tgacttgcct g                                              21

SEQ ID NO: 317          moltype = RNA  length = 21
FEATURE                 Location/Qualifiers
source                  1..21
                        mol_type = unassigned RNA
                        organism = Arabidopsis thaliana
SEQUENCE: 317
tgattgagcc gcgccaatat c                                              21

SEQ ID NO: 318          moltype = RNA  length = 21
FEATURE                 Location/Qualifiers
source                  1..21
                        mol_type = unassigned RNA
                        organism = Arabidopsis thaliana
SEQUENCE: 318
ttgagccgtg ccaatatcac g                                              21

SEQ ID NO: 319          moltype = RNA  length = 21
FEATURE                 Location/Qualifiers
source                  1..21
                        mol_type = unassigned RNA
                        organism = Medicago truncatula
SEQUENCE: 319
tgattgagcc gcgtcaatat c                                              21

SEQ ID NO: 320          moltype = RNA  length = 21
FEATURE                 Location/Qualifiers
source                  1..21
                        mol_type = unassigned RNA
                        organism = Zea mays
SEQUENCE: 320
ggattgagcc gcgtcaatat c                                              21

SEQ ID NO: 321          moltype = RNA  length = 21
FEATURE                 Location/Qualifiers
source                  1..21
```

```
                        mol_type = unassigned RNA
                        organism = Arabidopsis thaliana
SEQUENCE: 321
ttgagccgtg ccaatatcac g                                                21

SEQ ID NO: 322          moltype = RNA  length = 21
FEATURE                 Location/Qualifiers
source                  1..21
                        mol_type = unassigned RNA
                        organism = Medicago truncatula
SEQUENCE: 322
agattgagcc gcgccaatat c                                                21

SEQ ID NO: 323          moltype = RNA  length = 21
FEATURE                 Location/Qualifiers
source                  1..21
                        mol_type = unassigned RNA
                        organism = Medicago truncatula
SEQUENCE: 323
cgagccgaat caatatcact c                                                21

SEQ ID NO: 324          moltype = RNA  length = 21
FEATURE                 Location/Qualifiers
source                  1..21
                        mol_type = unassigned RNA
                        organism = Arabidopsis thaliana
SEQUENCE: 324
agaatcttga tgatgctgca t                                                21

SEQ ID NO: 325          moltype = RNA  length = 20
FEATURE                 Location/Qualifiers
source                  1..20
                        mol_type = unassigned RNA
                        organism = Arabidopsis thaliana
SEQUENCE: 325
gcagcaccat taagattcac                                                  20

SEQ ID NO: 326          moltype = RNA  length = 21
FEATURE                 Location/Qualifiers
source                  1..21
                        mol_type = unassigned RNA
                        organism = Arabidopsis thaliana
SEQUENCE: 326
agaatcttga tgatgctgca g                                                21

SEQ ID NO: 327          moltype = RNA  length = 21
FEATURE                 Location/Qualifiers
source                  1..21
                        mol_type = unassigned RNA
                        organism = Arabidopsis thaliana
SEQUENCE: 327
ggaatcttga tgatgctgca t                                                21

SEQ ID NO: 328          moltype = RNA  length = 21
FEATURE                 Location/Qualifiers
source                  1..21
                        mol_type = unassigned RNA
                        organism = Arabidopsis cebennensis
SEQUENCE: 328
ttggactgaa gggagctccc t                                                21

SEQ ID NO: 329          moltype = RNA  length = 21
FEATURE                 Location/Qualifiers
source                  1..21
                        mol_type = unassigned RNA
                        organism = Arabidopsis halleri
SEQUENCE: 329
ttggactgaa gggagctccc t                                                21

SEQ ID NO: 330          moltype = RNA  length = 21
FEATURE                 Location/Qualifiers
source                  1..21
                        mol_type = unassigned RNA
                        organism = Arabidospis lyrata
SEQUENCE: 330
ttggactgaa gggagctccc t                                                21

SEQ ID NO: 331          moltype = RNA  length = 21
FEATURE                 Location/Qualifiers
```

```
source                  1..21
                        mol_type = unassigned RNA
                        organism = Arabidopsis thaliana
SEQUENCE: 331
ttggactgaa gggagctccc t                                              21

SEQ ID NO: 332          moltype = RNA  length = 21
FEATURE                 Location/Qualifiers
source                  1..21
                        mol_type = unassigned RNA
                        organism = Brassica rapa
SEQUENCE: 332
ttggactgaa gggagctccc t                                              21

SEQ ID NO: 333          moltype = RNA  length = 21
FEATURE                 Location/Qualifiers
source                  1..21
                        mol_type = unassigned RNA
                        organism = Carica papaya
SEQUENCE: 333
ttggactgaa gggagctcct t                                              21

SEQ ID NO: 334          moltype = RNA  length = 19
FEATURE                 Location/Qualifiers
source                  1..19
                        mol_type = unassigned RNA
                        organism = Capsella rubella
SEQUENCE: 334
ttggactgaa gggagctcc                                                 19

SEQ ID NO: 335          moltype = RNA  length = 21
FEATURE                 Location/Qualifiers
source                  1..21
                        mol_type = unassigned RNA
                        organism = Eucalyptus grandis
SEQUENCE: 335
ttggactgaa gggagctccc t                                              21

SEQ ID NO: 336          moltype = RNA  length = 21
FEATURE                 Location/Qualifiers
source                  1..21
                        mol_type = unassigned RNA
                        organism = Gossypium raimondii
SEQUENCE: 336
ttggactgaa gggagctccc t                                              21

SEQ ID NO: 337          moltype = RNA  length = 22
FEATURE                 Location/Qualifiers
source                  1..22
                        mol_type = unassigned RNA
                        organism = Medicago truncatula
SEQUENCE: 337
ttggactgaa gggagtctcc ct                                             22

SEQ ID NO: 338          moltype = RNA  length = 21
FEATURE                 Location/Qualifiers
source                  1..21
                        mol_type = unassigned RNA
                        organism = Oryza sativa
SEQUENCE: 338
ttggactgaa gggtgctccc t                                              21

SEQ ID NO: 339          moltype = RNA  length = 20
FEATURE                 Location/Qualifiers
source                  1..20
                        mol_type = unassigned RNA
                        organism = Physcomitrella patens
SEQUENCE: 339
cttggactga agggagctcc                                                20

SEQ ID NO: 340          moltype = RNA  length = 20
FEATURE                 Location/Qualifiers
source                  1..20
                        mol_type = unassigned RNA
                        organism = Thellungiella halophila
SEQUENCE: 340
tggactcaag gaagctctct                                                20

SEQ ID NO: 341          moltype = RNA  length = 21
```

```
FEATURE                Location/Qualifiers
source                 1..21
                       mol_type = unassigned RNA
                       organism = Arabidopsis thaliana
SEQUENCE: 341
ttggactgaa gggagctccc t                                              21

SEQ ID NO: 342         moltype = RNA  length = 20
FEATURE                Location/Qualifiers
source                 1..20
                       mol_type = unassigned RNA
                       organism = Arabidopsis thaliana
SEQUENCE: 342
ttggcattct gtccacctcc                                                20

SEQ ID NO: 343         moltype = RNA  length = 21
FEATURE                Location/Qualifiers
source                 1..21
                       mol_type = unassigned RNA
                       organism = Arabidopsis thaliana
SEQUENCE: 343
ctgaagtgtt tgggggggact c                                             21

SEQ ID NO: 344         moltype = RNA  length = 21
FEATURE                Location/Qualifiers
source                 1..21
                       mol_type = unassigned RNA
                       organism = Arabidopsis thaliana
SEQUENCE: 344
ctgaagtgtt tgggggaact c                                              21

SEQ ID NO: 345         moltype = RNA  length = 21
FEATURE                Location/Qualifiers
source                 1..21
                       mol_type = unassigned RNA
                       organism = Arabidopsis thaliana
SEQUENCE: 345
tcattgagtg catcgttgat g                                              21

SEQ ID NO: 346         moltype = RNA  length = 21
FEATURE                Location/Qualifiers
source                 1..21
                       mol_type = unassigned RNA
                       organism = Arabidopsis thaliana
SEQUENCE: 346
tgtgttctca ggtcacccct g                                              21

SEQ ID NO: 347         moltype = RNA  length = 21
FEATURE                Location/Qualifiers
source                 1..21
                       mol_type = unassigned RNA
                       organism = Arabidopsis thaliana
SEQUENCE: 347
tgccaaagga gagttgccct g                                              21

SEQ ID NO: 348         moltype = RNA  length = 21
FEATURE                Location/Qualifiers
source                 1..21
                       mol_type = unassigned RNA
                       organism = Arabidopsis thaliana
SEQUENCE: 348
tgccaaagga gatttgcccc g                                              21

SEQ ID NO: 349         moltype = RNA  length = 21
FEATURE                Location/Qualifiers
source                 1..21
                       mol_type = unassigned RNA
                       organism = Arabidopsis thaliana
SEQUENCE: 349
ttagattcac gcacaaactc g                                              21

SEQ ID NO: 350         moltype = RNA  length = 22
FEATURE                Location/Qualifiers
source                 1..22
                       mol_type = unassigned RNA
                       organism = Arabidopsis thaliana
SEQUENCE: 350
ttggggacga gatgttttgt tg                                             22
```

```
SEQ ID NO: 351          moltype = RNA  length = 22
FEATURE                 Location/Qualifiers
source                  1..22
                        mol_type = unassigned RNA
                        organism = Arabidopsis thaliana
SEQUENCE: 351
ttggggacga gatgttttgt tg                                          22

SEQ ID NO: 352          moltype = RNA  length = 21
FEATURE                 Location/Qualifiers
source                  1..21
                        mol_type = unassigned RNA
                        organism = Arabidopsis thaliana
SEQUENCE: 352
ccccttacaa tgtcgagtaa a                                           21

SEQ ID NO: 353          moltype = RNA  length = 22
FEATURE                 Location/Qualifiers
source                  1..22
                        mol_type = unassigned RNA
                        organism = Drosophila melanogaster
SEQUENCE: 353
tggaatgtaa agaagtatgg ag                                          22

SEQ ID NO: 354          moltype = RNA  length = 23
FEATURE                 Location/Qualifiers
source                  1..23
                        mol_type = unassigned RNA
                        organism = Drosophila melanogaster
SEQUENCE: 354
taatactgtc aggtaaagat gtc                                         23

SEQ ID NO: 355          moltype = AA  length = 17
FEATURE                 Location/Qualifiers
source                  1..17
                        mol_type = protein
                        organism = Homo sapiens
SEQUENCE: 355
MEMALMVAQT RKGKSVV                                                17

SEQ ID NO: 356          moltype = DNA  length = 53
FEATURE                 Location/Qualifiers
source                  1..53
                        mol_type = unassigned DNA
                        organism = Homo sapiens
SEQUENCE: 356
tggagatggc tctaatggtg gcacaaacca ggaaggggaa atctgtggtt taa        53

SEQ ID NO: 357          moltype = DNA  length = 1500
FEATURE                 Location/Qualifiers
source                  1..1500
                        mol_type = unassigned DNA
                        organism = Homo sapiens
SEQUENCE: 357
gccgagcccg ggcccagcgc cgcctgcagc ctcgggaagg gagcggatag cggagccccg  60
agccgcccgc agagcaagcg cggggaacca aggagacgct cctggcactg cagataactt  120
gtctgcattt caagaacaac ctaccagaga ccttacctgt caccttggct ctcccaccca  180
atggagatgg ctctaatggt ggcacaaacc aggaagggga aatctgtggt ttaaattctt  240
tatgcctcat cctctgagtg ctgaaggctt gctgtaggct gtatgctgtt aatgctaatc  300
gtgatagggg tttttgcctc caactgactc ctacatatta gcattaacag tgtatgatgc  360
ctgttactag cattcacatg gaacaaattg ctgccgtggg aggatgacaa agaagcatga  420
gtcaccctgc tggataaact tagacttcag gctttatcat ttttcaatct gttaatcata  480
atctggtcac tgggatgttc aaccttaaac taagttttga aagtaaggtt atttaaaaga  540
tttatcagta gtatcctaaa tgcaaacatt ttcatttaaa tgtcaagccc atgtttgttt  600
ttatcattaa cagaaaatat attcatgtca ttcttaattg caggttttgg cttgttcatt  660
ataatgttca taaacacctt tgattcaact gttagaaatg tgggctaaac acaaatttct  720
ataatatttt tgtagttaaa aattagaagg actactaacc tccagttata tcatggattg  780
tctggcaacg ttttttaaaa gatttagaaa ctggtacttt cccccaggta acgatttttct 840
gttcaggcaa cttcagttta aaattaatac ttttatttga ctcttaaagg gaaactgaaa  900
ggctatgaag ctgaattttt ttaatgaaat atttttaaca gttagcaggg taaataacat  960
ctgacagcta atgagatatt ttttccatac aagataaaaa gatttaatca aaaaatttca  1020
tatttgaaat gaagtcccaa atctaggttc aagttcaata gcttagccac ataatacggt  1080
tgtgcgagca gagaatctac ctttccactt ctaagcctgt ttcttcctcc atatggggat  1140
aatactttac aaggttgttg tgaggcttag atgagataga gaattattcc ataagataat  1200
caagtgctac attaatgtta tagttagatt aatccaagaa ctagtcaccc tactttatta  1260
gagaagagaa aagctaatga tttgatttgc agaatattta aggtttggat ttctatgcag  1320
tttttctaaa taaccatcac ttacaaatat gtaaccaaac gtaattgtta gtatatttaa  1380
tgtaaacttg ttttaacaac tcttctcaac attttgtcca ggttattcac tgtaaccaaa  1440
taaatctcat gagtctttag ttgatttaaa ataaaaaaaa aaaaaaaaaa aaaaaaaaaa  1500
```

```
SEQ ID NO: 358         moltype = RNA  length = 23
FEATURE                Location/Qualifiers
source                 1..23
                       mol_type = unassigned RNA
                       organism = Homo sapiens
SEQUENCE: 358
taatactgtc aggtaaagat gtc                                          23

SEQ ID NO: 359         moltype = DNA  length = 337
FEATURE                Location/Qualifiers
source                 1..337
                       mol_type = unassigned DNA
                       organism = Medicago truncatula
SEQUENCE: 359
ttagggtttt cagctcatgg taataaaaat gtcatctaat gtcttgcatg tgggaatgag  60
gtcatatatg cagccaagga tgacttgccg gcgagcctct ttcgatactt ttatgacata  120
attaatcatg tggatagcca aggtactaaa ctcactttgc actaaaacaa atatttttgc  180
tttagtgcaa acttagttta ggcgcttcgc aacggctagt caaatgtcct agttccaatg  240
tgattggttg tccggcaagt cgtctctggc tacgtaaagg cctccttttt tcatgctaga  300
tttttgatga tttgatatag ccacacatat tttggaa                           337

SEQ ID NO: 360         moltype = DNA  length = 121
FEATURE                Location/Qualifiers
source                 1..121
                       mol_type = unassigned DNA
                       organism = Medicago truncatula
SEQUENCE: 360
aagaggcaga gagagtaatg cagccaagga tgacttgccg acaacattgg cgaatgttca  60
tgtgatttct gcctcattgt gccggcaagt tgtccttggc tatgttagtc tctcatcttc  120
t                                                                  121

SEQ ID NO: 361         moltype = DNA  length = 114
FEATURE                Location/Qualifiers
source                 1..114
                       mol_type = unassigned DNA
                       organism = Medicago truncatula
SEQUENCE: 361
tgaattcccc tccgcttttt gatgttggct tgtctcaatc aaatcaaagt tcttgaaatt  60
tgagttcttt agtctgattg agtcgtgcca atatcatatt aagcgataaa agtc        114

SEQ ID NO: 362         moltype = DNA  length = 367
FEATURE                Location/Qualifiers
source                 1..367
                       mol_type = unassigned DNA
                       organism = Medicago truncatula
SEQUENCE: 362
ccacaaaact ataactagct agaagcttta atcgccttat ttattataat aataataata  60
aatatggctt cagctgcaaa agtatacatg gcgtgatatt gatccggctc atctatatct  120
tcaagttcaa tcatccatat tcatatcaat ttcagacgag ccgaatcaat atcactcttg  180
tttgcttcat tgcatattaa ttatatactt catttataag ttatagtttg ccatatatat  240
attagattga ttctgcagaa gtagacagga gtggtgttgt ttctgctcat cttattaaat  300
aatgaatgaa tgaatgacat ttgcttactt ataagacgag ccgaatcaat atcactccag  360
tacacct                                                            367

SEQ ID NO: 363         moltype = DNA  length = 135
FEATURE                Location/Qualifiers
source                 1..135
                       mol_type = unassigned DNA
                       organism = Medicago truncatula
SEQUENCE: 363
aactgcaact tgaggaggca tccaaaggga tcgcattgat cctataatat ttcaacttta  60
gtcactttaa ttttctctca tataatactt aattgggatc atgccatccc tttggatttc  120
tcctttagta gctac                                                   135

SEQ ID NO: 364         moltype = DNA  length = 119
FEATURE                Location/Qualifiers
source                 1..119
                       mol_type = unassigned DNA
                       organism = Medicago truncatula
SEQUENCE: 364
aggcatccaa agggatcgca ttgatcccaa atctaattaa gtccctagct acttaattaa  60
caacttaatt tccttaatat ctcataatat ttgggatcat gctatccctt tggattcat   119

SEQ ID NO: 365         moltype = DNA  length = 93
FEATURE                Location/Qualifiers
source                 1..93
                       mol_type = unassigned DNA
                       organism = Medicago truncatula
```

```
SEQUENCE: 365
tgcttttcca cagctttctt gaacttcttt cgtatcttaa atctgttttc aagattaaaa  60
gtcctagaag ctcaagaaag ctgtgggaga ata                               93

SEQ ID NO: 366         moltype = DNA  length = 95
FEATURE                Location/Qualifiers
source                 1..95
                       mol_type = unassigned DNA
                       organism = Medicago truncatula
SEQUENCE: 366
tattcttcca cagctttctt gaactgcatc caaattgagt tcctttgcat tgccatggcc  60
attgttttgc ggttcaataa agctgtggga agata                             95

SEQ ID NO: 367         moltype = RNA  length = 21
FEATURE                Location/Qualifiers
source                 1..21
                       mol_type = unassigned RNA
                       organism = Medicago truncatula
SEQUENCE: 367
cagccaagga tgacttgccg g                                            21

SEQ ID NO: 368         moltype = RNA  length = 21
FEATURE                Location/Qualifiers
source                 1..21
                       mol_type = unassigned RNA
                       organism = Medicago truncatula
SEQUENCE: 368
cagccaagga tgacttgccg a                                            21

SEQ ID NO: 369         moltype = RNA  length = 21
FEATURE                Location/Qualifiers
source                 1..21
                       mol_type = unassigned RNA
                       organism = Medicago truncatula
SEQUENCE: 369
tgattgagtc gtgccaatat c                                            21

SEQ ID NO: 370         moltype = RNA  length = 20
FEATURE                Location/Qualifiers
source                 1..20
                       mol_type = unassigned RNA
                       organism = Medicago truncatula
SEQUENCE: 370
gagccgaatc aatatcactc                                              20

SEQ ID NO: 371         moltype = RNA  length = 21
FEATURE                Location/Qualifiers
source                 1..21
                       mol_type = unassigned RNA
                       organism = Medicago truncatula
SEQUENCE: 371
tccaaaggga tcgcattgat c                                            21

SEQ ID NO: 372         moltype = RNA  length = 21
FEATURE                Location/Qualifiers
source                 1..21
                       mol_type = unassigned RNA
                       organism = Medicago truncatula
SEQUENCE: 372
tccaaaggga tcgcattgat c                                            21

SEQ ID NO: 373         moltype = RNA  length = 21
FEATURE                Location/Qualifiers
source                 1..21
                       mol_type = unassigned RNA
                       organism = Medicago truncatula
SEQUENCE: 373
ttccacagct ttcttgaact t                                            21

SEQ ID NO: 374         moltype = RNA  length = 21
FEATURE                Location/Qualifiers
source                 1..21
                       mol_type = unassigned RNA
                       organism = Medicago truncatula
SEQUENCE: 374
ttccacagct ttcttgaact g                                            21

SEQ ID NO: 375         moltype = AA  length = 15
FEATURE                Location/Qualifiers
```

```
source                  1..15
                        mol_type = protein
                        organism = Arabidopsis thaliana
SEQUENCE: 375
MMLHITHRFE SDVGC                                                    15

SEQ ID NO: 376          moltype = AA  length = 4
FEATURE                 Location/Qualifiers
source                  1..4
                        mol_type = protein
                        organism = Arabidopsis thaliana
SEQUENCE: 376
MLYV                                                                4

SEQ ID NO: 377          moltype = AA  length = 14
FEATURE                 Location/Qualifiers
source                  1..14
                        mol_type = protein
                        organism = Arabidopsis thaliana
SEQUENCE: 377
MFMRRGLVYN NIYI                                                     14

SEQ ID NO: 378          moltype = AA  length = 17
FEATURE                 Location/Qualifiers
source                  1..17
                        mol_type = protein
                        organism = Arabidopsis thaliana
SEQUENCE: 378
MMKVCDEQDG EAGHVHY                                                  17

SEQ ID NO: 379          moltype = AA  length = 28
FEATURE                 Location/Qualifiers
source                  1..28
                        mol_type = protein
                        organism = Arabidopsis thaliana
SEQUENCE: 379
MKKRITRINL EEQIKKTLDD SRTRLHSP                                      28

SEQ ID NO: 380          moltype = AA  length = 10
FEATURE                 Location/Qualifiers
source                  1..10
                        mol_type = protein
                        organism = Arabidopsis thaliana
SEQUENCE: 380
MKKIGSIDSF                                                          10

SEQ ID NO: 381          moltype = AA  length = 6
FEATURE                 Location/Qualifiers
source                  1..6
                        mol_type = protein
                        organism = Arabidopsis thaliana
SEQUENCE: 381
MTCRFK                                                              6

SEQ ID NO: 382          moltype = AA  length = 11
FEATURE                 Location/Qualifiers
source                  1..11
                        mol_type = protein
                        organism = Arabidopsis thaliana
SEQUENCE: 382
MKNENLCGSQ G                                                        11

SEQ ID NO: 383          moltype = AA  length = 45
FEATURE                 Location/Qualifiers
source                  1..45
                        mol_type = protein
                        organism = Arabidopsis thaliana
SEQUENCE: 383
MKCMMKKRGL TWRKASCLVA KDDLPDLFRL HDSISNSCIL DYYTF                   45

SEQ ID NO: 384          moltype = AA  length = 7
FEATURE                 Location/Qualifiers
source                  1..7
                        mol_type = protein
                        organism = Arabidopsis thaliana
SEQUENCE: 384
MFPRESL                                                             7

SEQ ID NO: 385          moltype = AA  length = 29
```

```
FEATURE                Location/Qualifiers
source                 1..29
                       mol_type = protein
                       organism = Arabidopsis thaliana
SEQUENCE: 385
MTLSVFFHSF LELQNFFRFF FFSFDISYA                                    29

SEQ ID NO: 386         moltype = AA  length = 23
FEATURE                Location/Qualifiers
source                 1..23
                       mol_type = protein
                       organism = Arabidopsis thaliana
SEQUENCE: 386
MSLAKGELPC HCFRLNTVYN RFC                                          23

SEQ ID NO: 387         moltype = DNA  length = 48
FEATURE                Location/Qualifiers
source                 1..48
                       mol_type = unassigned DNA
                       organism = Arabidopsis thaliana
SEQUENCE: 387
atgatgttgc atatcacaca taggtttgag agtgatgttg gttgttga               48

SEQ ID NO: 388         moltype = DNA  length = 15
FEATURE                Location/Qualifiers
source                 1..15
                       mol_type = unassigned DNA
                       organism = Arabidopsis thaliana
SEQUENCE: 388
atgctgtatg tatag                                                   15

SEQ ID NO: 389         moltype = DNA  length = 45
FEATURE                Location/Qualifiers
source                 1..45
                       mol_type = unassigned DNA
                       organism = Arabidopsis thaliana
SEQUENCE: 389
atgttcatgc gtagaggttt ggtatacaac aatatataca tataa                  45

SEQ ID NO: 390         moltype = DNA  length = 54
FEATURE                Location/Qualifiers
source                 1..54
                       mol_type = unassigned DNA
                       organism = Arabidopsis thaliana
SEQUENCE: 390
atgatgaagg tgtgtgatga gcaagatgga gaagcagggc acgtgcatta ctag        54

SEQ ID NO: 391         moltype = DNA  length = 87
FEATURE                Location/Qualifiers
source                 1..87
                       mol_type = unassigned DNA
                       organism = Arabidopsis thaliana
SEQUENCE: 391
atgaagaaga gaatcactcg aattaatttg gaagaacaaa ttaagaaaac cctagatgat  60
tctcggacca ggcttcattc cccctaa                                      87

SEQ ID NO: 392         moltype = DNA  length = 33
FEATURE                Location/Qualifiers
source                 1..33
                       mol_type = unassigned DNA
                       organism = Arabidopsis thaliana
SEQUENCE: 392
atgaagaaga tcggtagtat tgattcattt taa                               33

SEQ ID NO: 393         moltype = DNA  length = 21
FEATURE                Location/Qualifiers
source                 1..21
                       mol_type = unassigned DNA
                       organism = Arabidopsis thaliana
SEQUENCE: 393
atgacttgcc gatttaaatg a                                            21

SEQ ID NO: 394         moltype = DNA  length = 12
FEATURE                Location/Qualifiers
source                 1..12
                       mol_type = unassigned DNA
                       organism = Arabidopsis thaliana
SEQUENCE: 394
atggtgacat ga                                                      12
```

```
SEQ ID NO: 395          moltype = DNA  length = 36
FEATURE                 Location/Qualifiers
source                  1..36
                        mol_type = unassigned DNA
                        organism = Arabidopsis thaliana
SEQUENCE: 395
atgaagaatg agaacttgtg tggtagccaa ggatga                            36

SEQ ID NO: 396          moltype = DNA  length = 138
FEATURE                 Location/Qualifiers
source                  1..138
                        mol_type = unassigned DNA
                        organism = Arabidopsis thaliana
SEQUENCE: 396
atgaagtgta tgatgaagaa gagaggtcta acatggcgga aagcgtcatg tttagtagcc  60
aaggatgact tgcctgatct ttttcgcctc cacgattcaa tttcaaattc atgcattttg  120
gattattata ccttttaa                                                138

SEQ ID NO: 397          moltype = DNA  length = 24
FEATURE                 Location/Qualifiers
source                  1..24
                        mol_type = unassigned DNA
                        organism = Arabidopsis thaliana
SEQUENCE: 397
atgtttccga gagagtccct ctga                                         24

SEQ ID NO: 398          moltype = DNA  length = 90
FEATURE                 Location/Qualifiers
source                  1..90
                        mol_type = unassigned DNA
                        organism = Arabidopsis thaliana
SEQUENCE: 398
atgaccctct ctgtattctt ccacagcttt cttgaactgc aaaacttctt cagatttttt  60
tttttttctt ttgatatctc ttacgcataa                                   90

SEQ ID NO: 399          moltype = DNA  length = 72
FEATURE                 Location/Qualifiers
source                  1..72
                        mol_type = unassigned DNA
                        organism = Arabidopsis thaliana
SEQUENCE: 399
atgtcacttg ccaaaggaga gttgccctgt cactgcttcc gcttaaacac agtctataac  60
cggttctgct aa                                                      72

SEQ ID NO: 400          moltype = DNA  length = 331
FEATURE                 Location/Qualifiers
source                  1..331
                        mol_type = unassigned DNA
                        organism = Arabidopsis thaliana
SEQUENCE: 400
ctttgtcact tcatacactc cctattgtct atatatatat atatacttac acatattcaa  60
acattataat acttaattac acatacatac tttatgatgt tgcatatcac acataggttt  120
gagagtgatg ttggttgttg acagaagata gagagcacta aggatgacat gcaagtacat  180
acatatatat catcacaccg catgtggatg ataaaatatg tataacaaat tcaaagaaag  240
agagggagag aaagagagag aacctgcatc tctactcttt tgtgctctct atacttctgt  300
caccaccttt atctcttctt ctctctaacc t                                 331

SEQ ID NO: 401          moltype = DNA  length = 304
FEATURE                 Location/Qualifiers
source                  1..304
                        mol_type = unassigned DNA
                        organism = Arabidopsis thaliana
SEQUENCE: 401
atttactctt caccgccctc tctctatata tagtctctat cctcacatat tatatatcaa  60
accgcaagaa tgctgtatgt atagtggagg gtgatagtgt ggttgctgac agaagataga  120
gagcactaag gatgctatgc aaaacagaca cagatatgtg tttctaattg tatttcatac  180
tttaacctca aagttgatat aaaaaaagaa agaaagatag aagagctaga agactatctg  240
catctctatt cctatgtgct ctctatgctt ctgtcatcac ctttctttct ctatttctct  300
ctac                                                               304

SEQ ID NO: 402          moltype = DNA  length = 245
FEATURE                 Location/Qualifiers
source                  1..245
                        mol_type = unassigned DNA
                        organism = Arabidopsis thaliana
SEQUENCE: 402
aaccaaaact cttcaacatt tctctctgac tacttcattt cctcttccca acagttaaaa  60
aaagttctga ttcgattcaa gccaagatcc acgtataaag atatgttcat gcgtagaggt  120
```

```
ttggtataca acaatatata catataatag tttgtcgtta tgcctggctc cctgtatgcc  180
acgagtggat accgattttg gttttaaaat cggctgccgg tggcgtacaa ggagtcaagc  240
atgac                                                              245

SEQ ID NO: 403         moltype = DNA  length = 240
FEATURE                Location/Qualifiers
source                 1..240
                       mol_type = unassigned DNA
                       organism = Arabidopsis thaliana
SEQUENCE: 403
atacattctc tctttctctc tctctctctc tctcatcccg gcccagttat gtggtcggag  60
agaatgatga aggtgtgtga tgagcaagat ggagaagcag ggcacgtgca ttactagctc  120
atatatacac tctcaccaca aatgcgtgta tatatgcgga attttgtgat atagatgtgt  180
gtgtgtgttg agtgtgatga tatggatgag ttagttcttc atgtgcccat cttcaccatc  240

SEQ ID NO: 404         moltype = DNA  length = 280
FEATURE                Location/Qualifiers
source                 1..280
                       mol_type = unassigned DNA
                       organism = Arabidopsis thaliana
SEQUENCE: 404
tcacacatac ctttctttct cttcttcttc ttacgaaaag tttcatcaca ttcacattat  60
ctttaacttt ggtctctttt cttttttgtc tcttttctct tcttgataac gtggttctag  120
tcttgattaa ttcattgttg tgcgatttag tgttgagagg attgttgtct ggctcgaggt  180
catgaagaag agaatcactc gaattaattt ggaagaacaa attaagaaaa ccctagatga  240
ttctcggacc aggcttcatt ccccctaacc tacttatcgc                        280

SEQ ID NO: 405         moltype = DNA  length = 179
FEATURE                Location/Qualifiers
source                 1..179
                       mol_type = unassigned DNA
                       organism = Arabidopsis thaliana
SEQUENCE: 405
atttagcttc ttcttcttct tcttcttctg tctacttaca taaagttatc cttgctttgg  60
tttagggttg agaggaatat tgtctggctc gaggtcatga agaagatcgg tagtattgat  120
tcattttaaa gagtgaaatc cctaaatgat tctcggacca ggcttcattc cccccaacc   179

SEQ ID NO: 406         moltype = DNA  length = 376
FEATURE                Location/Qualifiers
source                 1..376
                       mol_type = unassigned DNA
                       organism = Arabidopsis thaliana
SEQUENCE: 406
tagtattcat aagcaccaaa acaaatatgt agagatctcc tcttccattc tctattgtta  60
ctttcgagaa gaaacataca aaacacatac atttttcttt tgtttgtggt tttcatatat  120
acaagtgggt atagctagtg aaacgcgaat gtgacgaaag tagtgtgcag ccaaggatga  180
cttgccgatt taaatgatct ttctttatac tctattaaga caatttagtt tcaaactttt  240
ttttttttt ttttttgaag gattcaggaa gaaattagga tatattattc cgtataaaat  300
acaagatata taaaaccaaa aagaaaaagt aacatgatcg gcaagttgtc cttggctaca  360
cgttactttg tgtcgc                                                  376

SEQ ID NO: 407         moltype = DNA  length = 77
FEATURE                Location/Qualifiers
source                 1..77
                       mol_type = unassigned DNA
                       organism = Arabidopsis thaliana
SEQUENCE: 407
actcatcaac aacctcttca taaatacata aatcatataa gagaaaatgg tgacatgaag  60
aatgagaact tgtgtgg                                                 77

SEQ ID NO: 408         moltype = DNA  length = 248
FEATURE                Location/Qualifiers
source                 1..248
                       mol_type = unassigned DNA
                       organism = Arabidopsis thaliana
SEQUENCE: 408
aggcaaaaac atatagagag taatgaagtg tatgatgaag aagagaggtc taacatggcg  60
gaaagcgtca tgtttagtag ccaaggatga cttgcctgat ctttttcgcc tccacgattc  120
aatttcaaat tcatgcattt tggattatta tacctttttaa agtataatag gtcaaatatc  180
atgttgaatc ttgcgggtta ggtttcaggc agtctctttg gctatcttga catgcttttt  240
ccatccat                                                           248

SEQ ID NO: 409         moltype = DNA  length = 187
FEATURE                Location/Qualifiers
source                 1..187
                       mol_type = unassigned DNA
                       organism = Arabidopsis thaliana
SEQUENCE: 409
attcactccc ttcttcttct taatctcctt acagttacag acattctctc acttgcgttc  60
```

-continued

```
ttgtttcttt tacaaaacag atacactatg tttccgagag agtccctctg atattggcct  120
ggttcactca gattctcttt tactaactca tctgattgag ccgtgtcaat atctcagtcc  180
tctctcg                                                            187

SEQ ID NO: 410          moltype = DNA  length = 246
FEATURE                 Location/Qualifiers
source                  1..246
                        mol_type = unassigned DNA
                        organism = Arabidopsis thaliana
SEQUENCE: 410
tctcacaact tcaacttccc tctttctcta tattacgctt ttgcccctca ctccctcttt  60
ccacaattag ggtttcgtct gctctacatg accctctctg tattcttcca cagctttctt  120
gaactgcaaa acttcttcag attttttttt ttttcttttg atatctctta cgcataaaat  180
agtgattttc ttcatatctc tgctcgattg atttgcggtt caataaagct gtgggaagat  240
acagac                                                             246

SEQ ID NO: 411          moltype = DNA  length = 631
FEATURE                 Location/Qualifiers
source                  1..631
                        mol_type = unassigned DNA
                        organism = Arabidopsis thaliana
SEQUENCE: 411
gaataaccaa ccagccttct ctcaaagcaa accaaaaaga aaaaccaaca ttgaaagagg  60
aagttacgat aagcggagca gtaatagggc atctttctat tggcaggcga cttggctatt  120
tgtatctttt gtgttcttga ctattggcta tgtcacttgc caaaggagag ttgccctgtc  180
actgcttccg cttaaacaca gtctataacc ggttctgcta atatcaatcc ttcttttgga  240
catgtccaaa gccgagattg attgatagag aattggtctc tctggctaca aaactagtgc  300
ggttctctcg atttaagttt taatagcatt cactttgcac attgcatctt tcacatcaaa  360
tttccatttc atcaaccatc taaacctctt tgttagcttt gatataagca acgatctaaa  420
gtctaaaaac cattaatcct ctgaaaaaaa agacaatttc gatggttcta ttatgtttct  480
ccaatgcaga aattgtatcg tctgaattat agtagatttt ttctagacta aagtgtaaac  540
caagacgaat ctgcactaac aagacacacc aatagacttt acagagaaag gttacgagtt  600
ttgaaaatat taacggacca tagtcatcgc g                                 631

SEQ ID NO: 412          moltype = RNA  length = 21
FEATURE                 Location/Qualifiers
source                  1..21
                        mol_type = unassigned RNA
                        organism = Arabidopsis thaliana
SEQUENCE: 412
ttgacagaag atagagagca c                                            21

SEQ ID NO: 413          moltype = RNA  length = 20
FEATURE                 Location/Qualifiers
source                  1..20
                        mol_type = unassigned RNA
                        organism = Arabidopsis thaliana
SEQUENCE: 413
tgacagaaga tagagagcac                                              20

SEQ ID NO: 414          moltype = RNA  length = 21
FEATURE                 Location/Qualifiers
source                  1..21
                        mol_type = unassigned RNA
                        organism = Arabidopsis thaliana
SEQUENCE: 414
tgcctggctc cctgtatgcc a                                            21

SEQ ID NO: 415          moltype = RNA  length = 21
FEATURE                 Location/Qualifiers
source                  1..21
                        mol_type = unassigned RNA
                        organism = Arabidopsis thaliana
SEQUENCE: 415
tggagaagca gggcacgtgc a                                            21

SEQ ID NO: 416          moltype = RNA  length = 21
FEATURE                 Location/Qualifiers
source                  1..21
                        mol_type = unassigned RNA
                        organism = Arabidopsis thaliana
SEQUENCE: 416
tcggaccagg cttcattccc c                                            21

SEQ ID NO: 417          moltype = RNA  length = 21
FEATURE                 Location/Qualifiers
source                  1..21
                        mol_type = unassigned RNA
                        organism = Arabidopsis thaliana
```

-continued

```
SEQUENCE: 417
tcggaccagg cttcattccc c                                             21

SEQ ID NO: 418          moltype = RNA  length = 21
FEATURE                 Location/Qualifiers
source                  1..21
                        mol_type = unassigned RNA
                        organism = Arabidopsis thaliana
SEQUENCE: 418
cagccaagga tgacttgccg a                                             21

SEQ ID NO: 419          moltype = RNA  length = 21
FEATURE                 Location/Qualifiers
source                  1..21
                        mol_type = unassigned RNA
                        organism = Arabidopsis thaliana
SEQUENCE: 419
tagccaagga tgacttgcct g                                             21

SEQ ID NO: 420          moltype = RNA  length = 21
FEATURE                 Location/Qualifiers
source                  1..21
                        mol_type = unassigned RNA
                        organism = Arabidopsis thaliana
SEQUENCE: 420
tagccaagga tgacttgcct g                                             21

SEQ ID NO: 421          moltype = RNA  length = 21
FEATURE                 Location/Qualifiers
source                  1..21
                        mol_type = unassigned RNA
                        organism = Arabidopsis thaliana
SEQUENCE: 421
tgattgagcc gtgtcaatat c                                             21

SEQ ID NO: 422          moltype = RNA  length = 21
FEATURE                 Location/Qualifiers
source                  1..21
                        mol_type = unassigned RNA
                        organism = Arabidopsis thaliana
SEQUENCE: 422
ttccacagct ttcttgaact g                                             21

SEQ ID NO: 423          moltype = RNA  length = 21
FEATURE                 Location/Qualifiers
source                  1..21
                        mol_type = unassigned RNA
                        organism = Arabidopsis thaliana
SEQUENCE: 423
tgccaaagga gagttgccct g                                             21
```